US009738722B2

(12) United States Patent
Moore et al.

(10) Patent No.: US 9,738,722 B2
(45) Date of Patent: Aug. 22, 2017

(54) RAPID CLEARANCE OF ANTIGEN COMPLEXES USING NOVEL ANTIBODIES

(71) Applicants: Gregory L. Moore, Monrovia, CA (US); John Desjarlais, Pasadena, CA (US); Matthew Bernett, Rosemead, CA (US)

(72) Inventors: Gregory L. Moore, Monrovia, CA (US); John Desjarlais, Pasadena, CA (US); Matthew Bernett, Rosemead, CA (US)

(73) Assignee: Xencor, Inc., Monrovia, CA (US)

( * ) Notice: Subject to any disclaimer, the term of this patent is extended or adjusted under 35 U.S.C. 154(b) by 337 days.

(21) Appl. No.: 14/156,432

(22) Filed: Jan. 15, 2014

(65) Prior Publication Data

US 2014/0212436 A1 Jul. 31, 2014

Related U.S. Application Data

(60) Provisional application No. 61/752,955, filed on Jan. 15, 2013, provisional application No. 61/794,164, filed on Mar. 15, 2013, provisional application No. 61/794,386, filed on Mar. 15, 2013, provisional application No. 61/833,696, filed on Jun. 11, 2013.

(51) Int. Cl.

| *C07K 14/435* | (2006.01) |
| *C07K 14/705* | (2006.01) |
| *C07K 14/735* | (2006.01) |
| *C07K 16/18* | (2006.01) |
| *C07K 19/00* | (2006.01) |
| *A61K 38/17* | (2006.01) |
| *A61K 39/395* | (2006.01) |
| *C07K 16/28* | (2006.01) |
| *C07K 16/42* | (2006.01) |
| *C07K 16/10* | (2006.01) |
| *C07K 16/46* | (2006.01) |
| *A61K 39/00* | (2006.01) |

(52) U.S. Cl.
CPC ...... *C07K 16/2878* (2013.01); *C07K 16/1027* (2013.01); *C07K 16/2803* (2013.01); *C07K 16/4291* (2013.01); *A61K 38/17* (2013.01); *A61K 38/177* (2013.01); *A61K 38/1709* (2013.01); *A61K 38/1774* (2013.01); *A61K 39/395* (2013.01); *A61K 39/3955* (2013.01); *A61K 2039/505* (2013.01); *A61K 2039/54* (2013.01); *C07K 14/435* (2013.01); *C07K 16/18* (2013.01); *C07K 16/46* (2013.01); *C07K 2316/52* (2013.01); *C07K 2317/24* (2013.01); *C07K 2317/30* (2013.01); *C07K 2317/72* (2013.01); *C07K 2317/732* (2013.01); *C07K 2317/76* (2013.01); *C07K 2317/77* (2013.01); *C07K 2317/92* (2013.01); *C07K 2319/30* (2013.01); *C07K 2319/32* (2013.01)

(58) Field of Classification Search
CPC .......... A61K 2039/505; A61K 39/3955; A61K 39/0012; A61K 38/177; A61K 38/1774; C07K 2317/92; C07K 2317/94; C07K 16/00; C07K 2317/52; C07K 2317/72; C07K 16/18; C07K 2317/56; C07K 2317/62; C07K 2316/52; C07K 14/435; C07K 14/70535; C07K 2319/30; C07K 2319/32; C07K 16/44
See application file for complete search history.

(56) References Cited

U.S. PATENT DOCUMENTS

| 3,773,919 | A | 11/1973 | Boswell et al. |
| 4,169,888 | A | 10/1979 | Hanka et al. |
| 4,179,337 | A | 12/1979 | Davis et al. |
| 4,256,746 | A | 3/1981 | Miyashita et al. |
| 4,294,757 | A | 10/1981 | Asai |
| 4,301,144 | A | 11/1981 | Iwashita et al. |
| 4,307,016 | A | 12/1981 | Asai et al. |
| 4,313,946 | A | 2/1982 | Powell et al. |
| 4,315,929 | A | 2/1982 | Freedman et al. |
| 4,322,348 | A | 3/1982 | Asai et al. |
| 4,331,598 | A | 5/1982 | Hasegawa et al. |
| 4,361,650 | A | 11/1982 | Asai et al. |
| 4,362,663 | A | 12/1982 | Kida et al. |
| 4,364,866 | A | 12/1982 | Asai et al. |
| 4,364,935 | A | 12/1982 | Kung et al. |
| 4,371,533 | A | 2/1983 | Akimoto et al. |
| 4,424,219 | A | 1/1984 | Hashimoto et al. |

(Continued)

FOREIGN PATENT DOCUMENTS

| EP | 0 425 235 B1 | 9/1996 |
| EP | 1752471 | 2/2007 |

(Continued)

OTHER PUBLICATIONS

Cao et al. Oligomerization is required for the activity of recombinant soluble LOX-1. FEBS J 276: 4909-4920, 2009.*

(Continued)

*Primary Examiner* — Bridget E Bunner
(74) *Attorney, Agent, or Firm* — Robin M. Silva; Louis T. Nguyen; Morgan, Lewis & Bockius, LLP

(57) ABSTRACT

The present invention relates to rapid clearance molecules that bind target antigens and FcγRIIb with increased affinity as compared to parent molecules, the compositions being capable of causing accelerated clearance of such antigens. Such compositions are useful for treating a variety of disorders, including allergic diseases, atherosclerosis, and a variety of other conditions.

8 Claims, 61 Drawing Sheets

(56) References Cited

U.S. PATENT DOCUMENTS

| | | | |
|---|---|---|---|
| 4,450,254 A | 5/1984 | Isley et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 4,880,935 A | 11/1989 | Thorpe | |
| 4,923,990 A | 5/1990 | Nakano et al. | |
| 4,943,533 A | 7/1990 | Mendelsohn et al. | |
| 4,970,198 A | 11/1990 | Lee et al. | |
| 5,053,394 A | 10/1991 | Ellestad et al. | |
| 5,070,092 A | 12/1991 | Kanda et al. | |
| 5,084,468 A | 1/1992 | Saito et al. | |
| 5,101,038 A | 3/1992 | Nakano et al. | |
| 5,122,368 A | 6/1992 | Greenfield et al. | |
| 5,187,186 A | 2/1993 | Kanda et al. | |
| 5,208,020 A | 5/1993 | Chari et al. | |
| 5,264,586 A | 11/1993 | Nicolaou et al. | |
| 5,384,412 A | 1/1995 | Nicolaou et al. | |
| 5,416,064 A | 5/1995 | Chari et al. | |
| 5,475,092 A | 12/1995 | Chari et al. | |
| 5,500,362 A | 3/1996 | Robinson et al. | |
| 5,530,101 A | 6/1996 | Queen et al. | |
| 5,541,087 A | 7/1996 | Lo et al. | |
| 5,550,246 A | 8/1996 | Nicolaou et al. | |
| 5,558,864 A | 9/1996 | Bendig et al. | |
| 5,585,089 A | 12/1996 | Queen et al. | |
| 5,585,097 A | 12/1996 | Bolt et al. | |
| 5,585,499 A | 12/1996 | Chari et al. | |
| 5,622,929 A | 4/1997 | Willner et al. | |
| 5,635,483 A | 6/1997 | Pettit et al. | |
| 5,641,780 A | 6/1997 | Amishiro et al. | |
| 5,663,149 A | 9/1997 | Pettit et al. | |
| 5,677,171 A | 10/1997 | Hudziak et al. | |
| 5,693,761 A | 12/1997 | Queen et al. | |
| 5,693,762 A | 12/1997 | Queen et al. | |
| 5,703,080 A | 12/1997 | Nakakura et al. | |
| 5,712,374 A | 1/1998 | Kuntsmann et al. | |
| 5,714,586 A | 2/1998 | Kunstmann et al. | |
| 5,726,044 A | 3/1998 | Lo et al. | |
| 5,731,168 A | 3/1998 | Carter et al. | |
| 5,736,137 A | 4/1998 | Anderson et al. | |
| 5,739,116 A | 4/1998 | Hamann et al. | |
| 5,767,237 A | 6/1998 | Sakakibara et al. | |
| 5,767,285 A | 6/1998 | Hamann et al. | |
| 5,770,701 A | 6/1998 | McGahren et al. | |
| 5,770,710 A | 6/1998 | McGahren et al. | |
| 5,773,001 A | 6/1998 | Hamann et al. | |
| 5,780,588 A | 7/1998 | Pettit et al. | |
| 5,807,706 A | 9/1998 | Carter et al. | |
| 5,821,333 A | 10/1998 | Carter et al. | |
| 5,821,337 A | 10/1998 | Carter et al. | |
| 5,824,805 A | 10/1998 | King et al. | |
| 5,846,545 A | 12/1998 | Chari et al. | |
| 5,859,205 A | 1/1999 | Adair et al. | |
| 5,877,291 A | 3/1999 | Mezes et al. | |
| 5,877,296 A | 3/1999 | Hamann et al. | |
| 5,891,996 A | 4/1999 | Mateo de Acosta del Rio et al. | |
| 5,892,020 A | 4/1999 | Mezes et al. | |
| 5,945,311 A | 8/1999 | Lindhofer et al. | |
| 5,968,509 A | 10/1999 | Gorman et al. | |
| 6,054,297 A | 4/2000 | Carter et al. | |
| 6,071,515 A | 6/2000 | Mezes et al. | |
| 6,124,431 A | 9/2000 | Sakakibara et al. | |
| 6,180,370 B1 | 1/2001 | Queen et al. | |
| 6,214,345 B1 | 4/2001 | Firestone et al. | |
| 6,235,883 B1 | 5/2001 | Jakobovits et al. | |
| 6,329,507 B1 | 12/2001 | Mezes et al. | |
| 6,407,213 B1 | 6/2002 | Carter et al. | |
| 6,441,163 B1 | 8/2002 | Chari et al. | |
| 6,455,677 B1 | 9/2002 | Park et al. | |
| 6,506,883 B2 | 1/2003 | Meteo de Acosta del Rio et al. | |
| 6,602,684 B1 | 8/2003 | Umana et al. | |
| 6,632,927 B2 | 10/2003 | Adair et al. | |
| 6,706,265 B1 | 3/2004 | Bolt et al. | |
| 6,716,410 B1 * | 4/2004 | Witztum | A61K 41/0057 424/1.49 |
| 6,723,538 B2 | 4/2004 | Mack et al. | |
| 6,884,869 B2 | 4/2005 | Senter et al. | |
| 6,989,452 B2 | 1/2006 | Ng et al. | |
| 7,087,600 B2 | 8/2006 | Ng et al. | |
| 7,112,324 B1 | 9/2006 | Dorken et al. | |
| 7,129,261 B2 | 10/2006 | Ng et al. | |
| 7,276,497 B2 | 10/2007 | Chari et al. | |
| 7,303,749 B1 | 12/2007 | Chari | |
| 7,368,565 B2 | 5/2008 | Chari et al. | |
| 7,498,302 B2 | 3/2009 | Ng et al. | |
| 7,507,420 B2 | 3/2009 | Ng et al. | |
| 7,517,903 B2 | 4/2009 | Chen et al. | |
| 7,601,354 B2 | 10/2009 | Chari | |
| 7,642,228 B2 | 1/2010 | Carter et al. | |
| 7,691,962 B2 | 4/2010 | Boyd et al. | |
| 7,695,936 B2 | 4/2010 | Carter et al. | |
| 7,696,338 B2 | 4/2010 | Neville, Jr. et al. | |
| 7,728,114 B2 | 6/2010 | Mach et al. | |
| 8,063,187 B2 | 11/2011 | Chu et al. | |
| 8,114,967 B2 | 2/2012 | Bhatt et al. | |
| 8,216,805 B2 | 7/2012 | Carter et al. | |
| 8,236,308 B2 | 8/2012 | Kischel et al. | |
| 8,309,690 B2 | 11/2012 | Allan et al. | |
| 8,367,805 B2 | 2/2013 | Chamberlain et al. | |
| 8,409,568 B2 | 4/2013 | Gao et al. | |
| 8,592,562 B2 | 11/2013 | Kannan et al. | |
| 8,637,641 B2 | 1/2014 | Dahiyat et al. | |
| 8,946,387 B2 | 2/2015 | Koenig et al. | |
| 2001/0035606 A1 | 11/2001 | Schoen | |
| 2002/0076406 A1 | 6/2002 | Leung | |
| 2002/0103345 A1 | 8/2002 | Zhu | |
| 2002/0131968 A1 | 9/2002 | Waldmann et al. | |
| 2003/0003097 A1 | 1/2003 | Reff et al. | |
| 2003/0017979 A1 | 1/2003 | Mack et al. | |
| 2003/0091561 A1 | 5/2003 | Van de Winekl | |
| 2003/0157108 A1 | 8/2003 | Presta | |
| 2003/0223999 A1 | 12/2003 | Lindhofer | |
| 2004/0071696 A1 | 4/2004 | Adams et al. | |
| 2004/0162411 A1 | 8/2004 | Lanzavecchia | |
| 2004/0170626 A1 | 9/2004 | Schuurman et al. | |
| 2004/0242851 A1 | 12/2004 | Zhu | |
| 2005/0114037 A1 | 5/2005 | Desjarlais et al. | |
| 2005/0136050 A1 | 6/2005 | Kufer et al. | |
| 2005/0142133 A1 | 6/2005 | Lazar et al. | |
| 2005/0176028 A1 | 8/2005 | Hofmeister et al. | |
| 2005/0191702 A1 | 9/2005 | Mack et al. | |
| 2005/0238648 A1 | 10/2005 | Jacobs | |
| 2005/0238649 A1 | 10/2005 | Doronina | |
| 2006/0008883 A1 | 1/2006 | Lazar | |
| 2006/0018897 A1 | 1/2006 | Lee et al. | |
| 2006/0024298 A1 | 2/2006 | Lazar et al. | |
| 2006/0024317 A1 | 2/2006 | Boyd | |
| 2006/0073142 A1 | 4/2006 | Chan et al. | |
| 2006/0074008 A1 | 4/2006 | Senter | |
| 2006/0115481 A1 | 6/2006 | Lindhofer et al. | |
| 2006/0121032 A1 | 6/2006 | Dahiyat et al. | |
| 2006/0134105 A1 | 6/2006 | Lazar et al. | |
| 2006/0235208 A1 | 10/2006 | Lazar | |
| 2007/0071675 A1 | 3/2007 | Wu et al. | |
| 2007/0105199 A1 | 5/2007 | Yan et al. | |
| 2007/0123479 A1 | 5/2007 | Kufer et al. | |
| 2007/0148170 A1 | 6/2007 | Desjarlais | |
| 2007/0287170 A1 | 12/2007 | Davis et al. | |
| 2008/0044413 A1 | 2/2008 | Hammond et al. | |
| 2008/0050370 A1 | 2/2008 | Glaser et al. | |
| 2008/0138335 A1 | 6/2008 | Takahashi et al. | |
| 2008/0213273 A1 | 9/2008 | Burge | |
| 2008/0219974 A1 | 9/2008 | Bernett et al. | |
| 2008/0242845 A1 | 10/2008 | Lazar et al. | |
| 2009/0082213 A1 | 3/2009 | Horowitz et al. | |
| 2009/0163699 A1 | 6/2009 | Desjarlais | |
| 2009/0214539 A1 | 8/2009 | Grosmaire et al. | |
| 2009/0252683 A1 | 10/2009 | Kischel et al. | |
| 2009/0252729 A1 | 10/2009 | Farrington et al. | |
| 2009/0274692 A1 | 11/2009 | Tan et al. | |
| 2009/0311253 A1 | 12/2009 | Ghayur et al. | |
| 2009/0317869 A1 | 12/2009 | Alley et al. | |

(56) References Cited

U.S. PATENT DOCUMENTS

| | | |
|---|---|---|
| 2010/0015133 A1 | 1/2010 | Igawa et al. |
| 2010/0080814 A1 | 4/2010 | Desjarlais et al. |
| 2010/0150918 A1 | 6/2010 | Kufer et al. |
| 2010/0174053 A1 | 7/2010 | Johnson et al. |
| 2010/0178298 A1 | 7/2010 | Lindhofer |
| 2010/0183554 A1 | 7/2010 | Mach et al. |
| 2010/0226925 A1 | 9/2010 | Dillon et al. |
| 2010/0239567 A1* | 9/2010 | Esue .................. C07K 16/18 424/130.1 |
| 2010/0239582 A1 | 9/2010 | Humphreys et al. |
| 2010/0256339 A1 | 10/2010 | Bossenmaier et al. |
| 2010/0256340 A1 | 10/2010 | Brinkmann et al. |
| 2010/0298542 A1 | 11/2010 | Igawa et al. |
| 2010/0322933 A1 | 12/2010 | Lindhofer et al. |
| 2010/0330089 A1 | 12/2010 | Damle et al. |
| 2010/0331527 A1 | 12/2010 | Davis et al. |
| 2011/0054151 A1 | 3/2011 | Lazar et al. |
| 2011/0076275 A1 | 3/2011 | Igawa et al. |
| 2011/0177500 A1 | 7/2011 | Winther et al. |
| 2011/0189178 A1 | 8/2011 | Desjarlais et al. |
| 2011/0189209 A1 | 8/2011 | Neville, Jr. et al. |
| 2011/0201032 A1 | 8/2011 | Zeng et al. |
| 2011/0217302 A1 | 9/2011 | Odegard et al. |
| 2011/0262439 A1 | 10/2011 | Kufer et al. |
| 2011/0275787 A1 | 11/2011 | Kufer et al. |
| 2011/0293619 A1 | 12/2011 | Kufer et al. |
| 2012/0028304 A1 | 2/2012 | Dahiyat et al. |
| 2012/0034228 A1 | 2/2012 | Kufer et al. |
| 2012/0149876 A1 | 6/2012 | Von Kreudenstein et al. |
| 2012/0156207 A1 | 6/2012 | Chu et al. |
| 2012/0251531 A1 | 10/2012 | Baehner et al. |
| 2012/0251541 A1 | 10/2012 | Baurin et al. |
| 2013/0089541 A1 | 4/2013 | D'Angelo et al. |
| 2013/0095097 A1 | 4/2013 | Blakenship et al. |
| 2013/0101586 A1 | 4/2013 | Riegler et al. |
| 2013/0115208 A1 | 5/2013 | Ho et al. |
| 2013/0129723 A1 | 5/2013 | Blakenship et al. |
| 2013/0142793 A1 | 6/2013 | Ledbetter et al. |
| 2013/0171095 A1 | 7/2013 | Bernett et al. |
| 2013/0195849 A1 | 8/2013 | Von Kreudenstein et al. |
| 2013/0209355 A1 | 8/2013 | De Weers et al. |
| 2013/0336981 A1 | 12/2013 | de Kruif et al. |
| 2014/0024111 A1 | 1/2014 | Kannan et al. |
| 2014/0072581 A1 | 3/2014 | Dixit et al. |
| 2014/0086916 A1 | 3/2014 | Zha |
| 2014/0212435 A1 | 7/2014 | Moore et al. |
| 2014/0212436 A1 | 7/2014 | Moore et al. |
| 2014/0249297 A1 | 9/2014 | Lazar et al. |
| 2014/0288275 A1 | 9/2014 | Moore et al. |
| 2014/0294759 A1 | 10/2014 | Chu et al. |
| 2014/0294823 A1 | 10/2014 | Moore et al. |
| 2014/0294833 A1 | 10/2014 | Desjarlais et al. |
| 2014/0294835 A1 | 10/2014 | Moore et al. |
| 2014/0294836 A1 | 10/2014 | Chu et al. |
| 2014/0302064 A1 | 10/2014 | Moore |
| 2014/0322217 A1 | 10/2014 | Moore et al. |
| 2014/0356381 A1 | 12/2014 | Moore et al. |
| 2014/0363426 A1 | 12/2014 | Moore et al. |
| 2014/0370013 A1 | 12/2014 | Desjarlais et al. |
| 2014/0370020 A1 | 12/2014 | Kuramochi et al. |
| 2014/0377269 A1 | 12/2014 | Mabry et al. |
| 2014/0377270 A1 | 12/2014 | Moore et al. |
| 2015/0071948 A1 | 3/2015 | Lazar et al. |
| 2015/0307629 A1 | 10/2015 | Bernett et al. |
| 2016/0060360 A1 | 3/2016 | Moore et al. |
| 2016/0068588 A1 | 3/2016 | Bernett et al. |
| 2016/0176969 A1 | 6/2016 | Bernett et al. |
| 2016/0215063 A1 | 7/2016 | Bernett et al. |
| 2016/0229924 A1 | 8/2016 | Bernett et al. |

FOREIGN PATENT DOCUMENTS

| | | |
|---|---|---|
| EP | 1829895 | 5/2007 |
| EP | 2009101 | 10/2007 |
| EP | 2 006 381 | 12/2008 |
| EP | 2 009 101 A1 | 12/2008 |
| EP | 2 194 066 | 6/2010 |
| EP | 2 202 245 A1 | 6/2010 |
| EP | 2194066 | 9/2010 |
| EP | 2522724 | 6/2011 |
| EP | 2 155 788 | 2/2014 |
| WO | WO 87/05330 | 9/1987 |
| WO | WO 92/11018 | 7/1992 |
| WO | WO 93/21232 | 10/1993 |
| WO | WO 94/13804 | 5/1994 |
| WO | WO 95/20045 | 1/1995 |
| WO | WO 96/40210 | 6/1996 |
| WO | WO9627011 | 9/1996 |
| WO | WO 98/50431 | 11/1998 |
| WO | WO 99/37791 | 7/1999 |
| WO | WO9954440 | 10/1999 |
| WO | WO 99/66951 | 12/1999 |
| WO | WO 00/61739 A1 | 10/2000 |
| WO | WO2011005621 | 1/2001 |
| WO | WO 01/24763 A2 | 4/2001 |
| WO | WO 01/29246 A1 | 4/2001 |
| WO | WO 01/62931 A1 | 8/2001 |
| WO | WO 01/88138 | 11/2001 |
| WO | WO0183525 | 11/2001 |
| WO | WO0190192 | 11/2001 |
| WO | WO 02/16368 | 2/2002 |
| WO | WO 02/30954 A1 | 4/2002 |
| WO | WO 02/31140 A1 | 4/2002 |
| WO | WO 02/088172 A2 | 7/2002 |
| WO | WO02062850 | 8/2002 |
| WO | WO 02/083180 | 10/2002 |
| WO | WO 02/098883 | 12/2002 |
| WO | WO 2004/010957 | 2/2004 |
| WO | WO 2004/043493 | 5/2004 |
| WO | WO 2004/103272 | 12/2004 |
| WO | WO2004106383 | 12/2004 |
| WO | WO2005063816 | 7/2005 |
| WO | WO 2005/112919 A2 | 12/2005 |
| WO | WO2005118635 | 12/2005 |
| WO | WO2006020258 | 2/2006 |
| WO | WO 2006/034488 | 3/2006 |
| WO | WO2006036834 | 4/2006 |
| WO | WO2006072620 | 7/2006 |
| WO | WO 2006/110476 A2 | 10/2006 |
| WO | WO2006106905 | 12/2006 |
| WO | WO2007005612 | 1/2007 |
| WO | WO 2007/018431 A2 | 2/2007 |
| WO | WO2007042261 | 4/2007 |
| WO | WO2007047829 | 4/2007 |
| WO | WO 2007/059404 A2 | 5/2007 |
| WO | WO2007062037 | 5/2007 |
| WO | WO 2007/089149 A2 | 8/2007 |
| WO | WO2007093630 | 8/2007 |
| WO | WO2007098934 | 9/2007 |
| WO | WO2007110205 | 10/2007 |
| WO | WO 2007113648 | 10/2007 |
| WO | WO 2007/147901 | 12/2007 |
| WO | WO2008003103 | 1/2008 |
| WO | WO2008003115 | 1/2008 |
| WO | WO2008003116 | 1/2008 |
| WO | WO 2008/119566 | 10/2008 |
| WO | WO2008119096 | 10/2008 |
| WO | WO2008124858 | 10/2008 |
| WO | WO 2008/150494 | 12/2008 |
| WO | WO2008145142 | 12/2008 |
| WO | WO2009000006 | 12/2008 |
| WO | WO 2009/017394 A1 | 2/2009 |
| WO | WO2009017823 | 2/2009 |
| WO | WO2009030734 | 3/2009 |
| WO | WO2009032782 | 3/2009 |
| WO | WO 2013/180201 | 6/2009 |
| WO | WO 2009/086320 | 7/2009 |
| WO | WO2009089004 | 7/2009 |
| WO | WO2009106096 | 9/2009 |
| WO | WO2009106321 | 9/2009 |
| WO | WO 2010/028796 | 3/2010 |
| WO | WO 2010/033736 | 3/2010 |
| WO | WO 2010/037835 | 4/2010 |

(56) References Cited

FOREIGN PATENT DOCUMENTS

| WO | WO2010034441 | 4/2010 |
|---|---|---|
| WO | WO2010042904 | 4/2010 |
| WO | WO 2010/062171 A2 | 6/2010 |
| WO | WO2010085682 | 7/2010 |
| WO | WO 2010/106180 | 9/2010 |
| WO | WO 2010/0112193 | 10/2010 |
| WO | WO 2010/115551 | 10/2010 |
| WO | WO 2010/115552 | 10/2010 |
| WO | WO 2010/115553 | 10/2010 |
| WO | WO2010115589 | 10/2010 |
| WO | WO2010119119 | 10/2010 |
| WO | WO2011133886 | 10/2010 |
| WO | WO2010151792 | 12/2010 |
| WO | WO2010151808 | 12/2010 |
| WO | WO2011036183 | 3/2011 |
| WO | WO2011066342 | 3/2011 |
| WO | WO2011063348 | 5/2011 |
| WO | WO2011066501 | 6/2011 |
| WO | WO2011131746 | 10/2011 |
| WO | WO2011143545 | 11/2011 |
| WO | WO 2012/016227 | 2/2012 |
| WO | WO2012018687 | 2/2012 |
| WO | WO2012032080 | 3/2012 |
| WO | WO 2012/058768 | 5/2012 |
| WO | WO2012058768 | 5/2012 |
| WO | WO2012107417 | 8/2012 |
| WO | WO2012116453 | 9/2012 |
| WO | WO2012125495 | 9/2012 |
| WO | WO2012125850 | 9/2012 |
| WO | WO2012131555 | 10/2012 |
| WO | WO2012146628 | 11/2012 |
| WO | WO2012162067 | 11/2012 |
| WO | WO2013006544 | 1/2013 |
| WO | WO2013016714 | 1/2013 |
| WO | WO2013026833 | 2/2013 |
| WO | WO2013033008 | 3/2013 |
| WO | WO2013047748 | 4/2013 |
| WO | WO2013055809 | 4/2013 |
| WO | WO2013063702 | 5/2013 |
| WO | WO2013096828 | 6/2013 |
| WO | WO 2013/125667 | 8/2013 |
| WO | WO2014004586 | 1/2014 |
| WO | WO2014012085 | 1/2014 |
| WO | WO 2014079000 | 5/2014 |
| WO | WO 2014/110601 | 7/2014 |
| WO | WO 2014/113510 | 7/2014 |
| WO | WO 2014/145806 | 9/2014 |
| WO | WO 2014/145907 | 9/2014 |
| WO | WO 2014/164553 | 10/2014 |
| WO | WO 2015/063339 | 5/2015 |
| WO | WO 2015/149077 | 10/2015 |
| WO | WO 2016014984 | 1/2016 |
| WO | WO 2016086186 | 6/2016 |
| WO | WO 2016086189 | 6/2016 |
| WO | WO 2016086196 | 6/2016 |
| WO | WO 2016105450 | 6/2016 |

OTHER PUBLICATIONS

Chang et al. Monoclonal antibodies against oxidized low-density lipoprotein bind to apoptotic cells and inhibit their phagocytosis by elicited macrophages: evidence that oxidation-specific epitopes mediate macrophage recognition. Proc Natl Acad Sci USA 96: 6353-6358, 1999.*
Kakutani et al. Accumulation of LOX-1 ligand in plasma and atherosclerotic lesions of watanabe heritable hyperlipidemic rabbits: identification by a novel enzyme immunoassay. Biochem Biophys Res Comm 282: 180-185, 2001.*
Soumyarani et al. Oxidatively modified high density lipoprotein promotes inflammatory response in human monocytes-macrophages by enhanced production of ROS, TNFalpha, MMP-9, and MMP-2. Mol Cell Biochem 366: 277-285, 2012.*
Stewart et al. Recombinant CD36 inhibits oxLDL-induced ICAM-1-dependent monocyte adhesion. Mol Immunol 43: 255-267, 2006.*
Tedgui et al. Cytokines in atherosclerosis: pathogenic and regulatory pathways. Physiol Rev 86: 515-581, 2006.*
Thorne et al. CD36 is a receptor for oxidized high density lipoprotein: Implications for the development of atherosclerosis. FEBS Lett 581: 1227-1232, 2007.*
Ishigaki et al. Impact of plasma oxidized Low-density lipoprotein removal on atherosclerosis. Circulation 118: 75-83, 2008.*
Ziebig et al. Effect of the oxLDL binding protein Fc-CD68 on plaque extension and vulnerability in atherosclerosis. Circ Res 108: 695-703, 2011.*
Ganesan et al., FcγRIIb on Liver Sinusoidal Endothelium Clears Small Immune Complexes., The Journal of Immunology, Nov. 15, 2012, vol. 189 No. 10 4981-4988.
Cemerski et al., Suppression of mast cell degranulation through a dual-targeting tandem IgE-IgG Fc domain biologic engineered to bind with high affinity to FcγRllb., Immunol Lett. Mar. 30, 2012;143(1):34-43. doi: 10.1016/j.imlet.2012.01.008. Epub Jan. 25, 2012.
Yeung et al., Engineering human IgG1 affinity to human neonatal Fc receptor: impact of affinity improvement on pharmacokinetics in primates., J Immunol. Jun. 15, 2009 ;182(12):7663-71. doi: 10.4049/jimmunol.0804182.
Reddy et al., Elimination of Fc receptor-dependent effector functions of a modified IgG4 monoclonal antibody to human CD4., J Immunol. Feb. 15, 2000;164(4):1925-33.
Spies et al., Alternative molecular formats and therapeutic applications for bispecific antibodies., Mol Immunol. Jan. 27, 2015. pii: 50161-5890(15)00005-X. doi: 10.1016/j.molimm.2015.01.003.
Abbott Laboratories, Strategies and Current Approaches for Improving Drug-Like-Properties During Biologics Drug Candidate Selection, AAPS Webinar—Nov. 10, 2011.
Adams, et al., Avidity-Mediated Enhancement of In vivo Tumor Targeting by Single-Chain Fv Dimers, Clin Cancer Res, 2006, vol. 12(5), pp. 1599-1605, doi:10.1158/1078-0432.CCR-05-2217.
Alberola-Ila et al., Stimulation Through the TCR/CD3 Complex Up-Regulates the CD2 Srface Expression on Human T Lymphocytes, Feb. 15, 1991.
Alibaud et al., A New Monoclonal Anti-CD3? Antibody Reactive on Paraffin Sections, Journal of Histochemistry & Cytochemistry, 2000, vol. 48, p. 1609.
An, et al., IgG2m4, an engineered antibody isotype with reduced Fc function, mAbs, 2009, vol. 1, Issue 6, pp. 572-579, www.landesbioscience.com/journals/mabs/article/10185.
Arnett, et al., Crystal structure of a human CD3-ε/δ dimer in complex with a UCHT1 single-chain antibody fragment, PNAS, 2004, vol. 101, No. 46, pp. 16268-16273.
Asano, et al., Cytotoxic enhancement of a bispecific diabody (Db) by format conversion to tandem single-chain variable fragment (taFv): The Case of the hEx3 Diabody, JBC Papers in Press, 2010, http://www.jbc.org/cgi/doi/10.1074/jbc.M110.172957.
Asano, et al., Highly Effective Recombinant Format of a Humanized IgG-like Bispecific Antibody for Cancer Immunotherapy with Retargeting of Lymphocytes to Tumor Cells, The Journal of Biological Chemistry, 2007, vol. 282, No. 38, pp. 27659-27665.
Atwell, et al., Stable Heterodimers from Remodeling the Domain Interface of a Homodimer using a Phage Display Library, J. Mol. Biol., 1997, vol. 270, pp. 26-35.
Baeuerle, et al., Response to Letter, "Correct TandAb protein," Molecular Immunology, 2007, vol. 44, p. 3084.
Baeuerle, et al., Review—Bispecific T-Cell Engaging Antibodies for Cancer Therapy, Cancer Res, 2009, vol. 69: (12), pp. 4941-4944.
Bargou et al., Tumor Regression in Cancer Patients by Very Low Doses of a T Cell-Engaging Antibody, Science, 2008, vol. 321, pp. 974-977.
Bhatt, Sea Lane—DDD presentation, "Surrobodies™—A Novel Approach to Bispecifics . . . ," Aug. 8, 2012.
Bibollet-Ruche et al., The Quality of Chimpanzee T-Cell Activation and Simian Immunodeficiency Virus/Human Immunodeficiency

(56) References Cited

OTHER PUBLICATIONS

Virus Susceptibility Achieved via Antibody-Mediated T-Cell Receptor/CD3 Stimulation Is a Function of the Anti-CD3 Antibody Isotype, Jul. 30, 2008.

Bluemel, et al., Epitope distance to the target cell membrane and antigen size determine the potency of T cell-mediated lysis by BiTE antibodies specific for a large melanoma surface antigen, Cancer Immunol Immunother, 2010, vol. 59(8), pp. 1197-1209.

Borras, et al., Generic Approach for the Generation of Stable Humanized Single-chain Fv Fragments from Rabbit Monoclonal Antibodies, The Journal of Biological Chemistry, 2010, vol. 285, No. 12, pp. 9054-9066.

Brandi, et al., Bispecific antibody fragments with CD20 3 CD28 specificity allow effective autologous and allogeneic T-cell activation against malignant cells in peripheral blood and bone marrow cultures from patients with B-cell lineage leukemia and lymphoma, Experimental Hematology, 1999, vol. 27, pp. 1264-1270.

Brinkmann , et al., presentation slideshow—"Roche Penzberg & Roche Glycart, Schlieren: Centers of Excellence for Recombinant Proteins".

Brinkmann, et al., A recombinant immunotoxin containing a disulfide-stabilized Fv fragment, Proc. Natl. Acad. Sci. USA, 1993, vol. 90, pp. 7538-7542.

Carpenter, et al., Non-Fc Receptor-Binding Humanized Anti-CD3 Antibodies Induce Apoptosis of Activated Human T Cells, J. Immunol., 2000, vol. 165, No. 11, pp. 6205-6213.

Castoldi, et al., Molecular characterization of novel trispecific ErbB-cMet-IGF1R antibodies and their antigen-binding properties, Protein Engineering, Design & Selection, 2012, vol. 25, No. 10, pp. 551-559.

Cemerski, et al., Suppression of mast cell degranulation through a dual-targeting tandem IgE-IgG Fc domain biologic engineered to bind with high affinity to FcγRIIb., Immunol Lett. Mar. 30, 2012;143(1):34-43. doi: 10.1016/j.imlet.2012.01.008. Epub Jan. 25, 2012.

Chames et al., Bispecific antibodies for cancer therapy—The light at the end of the tunnel?, mAbs, 2009, vol. 1, Issue 6, pp. 1-9.

Chelius, et al., Structural and functional characterization of the trifunctional antibody catumaxomab, mAbs, 2010, vol. 2, Issue 3, pp. 309-319.

Chothia, et al., Structural Determinants in the Sequences of Immunoglobulin Variable Domain, J. Mol. Biol., 1998, vol. 278, pp. 457-479.

Conrad, et al., TCR and CD3 Antibody Cross-Reactivity in 44 Species, Cytometry Part A, 2007, vol. 71A, pp. 925-933.

Conrath, et al., Antigen Binding and Solubility Effects upon the Veneering of a Camel VHH in Framework-2 to Mimic a VH, J. Mol. Biol. , 2005, vol. 350, pp. 112-125.

Cuesta, et al., Multivalent antibodies: when design surpasses evolution, Trends in Biotechnology, 2010, vol. 28, No. 7, pp. 355-362, doi:10.1016/j.tibtech.2010.03.007.

d'Argouges, et al., Combination of rituximab with blinatumomab (MT103/MEDI-538), a T cell-engaging CD19-/CD3-bispecific antibody, for highly efficient lysis of human B lymphoma cells, Leukemia Research, 2009, vol. 33, pp. 465-473.

Davila, et al., Efficacy and Toxicity Management of 19-28z CAR T Cell Therapy in B Cell Acute Lymphoblastic Leukemia, Sci. Transl. Med., 2014, vol. 6, Issue 224, pp. 1-10, 224ra25.

Davis, et al., SEEDbodies: fusion proteins based on strand-exchange engineered domain (SEED) $C_H3$ heterodimers in an Fc analogue platform for asymmetric binders or immunofusions and bispecific antibodies, Protein Engineering, Design & Selection, 2010, vol. 23, No. 4 pp. 195-202.

Demarest et al., Antibody therapeutics, antibody engineering, and the merits of protein stability, Current Opinin in Drug Discovery & Development, 2008 11(5): 675-587, Sep. 11, 2008.

Deyev, et al., Multivalency: the hallmark of antibodies used for optimization of tumor targeting by design, BioEssays, 2008, vol. 30, pp. 904-918.

DiGiammarino et al., Ligand association rates to the inner-variable-domain of a dual-variable-domain immunoglobulin are significantly impacted by linker design, mAbs3:5, 1-8; Sep.-Oct.; 3(5):487-94, Landes Bioscience, Sep. 1, 2011.

Dixon, et al., Activation of Human T Lymphocytes by Crosslinking of Anti-CD3 Monoclonal Antibodies, Journal of Leukocyte Biology, 1989, vol. 46, pp. 214-220.

Dong et al., A stable IgG-like bispecific antibody targeting the epidermal growth factor receptor and the type I insulin-like growth factor receptor demonstrates superior anti-tumor activity, mAbs 3:3, May-Jun. 2011: 273- 288, May 1, 2011.

Dreier, et al., Extremely Potent, Rapid and Costimulation-Independent Cytotoxic T-cell Response Against Lymphoma Cells Catalyzed by a Single-Chain Bispecific Antibody, Int. J. Cancer, 2002, vol. 100, pp. 690-697.

Dreier, et al., T Cell Costimulus-Independent and Very Efficacious Inhibition of Tumor Growth in Mice Bearing Subcutaneous or Leukemic Human B Cell Lymphoma Xenografts by a CD19-/CD3-Bispecific Single-Chain Antibody Construct, The Journal of Immunology, 2003, vol. 170, pp. 4397-4402.

Dudgeon, et al., General strategy for the generation of human antibody variable domains with increased aggregation resistance, PNAS Early Edition, 2012, pp. 10879-10884, www.pnas.org/cgi/doi/10.1073/pnas.1202866109 & Supporting Information.

Duval, et al., A Bispecific Antibody Composed of a Nonneutralizing Antibody to the gp41 Immunodominant Region and an Anti-CD89 Antibody Directs Broad Human Immunodeficiency Virus Destruction by Neutrophils, Journal of Virology, 2008, pp. 4671-4674, doi:10.1128/JVI.02499-07.

Elliott, et al., Antiparallel Conformation of Knob and Hole Aglycosylated Half-Antibody Homodimers Is Mediated by a CH2—CH3 Hydrophobic Interaction, Journal of Molecular Biology, 2014, vol. 426, Issue 9, pp. 1947-1957.

Feldmann et al., Novel Humanized and Highly Efficient Bispecific Antibodies Mediate Killing of Prostate Stem Cell Antigen-Expressing Tumor Cells by CD8+ and CD4+ T cells, Aug. 8, 2012.

Feldmann et al., Retargeting of T Cells to Prostate Stem Cell Antigen Expressing Tumor Cells: Comparison of Different Antibody Formats, Dec. 28, 2010.

Fernandes, et al., T Cell Receptors are Structures Capable of Initiating Signaling in the Absence of Large Conformational Rearrangements, The Journal of Biological Chemistry, 2012, vol. 287, No. 16, pp. 13324-13335.

Foreman, et al., ErbB3 Inhibitory Surrobodies Inhibit Tumor Cell Proliferation In Vitro and In Vivo, Mol Cancer Ther, 2012, vol. 11(7) , pp. 1411-1420.

Foreman, et al., PEGS poster, "ErbB3 Inhibitory Surrobodies Inhibit Tumor Cell Proliferation In Vitro and In Vivo," 2012.

Francois, et al., Construction of a Bispecific Antibody Reacting with the α-and β-Chains of the Human IL-2 Receptor, The Journal of Immunology, May 15, 1993, vol. 150, No. 10, pp. 4610-4619.

F-star Modular Antibodies Fact Sheet, Apr. 2008, "Modular Antibody Technology" (w/ reference to Ruker WO 2006/072620 A1).

F-star Modular Antibodies Press Release, Mar. 28, 2008, "Antibody Engineering Company F-Star Buys Back Royalty Obligations. TVM Capital Joins Investor Syndicate."

Fudenberg, et al., Serologic Demonstration of Dual Specificity of Rabbit Bivalent Hybrid Antibody, The Journal of Experimental Medicine, 1964, vol. 119(1), pp. 151-166.

GenBank AAA38124.1, immunoglobulin heavy-chain VJ region [Mus musculus] Protein/NCBI Apr. 27, 1993.

GenBank AAA39180.1, immunoglobulin light-chain VJ region [Mus musculus] Protein/NCBI Apr. 27, 1993.

Ghendler et al., One of the CD3ε Subunits within a T Cell Receptor Complex Lies in Close Proximity to the Cβ FG Loop, J. Exp. Med.; 1998, vol. 187, No. 9. pp. 1529-1536.

Gilliland, et al., Universal bispecific antibody for targeting tumor cells for destruction by cytotoxic T cells, Proc. Natl. Acad. Sci. USA, 1988, vol. 85, pp. 7719-7723.

Gunasekaran et al., Enhancing Antibody Fc Heterodimer Formation through Electrostatic Steering Effects, Journal of Biological Cheministry, vol. 285, No. 25, pp. 19637-10946, Apr. 16, 2010 & Supplementary Tables.

(56) References Cited

OTHER PUBLICATIONS

Haagen, et al., The Efficacy of CD3 x CD19 Bispecific Monoclonal Antibody (BsAb) in a Clonogenic Assay: The Effect of Repeated Addition of BsAb, and Interleukin-2, Blood, 1995, vol. 85, No. 11, pp. 3208-3212.

Hamel, et al., The Role of the $V_L$ - and $V_H$- Segments in the Preferential Reassociation of Immunoglobulin Subunits, Molecular Immunology, 1986, vol. 23, No. 5, pp. 503-510.

Hayden-Ledbetter, et al., CD20-Directed Small Modular Immunopharmaceutical, TRU-015, Depletes Normal and Malignant B Cells, Clin Cancer Res, 2009, vol. 15(8), pp. 2739-2746.

Hernandez-Caselles, et al., A study of CD33 (SIGLEC-3) antigen expression and function on activated human T and NK cells: two isoforms of CD33 are generated by alternative splicing, J. Leukoc. Biol., 2006, vol. 79, pp. 46-58.

Hexham, et al., Influence of relative binding affinity on efficacy in a panel of anti-CD3 scFv immunotoxins, Molecular Immunology, 2001, vol. 38, pp. 397-408.

Hoffmann, et al., Serial killing of tumor cells by cytotoxic T cells redirected with a CD19-/CD3-bispecific single-chain antibody construct, Int. J. Cancer, 2005, vol. 115, pp. 98-104.

Houtenbos, et al., The novel bispecific diabody αCD40/αCD28 strengthens leukaemic dendritic cell-induced T-cell reactivity, British Journal of Haematology, 2008, vol. 142, pp. 273-283.

Igawa, $V_H/V_L$ interface engineering to promote selective expression and inhibit conformational isomerization of thrombopoietin receptor agonist single-chain diabody, Protein Engineering, Design & Selection, 2010, vol. 23, No. 8, pp. 667-677.

Jäger, et al., the Trifunctional Antibody Ertumaxomab Destroys Tumor Cells That Express Low Levels of Human Epidermal Growth Factor Receptor 2, Cancer Res, 2009, vol. 69(10), pp. 4270-4276.

Jespers, et al., Crystal Structure of HEL4, a Soluble, Refoldable Human $V_H$ Single Domain with a Germ-line Scaffold, J. Mol. Biol., 2004, vol. 337, pp. 893-903.

Jimenez, et al., A recombinant, fully human, bispecific antibody neutralizes the biological activities mediated by both vascular endothelial growth factor receptors 2 and 3, Mol Cancer Ther, 2005, vol. 4(3), pp. 427-434.

Jin, et al., MetMAb, the One-Armed 5D5 Anti-c-Met Antibody, Inhibits Orthotopic Pancreatic Tumor Growth and Improves Survival, Cancer Res 2008, vol. 68, pp. 4360-4368.

Johnson, et al., Effector Cell Recruitment with Novel Fv-based Dual-affinity Re-targeting Protein Leads to Potent Tumor Cytolysis and in Vivo B-cell Depletion, J. Mol. Biol., 2010, vol. 399, pp. 436-449.

Jordan et al., Structural understanding of stabilization patterns in engineered bispecific Ig-like antibody molecules, Proteins 2009; 77:832-841, Jun. 19, 2009.

Jung, et al., Design of interchain disulfide bonds in the framework region of the Fv fragment of the monoclonal antibody B3, Proteins, 1994, vol. 19(1), pp. 35-47.

Jung, et al., Target Cell-restricted Triggering of the CD95 (APO-1/Fas) Death Receptor with Bispecific Antibody Fragments, Cancer Research, 2001, vol. 61, pp. 1846-1848.

Kanakaraj, et al., Simultaneous targeting of TNF and Ang2 with a novel bispecific antibody enhances efficacy in an in vivo model of arthritis, mAbs, 2012, vol. 4, Issue 5, pp. 600-613, http://dx.doi.org/10.4161/mabs.21227 & Supplemental Data.

Keyna, et al., Surrogate Light Chain-Dependent Selection of Ig Heavy Chain V Regions, J. Immunol., 1995, vol. 155, pp. 5536-5542.

Kiewe, et al., Phase I Trial of the Trifunctional Anti-HER2 x Anti-CD3 Antibody Ertumaxomab in Metastatic Breast Cancer, Clin Cancer Res., 2006, vol. 12(10), pp. 3085-3091.

Kipriyanov, et al., Bispecific CD3 x CD19 Diabody for T Cell-Mediated Lysis of Malignant Human B Cells, Int. J. Cancer, 1998. vol. 77, pp. 763-772.

Kipriyanov, et al., Bispecific Tandem Diabody for Tumor Therapy with Improved Antigen Binding and Pharmacokinetics, J. Mol. Biol., 1999, vol. 293, pp. 41-56.

Kipriyanov, et al., Effect of Domain Order on the Activity of Bacterially Produced Bispecific Single-chain Fv Antibodies, J. Mol. Biol., 2003, vol. 330, pp. 99-111.

Kipriyanov, et al., Two amino acid mutations in an anti-human CD3 single chain Fv antibody fragment that affect the yield on bacterial secretion but not the affinity, Protein Engineering, 1997, vol. 10, No. 4, pp. 445-453.

Klein, et al., Progress in overcoming the chain association issue in bispecific heterodimeric IgG antibodies, mAbs, Nov.-Dec. 2012, vol. 4, issue 6, pp. 653-663, doi: 10.4161/mabs.21379, Epub Aug. 27, 2012.

Klinger, et al., Immunopharmacologic response of patients with B-lineage acute lymphoblastic leukemia to continuous infusion of T cell-engaging CD19/CD3-bispecific BiTE antibody blinatumomab, Blood, 2012, vol. 119, No. 26, pp. 6226-6233.

Koristka, et al., Retargeting of Human Regulatory T Cells by Single-Chain Bispecific Antibodies, The Journal of Immunology, 2012, vol. 188, pp. 1551-1558, www.jimmunol.org/cgi/doi/10.4049/jimmunol.1101760.

Kostelny, et al., Formation of a Bispecific Antibody by the Use of Leucine Zippers, The Journal of Immunology 1992, vol. 148, pp. 1547-1553.

Krupka, et al., CD33 target validation and sustained depletion of AML blasts in long-term cultures by the bispecific T-cell-engaging antibody AMG 330, Blood, 2014, vol. 123, No. 3, pp. 356-365, Prepublished online Dec. 3, 2013; doi:10.1182/blood-2013-08-523548 & Data Supplement.

Kung, et al., Monoclonal Antibodies Defining Distinctive Human T Cell Surface Antigens, Science, 1979, vol. 206, pp. 347-349.

Labrijn, et al., Efficient generation of stable bispecific IgG1 by controlled Fab-arm exchange, www.pnas.org/cgi/doi/10.1073/pnas.1220145110 & Supporting Information Proc Natl Acad Sci USA 110(13): 5145-5150, 2013.

Laszlo et al., Cellular determinants for preclinical activity of a novel CD33/CD3 bispecific T-cell engager (BiTE) antibody, AMG 330, against human AML, blood 2014 123: 554-561, Dec. 5, 2013.

Lewis, et al., Generation of bispecific IgG antibodies by structure-based design of an orthogonal Fab interface, Nature Biotechnology, 2014, doi:10.1038/nbt.2797 & Supplemental Information.

Li, et al., Construction and characterization of a humanized anti-human CD3 monoclonal antibody 12F6 with effective immunoregulation functions, Immunology, 2005, vol. 116, pp. 487-498.

Lindhofer, et al., Preferential Species-Restricted Heavy/Light Chain Pairing in Rat/Mouse Quadromas: Implications for a Single-Step Purification of Bispecific Antibodies, The Journal of Immunology, 1995, vol. 155, pp. 219-225.

Ling, et al., Interspecies Scaling of Therapeutic Monoclonal Antibodies: Initial Look, J Clin Pharmacol, 2009, vol. 49, pp. 1382-1402, doi: 10.1177/0091270009337134.

Link, et al., Production and Characterization of a Bispecific IgG Capable of Inducing T-Cell-Mediated Lysis of Malignant B Cells, Blood, 1993, vol. 81, No, 12, pp. 3343-3349.

Linke, et al., Catumaxomab, Clinical development and future directions, mAbs, 2010, vol. 2, Issue 2, pp. 129-136.

Little, et al., Letter to the Editor, "Flawed TandAb production," Molecular Immunology, 2007, vol. 44, p. 3083.

Liu et al, Asymmetrical Fc Engineering Greatly Enhances Antibody-dependent Cellular Cytotoxicity (ADCC) Effector Function and Stability of the Modified Antibodies, J. Biol. Chem. 2014, 289: 3571-3590, Dec. 5, 2013.

Liu, et al., Crystallization of a Deglycosylated T Cell Receptor (TCR) Complexed with an Anti-TCR Fab Fragment, The Journal of Biological Chemistry, 1996, vol. 271, No. 52, pp. 33639-33646.

Löffler, et al., A recombinant bispecific single-chain antibody, CD19xCD3, induces rapid, and high lymphoma-directed cytotoxicity by unstimulated T lymphocytes, Blood, 2000, vol. 95, No. 6, pp. 2098-2103.

Lu, et al., a Fully Human Recombinant IgG-like Bispecific Antibody to Both the Epidermal Growth Factor Receptor and the

(56) References Cited

OTHER PUBLICATIONS

Insulin-like Growth Factor Receptor for Enhanced Antitumor Activity, The Journal of Biological Chemistry, 2005, vol. 280, No. 20, pp. 19665-19672.
Lu, et al., Di-diabody: a novel tetravalent bispecific antibody molecule by design, Journal of Immunological Methods, 2003, vol. 279, pp. 219-232.
Lu, et al., Fab-scFv fusion protein: an efficient approach to production of bispecific antibody fragments, Journal of Immunological Methods, 2002, vol. 267, pp. 213-226.
Lu, et al., The effect of variable domain orientation and arrangement on the antigen-binding activity of a recombinant human bispecific diabody, Biochemical and Biophysical Research Communications, 2004, vol. 318, pp. 507-513.
Lum, et al., The new face of bispecific antibodies: targeting cancer and much more, Experimental Hematology, 2006, vol. 34, pp. 1-6.
Lutterbuese, et al., AACR Poster, "Conversion of Cetuximab, Panitumumab, Trastuzumab and Omalizumab into T Cell-engaging BiTE Antibodies Creates Novel Drug Candidates of High Potency," 2008.
Lutterbuese, et al., T cell-engaging BiTE antibodies specific for EGFR potently eliminate KRAS- and BRAF-mutated colorectal cancer cells, PNAS Early Edition, 2010, www.pnas.org/cgi/doi/10.1073/pnas.1000976107 & Supporting Information.
Ma, et al., Expression and Characterization of a Divalent Chimeric Anti-Human CD3 Single Chain Antibody, Scand.J.Immunol, 1996, vol. 43, pp. 134-139.
Mabry, et al., A dual-targeting PDGFβ/VEGF-A molecule assembled from stable antibody fragments demonstrates anti-angiogenic activity in vitro and in vivo, mAbs, 2010, vol. 2, Issue 1, pp. 20-34; www.landesbioscience.com/journals/mabs/article/10498 & Supplemental Information.
Mabry, et al., Engineering of stable bispecific antibodies targeting IL-17A and IL-23, Protein Engineering, Design & Selection, 2009, vol. 23, No. 3, pp. 115-127; doi:10.1093/protein/gzp073 & Supplementary Figures 1-8.
Mack, et al., A small bispecific antibody construct expressed as a functional single-chain molecule with high tumor cell cytotoxicity, Proc. Natl. Acad. Sci. USA, 1995, vol. 92, pp. 7021-7025.
Mack, et al., Biologic Properties of a Bispecific Single-Chain Antibody Directed Against 17-1A (EpCAM) and CD3-Tumor Cell-Dependent T Cell Stimulation and Cytotoxic Activity, The Journal of Immunology, 1997, vol. 158, pp. 3965-3970.
MacroGenics Factsheet, Dual Affinity Re-Targeting ("DART") Platform, 2010.
Mandy, et al., Effect of Reduction of Several Disulfide Bonds on the Properties and Recombination of Univalent Fragments of Rabbit Antibody, The Journal of Biological Chemistry, 1963, vol. 238, No. 1, pp. 206-213.
Mandy, et al., Recombination of Univalent Subunits Derived from Rabbit Antibody, The Journal of Biological Chemistry, 1961, vol. 236, No. 12, pp. 3221-3226.
Martin, et al., Generation of the Germline Peripheral B Cell Repertoire: VH81X-λ B Cells Are Unable to Complete All Developmental Programs, J. Immunol., 1998, vol. 160, pp. 3748-3758.
Martinez, et al., Characterization of a novel modification on IgG2 light chain: Evidence for the presence of O-linked mannosylation, J. Chromatogr. A, 2007, vol. 1156 pp. 183-187.
Marvin, Bispecific antibodies for dual-modality cancer therapy: killing two signaling cascades with one stone, Curr Opin Drug Discov Devel, 2006, vol. 9(2), pp. 184-193.
Marvin, et al., Recombinant approaches to IgG-like bispecific antibodies, Acta Pharmacologica Sinica, 2005, vol. 26 (6), pp. 649-658.
McPhee, Engineering human immunodeficiency virus 1 protease heterodimers as macromolecular inhibitors of viral maturation, Proc. Natl. Acad. Sci. USA, 1996, vol. 93, pp. 11477-11481.
Meijer, et al., Isolation of Human Antibody Repertoires with Preservation of the Natural Heavy and Light Chain Pairing, J. Mol. Biol., 2006, vol. 358, pp. 764-772.

Merchant, et al., An efficient route to human bispecific IgG, Nature Biotechnology, 1998, vol. 16, pp. 677-681.
Metz, et al., Bispecific antibody derivatives with restricted binding functionalities that are activated by proteolytic processing, Protein Engineering, Design & Selection, 2012, vol. 25, No. 10, pp. 571-580.
Metz, et al., Bispecific digoxigenin-binding antibodies for targeted payload delivery, PNAS, 2011, vol. 108, No. 20, pp. 8194-8199.
Michaelson et al., Anti-tumor activity of stability-engineered IgG-like bispecific antibodies targeting TRAIL-R2 and LTbetaR, [mAbs 1:2, 128-141; Mar./Apr. 2009]; Mar. 11, 2009.
Miller et al., Stability engineering of scFvs for the development of bispecific and multivalent antibodies, PEDS, 2010, vol. 23, No. 7, pp. 549-557 & Supplementary Data.
Miller, biogen idec Stability Engineering and Production of IgG-like Bispecifc Antibodies, AAPS National Biotechnology Conference, Jun. 24 to Jun. 27, 2007.
Milutinovic, et al., Sanford Burnham Medical Research Institute / AACR Poster, #4318, "Development of a novel dual agonist Surrobody™ that simultaneously activates both death receptors DR4 and DR5 and induces cancer cell death with high potency".
Mimoto, et al., Novel asymmetrically engineered antibody Fc variant with superior FcγR binding affinity and specificity compared with afucosylated Fc variant, mAbs, 2013, vol. 5, Issue 2, pp. 229-236.
Mølhøj, et al., CD19-/CD3-bispecific antibody of the BiTE class is far superior to tandem diabody with respect to redirected tumor cell lysis, Molecular Immunology 2007, vol. 44 , pp. 1935-1943.
Moore, et al., A novel bispecific antibody format enables simultaneous bivalent and monovalent co-engagement of distinct target antigens., MAbs. Nov.-Dec. 2011; 3(6): 546-557; Published online Nov 1, 2011. doi: 10.4161/mabs.3.6.18123.
Moore, et al., Application of dual affinity retargeting molecules to achieve optimal redirected T-cell killing of B-cell lymphoma, Blood, 2011, vol. 117, No. 17, pp. 4542-4551.
Moretti et al., BEAT® the bispecific challenge: a novel and efficient platform for the expression of bispecific IgGs. BMC Proceedings 2013 7(Suppl 6):O9.
Morrison, et al., News and Views: Two heads are better than one, Nature Biotechnology, 2007, vol. 25, No. 11, pp. 1233-1234.
Muda, et al., Therapeutic assessment of SEED: a new engineered antibody platform designed to generate mono and bispecific antibodies, Protein Engineering, Design & Selection, 2011, vol. 24, No. 5, pp. 447-454.
Nagorsen, et al., Blinatumomab: A historical perspective, Pharmacology & Therapeutics, 2012, vol. 136, pp. 334-342, http://dx.doi.org/10.1016/j.pharmthera.2012.07.013.
Nelson, et al., Point of View: Antibody fragments—Hope and hype, mAbs, 2010, vol. 2, Issue 1, pp. 77-83.
Nielsen, et al., Human T cells resistant to complement lysis by bivalent antibody can be efficiently lysed by dimers of monovalent antibody, Blood, 2002, vol. 100, No. 12, pp. 4067-4073.
Nisonoff, et al., Letters to the Editors: Recombination of a Mixture of Univalent Antibody Fragments of Different Specificity, Arch. Biochem. Biophys., 1961, pp. 460-462.
Nisonoff, et al., Quantitative Estimation of the Hybridization of Rabbit Antibodies, Nature, 1962, vol. 194, No. 4826, pp. 355-359.
North, et al., A New Clustering of Antibody CDR Loop Conformations, J. Mol. Biol., 2011, vol. 406, pp. 228-256, doi:10.1016/j.jmb.2010.10.030.
Olafsen, et al., Covalent disulfide-linked anti-CEA diabody allows site-specific conjugation and radiolabeling for tumor targeting applications, Protein Engineering, Design & Selection, 2004, vol. 17, No. 1, pp. 21-27.
Panke, et al., Quantification of cell surface proteins with bispecific antibodies, Protein Engineering, Design & Selection, 2013, vol. 26, No. 10, pp. 645-654.
Pessano, et al., The T3/T cell receptor complex: antigenic distinction between the two 20-kd T3 (T3-δ and T3-ε) subunits, The EMBO Journal, 1985, vol. 4, No. 2, pp. 337-344.
Pichler et al., Differences of T-Cell Activation by the Anti-CD3 Antibodies Leu4 and BMA030, Mar. 30, 1987.

(56) References Cited

OTHER PUBLICATIONS

Potapov et al., Protein-Protein Recognition: Juxtaposition of Domain and Interface Cores in Immunoglobulins and Other Sandwich-like Proteins, J. Mol. Biol., 2004, vol. 342, pp. 665-679.
Rattel, et al., AACR Poster, "Validation of Cynomolgus Monkeys as Relevant Species for Safety Assessment of a Novel Human BiTE Antibody Platform for Cancer Therapy," 2010.
Reiter et al., Disulfide stabilization of antibody Fv: computer predictions and experimental evaluation, Protein Eng., 1995, vol. 8(12), pp. 1323-1331.
Reiter et al., Engineering interchain disulfide bonds into conserved framework regions of Fv fragments: improved biochemical characteristics of recombinant immunotoxins containing disulfide-stabilized Fv, Protein Eng., 1994, vol. 7(5), pp. 697-704.
Repp, et al., Combined Fc-protein- and Fc-glyco-engineering of scFv-Fc fusion proteins synergistically enhances CD16a binding but does not further enhance NK-cell mediated ADCC, Journal of Immunological Methods, 2011, vol. 373, Issues 1-2, pp. 67-78.
Ridgway, et al., 'Knobs-into-holes' engineering of antibody CH3 domains for heavy chain heterodimerization, Protein Engineering, 1996, vol. 9, No. 7, pp. 617-621.
Riethmüller, Symmetry breaking: bispecific antibodies, the beginnings, and 50 years on, Cancer Immunity, 2012, vol. 12, p. 12, pp. 1-7.
Roosnek, et al., Triggering T Cells by Otherwise Inert Hybrid Anti-CD3/Antitumor Antibodies Requires Encounter with the Specific Target Cell, J . Exp. Med., 1989, vol. 170, pp. 297-302.
Rose, et al., Mutation of Y407 in the CH3 domain dramatically alters glycosylation and structure of human IgG, mAbs, 2013, vol. 5, Issue 2, pp. 219-228.
Rose, et al., Quantitative Analysis of the Interaction Strength and Dynamics of Human IgG4 Half Molecules by Native Mass Spectrometry, Structure , 2011, vol. 19, pp. 1274-1282.
Rossi, et al., A new class of bispecific antibodies to redirect T cells for cancer immunotherapy, mAbs 2014, vol. 6, Issue 2, pp. 381-391.
Roux, et al., Structural analysis of the nurse shark (new) antigen receptor (NAR): Molecular convergence of NAR and unusual mammalian immunoglobulins, Proc. Natl. Acad. Sci. USA, 1998, vol. 95, pp. 11804-11809.
Rudnick, et al., Affinity and Avidity in Antibody-Based Tumor Targeting, Cancer Biotherapy and Radiopharmaceuticals, 2009, vol. 24, No. 2, pp. 155-161, doi: 10.1089/cbr.2009.0627.
Röthlisberger, et al., Domain Interactions in the Fab Fragment: A Comparative Evaluation of the Single-chain Fv and Fab Format Engineered with Variable Domains of Different Stability, J. Mol. Biol. , 2005, vol. 347, pp. 773-789.
Salmeron et al., A conformational epitope expressed upon association of CD3-epsilon with either CD3-delta or CD3-gamma is the main target for recognition by anti-CD3 monoclonal antibodies, Nov. 1, 1991.
Sancho et al., CD3-Surface Expression Is Required for CD4-p56ickmediated Up-regulation of T Cell Antigen Receptor-CD3 Signaling in T Cells, Apr. 16, 1992.
Schaefer, et al., A Two-in-One Antibody against HER3 and EGFR Has Superior Inhibitory Activity Compared with Monospecific Antibodies, Cancer Cell, 2011, vol. 20, pp. 472-486 & Supplemental Information, pp. 1-21.
Schaefer, et al., Immunoglobulin domain crossover as a generic approach for the production of bispecific IgG antibodies, PNAS, 2011, vol. 108, No. 27, pp. 11187-11192.
Schlapschy, et al., Functional humanization of an anti-CD16 Fab fragment: obstacles of switching from murine λ to human λ or κ light chains, Protein Engineering, Design & Selection, 2009, vol. 22, No. 3, pp. 175-188, doi:10.1093/protein/gzn066.
Schlereth, et al., Eradication of Tumors from a Human Colon Cancer Cell Line and from Ovarian Cancer Metastases in Immunodeficient Mice by a Single-Chain Ep-CAM-/CD3-Bispecific Antibody Construct, Cancer Res 2005, vol. 65(7), pp. 2882-2889.
Schlereth, et al., T-cell activation and B-cell depletion in chimpanzees treated with a bispecific anti-CD19/anti-CD3 single-chain antibody construct, Cancer Immunol Immunother, 2006, vol. 55, pp. 503-514, doi:10.1007/s00262-005-0001-1.
Schoonjans, et al., Fab Chains As an Efficient Heterodimerization Scaffold for the Production of Recombinant Bispecific and Trispecific Antibody Derivatives, The Journal of Immunology, 2000, vol. 165, pp. 7050-7057.
Shalaby, et al., Development of Humanized Bispecific Antibodies Reactive with Cytotoxic Lymphocytes and Tumor Cells Overexpressing the HER2 Protooncogene, J.Exp.Med., 1992, vol. 175, pp. 217-225.
Shan, et al., Characterization of scFv-Ig Constructs Generated from the Anti-CD20 mAb 1F5 Using Linker Peptides of Varying Lengths, J Immunol, 1999, vol. 162, pp. 6589-6595.
Shearman, et al., Construction, Expression and Characterization of Humanized Antibodies Directed Against the Human α/β T Cell Receptor, The Journal of Immunology, 1991, vol. 147, No. 12, pp. 4366-4373.
Shen, et al., Catumaxomab, a rat/murine hybrid trifunctional bispecific monoclonal antibody for the treatment of cancer, Curr Opin Mol Ther, 2008, vol. 10(3), pp. 273-284.
Shen, et al., Single Variable Domain-IgG Fusion: A Novel Recombinant Approach to Fc Domain-Containing Bispecific Antibodies, The Journal of Biological Chemistry, 2006, vol. 281, No. 16, pp. 10706-10714.
Spiess, et al., Bispecific antibodies with natural architecture produced by co-culture of bacteria expressing two distinct half-antibodies, Nature Biotechnology, 2013, doi:10.1038/nbt.2621 & Supplemental Information.
Stamova, Unexpected recombinations in single chain bispecific anti-CD3- anti-CD33 antibodies can be avoided by a novel linker module, Oct. 29, 2011.
Stanfield, et al., Maturation of Shark Single-domain (IgNAR) Antibodies: Evidence for Induced-fit Binding, J. Mol. Biol., 2007, vol. 367, pp. 358-372.
Strop, P. et al., Generating Bispecific Human IgG1 and IgG2 Antibodies from Any Antibody Pair, J. Mol. Biol., 2012, doi:10.1016/j.jmb.2012.04.020.
Tan, Philip, Presentation at PepTalk, Jan. 25, 2013, "Bi-specific ADAPTIR Molecule Targeting CD86 and Delivering Monomeric IL10 to Inhibit Antigen Presenting Cells".
Tarcsa et al, Chapter 10 Dual-Variable Domain Immunoglobulin (DVD-Ig™) Technology: A Versatile, Novel Format for the Next Generation of Dual-Targeting Biologics, Bispecific Antibodies 2011, pp. 171-185, 2011.
Teachey, et al., Cytokine release syndrome after blinatumomab treatment related to abnormal macrophage activation and ameliorated with cytokine-directed therapy, Blood, 2013, vol. 121, No. 26, pp. 5154-5157.
Thompson, et al., An Anti-CD3 Single-chain Immunotoxin with a Truncated Diphtheria Toxin Avoids Inhibition by Pre-existing Antibodies in Human Blood, J.Biol.Chem., 1995, vol. 270, No. 47, pp. 28037-28041.
Thompson, et al., Improved binding of a bivalent single-chain immunotoxin results in increased efficacy for in vivo T-cell depletion, Protein Engineering, 2001, vol. 14, No. 12, pp. 1035-1041.
Topp, et al., Targeted Therapy With the T-Cell-Engaging Antibody Blinatumomab of Chemotherapy-Refractory Minimal Residual Disease in B-Lineage Acute Lymphoblastic Leukemia Patients Results in High Response Rate and Prolonged Leukemia-Free Survival, J Clin Oncol vol. 29, No. 18, pp. 2493-2498, 2011.
Traunecker, et al., Bispecific single chain molecules (Janusins) target cytotoxic lymphocytes on HIV infected cells, The EMBO Journal, 1991, vol. 1, No. 12, pp. 3655-3659.
Valliere-Douglass, et al., O-Fucosylation of an antibody light chain: Characterization of a modification occurring on an IgG1 molecule, Glycobiology, 2009, vol. 19, No. 2, pp. 144-152, doi:10.1093/glycob/cwn116.
van Boxel, et al., Some lessons from the systematic production and structural analysis of soluble αβ T-cell receptors, Journal of Immunological Methods, 2009, vol. 350, pp. 14-21.
van Wauwe, et al., OKT3: A Monoclonal Anti-Human T Lymphoctye Antibody with Potent Mitogenic Properties, The Journal of Immunology, 1980, vol. 124, No. 6, pp. 2708-2713.

(56) References Cited

OTHER PUBLICATIONS

Verdier, et al., Determination of lymphocyte subsets and cytokine levels in Cynomolgus monkeys, Toxicology, 1995, vol. 105, pp. 81-90.
Veri, et al., Therapeutic Control of B Cell Activation via Recruitment of Fcγ Receptor IIb (CD32B) Inhibitory Function With a Novel Bispecific Antibody Scaffold, Arthritis & Rheumatism, 2010, vol. 62, No. 7, pp. 1933-1943.
Vettermann, et al., Powered by pairing: The surrogate light chain amplifies immunoglobulin heavy chain signaling and pre-selects the antibody repertoire, Seminars in Immunology 18, 2006, pp. 44-55.
Von Kreudenstein, et al., Improving biophysical properties of a bispecific antibody scaffold to aid developability: Quality by molecular design, mAbs, 2013, vol. 5, Issue 5, pp. 1-9, http://dx.doi.org/10.4161/mabs.25632 & Supplemental Material.
Wang et al., Conserved amino acid networks involved in antibody variable domain interactions, Proteins, 2009, vol. 76, pp. 99-114.
Wang et al., Expression and characterization of recombinant soluble monkey CD3 molecules: mapping the FN18 polymorphic epitope, Molecular Immunology, 2004, vol. 40, pp. 1179-1188.
Wang, et al., A block in both early T lymphocyte and natural killer cell development in transgenic mice with high-copy numbers of the human CD3E gene, Proc. Natl. Acad. Sci. USA, 1994, vol. 91, pp. 9402-9406.
Ward, et al., Protein Engineering of Homodimeric Tyrosyl-tRNA Synthetase to Produce Active Heterodimers, The Journal of Biological Chemistry, 1986, vol. 261, No. 21, pp. 9576-9578.
Weatherill, et al., Towards a universal disulphide stabilised single chain Fv format: importance of interchain disulphide bond location and vL—vH orientation, Protein Engineering, Design & Selection, 2012, vol. 25, No. 7, pp. 321-329.
Weiner, et al., The Role of T Cell Activation Bispecific Antibody Therapy in Anti-CD3 X Antitumor, Journal of Immunology, 1994, vol. 152, pp. 2385-2392.
Wesolowski, et al., Single domain antibodies: promising experimental and therapeutic tools in infection and immunity, Med Microbiol Immunol, 2009, vol. 198, pp. 157-174.
Whitlow, et al., An improved linker for single-chain Fv with reduced aggregation and enhanced proteolytic stability, Protein Engineering, 1993, vol. 6 , No. 8, pp. 989-995.
Wong, et al., The Mechanism of Anti-CD3 Monoclonal Antibodies, Transplantation, 1990, vol. 50, No. 4, pp. 683-689.
Woods, et al., LC-MS characterization and purity assessment of a prototype bispecific antibody, mAbs, 2013, vol. 5, Issue 5, pp. 711-722, http://dx.doi.org/10.4161/mabs.25488.
Wu et al, Molecular construction and optimization of anti-human IL-11α/β dual variable domain immunoglobulin (DVD-Ig™) molecules, [mAbs 1:4, 339-347; Jul./Aug. 2009]; Landes Bioscience, Apr. 10, 2009.
Wu et al, Simultaneous targeting of multiple disease mediators by a dual-variable-domain immunoglobulin, (DVD-Ig™) molecules, Jul.-Aug. 2009; 339-347, Oct. 14, 2007.
Wu, et al., Multimerization of a chimeric anti-CD20 single-chain Fv-Fc fusion protein is mediated through variable domain exchange, Protein Engineering, 2001, vol. 14, No. 12, pp. 1025-1033.
Wucherpfennig, et al., Structural Biology of the T-cell Receptor: Insights into Receptor Assembly, Ligand Recognition, and Initiation of Signaling, Cold Spring Harb Perspect Biol 2010;2:a005140.
Xie, et al., A new format of bispecific antibody: highly efficient heterodimerization, expression and tumor cell lysis, Journal of Immunological Methods, 2005, vol. 296 , pp. 95-101, doi:10.1016/j.jim.2004.11.005.
Xu, et al., Combinatorial surrobody libraries, PNAS, 2008, vol. 105, No. 31, pp. 10756-10761.
Xu, et al., Rapid optimization and prototyping for therapeutic antibody-like molecules, mAbs, 2013, vol. 5, Issue 2, pp. 237-254.
Xu, et al., Surrobodies with Functional Tails, J. Mol. Biol., 2010, vol. 397, pp. 352-360.
Yang et al., Differential in vitro activation of CD8-CD4+ and CD4-CD8+ T lymphocytes by combinations of anti-CD2 and anti-CD3 antibodies, Apr. 1, 1988.
Yeung, et al., Engineering human IgG1 affinity to human neonatal Fc receptor: impact of affinity improvement on pharmacokinetics in primates, J Immunol. Jun. 15, 2009;182(12):7663-71. doi: 10.4049/jimmunol.0804182.
Yoshino et al., Upgrading of flow cytometric analysis for absolute counts, cytokines and other antigenic molecules of cynomolgus monkeys (*Macaca fascicularis* ) by using anti-human cross-reactive antibodies, Exp. Anim., 2000, vol. 49(2), pp. 97-100.
Zeidler, et al., The Fc-region of a new class of intact bispecific antibody mediates activation of accessory cells and NK cells and induces direct phagocytosis of tumour cells, Br J Cancer, 2000, vol. 83(2), pp. 261-266.
Zhu, et al., Identification of Heavy Chain Residues in a Humanized Anti-CD3 Antibody Important for Efficient Antigen Binding and T Cell Activation, The Journal of Immunology, 1995, vol. 155, pp. 1903-1910.
Zhu, et al., Remodeling domain interfaces to enhance heterodimer formation, Protein Science, 1997, vol. 6, pp. 781-788.
Zuo, et al., An efficient route to the production of an IgG-like bispecific antibody, Protein Engineering, 2000, vol. 13, No. 5, pp. 361-367.
Chu et al., Reduction of total IgE by targeted coengagement of IgE B-cell receptor and FcγRIIb with Fc-engineered antibody., J Allergy Clin Immunol. Apr. 2012;129(4):1102-15. doi: 10.1016/j.jaci.2011.11.029. Epub Jan. 16, 2012.
Del Nagro et al., A critical role for complement C3d and the B cell coreceptor (CD19/CD21) complex in the initiation of inflammatory arthritis., J Immunol. Oct. 15, 2005;175(8):5379-89.
Michalk et al., Characterization of a novel single-chain bispecific antibody for retargeting of T cells to tumor cells via the TCR co-receptor CD8., PLoS One. Apr. 21, 2014;9(4):e95517. doi: 10.1371/journal.pone.0095517.
Mimoto et al., Engineered antibody Fc variant with selectively enhanced FcγRIIb binding over both FcγRIIa(R131) and FcγRIIa(H131)., Protein Eng Des Sel. Oct. 2013;26(10):589-98. doi: 10.1093/protein/gzt022. Epub Jun. 5, 2013.
Moore et al., Tuning T Cell Affinity Improves Efficacy and Safety of Anti-CD38 x Anti-CD3 Bispecific Antibodies in Monkeys—a Potential Therapy for Multiple Myeloma., 57th ASH Annual Meeting and Exposition (Dec. 5-8, 2015), American Society of Hematology, Orlando, Florida.
Thurman et al., Detection of complement activation using monoclonal antibodies against C3d., J Clin Invest. May 2013;123(5):2218-30. doi: 10.1172/JCI65861. Epub Apr. 24, 2013.
U.S. Appl. No. 12/631,508, filed Dec. 4, 2009, Chari et al.
"Polythene Glycol and Derivatives for Advanced PEGylation", Catalog 2005-2006, Nektar Therapeutics.
Aplin et al. Preparation, properties, and applications of carbohydrate conjugates of proteins and lipids, 1981, CRC Crit. Rev. Biochem., pp. 259-306.
Baca et al., Antibody humanization using monovalent phage display, 1997, J. Biol. Chem. 272(16):10678-10684.
Barbas, et al. In vitro evolution of a neutralizing human antibody to human immunodeficiency virus type 1 to enhance affinity and broaden strain cross-reactivity, 1994, Proc. Nat. Acad. Sci, USA 91:3809-3813.
Biochemica, Your apoptosis specialist, 1999, No. 2, pp. 34-37 (Roche Molecular Biochemicals).
Bird et al., Single-chain antigen-binding proteins, 1988, Science 242:423-426.
Carter et al., Humanization of an anti-p185HER2 antibody for human cancer therapy, 1992, Proc Natl Acad Sci USA 89:4285-9.
Carter et al., Antibody-drug conjugates for cancer therapy, 2008, Cancer J. 14(3):154-169.
Chari et al., Immunoconjugates containing novel maytansinoids: promising anticancer drugs, 1992, Cancer Research 52: 127-131.
Chatal, 1989, Monoclonal Antibodies in Immunoscintigraphy, CRC Press (Book Abstract).
Chothia et al., Canonical structures for the hypervariable regions of immunoglobulins, 1987, J. Mol. Biol. 196:901-917.

(56) References Cited

OTHER PUBLICATIONS

Davies et al., Expression of GnTIII in recombinant anti-CD20 CHO production cell line: expression of antibodies with altered glycoforms leads to an increase in ADCC through higher affinity for FCγRIII, 2001, Biotechnol Bioeng 74:288-294.
De Pascalis et al., Grafting of "abbreviated" complementarity-determining regions containing specificity-determining residues essential for ligand contact to engineer a less immunogenic humanized monoclonal antibody, 2002, J. Immunol. 169:3076-3084.
Doronina, Development of potent monoclonal antibody auristatin conjugates for cancer therapy, 2003, Nat Biotechnol 21(7):778-784.
Dubowchik et al., Receptor-mediated and enzyme-dependent targeting of cytotoxic anticancer drugs, 1999, Pharm. Therapeutics 83:67-123.
Ducry et al., Antibody-drug conjugates: linking cytotoxic payloads to monoclonal antibodies, 2010, Bioconjugate Chem. 21:5-13.
Duke, et al., Measurement of apoptosis and other forms of cell death, 2004, Curr protocols immunol. 3.17.1-3.17.16.
Duksin et al., Relationship of the structure and biological activity of the natural homologues of tunicamycin, 1982, J. Biol. Chem. 257:3105.
Edge et al., Deglycosylation of glycoproteins by trifluoromethanesulfonic acid, 1981, Anal. Biochem. 118:131.
Fraker et al., Crystal structure of peptide cyclo-(D-VAL-L-PRO-L-VAL-D-PRO)$_3$, 1978, Biochem. Biophys. Res. Commun. 80(4):849-57.
Ghetie et al., Multiple roles for the major histocompatibility complex Class I-related receptor FcRn, 2000, Annu Rev Immunol 18:739-766.
Gorman et al., Reshaping a therapeutic CD4 antibody, Proc. Natl. Acad. Sci. USA 88:4181-4185 2007.
Hakimuddin et al., A chemical method for the deglycosylation of proteins, 1987, Arch. Biochem. Biophys. 259:52.
Hawkins et al, Selection of phage antibodies by binding affinity mimicking affinity maturation, 1992, J. Mol. Biol. 226:889-896.
He et al., Humanization and pharmacokinetics of a monoclonal antibody with specificity for both E- and P-selectin, 1998, J. Immunol. 160:1029-1035.
Hinman et al., Preparation and characterization of monoclonal antibody conjugates of the calicheamicins: a novel and potent family of antitumor antibodies, 1993 Cancer Res. 53:3336-3342.
Holliger et al., Engineering bispecific antibodies, 1993, Current Opinion Biotechnol. 4:446-449.
Holliger et al., "Diabodies": Small Bivalent and bispecific antibody fragments, 1993, Proc. Natl. Acad. Sci. U.S.A. 90:6444-6448.
Hu et al., Minibody: A novel engineered anti-carcinoembryonic antigen antibody fragment (single-chain Fv-$C_H$ 3) which exhibits rapid, high-level targeting of xenografts, 1996, Cancer Res. 56:3055-3061.
Huston et al., Protein engineering antibody binding sites: recovery of specific activity in an anti-digoxin single-chain Fv analogue produced in *Escherichia coli*, 1988, Proc. Natl. Acad. Sci. U.S.A. 85:5879-5883.
Igawa et al., Reduced elimination of IgG antibodies by engineering the variable region, 2010, PEDS. 23(5): 385-392.
Jackson et al., In vitro antibody maturation, 1995, J. Immunol. 154(7):3310-9.
Jefferis et al., Interaction sites on human IgG-Fc for FcγR: current models, 2002, Immunol Lett 82:57-65.
Johnson et al., Anti-tumor activity of CC49-doxorubicin immunoconguates, 1995, Anticancer Res. 15:1387-93.
Jones et al., Replacing the complementarity-determining regions in a human antibody with those from a mouse, 1986, Nature 321:522-525.
Jungbluth et al., A monoclonal antibody recognizing human cancers with amplification/overexpression of the human epidermal growth factor receptor, 2003, Proc Natl Acad Sci U S A. 100(2):639-44.
Kabat et al., 1991, Sequences of proteins of immunological interest, Department of Health and Human Services, Bethesda, vol. 1, 5$^{th}$ Ed.

Kettleborough et al., Humanization of a mouse monoclonal antibody by CDR-grafting: the importance of framework residues on loop conformation, 1991, Protein Eng. 4(7):773-83.
Klein et al., Progression of metastatic human prostate cancer to androgen independence in immunodeficient SDIC mice, 1997, Nature Medicine 3: 402-408.
Krauss et al., Specificity grafting of human antibody frameworks selected from a phage display library: generation of a highly stable humanized anti-CD22 single-chain Fv fragment, 2003, Protein Engineering 16(10):753-759.
Lau et al., Conjugation of Doxorubicin to monoclonal anti-carcinoembryonic antigen antibody via novel thiol-directed cross-linking regents, 1995, Bioorg-Med-Chem. 3(10):1299-1304.
Lau et al., Novel doxorubicin-monoclonal anti-carcinoembryonic antigen antibody immunoconjugate activity in vitro, 1995, Bioorg-Med-Chem. 3(10):1305-12.
Liu et al., Eradication of large colon tumor xenografts by targeted delivery of maytansinoids, 1996 Proc. Natl. Acad. Sci. USA 93:8618-8623.
Lode et al., Targeted therapy with a novel enediyne antibiotic calicheamicins o$^1_1$ effectively suppress growth and dissemination of liver metastases in a syngeneic model of murine neuroblastoma, 1998, Cancer Res. 58:2928.
Mandler et al., Synthesis and evaluation of antiproliferative activity of a geldanaymcin-herceptin™ immunoconjugates, 2000, Bioorganic & Med. Chem. Letters 10:1025-1028.
Mandler et al., Modifications in synthesis strategy improve the yield and efficacy of geldanamycin-herceptin immunoconjugates, 2002, Bioconjugate Chem. 13:786-791).
Mandler et al., Immunoconjugates of geldanamycin and anti-HER2 Monoclonal antibodies: antiproliferative activity on human breast carcinoma cell lines, 2000, J. Nat. Cancer Inst. 92(19):1573-1581.
Marks et al., By-passing immunization: building high affinity human antibodies by chain shuffling, 1992, Biotechnology 10:779-783.
Mateo et al, Humanization of a mouse nonclonal antibody that blocks the epidermal growth factor receptor: recovery of antagonistic activity, 1997, Immunotechnology, 3(1):71-81.
Modjtahedi et al, Phase I trial and tumour localization of the anti-EGFR monoclonal antibody ICR62 in head and neck or lung cancer, 1996, Br J Cancer, 73(2):228-35.
Modjtahedi et al, Targeting of cells expressing wild-type EGFR and type-III mutant EGFR (EGFRVIII) by anti-EGFR MaB ICR62: a two-pronged attack for tumor therapy, 2003, Int J Cancer, 105(2):273-80.
Modjtahedi et al., The human EGF receptor as a target for cancer therapy: six new rat mAbs against the receptor on the breast carcinoma MDA-MB 468, 1993, Br J Cancer. 1993, 67(2):247-53.
Modjtahedi et al., Antitumor activity of combinations of antibodies directed against different epitopes on the extracellular domain of the human EGF receptor, 1993, J. Cell Biophys. 1993, 22(1-3):129-46.
Mosmann, 1983, Rapid colorimetric assay for cellular growth and survival: application to proliferation and cytotoxicity assays, J. Immunol. Methods 65:55-63.
Murthy et al., Binding of an antagonistic monoclonal antibody to an intact and fragmented EGF-receptor polypeptide, 1987, Arch Biochem Biophys. 252(2):549-60.
Neville et al., Enhancement of immunotoxin efficacy by acid-cleavable cross-ling agents utilizing diphtheria toxin and toxin mutants, 1989, Biol. Chem. 264:14653-14661.
O'Connor et al., Humanization of an antibody against human protein C and calcium-dependence involving framework residues, 1998, Protein Eng 11:321-8.
Page et al., 1993, Intermantional. Journal of Oncology 3:473-476.
Pettit et al., Structure-activity studies with chiral isomers and with segments of the antimitotic marine peptide dolastatin 10, 1989, J. Am. Chem. Soc. 111:5463-5465.
Pettit et al., Dolastatins 24. Synthesis of (−)-dolastatin 10.1 X-ray molecular structure of N,N-dimethylvalyl-valyl-dolaisoleuine tert-butyl ester, 1996, J. Chem. Soc. Perkin Trans. 1 5:859-863.
Pettit et al., Antineoplastic agents 365. Dolastatin 10 SAR probes, 1998, Anti-Cancer Drug Design 13:243-277.

(56) References Cited

OTHER PUBLICATIONS

Pettit et al., Specific activities of dolastatin 10 and peptide derivatives against Cryptococcus neoformans, 1998, Antimicrob. Agents Chemother. 42(11):2961-2965.
Pettit, et al., The dolastatins; 18: Sterospecific synthesis of dolaproinel, 1996, Synthesis 719-725.
Presta et al., Humanization of an anti-vascular endothelial growth factor monoclonal antibody for the therapy of solid tumors and other disorders, 1997, Cancer Res.57(20):4593-9.
Queen et al., A humanized antibody that binds to the interleukin 2 receptor, 1989, Proc Natl Acad Sci, USA 86:10029-33.
Rader et al., A phage display approach for rapid antibody humanization: designed combinatorial V gene libraries, 1998, Proc. Natl. Acad. Sci. USA 95: 8910-8915.
Raghavan et al., Fc receptors and their interactios with immunoglobulins, 1996, Annu Rev Cell Dev Biol 12:181-220.
Remington's Pharmaceutical Sciences 16th edition, Osol, A. Ed. (1980) (Book Abstract).
Riechmann et al., Reshaping human antibodies for therapy, 1988, Nature 332:323-329.
Rodeck et al., Interactions between growth factor receptors and corresponding monoclonal antibodies in human tumors, 1987, J Cell Biochem. 35(4):315-20.
Roguska et al., Humanization of murine monoclonal antibodies through variable domain resurfacing, 1994, Proc. Natl. Acad. Sci. USA 91:969-973.
Roque et al., Antibodies and genetically engineered related molecules: production and purification, 2004, Biotechnol. Prog. 20:639-654.
Rosok et al., A combinatorial library strategy for the rapid humanization of anticarcinoma Br 96 Fab, 1996, J. Biol. Chem. 271(37): 22611-22618.
Schroder et al., The Peptides, vol. pp. 76-136, 1965, Academic Press.
Senter, Potent antibody drug conjugates for cancer therapy, 2009, Current Opin. Chem. Biol. 13:235.
Senter et al, Proceedings of the American Association for Cancer Research, 2004, vol. 45, Abstract No. 623.
Shields et al., Lack of fucose on human IgG1 N-linked oligosaccharide improves binding to human FcγRIII and antibody-dependent cellular toxicity, 2002, J Biol Chem 277:26733-26740.
Shier et al., Identification of functional and structural amino-acid residues by parsimonious mutagenesis, 1995, Gene 169:147-155.
Shinkawa et al., the absence of fucose but not the presence of galactose or bisecting N-acetylglucosamine of human IgG1 complex-type oligosaccharides shows the critical role of enhancing antibody-dependent cellular cytotoxicity, 2003, J Biol Chem 278:3466-3473.
Skehan et al., Identification of functional and structural amino-acid residues by parsimonious mutagenesis, 1990, J. Natl. Cancer Inst. 82(13):1107-12.
Tan et al., "Superhumanized" antibodies: reduction of immunogenic potential by complementarity-determining region grafting with human germline sequences: application to an anti-CD28, 2002, J. Immunol. 169:1119-1125.
Thorpe et al., New coupling agents for the synthesis of immunotoxins containing a hindered disulfide bond with improved stability in Vivo, 1987, Cancer Res. 47:5924-5931.
Thotakura et al., Enzymatic deglycosylating of glycoproteins, 1987, Meth. Enzymol. 138:350.
Tomlinson et. al., Methods for generating multivalent and bispecific antibody fragments, 2000, Methods Enzymol. 326:461-479.
Tsurushita et al., Humanization of monoclonal antibodies, 2004, Molecular Biology of B Cells 533-545.
Umaña et al., Engineered glycoforms of an antineuro-blastoma IgG1 with optimized antibody-dependent cellular cytotoxic activity, 1999, Nat Biotechnol 17:176-180.
Verhoeyen et al., Reshaping human antibodies: grafting an antilysozyme activity, 1988, Science, 239:1534-1536.
Wawrzynczak et al., Methods for preparing immunotoxins: Effect of the linkage on activity and stability. In Immunoconjugates. Antibody Conjugates in Radio imaging and Therapy of Cancer. (C.-W. Vogel, editor). New York, Oxford University Press, pp. 28-55, 1987.
Woyke et al., In vitro activities and postantifungal effects of the potent dolastation 10 derivative auristatin PHE, 2001, Antimicrob. Agents and Chemother. 45(12):3580-3584.
Wu et al., Humanization of a murine monoclonal antibody by simultaneous optimization of framework and CDR residues, 1999, J. Mol. Biol. 294:151-162.
Yelton et al., Affinity maturation of the BR96 anti-carcinoma antibody by codon-based mutagenesis, 1995, J. Immunol. 155:1994-2004.
Yu et al., The biosynthetic gene cluster of the maytansinoids antitumor agent ansamitocin from actinosynnema pretiosum, 2002, PNAS 99:7968-7973.
Boswell et al., Effects of Charge on Antibody Tissue Distribution and Pharmacokinetics, 2010, Bioconjugate Chem, 21(21):2153-2163.
De Groot et al., De-Immunization Of Therapeutic Proteins By T-Cell Epitope Modification, 2005, Dev. In Biologicals, 2005, 122:171-194.
Kim et al., "Localization of the site of murine IgG1 molecule that is involved in binding the murine intestinal Fc receptor," Eur. J. Immunol., 24:2429-2434, 1994.
Fischer, Nicolas et al., "Bispecifc antibodies: molecules that enable novel therapeutic strategies", 2007, vol. 74, pp. 3-14.
(No Author Name) "A method for making multispecific antibodies having heteromultimeric and common components", Expert Opinion on Therapeutic Patents, Genentech, Inc. (1999) 9(6): 785-790, pp. 785-790.
"Xencor Provides Data Updates on XmaB Bispecific Antibody Program and Announces Presentations at Upcoming American Society of Hematology 2014 Annual Meeting", Nov. 6, 2014, XP055255549, retrieved from the internet: http://files.shareholder.com/downloads/AMDA-2B2V8N/0x0x792404/77590b72-837a-4085-bc55-78fa500638dc/XNCR_News_2014_11_6_General_Releases.pdf.
Bortoletto, Nicola et al., "Optimizing anti-CD3 affinity for effective T cell targeting against tumor cells.", Eur J Immunol. Nov. 2002;32(11):3102-7.
Mertens, Nico, "Tribodies: Fab-scFv fusion proteins as a platform to create multifunctional pharmaceuticals.", SpringerLink 2011, 135-149.
Kuppen, Peter et al., The development and purification of a bispecific antibody for lymphokine-activated killer cell targeting against the rat colon carcinoma CC531., Cancer Immunol Immunother. Jun. 1993;36(6):403-8.
U.S. Appl. No. 12/875,015, Restriction Requirement, May 24, 2012, All.
U.S. Appl. No. 12/875,015, Non-Final Rejection, Sep. 17, 2012, All.
U.S. Appl. No. 12/875,015, Final Rejection, May 30, 2013, All.
U.S. Appl. No. 12/875,015, Non-Final Rejection, Dec. 17, 2015, All.
U.S. Appl. No. 12/875,015, Notice of Allowance, Jul. 1, 2016, All.
U.S. Appl. No. 13/648,951, Restriction Requirement, Apr. 23, 2013, All.
U.S. Appl. No. 13/648,951, Non-Final Rejection, Jan. 3, 2014, All.
U.S. Appl. No. 13/648,951, Final Rejection, Jan. 2, 2015, All.
U.S. Appl. No. 13/648,951, Non-Final Rejection, Feb. 11, 2016, All.
U.S. Appl. No. 13/194,904, Restriction Requirement, Sep. 14, 2012, All.
U.S. Appl. No. 13/194,904, Non-Final Rejection, Dec. 14, 2012, All.
U.S. Appl. No. 13/194,904, Notice of Allowance, Sep. 18, 2013, All.
U.S. Appl. No. 14/165,487, Restriction Requirement, Apr. 4, 2016, All.
U.S. Appl. No. 14/165,487, Notice of Allowance, Nov. 8, 2016, All.
U.S. Appl. No. 13/568,028, Restriction Requirement, Sep. 2, 2014, All.
U.S. Appl. No. 13/568,028, Non-Final Rejection, Mar. 12, 2015, All.

(56) References Cited

OTHER PUBLICATIONS

U.S. Appl. No. 14/156,431, Restriction Requirement, Mar. 30, 2016, All.
U.S. Appl. No. 14/156,431, Non-Final Rejection, Jun. 23, 2016, All.
U.S. Appl. No. 14/156,432, Restriction Requirement, Oct. 6, 2015, All.
U.S. Appl. No. 14/156,432, Non-Final Rejection, Feb. 23, 2016, All.
U.S. Appl. No. 14/156,432, Non-Final Rejection, Aug. 11, 2016, All.
U.S. Appl. No. 14/155,248, Restriction Requirement, Nov. 19, 2015, All.
U.S. Appl. No. 14/155,248, Non-Final Rejection, Jun. 23, 2016, All.
U.S. Appl. No. 14/155,334, Restriction Requirement, Nov. 20, 2015, All.
U.S. Appl. No. 14/155,334, Non-Final Rejection, Jun. 22, 2016, All.
U.S. Appl. No. 14/155,334, Final Rejection, Dec. 23, 2016, All.
U.S. Appl. No. 14/155,344, Restriction Requirement, Nov. 20, 2015, All.
U.S. Appl. No. 14/155,344, Non-Final Rejection, Sep. 2, 2016, All.
U.S. Appl. No. 14/205,227, Restriction Requirement, Apr. 29, 2015, All.
U.S. Appl. No. 14/205,227, Non-Final Rejection, Sep. 18, 2015, All.
U.S. Appl. No. 14/205,227, Final Rejection, Nov. 25, 2015, All.
U.S. Appl. No. 14/205,227, Non-Final Rejection, May 10, 2016, All.
U.S. Appl. No. 14/205,248, Restriction Requirement, Nov. 20, 2015, All.
U.S. Appl. No. 14/205,248, Notice of Allowance, Jun. 29, 2016, All.
U.S. Appl. No. 14/214,418, Restriction Requirement, Mar. 23, 2016, All.
U.S. Appl. No. 14/214,475, Restriction Requirement, Sep. 3, 2015, All.
U.S. Appl. No. 14/214,475, Non-Final Rejection, Apr. 7, 2016, All.
U.S. Appl. No. 14/214,475, Final Rejection, Nov. 1, 2016.
U.S. Appl. No. 14/217,166, Restriction Requirement, Aug. 27, 2015, All.
U.S. Appl. No. 14/217,166, Non-Final Rejection, Apr. 20, 2016, All.
U.S. Appl. No. 14/217,166, Final Rejection, Dec. 19, 2016, All.
U.S. Appl. No. 14/200,652, Restriction Requirement, Dec. 3, 2015, All.
U.S. Appl. No. 14/200,652, Non-Final Rejection, Jun. 30, 2016, All.
U.S. Appl. No. 14/200,652, Non-Final Rejection, Dec. 5, 2016, All.
U.S. Appl. No. 14/207,489, Restriction Requirement, Dec. 14, 2015, All.
U.S. Appl. No. 14/207,489, Non-Final Rejection, Aug. 31, 2016, All.
U.S. Appl. No. 14/207,489, Final Rejection, Dec. 29, 2016.
U.S. Appl. No. 14/210,236, Restriction Requirement, May 19, 2016, All.
U.S. Appl. No. 14/210,236, Non-Final Rejection, Dec. 15, 2016, All.
U.S. Appl. No. 14/200,821, Non-Final Rejection, Apr. 29, 2015, All.
U.S. Appl. No. 14/200,821, Final Rejection, Feb. 11, 2016, All.
U.S. Appl. No. 14/200,821, Notice of Allowance, Nov. 18, 2016.
U.S. Appl. No. 14/216,705, Restriction Requirement, Jun. 30, 2016, All.
U.S. Appl. No. 14/216,705, Non-Final Rejection, Aug. 5, 2016, All.
U.S. Appl. No. 14/757,809, Restriction Requirement, Jan. 19, 2017, All.
WO 2011/028952—PCT/US2010/047741 International Search Report mailed Dec. 14, 2010.
WO 2013/055809—PCT/US12/59582 International Search Report mailed Mar. 13, 2013.
WO 2012/016227—PCT/US11/46041 International Search Report mailed Mar. 15, 2012.
WO 2013/022855—PCT/US12/49789 International Search Report mailed Dec. 18, 2012.
WO 2014/113510—PCT/US14/11741 International Search Report mailed Jun. 6, 2014.
WO 2016/014984—PCT/US15/42072 International Search Report mailed Nov. 4, 2015.
WO 2014/110601—PCT/US14/11549 International Search Report and Written Opinion of the International Searching Authority mailed May 7, 2014.
WO 2014/145907—PCT/US14/30758 International Search Report mailed Aug. 6, 2014.
WO 2014/145806—PCT/US14/30634 International Search Report mailed Jan. 9, 2015.
WO 2015/149077—PCT/US15/23411 International Search Report mailed Sep. 2, 2015.
WO 2016/086186—PCT/US15/62769 International Search Report mailed Jun. 24, 2016.
WO 2016/086189—PCT/US15/62772 International Search Report mailed Jul. 18, 2016.
WO 2016/086196—PCT/US15/62786 62772 International Search Report mailed Jun. 22, 2016.
WO 2016/105450—PCT/US15/00155 62772 International Search Report mailed Jul. 20, 2016.
WO 2016/141387—PCT/US16/21277 International Search Report mailed Jun. 28, 2016.
Counterman et al., "Volumes of Individual Amino Acid Residues in Gas-Phase Peptide Ions.", J. Am. Chem. Soc., 1999, 121 (16), pp. 4031-4039.
Grodzki & Bernstein, "Antibody Purification: Ion-Exchange Chromatography.", Methods Mol Biol 2010 ;588:27-32.
Hennecke et al., "Non-repetitive single-chain Fv linkers selected by selectively infective phage (SIP) technology.", Protein Eng. May 1998;11(5):405-10.
Lazar Declaration, Dec. 27, 2010, pp. 1-4.
Jin et al. The Design and Engineering of IgG-Like Bispecific Antibodies., Chapter 9, Bispecific Antibodies, pp. 151-169.
Zamyatnin AA., Amino Acid, Peptide, and Protein Volume in Solution., Annu Rev Biophys Bioeng. 1984;13:145-65.
Zalevsky et al. "Enhanced antibody half-life improves in vivo activity." Nature Biotechnology, vol. 28, No. 2, Feb. 1, 2010, pp. 157-159.
Wigginton et al., An immunoglobulin E-reactive chimeric human immunoglobulin G1 anti-idiotype inhibits basophil degranulation through cross-linking of FcεRI with FcγRIIb., Clinical & Experimental Allergy, 38: 313-319. doi:10.1111/j.1365-2222.2007.02896.x.
Chu et al., Inhibition of B cell receptor-mediated activation of primary human B cells by coengagement of CD19 and FcgammaRIIb with Fc-engineered antibodies., Mol Immunol. Sep. 2008;45(15):3926-33. doi: 10.1016/j.molimm.2008.06.027. Epub Aug. 8, 2008.

\* cited by examiner

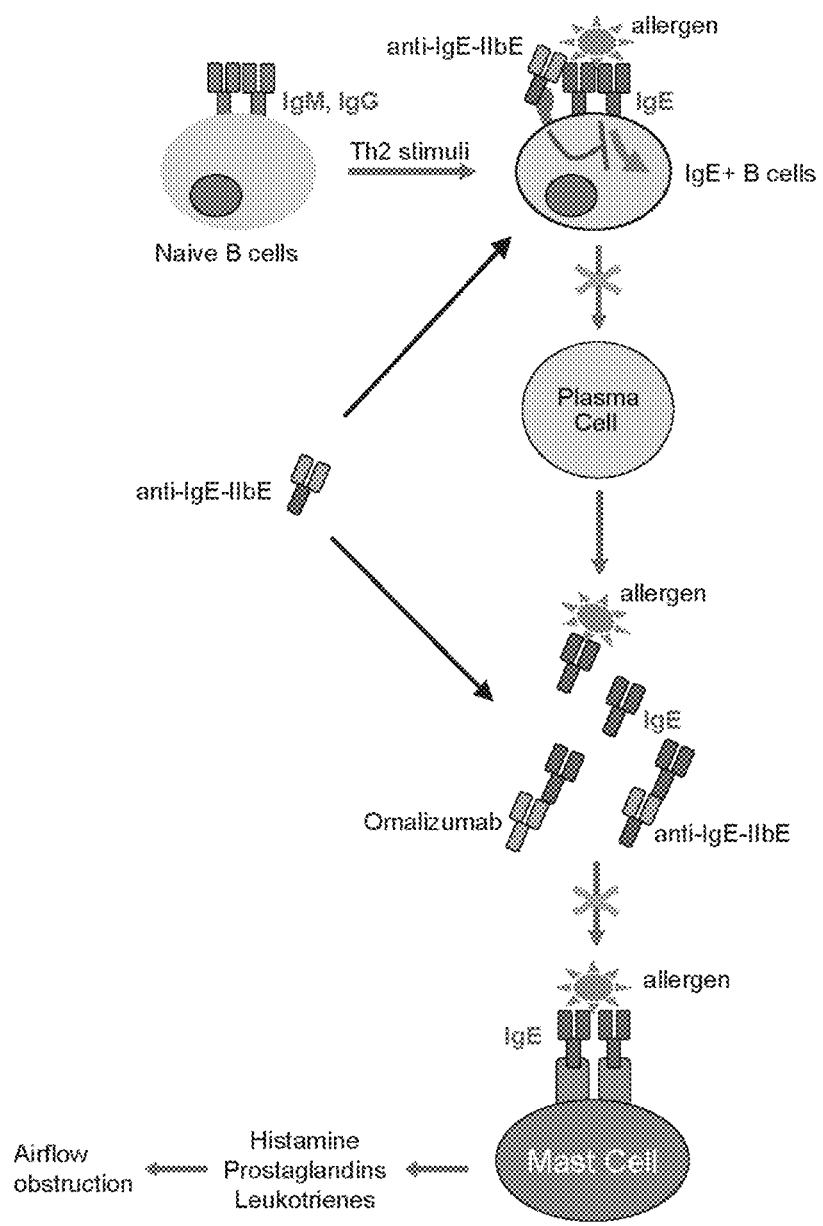

Figure 4

| Antibody | FcγRI | | H131 FcγRIIa | | FcγRIIb | | V158 FcγRIIIa | |
|---|---|---|---|---|---|---|---|---|
| | KD (M) | Fold | KD (M) | Fold | KD (M) | Fold | KD (M) | Fold |
| Native IgG1 | 2.8E-10 | 1.0 | 8.5E-07 | 1.0 | 1.8E-06 | 1.0 | 2.0E-07 | 1.0 |
| S267E | 2.6E-10 | 1.1 | 9.6E-07 | 0.89 | 6.0E-08 | 30 | 6.9E-07 | 0.29 |
| G236D/S267E | 3.2E-09 | 0.088 | 2.2E-06 | 0.39 | 2.5E-08 | 72 | n.d. | |
| S239D/S267E | 1.7E-10 | 1.6 | 7.0E-07 | 1.2 | 1.2E-08 | 150 | 6.2E-08 | 3 |
| S267E/L328F | 2.3E-10 | 1.2 | 8.8E-07 | 0.97 | 4.2E-09 | 429 | n.d. | |
| S239D/I332E | 1.4E-10 | 2.0 | 2.2E-07 | 3.9 | 8.8E-08 | 20 | 6.8E-09 | 29 |
| G236R/L328R | n.d. | | n.d. | | n.d. | | n.d. | |

Figure 5A

Omalizumab VH (SEQ ID NO:1)

EVQLVESGGGLVQPGGSLRLSCAVSGYSITSGYSWNWIRQAPGKGLEWVASITYDGSTNY
NPSVKGRITISRDDSKNTFYLQMNSLRAEDTAVYYCARGSHYFGHWHFAVWGQGTLVTVS
S

Omalizumab VH CDR1 (SEQ ID NO:2)

YSITSGYSW

Omalizumab VH CDR2 (SEQ ID NO:3)

TYDGS

Omalizumab VH CDR3 (SEQ ID NO:4)

GSHYFGHWHFAV

Omalizumab VL (SEQ ID NO:5)

DIQLTQSPSSLSASVGDRVTITCRASQSVDYDGDSYMNWYQQKPGKAPKLLIYAASYLESG
VPSRFSGSGSGTDFTLTISSLQPEDFATYYCQQSHEDPYTFGQGTKVEIK

Omalizumab VL CDR1 (SEQ ID NO:6)

QSVDYDGDSY

Omalizumab VL CDR2 (SEQ ID NO:7)

AASYLES

Omalizumab VL CDR3 (SEQ ID NO:8)

SHEDPYT

MaE11 VH (SEQ ID NO:9)

DVQLQESGPGLVKPSQSLSLACSVTGYSITSGYSWNWIRQFPGNKLEWMGSITYDGSSNY
NPSLKNRISVTRDTSQNQFFLKLNSATAEDTATYYCARGSHYFGHWHFAVWGAGTTVTVS
S

MaE11 VH CDR1 (SEQ ID NO:10)

YSITSGYSW

MaE11 VH CDR2 (SEQ ID NO:11)

TYDGS

Figure 5B

MaE11 VH CDR3 (SEQ ID NO:12)

GSHYFGHWHFAV

MaE11 VL (SEQ ID NO:13)

DIQLTQSPASLAVSLGQRATISCKASQSVDYDGDSYMNWYQQKPGQPPILLIYAASYLGSEI
PARFSGSGSGTDFTLNIHPVEEEDAATFYCQQSHEDPYTFGAGTKLEIK

MaE11 VL CDR1 (SEQ ID NO:14)

QSVDYDGDSY

MaE11 VL CDR2 (SEQ ID NO:15)

AASYLGS

MaE11 VL CDR3 (SEQ ID NO:16)

SHEDPYT

H1L1MaE11 VH (SEQ ID NO:17)

QVQLQESGPGLVKPSETLSLTCAVSGYSITSGYSWNWIRQPPGKKLEWIGSITYDGSSNYNPSLKSRVTIS
RDTSKNQFSLKLSSVTAADTAVYYCARGSHYFGHWHFAVWGAGTLVTVSS

H1L1 MaE11 VH CDR1 (SEQ ID NO:18)

YSITSGYSW

H1L1 MaE11 VH CDR2 (SEQ ID NO:19)

TYDGS

H1L1 MaE11 VH CDR3 (SEQ ID NO:20)

GSHYFGHWHFAV

H1L1 MaE11 VL (SEQ ID NO:21)

DIQLTQSPSSLSASVGDRVTITCRASQSVDYDGDSYMNWYQQKPGQPPKLLIYAASYLGSE
IPARFSGSGSGTDFTLTISSLQPEDFATYYCQQSHEDPYTFGAGTKLEIK

H1L1 MaE11 VL CDR1 (SEQ ID NO:22)

QSVDYDGDSY

H1L1 MaE11 VL CDR2 (SEQ ID NO:23)

AASYLGS

H1L1 MaE11 VL CDR3 (SEQ ID NO:24)

SHEDPYT

TES-C21 VH (SEQ ID NO:25)

QVQLQQSGAELMKPGASVKISCKTTGYTFSMYWLEWVKQRPGHGLEWVGEISPGTFTTN
YNEKFKAKATFTADTSSNTAYLQLSGLTSEDSAVYFCARFSHFSGSNYDYFDYWGQGTSLT
VSS

TES-C21 VH CDR1 (SEQ ID NO:26)

YTFSMYW

TES-C21 VH CDR2 (SEQ ID NO:27)

SPGTFT

Figure 5C

TES-C21 VH CDR3 (SEQ ID NO:28)

FSHFSGSNYDYFDY

TES-C21 VL (SEQ ID NO:29)

DILLTQSPAILSVSPGERVSFSCRASQSIGTNIHWYQQRTDGSPRLLIKYASESISGIPSRFSG
SGSGTEFTLNINSVESEDIADYYCQQSDSWPTTFGGGTKLEIK

TES-C21 VL CDR1 (SEQ ID NO:30)

QSIGTN

TES-C21 VL CDR2 (SEQ ID NO:31)

YASESIS

TES-C21 VL CDR3 (SEQ ID NO:32)

SDSWPTT

Figure 6

Ckappa light chain (SEQ ID NO:33)

RTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

Native IgG1 constant chain (SEQ ID NO:34)

ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK

S267E/L328F IgG1 constant chain (SEQ ID NO:35)

ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVEHEDPEVKFNWYVDGVEVHNAKTKPREEQYNSTY
RVVSVLTVLHQDWLNGKEYKCKVSNKAFPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK

G236D/S267E IgG1 constant chain (SEQ ID NO:36)

ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLDGPS
VFLFPPKPKDTLMISRTPEVTCVVVDVEHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK

Figure 7

Omalizumab light chain (VH-Cκ) (SEQ ID NO:37)

DIQLTQSPSSLSASVGDRVTITCRASQSVDYDGDSYMNWYQQKPGKAPKLLIYAASYLESG
VPSRFSGSGSGTDFTLTISSLQPEDFATYYCQQSHEDPYTFGQGTKVEIKRTVAAPSVFIFP
PSDEQLKSGTASVVCLLNNFYPREAKVQWKVDNALQSGNSQESVTEQDSKDSTYSLSSTL
TLSKADYEKHKVYACEVTHQGLSSPVTKSFNRGEC

Omalizumab IgG1 heavy chain (SEQ ID NO:38)

EVQLVESGGGLVQPGGSLRLSCAVSGYSITSGYSWNWIRQAPGKGLEWVASITYDGSTNY
NPSVKGRITISRDDSKNTFYLQMNSLRAEDTAVYYCARGSHYFGHWHFAVWGQGTLVTVS
SASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGP
SVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVDKSRWQQG
NVFSCSVMHEALHNHYTQKSLSLSPGK

Omalizumab S267E/L328F heavy chain (SEQ ID NO:39)

EVQLVESGGGLVQPGGSLRLSCAVSGYSITSGYSWNWIRQAPGKGLEWVASITYDGSTNY
NPSVKGRITISRDDSKNTFYLQMNSLRAEDTAVYYCARGSHYFGHWHFAVWGQGTLVTVS
SASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGP
SVFLFPPKPKDTLMISRTPEVTCVVVDVEHEDPEVKFNWYVDGVEVHNAKTKPREEQYNST
YRVVSVLTVLHQDWLNGKEYKCKVSNKAFPAPIEKTISKAKGQPREPQVYTLPPSREEMTK
NQVSLTCLVKGFYPSDIAVEWESNGQPENNYKTTPPVLDSDGSFFLYSKLTVDKSRWQQG
NVFSCSVMHEALHNHYTQKSLSLSPGK

H1L1 MaE11 light chain (VH-Cκ) (SEQ ID NO:40)

DIQLTQSPSSLSASVGDRVTITCRASQSVDYDGDSYMNWYQQKPGQPPKLLIYAASYLGSE
IPARFSGSGSGTDFTLTISSLQPEDFATYYCQQSHEDPYTFGAGTKLEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

H1L1 MaE11 IgG1 heavy chain (SEQ ID NO:41)

QVQLQESGPGLVKPSETLSLTCAVSGYSITSGYSWNWIRQPPGKKLEWIGSITYDGSSNYNPSLKSRVTIS
RDTSKNQFSLKLSSVTAADTAVYYCARGSHYFGHWHFAVWGAGTLVTVSSASTKGPSVFPLAPSSKS
TSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYT
QKSLSLSPGK

H1L1 MaE11 S267E/L328F heavy chain (SEQ ID NO:42)

QVQLQESGPGLVKPSETLSLTCAVSGYSITSGYSWNWIRQPPGKKLEWIGSITYDGSSNYNPSLKSRVTIS
RDTSKNQFSLKLSSVTAADTAVYYCARGSHYFGHWHFAVWGAGTLVTVSSASTKGPSVFPLAPSSKS
TSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTP
EVTCVVVDVEHEDPEVKFNWYVDGVEVHNAKTKPREEQYNSTYRVVSVLTVLHQDWLNG
KEYKCKVSNKAFPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYT
QKSLSLSPGK

| Antibody | IgE KD (M) | FcγRIIb KD (M) | FcγRIIb Fold |
|---|---|---|---|
| Omalizumab_IgG1_WT | 2.2E-10 | 1.94E-06 | 1.0 |
| Omalizumab_IgG1_S267E/L328F | 2.0E-10 | 1.4E-08 | 135 |
| MaE11_H1L1_IgG1_WT | 6.1E-11 | 2.0E-06 | 1.0 |
| MaE11_H1L1_IgG1_S267E/L328F | 6.3E-11 | 5.6E-09 | 366 |
| MaE11_H1L1_IgG1_G236R/L328R | 6.4E-11 | NB | |

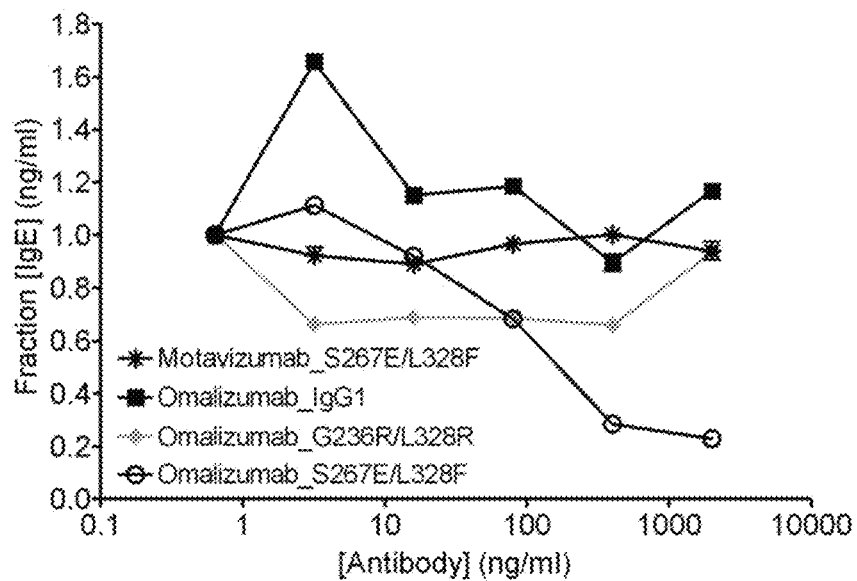
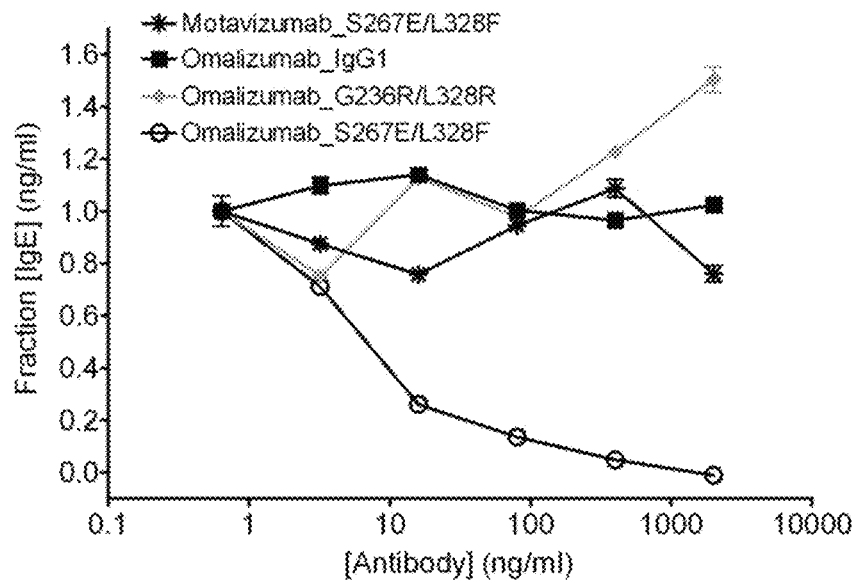

Figure 30A

| FcyRIIb variant |
|---|
| 267D |
| 267E |
| 267E/328F |
| 236N/267E |
| G236D/S267E |
| L235Y/S267E |
| S239D/S267E |
| L235D/S267E |
| L235Y/S267D |
| L235Y/S267E |
| G235D/S267E |
| G235D/H268D |
| S239D/S267D |
| S239D/S267E |
| S239D/H268D |
| V266M/S267E |
| S267D/H268D |
| S267D/H268E |
| S267D/A327D |
| S267E/H268D |
| S267E/H268E |
| S267E/L328F |
| H268D/A327D |
| L235S/S267E |
| L234F/S267E |
| L235Y/G236D/S267E |
| L235Y/S267E/H268E |
| L235Y/S239D/S267E |
| L235Y/S267E/L328F |
| G236D/S239D/S267E |
| G236D/S267E/H268E |
| G236D/S267E/L328F |
| S239D/S267E/H268E |
| S239D/S267E/L328F |
| S267E/H268E/L328F |
| P238D |
| L234Y/G237D/P238D/K326A/A330R |
| E233D/L234Y/G237D/P238D/K326A/A330R |
| E233D/L234Y/G237D/P238D/Y296D/K326A/A330R |
| E233D/L234Y/G237D/P238D/P271G/K326D/A330R |
| E233D/G237D/P238D/P271G/A330R |

Figure 30B

| P238D/S267E |
| L328E |
| 267E/L328F |
| E233D/G237D/P238D/H268D/P271G/A330R |
| P238D/S267E/L328F |

Figure 33A

FVIII_A2_IgG1_C220S/S267E/L328F  (SEQ ID NO: 43)

SVAKKHPKTWVHYIAAEEEDWDYAPLVLAPDDRSYKSQYLNNGPQRIGRKYKKVRFMAYTDE
TFKTREAIQHESGILGPLLYGEVGDTLLIIFKNQASRPYNIYPHGITDVRPLYSRRLPKGVKHLKD
FPILPGEIFKYKWTVTVEDGPTKSDPRCLTRYYSSFVNMERDLASGLIGPLLICYKESVDQRGN
QIMSDKRNVILFSVFDENRSWYLTENIQRFLPNPAGVQLEDPEFQASNIMHSINGYVFDSLQLS
VCLHEVAYWYILSIGAQTDFLSVFFSGYTFKHKMVYEDTLTLFPFSGETVFMSMENPGLWILGC
HNSDFRNRGMTALLKVSSCDKEPKSSDKTHTCPPCPAPELLGGPSVFLFPPKPKDTLMISRTP
EVTCVVVDVEHEDPEVKFNWYVDGVEVHNAKTKPREEQYNSTYRVVSVLTVLHQDWLNGKEY
KCKVSNKAFPAPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHYTQKSLSLSP
GK

Figure 33B

FVIII_C2_IgG1_C220S/S267E/L328F  (SEQ ID NO: 44)

DLNSCSMPLGMESKAISDAQITASSYFTNMFATWSPSKARLHLQGRSNAWRPQVNNPKEWLQ
VDFQKTMKVTGVTTQGVKSLLTSMYVKEFLISSSQDGHQWTLFFQNGKVKVFQGNQDSFTPV
VNSLDPPLLTRYLRIHPQSWVHQIALRMEVLGCEAQDLYEPKSSDKTHTCPPCPAPELLGGPS
VFLFPPKPKDTLMISRTPEVTCVVVDVEHEDPEVKFNWYVDGVEVHNAKTKPREEQYNSTYRV
VSVLTVLHQDWLNGKEYKCKVSNKAFPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

Figure 33C

FVIII_A2_C2_IgG1_pI_ISO(-)-pI_ISO(+RR)_C220S/S267E/L328F  (SEQ ID NO: 45)

Heavy chain 1:

SVAKKHPKTWVHYIAAEEEDWDYAPLVLAPDDRSYKSQYLNNGPQRIGRKYKKVRFMAYTDE
TFKTREAIQHESGILGPLLYGEVGDTLLIIFKNQASRPYNIYPHGITDVRPLYSRRLPKGVKHLKD
FPILPGEIFKYKWTVTVEDGPTKSDPRCLTRYYSSFVNMERDLASGLIGPLLICYKESVDQRGN
QIMSDKRNVILFSVFDENRSWYLTENIQRFLPNPAGVQLEDPEFQASNIMHSINGYVFDSLQLS
VCLHEVAYWYILSIGAQTDFLSVFFSGYTFKHKMVYEDTLTLFPFSGETVFMSMENPGLWILGC
HNSDFRNRGMTALLKVSSCDKEPKSSDKTHTCPPCPAPELLGGPSVFLFPPKPKDTLMISRTP
EVTCVVVDVEHEDPEVQFNWYVDGVEVHNAKTKPREEQYNSTYRVVSVLTVLHQDWLNGKE
YKCKVSNKAFPAPIEKTISKAKGQPREPQVYTLPPSQEEMTKNQVSLTCLVKGFYPSDIAVEWE
SSGQPENNYNTTPPMLDSDGSFFLYSKLTVDKSRWQEGNVFSCSVMHEALHNHYTQKSLSLS
PG

Figure 33D

Heavy chain 2: (SEQ ID NO: 46)

DLNSCSMPLGMESKAISDAQITASSYFTNMFATWSPSKARLHLQGRSNAWRPQVNNPKEWLQ
VDFQKTMKVTGVTTQGVKSLLTSMYVKEFLISSSQDGHQWTLFFQNGKVKVFQGNQDSFTPV
VNSLDPPLLTRYLRIHPQSWVHQIALRMEVLGCEAQDLYEPKSSDKTHTCPPCPAPELLGGPS
VFLFPPKPKDTLMISRTPEVTCVVVDVEHEDPEVKFKWYVDGVEVHNAKTKPREEQYNSTYRV
VSVLTVLHQDWLNGKEYKCKVSNKAFPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

Figure 33E

FVIII_A2-C2_IgG1_C220S/S267E/L328F (SEQ ID NO: 47)

SVAKKHPKTWVHYIAAEEEDWDYAPLVLAPDDRSYKSQYLNNGPQRIGRKYKKVRFMAYTDE
TFKTREAIQHESGILGPLLYGEVGDTLLIIFKNQASRPYNIYPHGITDVRPLYSRRLPKGVKHLKD
FPILPGEIFKYKWTVTVEDGPTKSDPRCLTRYYSSFVNMERDLASGLIGPLLICYKESVDQRGN
QIMSDKRNVILFSVFDENRSWYLTENIQRFLPNPAGVQLEDPEFQASNIMHSINGYVFDSLQLS
VCLHEVAYWYILSIGAQTDFLSVFFSGYTFKHKMVYEDTLTLFPFSGETVFMSMENPGLWILGC
HNSDFRNRGMTALLKVSSCDKNTGDYYEDSYEDLNSCSMPLGMESKAISDAQITASSYFTNMF
ATWSPSKARLHLQGRSNAWRPQVNNPKEWLQVDFQKTMKVTGVTTQGVKSLLTSMYVKEFLI
SSSQDGHQWTLFFQNGKVKVFQGNQDSFTPVVNSLDPPLLTRYLRIHPQSWVHQIALRMEVL
GCEAQDLYEPKSSDKTHTCPPCPAPELLGGPSVFLFPPKPKDTLMISRTPEVTCVVVDVEHED
PEVKFNWYVDGVEVHNAKTKPREEQYNSTYRVVSVLTVLHQDWLNGKEYKCKVSNKAFPAPI
EKTISKAKGQPREPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSPGK

1 = FVIII_A2_C220S/S267E/L328F
2 = FVIII_C2_C220S/S267E/L328F

Figure 36A

| Substitution(s) | FcγRI Kd (pM) | FcγRIIaH Kd (nM) | FcγRIIaR Kd (nM) | FcγRIIb Kd (nM) | FcγRIIIaV Kd (nM) | FcγRIIIaF Kd (nM) |
|---|---|---|---|---|---|---|
| IgG1 WT | 329 | 646 | 859 | 1467 | 191 | 1352 |
| L234D/G236N/S267E | | | 1180 | 287 | | |
| L234D/S267E | 11500 | | 67.7 | 67.8 | 1370 | |
| L234E/H268D | | | | 249 | | |
| L234E/S267E | 2510 | n.d. | 80.4 | 97 | n.d. | |
| L234E/S267E/L328F | 7750 | 8920 | 4.93 | 7.53 | n.d. | |
| L234F | 9110 | n.d. | 3760 | 3590 | n.d. | |
| L234F/G236N | | | n.d. | n.d. | | |
| L234F/S236D | | | n.d. | n.d. | | |
| L234F/S267E | 498 | 1270 | 41.6 | 55.7 | 2040 | |
| L234G | | | 10000 | 10000 | | |
| L234I | | | 15500 | 13600 | | |
| L234K | | | 100000 | 100000 | | |
| L234N | | | n.d. | n.d. | | |
| L234P | | | 60700 | 22800 | | |
| L234Q | | | 23100 | 10000 | | |
| L234S | | | 1240 | 7640 | | |
| L234V | | | 6425 | 3221 | | |
| L234W | 10500 | 1160 | 1897 | 1771 | 6590 | |
| L234W/G236D/S239E/S267E | | | 151 | 129 | | |
| L234W/H268D/L328Y | | | | 248 | | |
| L234W/L328Y/I332E | | | | 232 | | |
| L234W/S239D/L328Y | | | | 44.8 | | |
| L234W/S239E/S267E | | | 8.72 | 34.7 | | |
| L234Y | | | 16800 | 61900 | | |
| L235A | 18400 | 13300 | 5178 | 4183 | 609 | |
| L235D/S239D | | | | 357 | | |
| L235D/S267E | 854000 | n.d. | 66.1 | 88.1 | n.d. | |
| L235D/S267E/L328F | 573000 | 2350 | 6.45 | 18.2 | n.d. | |
| L235E | | | 2580 | 2668 | | |
| L235F/H268D/L328Y | | | | 370 | | |
| L235F/L328Y/I332E | | | | 443 | | |
| L235F/S239D/L328Y | | | | 215 | | |
| L235F/S267E | 18700 | 1610 | 26.4 | 51.7 | n.d. | |
| L235H | | | 1136 | 1998 | | |
| L235I | 16700 | 3580 | 1289 | 1615 | 212 | |
| L235N | | | 24100 | 10000 | | |
| L235P | | | 7013 | 251022 | | |
| L235Q | | | 420 | n.d. | | |
| L235R | | | 838 | 263 | | |
| L235S | | | 100000 | 100000 | | |
| L235S/S267E | | | 1200 | 37800 | | |
| L235T/S267E | | | 281 | 619 | | |

Figure 36B

| Substitution(s) | FcγRI Kd (pM) | FcγRIIaH Kd (nM) | FcγRIIaR Kd (nM) | FcγRIIb Kd (nM) | FcγRIIIaV Kd (nM) | FcγRIIIaF Kd (nM) |
|---|---|---|---|---|---|---|
| S239D/A327D/L328Y | | | | 123 | | |
| S239D/H268D | | | | 102 | | |
| S239D/H268D/L328F | | | | 167 | | |
| S239D/H268D/L328F/I332E | | | | 27.6 | | |
| S239D/H268D/L328W | | | | 28.7 | | |
| S239D/H268D/L328W/I332E | | | | 52.7 | | |
| S239D/H268D/L328Y | | | | 60.1 | | |
| S239D/H268D/L328Y/I332E | | | | 27.1 | | |
| S239D/H268E/L328Y | | | | 67.7 | | |
| S239D/I332E | 37.4 | 163 | 68.6 | 101 | 7.07 | 28.2 |
| S239D/K326D/L328Y | | | | 113 | | |
| S239D/L328F/I332E | | | | 176 | | |
| S239D/L328Y | | | | 264 | | |
| S239D/L328Y/I332E | | | | 198 | | |
| S239D/S267A/L328Y | | | | 74.1 | | |
| S239D/S267D | | | | 65.9 | | |
| S239D/S267E | 14.2 | 510 | 7.16 | 13.3 | 51.2 | 516 |
| S239D/S267E/H268E | 326 | 817 | 7.52 | 6.91 | 18.6 | |
| S239D/S267E/I332E | | | | 11.8 | | |
| S239D/S267E/L328F | 227 | 378 | 2.06 | 3.43 | 887 | |
| S239E | 200 | 1320 | 1249 | 1828 | 54.8 | |
| S239N | | | 990 | 1013 | | |
| S239Q | | | 1007 | 2012 | | |
| D265E | | | 2794 | 3517 | | |
| V266D | | | 1220 | 10000 | | |
| V266I | | | n.d. | n.d. | | |
| V266M | 264 | 553 | 274 | 770 | 350 | |
| V266M/S267E | 166 | 59.2 | 28 | 50.2 | 4270 | |
| S267A | 287 | 530 | 200 | 408 | 201 | |
| S267A/H268D/L328Y | | | | 137 | | |
| S267A/L328Y/I332E | | | | 109 | | |
| S267D | 156 | 695 | 95.5 | 330 | 127 | |
| S267D/A327D | | | | 213 | | |
| S267D/A327E | | | | 121 | | |
| S267D/H268D | | | | 103 | | |
| S267D/H268E | | | | 82.6 | | |
| S267E | 117 | 859 | 29.1 | 71.9 | 503 | n.d. |
| S267E/A327D | 198 | | 51.3 | 69.1 | 96300 | |
| S267E/A327E | 143 | 243 | 29.3 | 47.5 | 21400 | |
| S267E/H268D | | | | 44 | | |
| S267E/H268E | 93.5 | 845 | 20.6 | 36.1 | 60.8 | |
| S267E/H268E/L328F | 333 | 783 | 3.4 | 4.26 | 2080 | |
| S267E/L328F | 220 | 923 | 3.12 | 6.06 | 5040 | n.d. |
| S267E/L328H | | | 185 | 284 | | |
| S267E/L328I | | | 11.6 | 27.5 | | |

Figure 36C

| Substitution(s) | FcγRI Kd (pM) | FcγRIIaH Kd (nM) | FcγRIIaR Kd (nM) | FcγRIIb Kd (nM) | FcγRIIIaV Kd (nM) | FcγRIIIaF Kd (nM) |
|---|---|---|---|---|---|---|
| L235W | | | n.d. | n.d. | | |
| L235Y | 142000 | 479 | 669 | 1400 | 380 | |
| L235Y/G236D/S267E | n.d. | n.d. | 88.8 | 58.7 | n.d. | |
| L235Y/S239D/S267E | 307 | 617 | 8.68 | 12.6 | 73.5 | |
| L235Y/S267D | | | | 92.2 | | |
| L235Y/S267E | 95000 | 687 | 22.9 | 39.4 | n.d. | |
| L235Y/S267E/H268E | 32100 | 4130 | 17.8 | 21 | 447 | |
| L235Y/S267E/L328F | 75539 | 853 | 5.02 | 7.83 | n.d. | |
| G236A/G237A | | | | 25400 | | |
| G236D | 15631 | 3871 | 1133 | 953 | n.d. | n.d. |
| G236D/H268D | | | | 126 | | |
| G236D/S239D/S267E | 4810 | 2980 | 32.2 | 17.3 | n.d. | |
| G236D/S267E | 3705 | 2728 | 34.0 | 26.6 | 579 | n.d. |
| G236D/S267E/H268E | 3650 | 6300 | 28.7 | 13.4 | n.d. | |
| G236D/S267E/L328F | 4478 | 21500 | 14.3 | 9.87 | n.d. | |
| G236E/S267E | | | 23.5 | 129 | | |
| G236F | | | 100000 | 100000 | | |
| G236H | | | 6350 | n.d. | | |
| G236I | | | n.d. | n.d. | | |
| G236K | | | 100000 | 100000 | | |
| G236L | | | n.d. | n.d. | | |
| G236M | | | 10000 | 10000 | | |
| G236N/S267E | 9270 | n.d. | 263 | 74.2 | n.d. | |
| G236P | | | 10000 | 10000 | | |
| G236Q | | | 10000 | 10000 | | |
| G236R | | | 100000 | 100000 | | |
| G236S | 12300 | 172 | 369 | 1441 | 52200 | |
| G236S/G237A | | | | 18400 | | |
| G236T | 21000 | 1330 | 2456 | 651920 | n.d. | |
| G236V | | | 8080 | 100000 | | |
| G236W | | | 10000 | 10000 | | |
| G236Y | | | n.d. | n.d. | | |
| G237A | 30500 | n.d. | 1220 | 7676 | n.d. | |
| G237D/S267E | 3770 | n.d. | 63.1 | 86.1 | n.d. | |
| G237E | | | 100000 | 100000 | | |
| G237H | | | n.d. | n.d. | | |
| G237K | | | 100000 | 100000 | | |
| G237L | | | n.d. | n.d. | | |
| G237N/S267E | 3250 | | 14 | 36.2 | n.d. | |
| G237P | | | 100000 | 100000 | | |
| G237Q | | | 10000 | 10000 | | |
| G237S | | | 10600 | 10000 | | |
| G237V | | | 25100 | 10000 | | |
| G237Y | | | 952 | 4450 | | |
| S239D | 93.4 | 590 | 230 | 408 | 23.5 | 214 |

Figure 36D

| Substitution(s) | FcγRI Kd (pM) | FcγRIIaH Kd (nM) | FcγRIIaR Kd (nM) | FcγRIIb Kd (nM) | FcγRIIIaV Kd (nM) | FcγRIIIaF Kd (nM) |
|---|---|---|---|---|---|---|
| S267E/L328Q | | | | 121 | | |
| S267E/L328Y | 1470 | 481 | 7.06 | 34.1 | n.d. | |
| S267E/N325L | | | 20.7 | 46.6 | | |
| S267G | 626 | 2120 | 517 | 1450 | 2120 | |
| H268D | 140 | 342 | 205 | 480 | 62.2 | |
| H268D/A327D | | | | 191 | | |
| H268D/A327D/L328Y | | | | 420 | | |
| H268D/K326D/L328Y | | | | 78.9 | | |
| H268D/L328F/I332E | | | | 119 | | |
| H268D/L328W/I332E | | | | 36.9 | | |
| H268D/L328Y | | | | 767 | | |
| H268D/L328Y/I332E | | | | 300 | | |
| H268E | 120 | 453 | 269 | 560 | 87.5 | |
| H268E/L328Y/I332E | | | | 172 | | |
| H268N | | | 481 | 1250 | | |
| H268Q | | | 544 | n.d. | | |
| S298D | | | 592 | 1840 | | |
| S298E | | | n.d. | n.d. | | |
| S298L | | | | n.d. | | |
| S298M | | | | n.d. | | |
| S298Q | | | n.d. | n.d. | | |
| K326A | | | | n.d. | | |
| K326D/L328Y/I332E | | | | 553 | | |
| K326E | | | | 241 | | |
| K326W | | | | 483 | | |
| A327D | 160 | 882 | 536 | 1100 | 481 | |
| A327D/L328Y/I332E | | | | 636 | | |
| A327G | | | 2692 | 4159 | | |
| A327L | | | | n.d. | | |
| A327N | 11800 | n.d. | 1410 | 1740 | n.d. | |
| A327Q | | | 1354 | 133661 | | |
| L328E | | | | n.d. | | |
| L328F | 452 | 2360 | 166 | 541 | 58408 | 5109 |
| L328Y/I332E | | | | 705 | | |
| P329E | | | 10000 | 10000 | | |
| A330D | | | | n.d. | | |
| A330H | | | | n.d. | | |
| A330K | | | | 947 | | |
| A330S | | | | 23100 | | |
| P331S | | | | 39400 | | |
| IgG1/2ELLGG | 161 | 428 | 481 | 563 | 667 | |
| IgG1/2ELLGG_S267E/L328F | 140 | 651 | 3.19 | 6.63 | n.d. | |
| G236R/L328R | n.d. | n.d. | n.d. | n.d. | n.d. | n.d. |
| ^236R/L328R | n.d. | n.d. | n.d. | n.d. | n.d. | n.d. |

Figure 37A

| Substitution(s) | Fold FcγRI | Fold FcγRIIaH | Fold FcγRIIaR | Fold FcγRIIb | Fold FcγRIIIaV | Fold FcγRIIIaF |
|---|---|---|---|---|---|---|
| IgG1 WT | 1 | 1 | 1 | 1 | 1 | 1 |
| L234D/G236N/S267E | | | 0.728 | 5.11 | | |
| L234D/S267E | 0.0286 | | 12.7 | 21.7 | 0.14 | |
| L234E/H268D | | | | 5.89 | | |
| L234E/S267E | 0.131 | n.d. | 10.7 | 15.1 | n.d. | |
| L234E/S267E/L328F | 0.0425 | 0.0725 | 174 | 195 | n.d. | |
| L234F | 0.0362 | n.d. | 0.228 | 0.409 | n.d. | |
| L234F/G236N | | | n.d. | n.d. | | |
| L234F/S236D | | | n.d. | n.d. | | |
| L234F/S267E | 0.661 | 0.509 | 20.7 | 26.4 | 0.0938 | |
| L234G | | | 0.0859 | 0.147 | | |
| L234I | | | 0.0554 | 0.108 | | |
| L234K | | | 0.00859 | 0.0147 | | |
| L234N | | | n.d. | n.d. | | |
| L234P | | | 0.0141 | 0.0644 | | |
| L234Q | | | 0.0372 | 0.147 | | |
| L234S | | | 0.693 | 0.192 | | |
| L234V | | | 0.134 | 0.456 | | |
| L234W | 0.0314 | 0.557 | 0.453 | 0.829 | 0.029 | |
| L234W/G236D/S239E/S267E | | | 5.69 | 11.4 | | |
| L234W/H268D/L328Y | | | | 5.92 | | |
| L234W/L328Y/I332E | | | | 6.32 | | |
| L234W/S239D/L328Y | | | | 32.8 | | |
| L234W/S239E/S267E | | | 98.5 | 42.3 | | |
| L234Y | | | 0.0511 | 0.0237 | | |
| L235A | 0.0179 | 0.0486 | 0.166 | 0.351 | 0.314 | |
| L235D/S239D | | | | 4.11 | | |
| L235D/S267E | 0.00039 | n.d. | 13 | 16.7 | n.d. | |
| L235D/S267E/L328F | 0.00057 | 0.275 | 133 | 80.4 | n.d. | |
| L235E | | | 0.333 | 0.55 | | |
| L235F/H268D/L328Y | | | | 3.97 | | |
| L235F/L328Y/I332E | | | | 3.31 | | |
| L235F/S239D/L328Y | | | | 6.82 | | |
| L235F/S267E | 0.0176 | 0.402 | 32.5 | 28.4 | n.d. | |
| L235H | | | 0.756 | 0.734 | | |
| L235I | 0.0197 | 0.181 | 0.666 | 0.908 | 0.903 | |
| L235N | | | 0.0356 | 0.147 | | |
| L235P | | | 0.122 | 0.00585 | | |
| L235Q | | | 2.04 | n.d. | | |
| L235R | | | 1.02 | 5.58 | | |
| L235S | | | 0.00859 | 0.0147 | | |
| L235S/S267E | | | 0.716 | 0.0388 | | |
| L235T/S267E | | | 3.06 | 2.37 | | |
| L235W | | | n.d. | n.d. | | |

Figure 37B

| Substitution(s) | Fold FcγRI | Fold FcγRIIaH | Fold FcγRIIaR | Fold FcγRIIb | Fold FcγRIIIaV | Fold FcγRIIIaF |
|---|---|---|---|---|---|---|
| L235Y | 0.00232 | 1.35 | 1.28 | 1.05 | 0.504 | |
| L235Y/G236D/S267E | n.d. | n.d. | 9.67 | 25 | n.d. | |
| L235Y/S239D/S267E | 1.07 | 1.05 | 98.9 | 116 | 2.6 | |
| L235Y/S267D | | | | 15.9 | | |
| L235Y/S267E | 0.00347 | 0.941 | 37.5 | 37.2 | n.d. | |
| L235Y/S267E/H268E | 0.0103 | 0.157 | 48.2 | 69.9 | 0.428 | |
| L235Y/S267E/L328F | 0.00436 | 0.758 | 171 | 187 | n.d. | |
| G236A/G237A | | | | 0.0578 | | |
| G236D | 0.0211 | 0.167 | 0.758 | 1.54 | n.d. | n.d. |
| G236D/H268D | | | | 11.6 | | |
| G236D/S239D/S267E | 0.0685 | 0.217 | 26.7 | 84.8 | n.d. | |
| G236D/S267E | 0.0889 | 0.237 | 25.2 | 55.1 | 0.331 | n.d. |
| G236D/S267E/H268E | 0.0902 | 0.103 | 29.9 | 110 | n.d. | |
| G236D/S267E/L328F | 0.0736 | 0.0301 | 59.9 | 149 | n.d. | |
| G236E/S267E | | | 36.5 | 11.4 | | |
| G236F | | | 0.00859 | 0.0147 | | |
| G236H | | | 0.135 | n.d. | | |
| G236I | | | n.d. | n.d. | | |
| G236K | | | 0.00859 | 0.0147 | | |
| G236L | | | n.d. | n.d. | | |
| G236M | | | 0.0859 | 0.147 | | |
| G236N/S267E | 0.0355 | n.d. | 3.27 | 19.8 | n.d. | |
| G236P | | | 0.0859 | 0.147 | | |
| G236Q | | | 0.0859 | 0.147 | | |
| G236R | | | 0.00859 | 0.0147 | | |
| G236S | 0.0268 | 3.76 | 2.33 | 1.02 | 0.00367 | |
| G236S/G237A | | | | 0.0797 | | |
| G236T | 0.0157 | 0.486 | 0.35 | 0.00225 | n.d. | |
| G236V | | | 0.106 | 0.0147 | | |
| G236W | | | 0.0859 | 0.147 | | |
| G236Y | | | n.d. | n.d. | | |
| G237A | 0.0108 | n.d. | 0.704 | 0.191 | n.d. | |
| G237D/S267E | 0.0874 | n.d. | 13.6 | 17 | n.d. | |
| G237E | | | 0.00859 | 0.0147 | | |
| G237H | | | n.d. | n.d. | | |
| G237K | | | 0.00859 | 0.0147 | | |
| G237L | | | n.d. | n.d. | | |
| G237N/S267E | 0.101 | | 61.5 | 40.5 | n.d. | |
| G237P | | | 0.00859 | 0.0147 | | |
| G237Q | | | 0.0859 | 0.147 | | |
| G237S | | | 0.081 | 0.147 | | |
| G237V | | | 0.0342 | 0.147 | | |
| G237Y | | | 0.902 | 0.33 | | |
| S239D | 3.53 | 1.1 | 3.73 | 3.6 | 8.14 | 6.32 |
| S239D/A327D/L328Y | | | | 11.9 | | |
| S239D/H268D | | | | 14.4 | | |

Figure 37C

| Substitution(s) | Fold FcγRI | Fold FcγRIIaH | Fold FcγRIIaR | Fold FcγRIIb | Fold FcγRIIIaV | Fold FcγRIIIaF |
|---|---|---|---|---|---|---|
| S239D/H268D/L328F | | | | 8.79 | | |
| S239D/H268D/L328F/I332E | | | | 53.2 | | |
| S239D/H268D/L328W | | | | 51.1 | | |
| S239D/H268D/L328W/I332E | | | | 27.8 | | |
| S239D/H268D/L328Y | | | | 24.4 | | |
| S239D/H268D/L328Y/I332E | | | | 54.1 | | |
| S239D/H268E/L328Y | | | | 21.7 | | |
| S239D/I332E | 8.81 | 3.98 | 12.5 | 14.6 | 27.1 | 48 |
| S239D/K326D/L328Y | | | | 13 | | |
| S239D/L328F/I332E | | | | 8.34 | | |
| S239D/L328Y | | | | 5.56 | | |
| S239D/L328Y/I332E | | | | 7.41 | | |
| S239D/S267A/L328Y | | | | 19.8 | | |
| S239D/S267D | | | | 22.3 | | |
| S239D/S267E | 23.2 | 1.27 | 120 | 111 | 3.74 | 2.62 |
| S239D/S267E/H268E | 1.01 | 0.791 | 114 | 212 | 10.3 | |
| S239D/S267E/I332E | | | | 124 | | |
| S239D/S267E/L328F | 1.45 | 1.71 | 416 | 428 | 0.216 | |
| S239E | 1.65 | 0.49 | 0.688 | 0.803 | 3.49 | |
| S239N | | | 0.867 | 1.45 | | |
| S239Q | | | 0.853 | 0.729 | | |
| D265E | | | 0.307 | 0.417 | | |
| V266D | | | 0.704 | 0.147 | | |
| V266I | | | n.d. | n.d. | | |
| V266M | 1.25 | 1.17 | 3.13 | 1.91 | 0.547 | |
| V266M/S267E | 1.98 | 10.9 | 30.7 | 29.2 | 0.0448 | |
| S267A | 1.15 | 1.22 | 4.29 | 3.6 | 0.952 | |
| S267A/H268D/L328Y | | | | 10.7 | | |
| S267A/L328Y/I332E | | | | 13.5 | | |
| S267D | 2.11 | 0.93 | 8.99 | 4.45 | 1.51 | |
| S267D/A327D | | | | 6.89 | | |
| S267D/A327E | | | | 12.1 | | |
| S267D/H268D | | | | 14.2 | | |
| S267D/H268E | | | | 17.8 | | |
| S267E | 2.81 | 0.753 | 29.5 | 20.4 | 0.381 | n.d. |
| S267E/A327D | 1.66 | | 16.7 | 21.2 | 0.00199 | |
| S267E/A327E | 2.3 | 2.66 | 29.3 | 30.9 | 0.00894 | |
| S267E/H268D | | | | 33.3 | | |
| S267E/H268E | 3.52 | 0.765 | 41.7 | 40.6 | 3.15 | |
| S267E/H268E/L328F | 0.991 | 0.826 | 253 | 344 | 0.092 | |
| S267E/L328F | 1.5 | 0.7 | 275 | 242 | 0.038 | n.d. |
| S267E/L328H | | | 4.64 | 5.17 | | |
| S267E/L328I | | | 74 | 53.4 | | |
| S267E/L328Q | | | | 12.1 | | |
| S267E/L328Y | 0.224 | 1.34 | 122 | 43.1 | n.d. | |
| S267E/N325L | | | 41.5 | 31.5 | | |

Figure 37D

| Substitution(s) | Fold FcγRI | Fold FcγRIIaH | Fold FcγRIIaR | Fold FcγRIIb | Fold FcγRIIIaV | Fold FcγRIIIaF |
|---|---|---|---|---|---|---|
| S267G | 0.526 | 0.305 | 1.66 | 1.01 | 0.0903 | |
| H268D | 2.35 | 1.89 | 4.19 | 3.06 | 3.08 | |
| H268D/A327D | | | | 7.68 | | |
| H268D/A327D/L328Y | | | | 3.49 | | |
| H268D/K326D/L328Y | | | | 18.6 | | |
| H268D/L328F/I332E | | | | 12.3 | | |
| H268D/L328W/I332E | | | | 39.8 | | |
| H268D/L328Y | | | | 1.91 | | |
| H268D/L328Y/I332E | | | | 4.89 | | |
| H268E | 2.74 | 1.43 | 3.19 | 2.62 | 2.19 | |
| H268E/L328Y/I332E | | | | 8.53 | | |
| H268N | | | 1.79 | 1.17 | | |
| H268Q | | | 1.58 | n.d. | | |
| S298D | | | 1.45 | 0.797 | | |
| S298E | | | n.d. | n.d. | | |
| S298L | | | | n.d. | | |
| S298M | | | | n.d. | | |
| S298Q | | | n.d. | n.d. | | |
| K326A | | | | n.d. | | |
| K326D/L328Y/I332E | | | | 2.65 | | |
| K326E | | | | 6.09 | | |
| K326W | | | | 3.04 | | |
| A327D | 2.06 | 0.733 | 1.6 | 1.33 | 0.398 | |
| A327D/L328Y/I332E | | | | 2.31 | | |
| A327G | | | 0.319 | 0.353 | | |
| A327L | | | | n.d. | | |
| A327N | 0.0279 | n.d. | 0.609 | 0.843 | n.d. | |
| A327Q | | | 0.634 | 0.011 | | |
| L328E | | | | n.d. | | |
| L328F | 0.728 | 0.274 | 5.16 | 2.71 | 0.00328 | 0.265 |
| L328Y/I332E | | | | 2.08 | | |
| P329E | | | 0.0859 | 0.147 | | |
| A330D | | | | n.d. | | |
| A330H | | | | n.d. | | |
| A330K | | | | 1.55 | | |
| A330S | | | | 0.0635 | | |
| P331S | | | | 0.0372 | | |
| IgG1/2ELLGG | 2.05 | 1.51 | 1.79 | 2.61 | 0.287 | |
| IgG1/2ELLGG_S267E/L328F | 2.35 | 0.993 | 269 | 221 | n.d. | |
| G236R/L328R | n.d. | n.d. | n.d. | n.d. | n.d. | n.d. |
| ^236R/L328R | n.d. | n.d. | n.d. | n.d. | n.d. | n.d. |

Figure 39A. Binding of human CR2-Fc constructs to purified human C3d using SPR
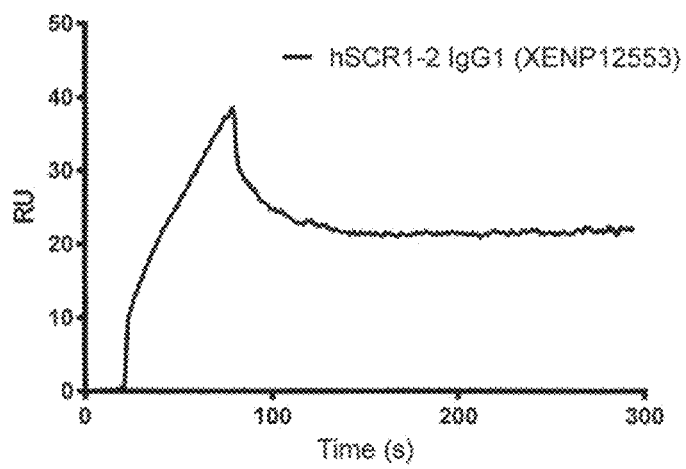
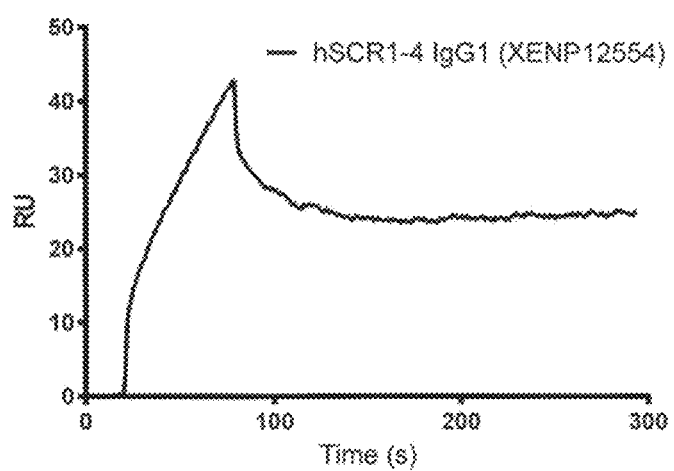

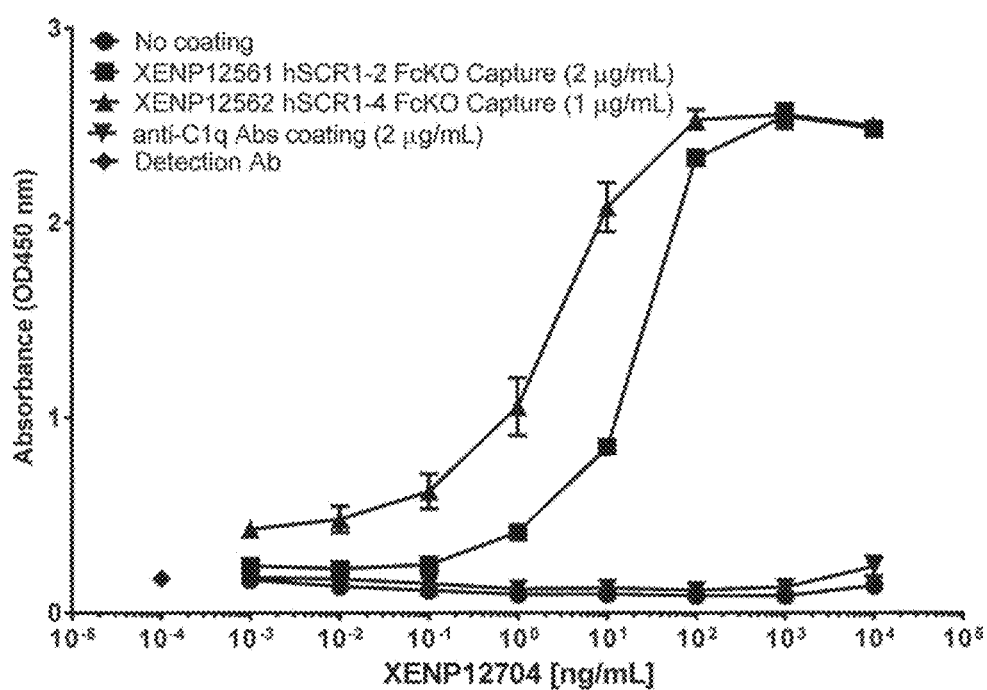
Figure 39B. Binding of human CR2-Fc constructs to recombinant C3d measured by ELISA

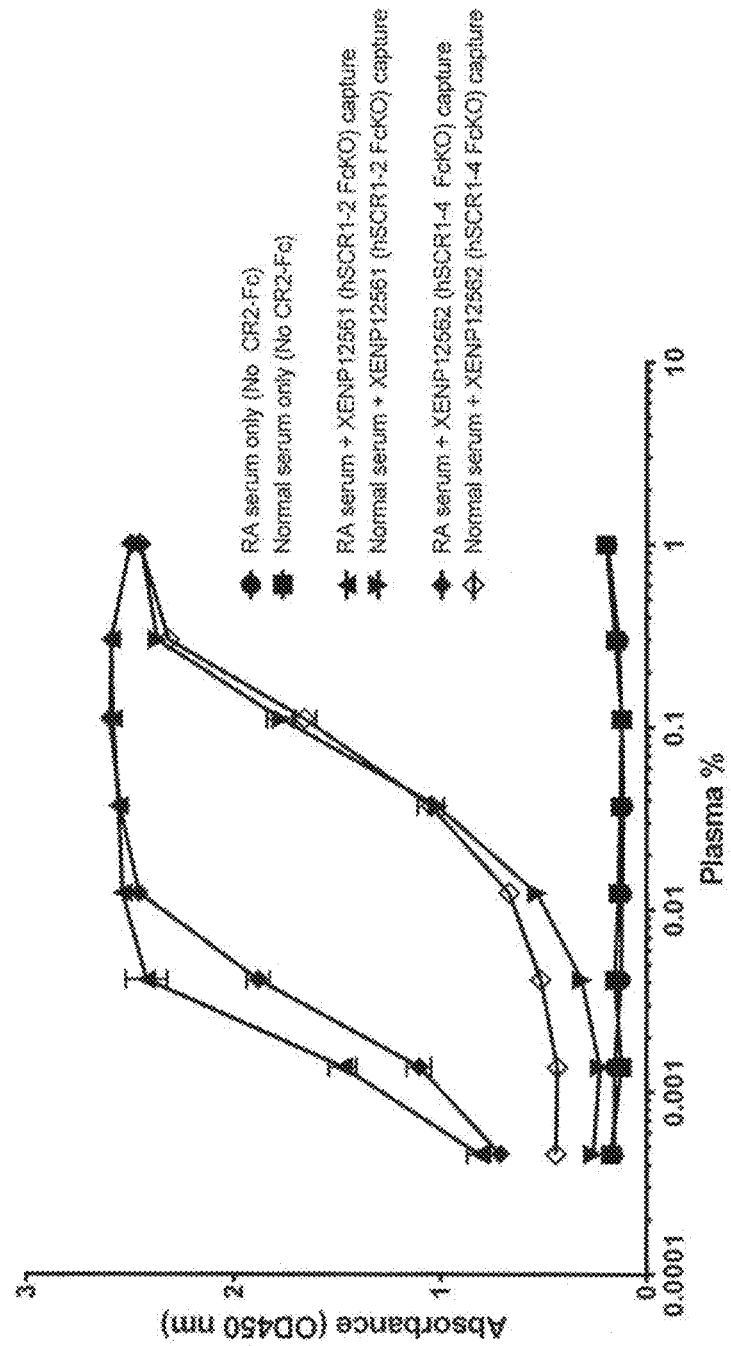
Figure 39C. Binding of human CR2-Fc constructs to C3d-tagged immune complexes present in normal and RA patient sera measured by ELISA Figure 40A. Amino acid sequences of human and mouse CR2 variants Signal sequences are underlined

Human CR2 SCR1-2 domains     (SEQ ID NO: 48)

MGAAGLLGVFLALVAPGVLGISCGSPPPILNGRISYYSTPIAVGTVIRYSCSGTFRLIGEKSLLCITKDKVDGTWDKPAPKC
EYFNKYSSCPEPIVPGGYKIRGSTPYRHGDSVTFACKTNFSMNGNKSVWCQANNMWGPTRLPTCVS

Human CR2 SCR1-4 domains     (SEQ ID NO: 49)

MGAAGLLGVFLALVAPGVLGISCGSPPPILNGRISYYSTPIAVGTVIRYSCSGTFRLIGEKSLLCITKDKVDGTWDKPAPKC
EYFNKYSSCPEPIVPGGYKIRGSTPYRHGDSVTFACKTNFSMNGNKSVWCQANNMWGPTRLPTCVSFPLECPALPMI
HNGHHTSENVGSIAPGLSVTYSCESGYLLVGEKIINCLSSGKWSAVPPTCEEARCKSLGRFPNGKVKEPPILRVGVTANFF
CDEGYRLQGPPSSRCVIAGQGVAWTKMPVCEE

Mouse CR2 SCR1-2 domains     (SEQ ID NO: 50)

MLTWFLFYFSEISCDPPPEVKNARKPYYSLPIVPGTVLRYTCSPSYRLIGEKAIFCISENQVHATWDKAPPICESVNKTISCS
DPIVPGGFMNKGSKAPFRHGDSVTFTCKANFTMKGSKTVWCQANEMWGPTALPVCES

Mouse CR2 SCR1-4 domains     (SEQ ID NO: 51)

MLTWFLFYFSEISCDPPPEVKNARKPYYSLPIVPGTVLRYTCSPSYRLIGEKAIFCISENQVHATWDKAPPICESVNKTISCS
DPIVPGGFMNKGSKAPFRHGDSVTFTCKANFTMKGSKTVWCQANEMWGPTALPVCESDFPLECPSLPTIHNGHHTG
QHVDQFVAGLSVTYSCEPGYLLTGKKTIKCLSSGDWDGVIPTCKEAQCEHPGKFPNGQVKEPLSLQVGTTVYFSCNEGY
QLQGQPSSQCVIVEQKAIWTKKPVCKE

Human CR2 SCR1-2 IgG1 (XENP12553)   (SEQ ID NO: 52)

MGAAGLLGVFLALVAPGVLGISCGSPPPILNGRISYYSTPIAVGTVIRYSCSGTFRLIGEKSLLCITKDKVDGTWDKPAPKC
EYFNKYSSCPEPIVPGGYKIRGSTPYRHGDSVTFACKTNFSMNGNKSVWCQANNMWGPTRLPTCVSEPKSSDKTHTCP
PCPAPELLGGPSVFLFPPKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Human CR2 SCR1-2 IgG1 S267E   (SEQ ID NO: 53)

MGAAGLLGVFLALVAPGVLGISCGSPPPILNGRISYYSTPIAVGTVIRYSCSGTFRLIGEKSLLCITKDKVDGTWDKPAPKC
EYFNKYSSCPEPIVPGGYKIRGSTPYRHGDSVTFACKTNFSMNGNKSVWCQANNMWGPTRLPTCVSEPKSSDKTHTCP
PCPAPELLGGPSVFLFPPKPKDTLMISRTPEVTCVVVDVEHEDPEVKFNWYVDGVEVHNAKTKPREEQYNSTYRVVSVL
TVLHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Human CR2 SCR1-2 IgG1 S267E/L328F   (SEQ ID NO: 54)

Figure 40B

MGAAGLLGVFLALVAPGVLGISCGSPPPILNGRISYYSTPIAVGTVIRYSCSGTFRLIGEKSLLCITKDKVDGTWDKPAPKC
EYFNKYSSCPEPIVPGGYKIRGSTPYRHGDSVTFACKTNFSMNGNKSVWCQANNMWGPTRLPTCVSEPKSSDKTHTCP
PCPAPELLGGPSVFLFPPKPKDTLMISRTPEVTCVVVDVEHEDPEVKFNWYVDGVEVHNAKTKPREEQYNSTYRVVSVL
TVLHQDWLNGKEYKCKVSNKAFPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Human CR2 SCR1-2 IgG1 G236N/S267E   (SEQ ID NO: 55)

MGAAGLLGVFLALVAPGVLGISCGSPPPILNGRISYYSTPIAVGTVIRYSCSGTFRLIGEKSLLCITKDKVDGTWDKPAPKC
EYFNKYSSCPEPIVPGGYKIRGSTPYRHGDSVTFACKTNFSMNGNKSVWCQANNMWGPTRLPTCVSEPKSSDKTHTCP
PCPAPELLNGPSVFLFPPKPKDTLMISRTPEVTCVVVDVEHEDPEVKFNWYVDGVEVHNAKTKPREEQYNSTYRVVSVL
TVLHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Human CR2 SCR1-2 IgG1 G236D/S267E   (SEQ ID NO: 56)

MGAAGLLGVFLALVAPGVLGISCGSPPPILNGRISYYSTPIAVGTVIRYSCSGTFRLIGEKSLLCITKDKVDGTWDKPAPKC
EYFNKYSSCPEPIVPGGYKIRGSTPYRHGDSVTFACKTNFSMNGNKSVWCQANNMWGPTRLPTCVSEPKSSDKTHTCP
PCPAPELLDGPSVFLFPPKPKDTLMISRTPEVTCVVVDVEHEDPEVKFNWYVDGVEVHNAKTKPREEQYNSTYRVVSVL
TVLHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Human CR2 SCR1-2 IgG1 G236R/L328R (XENP12561)   (SEQ ID NO: 57)

MGAAGLLGVFLALVAPGVLGISCGSPPPILNGRISYYSTPIAVGTVIRYSCSGTFRLIGEKSLLCITKDKVDGTWDKPAPKC
EYFNKYSSCPEPIVPGGYKIRGSTPYRHGDSVTFACKTNFSMNGNKSVWCQANNMWGPTRLPTCVSEPKSSDKTHTCP
PCPAPELLRGPSVFLFPPKPKDTLMISRTPEVTCVVVDVSHEDPEVKFNWYVDGVEVHNAKTKPREEQYNSTYRVVSVL
TVLHQDWLNGKEYKCKVSNKARPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Human CR2 SCR1-4 IgG1 (XENP12554)   (SEQ ID NO: 58)

MGAAGLLGVFLALVAPGVLGISCGSPPPILNGRISYYSTPIAVGTVIRYSCSGTFRLIGEKSLLCITKDKVDGTWDKPAPKC
EYFNKYSSCPEPIVPGGYKIRGSTPYRHGDSVTFACKTNFSMNGNKSVWCQANNMWGPTRLPTCVSVFPLECPALPMI
HNGHHTSENVGSIAPGLSVTYSCESGYLLVGEKIINCLSSGKWSAVPPTCEEARCKSLGRFPNGKVKEPPILRVGVTANFF
CDEGYRLQGPPSSRCVIAGQGVAWTKMPVCEEEPKSSDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK

Figure 40C

Human CR2 SCR1-4 IgG1 S267E (SEQ ID NO: 59)

MGAAGLLGVFLALVAPGVLGISCGSPPPILNGRISYYSTPIAVGTVIRYSCSGTFRLIGEKSLLCITKDKVDGTWDKPAPKC
EYFNKYSSCPEPIVPGGYKIRGSTPYRHGDSVTFACKTNFSMNGNKSVWCQANNMWGPTRLPTCVSVFPLECPALPMI
HNGHHTSENVGSIAPGLSVTYSCESGYLLVGEKIINCLSSGKWSAVPPTCEEARCKSLGRFPNGKVKEPPILRVGVTANFF
CDEGYRLQGPPSSRCVIAGQGVAWTKMPVCEEEPKSSDKTHTCPPCPAPELLGGPSVFLFPPKPKDTLMISRTPEVTCV
VVDVEHEDPEVKFNWYVDGVEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK

Human CR2 SCR1-4 IgG1 S267E/L328F (SEQ ID NO: 60)

MGAAGLLGVFLALVAPGVLGISCGSPPPILNGRISYYSTPIAVGTVIRYSCSGTFRLIGEKSLLCITKDKVDGTWDKPAPKC
EYFNKYSSCPEPIVPGGYKIRGSTPYRHGDSVTFACKTNFSMNGNKSVWCQANNMWGPTRLPTCVSVFPLECPALPMI
HNGHHTSENVGSIAPGLSVTYSCESGYLLVGEKIINCLSSGKWSAVPPTCEEARCKSLGRFPNGKVKEPPILRVGVTANFF
CDEGYRLQGPPSSRCVIAGQGVAWTKMPVCEEEPKSSDKTHTCPPCPAPELLGGPSVFLFPPKPKDTLMISRTPEVTCV
VVDVEHEDPEVKFNWYVDGVEVHNAKTKPREEQYNSTYRVVSVLTVLHQDWLNGKEYKCKVSNKAFPAPIEKTISKAK
GQPREPQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK

Human CR2 SCR1-4 IgG1 G236N/S267E (SEQ ID NO: 61)

MGAAGLLGVFLALVAPGVLGISCGSPPPILNGRISYYSTPIAVGTVIRYSCSGTFRLIGEKSLLCITKDKVDGTWDKPAPKC
EYFNKYSSCPEPIVPGGYKIRGSTPYRHGDSVTFACKTNFSMNGNKSVWCQANNMWGPTRLPTCVSVFPLECPALPMI
HNGHHTSENVGSIAPGLSVTYSCESGYLLVGEKIINCLSSGKWSAVPPTCEEARCKSLGRFPNGKVKEPPILRVGVTANFF
CDEGYRLQGPPSSRCVIAGQGVAWTKMPVCEEEPKSSDKTHTCPPCPAPELLNGPSVFLFPPKPKDTLMISRTPEVTCV
VVDVEHEDPEVKFNWYVDGVEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK

Human CR2 SCR1-4 IgG1 G236D/S267E (SEQ ID NO: 62)

MGAAGLLGVFLALVAPGVLGISCGSPPPILNGRISYYSTPIAVGTVIRYSCSGTFRLIGEKSLLCITKDKVDGTWDKPAPKC
EYFNKYSSCPEPIVPGGYKIRGSTPYRHGDSVTFACKTNFSMNGNKSVWCQANNMWGPTRLPTCVSVFPLECPALPMI
HNGHHTSENVGSIAPGLSVTYSCESGYLLVGEKIINCLSSGKWSAVPPTCEEARCKSLGRFPNGKVKEPPILRVGVTANFF
CDEGYRLQGPPSSRCVIAGQGVAWTKMPVCEEEPKSSDKTHTCPPCPAPELLDGPSVFLFPPKPKDTLMISRTPEVTCV
VVDVEHEDPEVKFNWYVDGVEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK

*Figure 40D*

Human CR2 SCR1-4 IgG1 G236R/L328R (XENP12562) (SEQ ID NO: 63)

MGAAGLLGVFLALVAPGVLGISCGSPPPILNGRISYYSTPIAVGTVIRYSCSGTFRLIGEKSLLCITKDKVDGTWDKPAPKC
EYFNKYSSCPEPIVPGGYKIRGSTPYRHGDSVTFACKTNFSMNGNKSVWCQANNMWGPTRLPTCVSVFPLECPALPMI
HNGHHTSENVGSIAPGLSVTYSCESGYLLVGEKIINCLSSGKWSAVPPTCEEARCKSLGRFPNGKVKEPPILRVGVTANFF
CDEGYRLQGPPSSRCVIAGQGVAWTKMPVCEEEPKSSDKTHTCPPCPAPELLRGPSVFLFPPKPKDTLMISRTPEVTCV
VVDVSHEDPEVKFNWYVDGVEVHNAKTKPREEQYNSTYRVVSVLTVLHQDWLNGKEYKCKVSNKARPAPIEKTISKAK
GQPREPQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK

Mouse CR2 SCR1-2 IgG1 (SEQ ID NO: 64)

MLTWFLFYFSEISCDPPPEVKNARKPYYSLPIVPGTVLRYTCSPSYRLIGEKAIFCISENQVHATWDKAPPICESVNKTISCS
DPIVPGGFMNKGSKAPFRHGDSVTFTCKANFTMKGSKTVWCQANEMWGPTALPVCESEPKSSDKTHTCPPCPAPELL
GGPSVFLFPPKPKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK

Mouse CR2 SCR1-2 IgG1 S267E (SEQ ID NO: 65)

MLTWFLFYFSEISCDPPPEVKNARKPYYSLPIVPGTVLRYTCSPSYRLIGEKAIFCISENQVHATWDKAPPICESVNKTISCS
DPIVPGGFMNKGSKAPFRHGDSVTFTCKANFTMKGSKTVWCQANEMWGPTALPVCESEPKSSDKTHTCPPCPAPELL
GGPSVFLFPPKPKDTLMISRTPEVTCVVVDVEHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK

Mouse CR2 SCR1-2 IgG1 S267E/L328F (SEQ ID NO: 66)

MLTWFLFYFSEISCDPPPEVKNARKPYYSLPIVPGTVLRYTCSPSYRLIGEKAIFCISENQVHATWDKAPPICESVNKTISCS
DPIVPGGFMNKGSKAPFRHGDSVTFTCKANFTMKGSKTVWCQANEMWGPTALPVCESEPKSSDKTHTCPPCPAPELL
GGPSVFLFPPKPKDTLMISRTPEVTCVVVDVEHEDPEVKFNWYVDGVEVHNAKTKPREEQYNSTYRVVSVLTVLHQD
WLNGKEYKCKVSNKAFPAPIEKTISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK

Mouse CR2 SCR1-2 IgG1 G236N/S267E (SEQ ID NO: 67)

MLTWFLFYFSEISCDPPPEVKNARKPYYSLPIVPGTVLRYTCSPSYRLIGEKAIFCISENQVHATWDKAPPICESVNKTISCS
DPIVPGGFMNKGSKAPFRHGDSVTFTCKANFTMKGSKTVWCQANEMWGPTALPVCESEPKSSDKTHTCPPCPAPELL
NGPSVFLFPPKPKDTLMISRTPEVTCVVVDVEHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK

Figure 40E

Mouse CR2 SCR1-2 IgG1 G236D/S267E (SEQ ID NO: 68)

MLTWLFLYFSEISCDPPPEVKNARKPYYSLPIVPGTVLRYTCSPSYRLIGEKAIFCISENQVHATWDKAPPICESVNKTISCS
DPIVPGGFMNKGSKAPFRHGDSVTFTCKANFTMKGSKTVWCQANEMWGPTALPVCESEPKSSDKTHTCPPCPAPELL
DGPSVFLFPPKPKDTLMISRTPEVTCVVVDVEHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK

Mouse CR2 SCR1-2 IgG1 G236R/L328R (SEQ ID NO: 69)

MLTWLFLYFSEISCDPPPEVKNARKPYYSLPIVPGTVLRYTCSPSYRLIGEKAIFCISENQVHATWDKAPPICESVNKTISCS
DPIVPGGFMNKGSKAPFRHGDSVTFTCKANFTMKGSKTVWCQANEMWGPTALPVCESEPKSSDKTHTCPPCPAPELL
RGPSVFLFPPKPKDTLMISRTPEVTCVVVDVSHEDPEVKFNWYVDGVEVHNAKTKPREEQYNSTYRVVSVLTVLHQDW
LNGKEYKCKVSNKARPAPIEKTISKAKGQPREPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSLSLSPGK

Mouse CR2 SCR1-4 IgG1 (SEQ ID NO: 70)

MLTWLFLYFSEISCDPPPEVKNARKPYYSLPIVPGTVLRYTCSPSYRLIGEKAIFCISENQVHATWDKAPPICESVNKTISCS
DPIVPGGFMNKGSKAPFRHGDSVTFTCKANFTMKGSKTVWCQANEMWGPTALPVCESDFPLECPSLPTIHNGHHTG
QHVDQFVAGLSVTYSCEPGYLLTGKKTIKCLSSGDWDGVIPTCKEAQCEHPGKFPNGQVKEPLSLQVGTTVYFSCNEGY
QLQGQPSSQCVIVEQKAIWTKKPVCKEEPKSSDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFFLYSKLTVDKSRWQQGNVFS
CSVMHEALHNHYTQKSLSLSPGK

Mouse CR2 SCR1-4 IgG1 S267E (SEQ ID NO: 71)

MLTWLFLYFSEISCDPPPEVKNARKPYYSLPIVPGTVLRYTCSPSYRLIGEKAIFCISENQVHATWDKAPPICESVNKTISCS
DPIVPGGFMNKGSKAPFRHGDSVTFTCKANFTMKGSKTVWCQANEMWGPTALPVCESDFPLECPSLPTIHNGHHTG
QHVDQFVAGLSVTYSCEPGYLLTGKKTIKCLSSGDWDGVIPTCKEAQCEHPGKFPNGQVKEPLSLQVGTTVYFSCNEGY
QLQGQPSSQCVIVEQKAIWTKKPVCKEEPKSSDKTHTCPPCPAPELLGGPSVFLFPPKPKDTLMISRTPEVTCVVVDVEH
EDPEVKFNWYVDGVEVHNAKTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFFLYSKLTVDKSRWQQGNVFS
CSVMHEALHNHYTQKSLSLSPGK

Mouse CR2 SCR1-4 IgG1 S267E/L328F (SEQ ID NO: 72)

MLTWLFLYFSEISCDPPPEVKNARKPYYSLPIVPGTVLRYTCSPSYRLIGEKAIFCISENQVHATWDKAPPICESVNKTISCS
DPIVPGGFMNKGSKAPFRHGDSVTFTCKANFTMKGSKTVWCQANEMWGPTALPVCESDFPLECPSLPTIHNGHHTG
QHVDQFVAGLSVTYSCEPGYLLTGKKTIKCLSSGDWDGVIPTCKEAQCEHPGKFPNGQVKEPLSLQVGTTVYFSCNEGY
QLQGQPSSQCVIVEQKAIWTKKPVCKEEPKSSDKTHTCPPCPAPELLGGPSVFLFPPKPKDTLMISRTPEVTCVVVDVEH
EDPEVKFNWYVDGVEVHNAKTKPREEQYNSTYRVVSVLTVLHQDWLNGKEYKCKVSNKAFPAPIEKTISKAKGQPREP

Figure 40F

QVYTLPPSREEMTKNQVSLTCLVKGFYPSDIAVEWESNGQPENNYKTTPPVLDSDGSFFLYSKLTVDKSRWQQGNVFS
CSVMHEALHNHYTQKSLSLSPGK

Mouse CR2 SCR1-4 IgG1 G236N/S267E (SEQ ID NO: 73)

<u>MLTWFLFYFSE</u>ISCDPPPEVKNARKPYYSLPIVPGTVLRYTCSPSYRLIGEKAIFCISENQVHATWDKAPPICESVNKTISCS
DPIVPGGFMNKGSKAPFRHGDSVTFTCKANFTMKGSKTVWCQANEMWGPTALPVCESDFPLECPSLPTIHNGHHTG
QHVDQFVAGLSVTYSCEPGYLLTGKKTIKCLSSGDWDGVIPTCKEAQCEHPGKFPNGQVKEPLSLQVGTTVYFSCNEGY
QLQGQPSSQCVIVEQKAIWTKKPVCKEEPKSSDKTHTCPPCPAPELLNGPSVFLFPPKPKDTLMISRTPEVTCVVVDVEH
EDPEVKFNWYVDGVEVHNAKTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFFLYSKLTVDKSRWQQGNVFS
CSVMHEALHNHYTQKSLSLSPGK

Mouse CR2 SCR1-4 IgG1 G236D/S267E (SEQ ID NO: 74)

<u>MLTWFLFYFSE</u>ISCDPPPEVKNARKPYYSLPIVPGTVLRYTCSPSYRLIGEKAIFCISENQVHATWDKAPPICESVNKTISCS
DPIVPGGFMNKGSKAPFRHGDSVTFTCKANFTMKGSKTVWCQANEMWGPTALPVCESDFPLECPSLPTIHNGHHTG
QHVDQFVAGLSVTYSCEPGYLLTGKKTIKCLSSGDWDGVIPTCKEAQCEHPGKFPNGQVKEPLSLQVGTTVYFSCNEGY
QLQGQPSSQCVIVEQKAIWTKKPVCKEEPKSSDKTHTCPPCPAPELLDGPSVFLFPPKPKDTLMISRTPEVTCVVVDVEH
EDPEVKFNWYVDGVEVHNAKTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFFLYSKLTVDKSRWQQGNVFS
CSVMHEALHNHYTQKSLSLSPGK

Mouse CR2 SCR1-4 IgG1 G236R/L328R (SEQ ID NO: 75)

<u>MLTWFLFYFSE</u>ISCDPPPEVKNARKPYYSLPIVPGTVLRYTCSPSYRLIGEKAIFCISENQVHATWDKAPPICESVNKTISCS
DPIVPGGFMNKGSKAPFRHGDSVTFTCKANFTMKGSKTVWCQANEMWGPTALPVCESDFPLECPSLPTIHNGHHTG
QHVDQFVAGLSVTYSCEPGYLLTGKKTIKCLSSGDWDGVIPTCKEAQCEHPGKFPNGQVKEPLSLQVGTTVYFSCNEGY
QLQGQPSSQCVIVEQKAIWTKKPVCKEEPKSSDKTHTCPPCPAPELLRGPSVFLFPPKPKDTLMISRTPEVTCVVVDVSH
EDPEVKFNWYVDGVEVHNAKTKPREEQYNSTYRVVSVLTVLHQDWLNGKEYKCKVSNKARPAPIEKTISKAKGQPREP
QVYTLPPSREEMTKNQVSLTCLVKGFYPSDIAVEWESNGQPENNYKTTPPVLDSDGSFFLYSKLTVDKSRWQQGNVFS
CSVMHEALHNHYTQKSLSLSPGK

Figure 42

Human LOX-1 (SEQ ID NO: 76)

MTFDDLKIQTVKDQPDEKSNGKKAKGLQFLYSPWWCLAAATLGVLCLGLVVTIMVLGMQLSQVSDLLTQEQANLTHQ
KKELEGQISARQQAEEASQESENELKEMIETLARKLNEKSKEQMELHHQNLNLQETLKRVANCSAPCPQDWIWHGEN
CYLFSSGSFNWEKSQEKCLSLDAKLLKINSTADLDFIQQAISYSSFPFWMGLSRRNPSYPWLWEDGSPLMPHLFRVRGA
VSQTYPSGTCAYIQRGAVYAENCILAAFSICQKKANLRAQ

Mouse LOX-1 (SEQ ID NO: 77)

MTFDDKMKPANDEPDQKSCGKKPKGLHLLSSPWWFPAAMTLVILCLVLSVTLIVQWTQLRQVSDLLKQYQANLTQQ
DRILEGQMLAQQKAENASQESKKELKGKIDTLTQKLNEKSKEQEELLQKNQNLQEALQRAANSSEESQRELKGKIDTITR
KLDEKSKEQEELLQMIQNLQEALQRAANSSEESQRELKGKIDTLTLKLNEKSKEQEELLQKNQNLQEALQRAANFSGPCP
QDWLWHKENCYLFHGPFSWEKNRQTCQSLGGQLLQINGADDLTFILQAISHTTSPFWIGLHRKKPGQPWLWENGTP
LNFQFFKTRGVSLQLYSSGNCAYLQDGAVFAENCILIAFSICQKKTNHLQI

Human CD36 (SEQ ID NO: 78)

MGCDRNCGLIAGAVIGAVLAVFGGILMPVGDLLIQKTIKKQVVLEEGTIAFKNWVKTGTEVYRQFWIFDVQNPQEVM
MNSSNIQVKQRGPYTYRVRFLAKENVTQDAEDNTVSFLQPNGAIFEPSLSVGTEADNFTVLNLAVAAASHIYQNQFVQ
MILNSLINKSKSSMFQVRTLRELLWGYRDPFLSLVPYPVTTTVGLFYPYNNTADGVYKVFNGKDNISKVAIIDTYKGKRNL
SYWESHCDMINGTDAASFPPPFVEKSQVLQFFSSDICRSIYAVFESDVNLKGIPVYRFVLPSKAFASPVENPDNYCFCTEKII
SKNCTSYGVLDISKCKEGRPVYISLPHFLYASPDVSEPIDGLNPNEEEHRTYLDIEPITGFTLQFAKRLQVNLLVKPSEKIQVL
KNLKRNYIVPILWLNETGTIGDEKANMFRSQVTGKINLLGLIEMILLSVGVVMFVAFMISYCACRSKTIK

Mouse CD36 (SEQ ID NO: 79)

MGCDRNCGLIAGAVIGAVLAVFGGILMPVGDMLIEKTIKREVVLEEGTTAFKNWVKTGTTVYRQFWIFDVQNPQDVA
KNSSKIKVKQRGPYTYRVRYLAKENITQDPEDHTVSFVQPNGAIFEPSLSVGTEDDNFTVLNLAVAAAPHIYQNSFVQVV
LNSLIKKSKSSMFQTRSLKELLWGYKDPFLSLVPYPISTTVGVFYPYNDTVDGVYKVFNGKDNISKVAIIESYKGKRNLSYW
PSYCDMINGTDAASFPPPFVEKSRTLRFFSSDICRSIYAVFGSEIDLKGIPVYRFVLPANAFASPLQNPDNHCFCTEKVISNN
CTSYGVLDIGKCKEGKPVYISLPHFLHASPDVSEPIEGLHPNEDEHRTYLDVEPITGFTLQFAKRLQVNILVKPARKIEALKN
LKRPYIVPILWLNETGTIGDEKAEMFKTQVTGKIKLLGMVEMALLGIGVVMFVAFMISYCACKSKNGK

Figure 43A

XENP13514 E06_H0L0_IgG1_WT HC (SEQ ID NO: 80)

EVKLVESGGGLVQPGGSLRLSCATSGFTFSDFYMEWVRQPPGKRLEWIAASRNKANDYTTEYSASVKGRFIVSRDTSQS
ILYLQMNALRAEDTAIYYCARDYYGSSYWYFDVWGAGTTVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCPAPE
LLGGPSVFLFPPKPKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK

XENP13514 E06_H0L0_IgG1_WT LC (SEQ ID NO: 81)

DIVMTQSPTFLAVTASKKVTISCTASESLYSSKHKVHYLAWYQKKPEQSPKLLIYGASNRYIGVPDRFTGSGSGTDFTLTIS
SVQVEDLTHYYCAQFYSYPLTFGAGTKLELKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSFNRGEC

XENP13515 2D03_H0L0_IgG1_WT HC (SEQ ID NO: 82)

EVQLLESGGGLVQPGGSLRLSCAASGFTFSNAWMSWVRQAPGKGLEWVSSISVGGHRTYYADSVKGRSTISRDNSKN
TLYLQMNSLRAEDTAVYYCARIRVGPSGGAFDYWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLSPGK

XENP13515 2D03_H0L0_IgG1_WT LC (SEQ ID NO: 83)

QSVLTQPPSASGTPGQRVTISCSGSNTNIGKNYVSWYQQLPGTAPKLLIYANSNRPSGVPDRFSGSKSGTSASLAISGLRS
EDEADYYCASWDASLNGWVFGGGTKLTVLGQPKAAPSVTLFPPSSEELQANKATLVCLISDFYPGAVTVAWKADSSPV
KAGVETTTPSKQSNNKYAASSYLSLTPEQWKSHRSYSCQVTHEGSTVEKTVAPTECS

XENP013516 huLOX1(137-237)-(G4S)2-Fc(216)_IgG1_C220S (SEQ ID NO: 84)

VANCSAPCPQDWIWHGENCYLFSSGSFNWEKSQEKCLSLDAKLLKINSTADLDFIQQAISYSSFPFWMGLSRRNPSYP
WLWEDGSPLMPHLFRVRGAVSQTYPSGTCAYIQRGAVYAENCILAAFSICQKKANLRAQGGGGSGGGGSEPKSSDKT
HTCPPCPAPELLGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHNHYTQKSLSLSPGK

XENP013517 huCD36(30-439)-(G4S)2-Fc(216)_IgG1_C220S (SEQ ID NO: 85)

GDLLIQKTIKKQVVLEEGTIAFKNWVKTGTEVYRQFWIFDVQNPQEVMMNSSNIQVKQRGPYTYRVRFLAKENVTQD
AEDNTVSFLQPNGAIFEPSLSVGTEADNFTVLNLAVAAASHIYQNQFVQMILNSLINKSKSSMFQVRTLRELLWGYRDP
FLSLVPYPVTTTVGLFYPYNNTADGVYKVFNGKDNISKVAIIDTYKGKRNLSYWESHCDMINGTDAASFPPFVEKSQVLQ
FFSSDICRSIYAVFESDVNLKGIPVYRFVLPSKAFASPVENPDNYCFCTEKIISKNCTSYGVLDISKCKEGRPVYISLPHFLYAS

Figure 43B

PDVSEPIDGLNPNEEEHRTYLDIEPITGFTLQFAKRLQVNLLVKPSEKIQVLKNLKRNYIVPILWLNETGTIGDEKANMFRS
QVTGKINGGGGSGGGGSEPKSSDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRWQQGNVFSCSVMHEAL
HNHYTQKSLSLSPGK

XENP13518 empty-Fc(216)_IgG1_C220S-(G4S)2-huLOX1(137-237)  (SEQ ID NO: 86)

EPKSSDKTHTCPPCPAPELLGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSVMHEALHNHYTQKSLSLSPGKGGG
GSGGGGSVANCSAPCPQDWIWHGENCYLFSSGSFNWEKSQEKCLSLDAKLLKINSTADLDFIQQAISYSSFPFWMGLS
RRNPSYPWLWEDGSPLMPHLFRVRGAVSQTYPSGTCAYIQRGAVYAENCILAAFSICQKKANLRAQ

Figure 45

E06_HOLO_IgG1_S267E/L328F HC (SEQ ID NO: 87)
EVKLVESGGGLVQPGGSLRLSCATSGFTFSDFYMEWVRQPPGKRLEWIAASRNKANDYTTEYSASVKGRFIVSRDTSQS
ILYLQMNALRAEDTAIYYCARDYYGSSYWYFDVWGAGTTVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCPAPE
LLGGPSVFLFPPKPKDTLMISRTPEVTCVVVDVEHEDPEVKFNWYVDGVEVHNAKTKPREEQYNSTYRVVSVLTVLHQ
DWLNGKEYKCKVSNKAFPAPIEKTISKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLSPGK

2D03_HOLO_IgG1_S267E/L328F HC (SEQ ID NO: 88)
EVQLLESGGGLVQPGGSLRLSCAASGFTFSNAWMSWVRQAPGKGLEWVSSISVGGHRTYYADSVKGRSTISRDNSKN
TLYLQMNSLRAEDTAVYYCARIRVGPSGGAFDYWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVEHEDPEVKFNWYVDGVEVHNAKTKPREEQYNSTYRVVSVLTVLHQ
DWLNGKEYKCKVSNKAFPAPIEKTISKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLSPGK huLOX1(137-237)-(G4S)2-Fc(216)_IgG1_C220S/S267E/L328F (SEQ ID NO: 89)
VANCSAPCPQDWIWHGENCYLFSSGSFNWEKSQEKCLSLDAKLLKINSTADLDFIQQAISYSSFPFWMGLSRRNPSYP
WLWEDGSPLMPHLFRVRGAVSQTYPSGTCAYIQRGAVYAENCILAAFSICQKKANLRAQGGGGSGGGGSEPKSSDKT
HTCPPCPAPELLGGPSVFLFPPKPKDTLMISRTPEVTCVVVDVEHEDPEVKFNWYVDGVEVHNAKTKPREEQYNSTYRV
VSVLTVLHQDWLNGKEYKCKVSNKAFPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLSPGK huCD36(30-439)-(G4S)2-Fc(216)_IgG1_C220S/S267E/L328F (SEQ ID NO: 90)
GDLLIQKTIKKQVVLEEGTIAFKNWVKTGTEVYRQFWIFDVQNPQEVMMNSSNIQVKQRGPYTYRVRFLAKENVTQD
AEDNTVSFLQPNGAIFEPSLSVGTEADNFTVLNLAVAAASHIYQNQFVQMILNSLINKSKSSMFQVRTLRELLWGYRDP
FLSLVPYPVTTTVGLFYPYNNTADGVYKVFNGKDNISKVAIIDTYKGKRNLSYWESHCDMINGTDAASFPPFVEKSQVLQ
FFSSDICRSIYAVFESDVNLKGIPVYRFVLPSKAFASPVENPDNYCFCTEKIISKNCTSYGVLDISKCKEGRPVYISLPHFLYAS
PDVSEPIDGLNPNEEEHRTYLDIEPITGFTLQFAKRLQVNLLVKPSEKIQVLKNLKRNYIVPILWLNETGTIGDEKANMFRS
QVTGKINGGGGSGGGGSEPKSSDKTHTCPPCPAPELLGGPSVFLFPPKPKDTLMISRTPEVTCVVVDVEHEDPEVKFN
WYVDGVEVHNAKTKPREEQYNSTYRVVSVLTVLHQDWLNGKEYKCKVSNKAFPAPIEKTISKAKGQPREPQVYTLPPS
REEMTKNQVSLTCLVKGFYPSDIAVEWESNGQPENNYKTTPPVLDSDGSFFLYSKLTVDKSRWQQGNVFSCSVMHEAL
HNHYTQKSLSLSPGK empty-Fc(216)_IgG1_C220S/S267E/L328F-(G4S)2-huLOX1(137-237) (SEQ ID NO: 91)
EPKSSDKTHTCPPCPAPELLGGPSVFLFPPKPKDTLMISRTPEVTCVVVDVEHEDPEVKFNWYVDGVEVHNAKTKPREE
QYNSTYRVVSVLTVLHQDWLNGKEYKCKVSNKAFPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSVMHEALHNHYTQKSLSLSPGKGGG
GSGGGGSVANCSAPCPQDWIWHGENCYLFSSGSFNWEKSQEKCLSLDAKLLKINSTADLDFIQQAISYSSFPFWMGLS
RRNPSYPWLWEDGSPLMPHLFRVRGAVSQTYPSGTCAYIQRGAVYAENCILAAFSICQKKANLRAQ

Figure 46

E06_H1 VH    (SEQ ID NO: 92)

EVQLVESGGGLVQPGGSLRLSCATSGFTFSDFYMEWVRQAPGKGLEWVGASRNKANDYTTEYSASVKGRFTITRDTSA
STLYLQMNSLKTEDTAVYYCARDYYGSSYWYFDVWGAGTLVTVSS

E06_H2 VH    (SEQ ID NO: 93)

EVQLVESGGGLVQPGGSLRLSCATSGFTFSDFYMEWVRQAPGQRLEWVGASRNKANDYTTEYSASVKGRFTISRDTSK
SSLYLQMNSLRAEDTAVYYCARDYYGSSYWYFDVWGAGTLVTVSS

E06_L1 VL    (SEQ ID NO: 94)

DIVMTQSPLSLPVTPGEPASISCRASESLYSSKHKVHYLAWYQKKPGQSPQLLIYGASNRYIGVPDRFTGSGSGTDFTLKIS
RVEAEDVGVYYCAQFYSYPLTFGAGTKLEIK

E06_L2 VL    (SEQ ID NO: 95)

DIVMTQSPSSLSASVGDRVTITCRASESLYSSKHKVHYLAWYQKKPGKSPKLLIYGASNRYIGVPDRFTGSGSGTDFTLTIS
SLQPEDFATYYCAQFYSYPLTFGAGTKLEIK

FIGURE 47A

| Variant |
|---|
| v90 |
| V266M/S267E |
| V266M |
| V266I |
| V266D |
| S298Q |
| S298E |
| S298D |
| S267G |
| S267E/N325L |
| S267E/L328Y |
| S267E/L328Q |
| S267E/L328I |
| S267E/L328H |
| S267E/L328F |
| S267E/H268E/L328F |
| S267E/H268E |
| S267E/H268D |
| S267E/A327E |
| S267E/A327D |
| S267E |
| S267D/H268E |
| S267D/H268D |
| S267D/A327E |
| S267D/A327D |
| S267D |
| S267A |
| S239Q |
| S239N |
| S239E |
| S239D/S267E/L328F |
| S239D/S267E/H268E |
| S239D/S267E |
| S239D/S267D |
| S239D/H268D |
| S239D |
| P329E |
| P238D/S267E |
| L328F |
| L235Y/S267E/L328F |
| L235Y/S267E/H268E |
| L235Y/S267E |
| L235Y/S267D |
| L235Y/S239D/S267E |
| L235Y/G236D/S267E |
| L235Y |
| L235W |
| L235T/S267E |
| L235S/S267E |
| L235S |
| L235R |
| L235Q |
| L235P |
| L235N |
| L235I |
| L235H |

FIGURE 47B

| |
|---|
| L235F/S267E |
| L235E |
| L235D/S267E/L328F |
| L235D/S267E |
| L235D/S239D |
| L235A |
| L234Y/G237D/P238D/K326A/A330R |
| L234Y |
| L234W |
| L234V |
| L234S |
| L234Q |
| L234P |
| L234N |
| L234K |
| L234I |
| L234G |
| L234F/S267E |
| L234F/G236N |
| L234F/G236D |
| L234F |
| L234E/S267E/L328F |
| L234E/S267E |
| L234E/H268D |
| L234D/S267E |
| IgG1/2ELLGG_S267E/L328F |
| IgG1/2ELLGG |
| IgG1 WT |
| H268Q |
| H268N |
| H268E |
| H268D/A327D |
| H268D |
| G237Y |
| G237V |
| G237S |
| G237Q |
| G237P |
| G237N/S267E |
| G237L |
| G237K |
| G237H |
| G237E |
| G237D/S267E |
| G237A |
| G236Y |
| G236W |
| G236V |
| G236T |
| G236S |
| G236R |
| G236Q |
| G236P |
| G236N/S267E |
| G236M |
| G236L |
| G236K |
| G236I |
| G236H |
| G236F |
| G236E/S267E |

FIGURE 47C

| |
|---|
| G236D/S267E/L328F |
| G236D/S267E/H268E |
| G236D/S267E |
| G236D/S239D/S267E |
| G236D/H268D |
| G236D |
| E233D/L234Y/G237D/P238D/Y296D/K326A/A330R |
| E233D/L234Y/G237D/P238D/P271G/K326D/A330R |
| E233D/L234Y/G237D/P238D/K326A/A330R |
| E233D/G237D/P238D/P271G/A330R |
| D265E |
| A327Q |
| A327N |
| A327G |
| A327D |
| V305A |
| T307A |
| T256A |
| S337A |
| S298L |
| S267A/R255A |
| S267A/H268A |
| S267A/E272A |
| S267A/E258A/D280A/R255A |
| S267A/E258A |
| S267A/D280A |
| S267A |
| R301M |
| R301A |
| R255A |
| P331A |
| N315A |
| N286S |
| N286Q |
| N286D |
| N286A |
| N276A |
| L398A |
| L309A |
| K360A |
| K340M |
| K340A |
| K326D |
| K326A |
| K322R |
| K322Q |
| K322N |
| K322E |
| K322A |
| K320Q |
| K320M |
| K320E |
| K320A |
| K290A |
| H285A |
| H268Y |
| H268S |
| H268N |
| H268A |

FIGURE 47D

| |
|---|
| E430A |
| E283S |
| E283Q |
| E283N |
| E283D |
| E283A |
| E272Q |
| E272A |
| E258A |
| D312A |
| D280S |
| D280N |
| D280A |
| A378Q |
| A339T |
| A330K |
| S267E/L328F |
| S267E |
| S239D |
| P238N |
| P238D/S267E/L328F |
| P238D/S239D |
| P238D/P271G |
| P238D/P271G |
| P238D/L328E |
| P238D/L234Y |
| P238D/L234W |
| P238D/H268D |
| P238D/G237Y |
| P238D/G237W |
| P238D/G237M |
| P238D/G237L |
| P238D/G237F |
| P238D/G237E |
| P238D/G237D/P271G/A330R |
| P238D/G237D/H268D/P271G/A330R |
| P238D/G237D/H268D/P271G |
| P238D/G237D |
| P238D/G237D |
| P238D/G237A |
| P238D/E233D/P271G/A330R |
| P238D/E233D/H268D/P271G/A330R |
| P238D/E233D/G237D/H268D/P271G/A330R |
| P238D/E233D/A330R |
| P238D/E233D |
| P238D/A330R |
| P238D |
| L328F |
| L328E |
| L328E |
| L234Y |
| L234W |
| G237Y |
| G237W |
| G237M |
| G237L |
| G237F |
| G237E |
| G237D |
| G237A |

Figure 48A

Combinations of FcγRIIb Variants

| FcγRIIb Variants | FcRn variants | Scaffold | Fv | Combinations (See Legend D) |
|---|---|---|---|---|
| G236N/S267E | See Legend A | See Legend B | See Legend C | 1), 2), 3), 4), 5),6), 7), 8), 9) and 10) |
| S267E/L328F | See Legend A | See Legend B | See Legend C | 1), 2), 3), 4), 5),6), 7), 8), 9) and 10) |
| S267E | See Legend A | See Legend B | See Legend C | 1), 2), 3), 4), 5),6), 7), 8), 9) and 10) |
| S267D | See Legend A | See Legend B | See Legend C | 1), 2), 3), 4), 5),6), 7), 8), 9) and 10) |
| S239D | See Legend A | See Legend B | See Legend C | 1), 2), 3), 4), 5),6), 7), 8), 9) and 10) |
| A327D | See Legend A | See Legend B | See Legend C | 1), 2), 3), 4), 5),6), 7), 8), 9) and 10) |
| H268D | See Legend A | See Legend B | See Legend C | 1), 2), 3), 4), 5),6), 7), 8), 9) and 10) |
| H268E | See Legend A | See Legend B | See Legend C | 1), 2), 3), 4), 5),6), 7), 8), 9) and 10) |
| L234D/S267E | See Legend A | See Legend B | See Legend C | 1), 2), 3), 4), 5),6), 7), 8), 9) and 10) |
| L234G/S267E | See Legend A | See Legend B | See Legend C | 1), 2), 3), 4), 5),6), 7), 8), 9) and 10) |
| L234E/H268D | See Legend A | See Legend B | See Legend C | 1), 2), 3), 4), 5),6), 7), 8), 9) and 10) |
| L235D/S267E | See Legend A | See Legend B | See Legend C | 1), 2), 3), 4), 5),6), 7), 8), 9) and 10) |
| L235Y/S267E | See Legend A | See Legend B | See Legend C | 1), 2), 3), 4), 5),6), 7), 8), 9) and 10) |
| L235Y/S267E | See Legend A | See Legend B | See Legend C | 1), 2), 3), 4), 5),6), 7), 8), 9) and 10) |
| G236D/S267E | See Legend A | See Legend B | See Legend C | 1), 2), 3), 4), 5),6), 7), 8), 9) and 10) |
| G236D/H268D | See Legend A | See Legend B | See Legend C | 1), 2), 3), 4), 5),6), 7), 8), 9) and 10) |
| S239D/S267D | See Legend A | See Legend B | See Legend C | 1), 2), 3), 4), 5),6), 7), 8), 9) and 10) |
| S239D/S267E | See Legend A | See Legend B | See Legend C | 1), 2), 3), 4), 5),6), 7), 8), 9) and 10) |
| S239D/H268D | See Legend A | See Legend B | See Legend C | 1), 2), 3), 4), 5),6), 7), 8), 9) and 10) |
| V266M/S267E | See Legend A | See Legend B | See Legend C | 1), 2), 3), 4), 5),6), 7), 8), 9) and 10) |
| S267D/H268D | See Legend A | See Legend B | See Legend C | 1), 2), 3), 4), 5),6), 7), 8), 9) and 10) |
| S267D/H268E | See Legend A | See Legend B | See Legend C | 1), 2), 3), 4), 5),6), 7), 8), 9) and 10) |
| S267D/A327D | See Legend A | See Legend B | See Legend C | 1), 2), 3), 4), 5),6), 7), 8), 9) and 10) |
| S267E/H268D | See Legend A | See Legend B | See Legend C | 1), 2), 3), 4), 5),6), 7), 8), 9) and 10) |
| S267E/H268E | See Legend A | See Legend B | See Legend C | 1), 2), 3), 4), 5),6), 7), 8), 9) and 10) |
| S267E/A327D | See Legend A | See Legend B | See Legend C | 1), 2), 3), 4), 5),6), 7), 8), 9) and 10) |
| S267E/L328F | See Legend A | See Legend B | See Legend C | 1), 2), 3), 4), 5),6), 7), 8), 9) and 10) |
| S267E/L328Q | See Legend A | See Legend B | See Legend C | 1), 2), 3), 4), 5),6), 7), 8), 9) and 10) |
| H268D/A327D | See Legend A | See Legend B | See Legend C | 1), 2), 3), 4), 5),6), 7), 8), 9) and 10) |

Figure 48B

| FcγRIIb Variants | FcRn variants | Scaffold | Fv | Combinations (See Legend D) |
|---|---|---|---|---|
| G236D/S267E/L328F | See Legend A | See Legend B | See Legend C | 1), 2), 3), 4), 5), 6), 7), 8), 9) and 10) |
| L235Y/G236D/S267E | See Legend A | See Legend B | See Legend C | 1), 2), 3), 4), 5), 6), 7), 8), 9) and 10) |
| L235Y/S267E/H268E | See Legend A | See Legend B | See Legend C | 1), 2), 3), 4), 5), 6), 7), 8), 9) and 10) |
| L235Y/S267E/L328F | See Legend A | See Legend B | See Legend C | 1), 2), 3), 4), 5), 6), 7), 8), 9) and 10) |
| G236D/S267E/S267E | See Legend A | See Legend B | See Legend C | 1), 2), 3), 4), 5), 6), 7), 8), 9) and 10) |
| G236D/S267E/H268E | See Legend A | See Legend B | See Legend C | 1), 2), 3), 4), 5), 6), 7), 8), 9) and 10) |
| S239D/S267E/H268E | See Legend A | See Legend B | See Legend C | 1), 2), 3), 4), 5), 6), 7), 8), 9) and 10) |
| S239D/S267E/L328F | See Legend A | See Legend B | See Legend C | 1), 2), 3), 4), 5), 6), 7), 8), 9) and 10) |
| S267E/H268E/L328F | See Legend A | See Legend B | See Legend C | 1), 2), 3), 4), 5), 6), 7), 8), 9) and 10) |
| L234E/S267E/L328F | See Legend A | See Legend B | See Legend C | 1), 2), 3), 4), 5), 6), 7), 8), 9) and 10) |
| L235D/S267E/L328F | See Legend A | See Legend B | See Legend C | 1), 2), 3), 4), 5), 6), 7), 8), 9) and 10) |
| L335S/S267E | See Legend A | See Legend B | See Legend C | 1), 2), 3), 4), 5), 6), 7), 8), 9) and 10) |
| G236E/S267E | See Legend A | See Legend B | See Legend C | 1), 2), 3), 4), 5), 6), 7), 8), 9) and 10) |
| G236N/S267E | See Legend A | See Legend B | See Legend C | 1), 2), 3), 4), 5), 6), 7), 8), 9) and 10) |
| S267E/L328H | See Legend A | See Legend B | See Legend C | 1), 2), 3), 4), 5), 6), 7), 8), 9) and 10) |
| S267E/L328I | See Legend A | See Legend B | See Legend C | 1), 2), 3), 4), 5), 6), 7), 8), 9) and 10) |
| S267E/L336Y | See Legend A | See Legend B | See Legend C | 1), 2), 3), 4), 5), 6), 7), 8), 9) and 10) |
| L234F/S267E | See Legend A | See Legend B | See Legend C | 1), 2), 3), 4), 5), 6), 7), 8), 9) and 10) |
| G237N/S267E | See Legend A | See Legend B | See Legend C | 1), 2), 3), 4), 5), 6), 7), 8), 9) and 10) |
| S267E/N325L | See Legend A | See Legend B | See Legend C | 1), 2), 3), 4), 5), 6), 7), 8), 9) and 10) |

RAPID CLEARANCE OF ANTIGEN COMPLEXES USING NOVEL ANTIBODIES

PRIORITY CLAIM

This application claims priority to U.S. Provisional Application Ser. Nos. 61/752,955, filed Jan. 15, 2013; 61/794,164, filed Mar. 15, 2013, 61/794,386, filed Mar. 15, 2013, and 61/833,696, filed Jun. 11, 2013, each of which is expressly incorporated by reference in the entirety.

RELATED APPLICATIONS

U.S. Ser. Nos. 11/124,620, 13/294,103, 12/341,769 and 12/156,183 are all expressly incorporated by reference in their entirety, particularly for the recitation of amino acid positions and substitutions, and all data, figures and legends relating thereto.

TECHNICAL FIELD

The present disclosure relates to methods of using polypeptides with two domains, a first domain that bind a ligand (such as the variable region of an immunoglobulin or a fusion partner) and a second domain, an Fc domain, that binds FcγRIIb, particularly human FcγRIIb, with high affinity. These methods resulting in rapid and accelerated clearance of the polypeptide-ligand complexes, e.g. the antibody-antigen complexes in the case of antibody polypeptides. Such methods are useful for treating a variety of conditions.

BACKGROUND OF THE INVENTION

Antigen recognition by B cells is mediated by the B cell receptor (BCR), a surface-bound immunoglobulin in complex with signaling components CD79a (Igα) and CD79b (10). Crosslinking of BCR upon engagement of antigen results in phosphorylation of immunoreceptor tyrosine-based activation motifs (ITAMs) within CD79a and CD79b, initiating a cascade of intracellular signaling events that recruit downstream molecules to the membrane and stimulate calcium mobilization. This leads to the induction of diverse B cell responses (e.g., cell survival, proliferation, antibody production, antigen presentation, differentiation, etc.) which lead to a humoral immune response (DeFranco, A. L., 1997, Curr. Opin. Immunol. 9, 296-308; Pierce, S. K., 2002, Nat. Rev. Immunol. 2, 96-105; Ravetch, J. V. & Lanier, L. L., 2000, Science 290, 84-89). Other components of the BCR coreceptor complex enhance (e.g., CD19, CD21, and CD81) or suppress (e.g., CD22 and CD72) BCR activation signals (Doody, G. M. et al., 1996, Curr. Opin. Immunol. 8, 378-382; L1, D. H. et al., 2006, J. Immunol. 176, 5321-5328). In this way, the immune system maintains multiple BCR regulatory mechanisms to ensure that B cell responses are tightly controlled.

When antibodies are produced to an antigen, the circulating level of immune complexes (e.g., antigen bound to antibody) increases. These immune complexes downregulate antigen-induced B cell activation. It is believed that these immune complexes downregulate antigen-induced B cell activation by coengaging cognate BCR with the low-affinity inhibitory receptor FcγRIIb, the only IgG receptor on B cells (Heyman, B., 2003, Immunol. Lett. 88, 157-161). It is also believed that this negative feedback of antibody production requires interaction of the antibody Fc domain with FcγRIIb since immune complexes containing F(ab')$_2$ antibody fragments are not inhibitory (Chan, P. L. & Sinclair, N. R., 1973, Immunology 24, 289-301). The intracellular immunoreceptor tyrosine-based inhibitory motif (ITIM) of FcγRIIb is necessary to inhibit BCR-induced intracellular signals (Amigorena, S. et al., 1992, Science 256, 1808-1812; Muta, T., et al., 1994, Nature 368, 70-73). This inhibitory effect occurs through phosphorylation of the FcγRIIb ITIM, which recruits SH2-containing inositol polyphosphate 5-phosphatase (SHIP) to neutralize ITAM-induced intracellular calcium mobilization (Kiener, P. A., et al., 1997, J. Biol. Chem. 272, 3838-3844; Ono, M., et al., 1996, Nature 383, 263-266; Ravetch, J. V. & Lanier, L. L., 2000, Science 290, 84-89). In addition, FcγRIIb-mediated SHIP phosphorylation inhibits the downstream Ras-MAPK proliferation pathway (Tridandapani, S. et al., 1998, Immunol. 35, 1135-1146).

A recently recognized function of FcγRIIb is to serve as a scavenger receptor in the liver, clearing antibody:antigen immune complexes from circulation. FcγRIIb is thus an important component of the classical reticulo-endothelial system. For example, Anderson and colleagues (Ganesan et al., J Immunol 2012) published a study demonstrating that three quarters of mouse FcγRIIb is expressed in the liver, with 90% of it being expressed in Liver Sinusoidal Endothelial Cells (LSEC). Moreover, the authors demonstrated that clearance of radiolabeled small immune complexes (SIC) is significantly impaired in an FcγRIIb knockout strain compared to wild-type mice. This is therefore a natural property of the immune system, which can be accentuated by Fc engineering for enhanced affinity to FcγRIIb.

Of relevance in the present invention are allergic diseases. Allergic diseases and conditions, such as asthma, allergic rhinitis, atopic dermatitis, and food allergy, have become increasingly prevalent over the past few decades and now affect 10-40% of the population in industrialized countries. Allergic diseases profoundly affect the quality of life, and can result in serious complications, including death, as may occur in serious cases of asthma and anaphylaxis. Allergies are prevalent, and are the largest cause of time lost from work and school and their impact on personal lives as well as their direct and indirect costs to the medical systems and economy are enormous. For example, allergic rhinitis (hay fever) affects 22% or more of the population of the USA, whereas allergic asthma is thought to affect at least 20 million residents of the USA. The economic impact of allergic diseases in the United States, including health care costs and lost productivity, has been estimated to amount to $6.4 billion in the early nineties alone.

Most allergic diseases are caused by immunoglobulin E (IgE)-mediated hypersensitivity reactions. IgE is a class of antibody normally present in the serum at minute concentrations. It is produced by IgE-secreting plasma cells that express the antibody on their surface at a certain stage of their maturation. Allergic patients produce elevated levels of IgE with binding specificity for ordinarily innocuous antigens to which they are sensitive. These IgE molecules circulate in the blood and bind to IgE-specific receptors on the surface of basophils in the circulation and mast cells along mucosal linings and underneath the skin. Binding of antigen or allergen to IgE on mast cells, basophils, and other cell types, crosslink the IgE molecules, and aggregate the underlying receptors, thus triggering the cells to release vasoactive and neuronal stimulatory mediators such as histamines, leukotrienes, prostaglandins, brakykinin, and platelet-activating factor. The rapid reaction of the immune system to antigen caused by antibody immune complexes has led to the term immediate or antibody-mediated hypersensitivity reaction, in contrast to delayed or cell-mediated hypersensitivity reactions that are mediated by T cells. IgE-mediated immune reactions are specifically referred to as type I hypersensitivity reactions.

The high affinity receptor for IgE (FcεRI) is a key mediator for immediate allergic manifestations. In addition to mast cells and basophils, the primary mediators of allergic reactions, FcεRI is found on a number of other cell types including eosinophils, platelets and on antigen-presenting cells such as monocytes and dendritic cells. An additional receptor for IgE is FcεRII, also known as CD23 or the low-affinity IgE Fc receptor. FcεRII is expressed broadly on B lymphocytes, macrophages, platelets, and many other cell types such as airway smooth muscle. FcεRII may play a role in the feedback regulation of IgE expression and subsequently FcεRII surface expression.

Since IgE plays a central role in mediating most allergic reactions, devising treatments to control IgE levels in the body and regulating IgE synthesis has been of great interest. Several strategies have been proposed to treat IgE-mediated allergic diseases by downregulating IgE levels. One strategy involves neutralizing the IgE molecules by binding the ε-chain of IgE in or near the Fc-receptor binding site. For example, Omalizumab (Xolair) is a recombinant humanized monoclonal anti-IgE antibody that binds to IgE on the same Fc site as FcεRI. Omalizumab causes a reduction in total serum or circulating IgE in atopic patients, which attenuates the amount of antigen-specific IgE that can bind to and sensitize tissue mast cells and basophils. This, in turn, leads to a decrease in symptoms of allergic diseases. Interestingly, serum IgE levels increase after start of therapy because of omalizumab-IgE complex formation and may remain high up to a year after stopping therapy. Consequently, this issue may lead to false-negatives on diagnostic tests and therefore IgE levels must be routinely checked. Accordingly, there exists a need for improved methods and compositions to reduce IgE-mediated diseases and disease symptoms.

Of additional relevance in the present invention is the fact that antibody/antigen immune complexes are well established mediators of inflammation in various autoimmune diseases. Moreover, circulating immune complexes can be deposited in the kidney, ultimately resulting in nephritis, the leading cause of death in systemic lupus erythematosus (SLE). Finally, nucleic-acid (RNA or DNA) containing immune complexes, observed most notably in SLE, can interact with toll-like receptors (TLRs) on immune cells, inducing the release of inflammatory cytokines such as interferon alpha, contributing to disease pathogenesis. The complement system naturally recognizes these antibody-antigen immune complexes (ICs), resulting in complement-component C3 'tagging' of the immune complexes with a variety of fragments of C3 (including C3b, C3b(i), C3d, and C3g). Under healthy conditions, these tagged immune complexes are cleared through interaction with a variety of complement receptors and FcγRs. C3b-C3b-IgG covalent complexes are immediately formed on interaction of serum C3 with IgG-IC. These C3b-C3b dimers constitute the core for the assembly of C3/C5-convertase on the IC, which are subsequently converted into iC3b-iC3b-IgG by the complement regulators. Further processing of iC3b can occur through interaction with these regulators, to produce C3d and C3g. ICs tagged with various forms of C3 have been detected in a variety of autoimmune disease, and C3d-IC levels in particular have been shown to correlate directly with disease activity level in SLE. See Toong C, Adelstein S, Phan T G (2011) *Int J Nephrol Renovasc Dis "Clearing the complexity: immune complexes and their treatment in lupus nephritis,"* 4:17-28, which is hereby incorporated by reference in its entirety and in particular all figures, legends and disclosure related to models of DNA-anti-DNA immune complex generation and glomerular damage in lupus nephritis and potential therapeutic targets. See also Sekita K, Doi T, Muso E, Yoshida H, Kanatsu K, Hamashima Y (1984) *Clin Exp Immunol "Correlation of C3d fixing circulating immune complexes with disease activity and clinical parameters in patients with systemic lupus erythematosus,"* 55(3): 487-494, which is hereby incorporated by reference in its entirety and in particular all figures, legends and disclosure related to CIC levels and anti-C3d assays from patients with various diseases.

The natural receptor for C3d is the complement receptor 2 (CR2), also known as CD21, expressed on the surface of B cells. CR2 serves as a link to from the innate to the adaptive immune system, and in healthy conditions, the interaction of C3d-tagged immune complexes leads to an amplified B cell/antibody response to the offending antigen. Unfortunately, in autoimmune diseases this amplification can lead to continuation of an auto-antibody response to autoantigen, further exacerbating the disease.

Soluble CRs and CR-Fc fusions have been described for therapeutic purposes. These include CR1, CR2-Fc (U.S. Pat. No. 6,458,360), CR2-fH (CR2-factor H), and others. However, while these approaches generally block interaction of C3-tagged ICs with their associated receptors, they do not necessarily remove the immune complexes from circulation. Most of the complement receptors and regulatory proteins are composed of one or more so-called short complement repeat (SCR) domains, also called complement control protein (CCP) modules or Sushi domains. Typically, only a subset of the domains is involved in direct recognition of the associated complement fragment ligand. For example, it has been demonstrated that only the first two SCRs of CR2 are essential for C3d binding. The SCR domains are stable and well-behaved, making them suitable for use in the development of therapeutic proteins.

Of further relevance to the present invention relates to the mechanisms of hemophilia. One issue with hemophiliacs is the effect that Factor VIII (FVIII (not to be confused with "Fv")) inhibitors play in disease. Currently, these FVIII inhibitors (generally FVIII antibodies, as shown in FIG. 28) are a huge problem for hemophiliacs.

SUMMARY OF THE INVENTION

Accordingly, in one aspect the present invention provides compositions and methods for rapidly lowering the serum concentration of an antigen in a patient comprising administering an antibody comprising a variable region that binds the antigen and a variant Fc domain comprising an amino acid substitution as compared to a parent Fc domain wherein said variant Fc domain binds human FcγRIIb with increased affinity as compared to said parent Fc domain. These antibodies bind to said antigen to form an antibody-antigen complex and said complex is cleared at least two fold faster than the antigen alone.

In a further aspect, the present invention provides compositions and methods for lowering the free antigen in a patient comprising administering an antibody comprising a variable region that binds the antigen and a variant Fc domain comprising an amino acid substitution as compared to a parent Fc domain wherein said variant Fc domain binds FcγRIIb with increased affinity as compared to said parent Fc domain. The administration results in the concentration of said free antigen decreasing at least 50% more rapidly than the decrease in concentration seen with an antibody comprising the parent Fc domain.

In a further aspect, the present invention provides compositions and methods for differentially clearing an antibody-antigen complex in a patient compared to antibody alone, comprising administering an antibody comprising a variable region that binds the antigen and a variant Fc domain comprising an amino acid substitution as compared to a parent Fc domain wherein said variant Fc domain binds FcγRIIb with increased affinity as compared to said parent Fc domain. These antibodies bind to the antigen to form an antibody-antigen complex and the complex is cleared at least two fold faster than the antigen alone.

In one embodiment and in accordance with any of the above, the invention provides methods wherein the variant Fc domain comprises amino acid substitutions selected from the group consisting of those of FIG. 30, FIG. 47, and FIG. 48.

In a further embodiment and in accordance with any of the above, the present invention provides compositions and methods wherein the variant Fc domain further comprises amino acid substitutions selected from the group consisting of 434S, 434A, 428L, 308F, 259I, 428L/434S, 259I/308F, 436I/428L, 436I or V/434S, 436V/428L and 259I/308F/428L.

In a yet further embodiment and in accordance with any of the above, according to any previous claim, the present invention provides compositions and methods wherein the increased affinity seen with the variant Fc domain is at least a 5-fold or a 10-fold increase as compared to the parent Fc domain as measured by a Biacore assay.

In a still further embodiment and in accordance with any of the above, the present invention provides compositions and methods that lower serum concentration of antigen, where the antigen is selected from the group consisting of IgE, oxoLDL, and FVIII inhibitor.

In a still further embodiment and in accordance with any of the above, the present invention provides compositions and methods in which the antibody includes a variable region VH domain that comprises a CDR1 of SEQ ID NO:2, a CDR2 of SEQ ID NO:3 and a CDR3 of SEQ ID NO:4 and a variable region VL domain that comprises a CDR1 of SEQ ID NO:6, a CDR2 of SEQ ID NO:7 and a CDR3 of SEQ ID NO:8.

In a still further embodiment and in accordance with any of the above, the present invention provides compositions and methods in which the antibody includes a variable region VH domain that comprises a CDR1 of SEQ ID NO:18, a CDR2 of SEQ ID NO:19 and a CDR3 of SEQ ID NO:20 and a variable region VL domain that comprises a CDR1 of SEQ ID NO:22, a CDR2 of SEQ ID NO:23 and a CDR3 of SEQ ID NO:24.

In a still further embodiment and in accordance with any of the above, the present invention provides compositions and methods in which the variant Fc domain comprises amino acid substitutions selected from the group consisting of S267E, S267D, L328F, P238D, S267E/L328F, G236N/S267E, G236D/S267E.

In a further aspect, the present invention provides a method of rapidly lowering the serum concentration of an antigen in a patient, where the method includes the step of: administering an Fc fusion protein comprising: (i) a binding moiety that binds the antigen; and (ii) a variant Fc domain comprising an amino acid substitution as compared to a parent Fc domain, wherein the variant Fc domain binds FcγRIIb with increased affinity as compared to the parent Fc domain and the Fc fusion protein binds to the antigen to form a protein-antigen complex that is cleared at least two fold faster than the antigen alone.

In a further aspect, the present invention provides compositions and methods for lowering the free antigen in a patient comprising administering an Fc fusion protein comprising a binding moiety that binds the antigen and a variant Fc domain comprising an amino acid substitution as compared to a parent Fc domain wherein said variant Fc domain binds FcγRIIb with increased affinity as compared to said parent Fc domain. The administration results in the concentration of said free antigen decreasing at least 50% more rapidly than the decrease in concentration seen with an antibody comprising the parent Fc domain.

In a further aspect, the present invention provides compositions and methods for clearing an antibody-antigen complex in a patient compared to antibody alone, by administering an Fc fusion protein comprising: (i) a binding moiety that binds to the antigen; and (ii) a variant Fc domain comprising an amino acid substitution as compared to a parent Fc domain, wherein the variant Fc domain binds FcγRIIb with increased affinity as compared to said parent Fc domain; and wherein the Fc fusion protein binds to said antigen to form a protein-antigen complex and said complex is cleared at least two fold faster than the protein alone.

In a further embodiment in accordance with any of the above, the methods and compositions of the invention include the use of a fusion protein containing a binding moiety that has a sequence selected from FIG. 33A or 33B.

In a further embodiment in accordance with any of the above, the methods and compositions of the invention include the use of an Fc fusion protein that has a first monomer and a second monomer, and the first monomer comprises the sequence shown in FIG. 33C and the second monomer has the sequence shown in FIG. 33D.

In a further embodiment in accordance with any of the above, the methods and compositions of the invention include the use of an Fc fusion protein that has a first monomer and a second monomer, and the first monomer comprises the sequence shown in FIG. 33E and the second monomer has the sequence shown in FIG. 33D.

In a yet further embodiment in accordance with any of the above, the methods and compositions of the invention include the use of an Fc fusion protein that has a first domain comprising a CR2 sequence and a second domain comprising an engineered Fc domain. In still further embodiments, the fusion protein sequence is selected from the sequences depicted in FIG. 40.

In a further aspect, the present invention provides methods and compositions for treating an IgE-mediated disease in a patient by rapidly lowering serum concentration of IgE in said patient by administering an antibody that has (i) a variable region that binds IgE; and (ii) a variant Fc domain comprising an amino acid substitution as compared to a parent Fc domain, where variant Fc domain binds FcγRIIb with increased affinity as compared to the parent Fc domain, and where the antibody binds to the IgE to form an antibody-IgE complex and the complex is cleared at least two fold faster than IgE alone. In certain embodiments, the variant Fc domain comprises amino acid substitutions selected from the group consisting of S267E, S267D, L238F, P238D, S267E/L328F, G236N/S267E, G236D/S267E. In further embodiments, the IgE mediated disease is selected from the group consisting of: asthma, allergic rhinitis, atopic dermatitis, and food allergy.

In a further aspect, the present invention provides methods and compositions for treating an autoimmune disorder in a patient by rapidly lowering serum concentration of C3d in the patient by administering a rapid clearance molecule comprising: (i) a variable region that binds C3d; and (ii) a variant Fc domain comprising an amino acid substitution as compared to a parent Fc domain, where the variant Fc domain binds FcγRIIb with increased affinity as compared to said parent Fc domain, and where the rapid clearance molecule binds to the C3d to form a molecule-C3d complex and the complex is cleared at least two fold faster than C3d alone. In certain embodiments, the variant Fc domain comprises amino acid substitutions selected from the group consisting of S267E, S267D, L238F, P238D, S267E/L328F, G236N/S267E, G236D/S267E. In further embodiments, the autoimmune disorder is selected from the group consisting of: systemic lupus erythematosus and rheumatoid arthritis. In yet further embodiments, the rapid clearance molecule is an antibody or an Fc fusion protein.

In a further aspect, the present invention provides methods and compositions for treating atherosclerosis in a patient by rapidly lowering serum concentration of oxLDL in the patient by administering a rapid clearance molecule that has: (i) a variable region that binds oxLDL; and (ii) a variant Fc domain comprising an amino acid substitution as compared to a parent Fc domain, where the variant Fc domain binds FcγRIIb with increased affinity as compared to the parent Fc domain; and where the rapid clearance molecule binds to the oxLDL to form a molecule-oxLDL complex that is cleared at least two fold faster than oxLDL alone. In certain embodiments, the variant Fc domain comprises amino acid substitutions selected from the group consisting of S267E, S267D, L238F, P238D, S267E/L328F, G236N/S267E, G236D/S267E. In yet further embodiments, the rapid clearance molecule is an antibody or an Fc fusion protein.

In a further aspect, the present invention provides methods and compositions for treating hemophilia in a patient by rapidly lowering serum concentration of FVIII inhibitor in said patient by administering a rapid clearance molecule comprising (i) a variable region that binds said FVIII inhibitor; and (ii) a variant Fc domain comprising an amino acid substitution as compared to a parent Fc domain, wherein the variant Fc domain binds FcγRIIb with increased affinity as compared to the parent Fc domain and wherein the rapid clearance molecule binds to the FVIII inhibitor to form a molecule-inhibitor complex and the complex is cleared at least two fold faster than FVIII inhibitor alone. In certain embodiments, the variant Fc domain comprises amino acid substitutions selected from the group consisting of S267E, S267D, L238F, P238D, S267E/L328F, G236N/S267E, G236D/S267E. In yet further embodiments, the rapid clearance molecule is an antibody or an Fc fusion protein.

BRIEF DESCRIPTION OF THE DRAWINGS

FIGS. 1A and B. FIG. 1A Illustrates the novel mechanistic approach for inhibiting IgE+ FcγRIIb+ B cells. Under appropriate stimuli, naive B cells can differentiate into IgE+ B cells. Engagement of antigen with the IgE B cell receptor activates these cells, which can then differentiate into plasma cells that release circulating IgE. Binding of circulating IgE binds to FcεR's, for example on mast cells, basophils, and eosinophils, activates these cells. Release of histamine, prostaglandins, and other chemical mediators ultimately results in the clinical symptoms of allergy and asthma. Omalizumab, having a native IgG1 Fc region, is capable of blocking binding of IgE to FcεR. Anti-IgE antibodies with high affinity for FcγRIIb, referred to as Anti-IgE-IIbE in the figure, are capable of not only blocking binding of IgE to FcεR, but also of inhibiting activation of IgE+ B cells by mIgE FcγRIIb coengagement.

FIG. 4. Affinities of Fc variant antibodies for human FcγRs as determined by Biacore surface plasmon resonance. The table provides equilibrium $K_D$'s for binding of variant and WT IgG1 antibodies to human FcγRI, H131 FcγRIIa FcγRIIb, and V158 FcγRIIIa, and the fold binding for each relative to native (WT) IgG1. n.d.=not detectable.

FIGS. 5A-C. Amino acid sequences of the heavy (VH) and light (VL) chain variable regions and CDRs of anti-IgE antibodies. CDR boundaries were defined as described previously based on a structural alignment of antibody variable regions (Lazar et al., 2007, Mol Immunol 44:1986-1998).

FIG. 6. Amino acid sequences of the heavy and light chain WT and variant constant regions.

FIG. 7. Amino acid sequences of anti-IgE full length antibodies that may be used to target IgE+ B cells.

FIG. 14. Inhibition of class-switched IgE+ B cells with variant anti-IgE antibodies enhanced for FcγRIIb affinity. The plot shows the concentration of IgE released from PBMCs after 14 days incubation with IL-4, anti-CD40 (α-CD40) agonist antibody, and varying concentrations of the antibodies shown. Data were normalized to the lowest concentration of antibody.

FIG. 15. Inhibition of class-switched IgE+ B cells with variant anti-IgE antibodies enhanced for FcγRIIb affinity. The plot shows the concentration of IgE released from PBMCs after 14 days incubation with IL-4, anti-CD40 (α-CD40) agonist antibody, anti-CD79b BCR cross-linking antibody, and varying concentrations of the antibodies shown. Data were normalized to the lowest concentration of antibody.

FIG. 30A-B. List of suitable Fc domain FcγRIIb amino acid substitutions for increased FcγRIIb binding.

FIG. 33A-E. Sequences of Factor VIII inhibitor constructs.

FIG. 36A-D. Affinities of Fc variant antibodies for human FcγRs as determined by Biacore surface plasmon resonance. FIG. 36A is a table listing the dissociation constant (Kd) for binding anti-CD19 variant antibodies to human FcγRI, FcγRIIa (131R), FcγRIIa (131H), FcγRIIb, FcγRIIIa (158V), and FcγRIIIa (158F). FIG. 36B is a continuation of the list in FIG. 36A. FIG. 36C is a continuation of the list in FIG. 36A and FIG. 36B. FIG. 36D is a continuation of the list in FIG. 36A, FIG. 36B, and FIG. 36C. Multiple observations have been averaged. n.d.=no detectable binding.

FIG. 37A-D. Fold affinities of Fc variant antibodies for human FcγRs as determined by Biacore surface plasmon resonance. FIG. 37A is a table listing the fold improvement or reduction in affinity relative to WT IgG1 for binding of anti-CD19 variant antibodies to human FcγRI, FcγRIIa (131R), FcγRIIa (131H), FcγRIIb, FcγRIIIa (158V), and FcγRIIa (158F). FIG. 37B is a continuation of the list in FIG. 37A. FIG. 37C is a continuation of the list in FIG. 37A and FIG. 37B. FIG. 37D is a continuation of the list in FIG. 37A, FIG. 37B, and FIG. 37C. Fold=KD(Native IgG1)/KD(variant). n.d.=no detectable binding.

FIGS. 39A-C. Binding data of CR2-Fc constructs.

FIGS. 40A-F. Sequences for the CR embodiments of the invention.

FIG. 42. Amino acid sequences for oxLDL-binding proteins.

FIG. 43A-B. Amino acid sequences for Fc-containing oxLDL-binding proteins.

FIG. 45. Amino acid sequences for Fc-containing oxLDL-binding proteins with enhanced FcγRIIb affinity.

FIG. 46. Amino acid sequences for humanized variable regions derived from the EO6 parental antibody.

FIG. 47A-D. List of a variety of suitable Fc domain FcγRIIb amino acid substitutions for increased FcγRIIb binding.

FIG. 48A-B. Matrix of possible combinations of FcγRIIb variants, FcRn variants, Scaffolds, Fvs and combinations, with each variant being independently and optionally combined from the appropriate source Legend: Legend A are suitable FcRn variants: 434A, 434S, 428L, 308F, 259I, 428L/434S, 259I/308F, 436I/428L, 436I or V/434S, 436V/428L, 252Y, 252Y/254T/256E, 259I/308F/428L. Legend B are suitable scaffolds and include IgG1, IgG2, IgG3, IgG4, and IgG1/2. Sequences for such scaffolds can be found for example in US Patent Publication No. 2012/0128663, published on May 24, 2012, which is hereby incorporated by reference in its entirety for all purposes and in particular for all teachings, figures and legends related to scaffolds and their sequences. Legend C are suitable exemplary target antigens: IgE, IL-4, IL-6, IL-13, TNFα, MCP-1, RANTES, TARC, MDC, VEGF, HGF, and NGF, immune complexes, FVIII inhibitors, LDL, oxidized LDL (OxLDL), Lp(a), SOST, and DKK1. Legend D reflects the following possible combinations, again, with each variant being independently and optionally combined from the appropriate source Legend: 1) FcγRIIb variants plus FcRn variants; 2) FcγRIIb variants plus FcRn variants plus Scaffold; 3) FcγRIIb variants plus FcRn variants plus Scaffold plus Fv; 4) FcγRIIb variants plus Scaffold 5) FcγRIIb variants plus Fv; 6) FcRn variants plus Scaffold; 7) FcRn variants plus Fv; 8) Scaffold plus Fv; 9) FcγRIIb variants plus Scaffold plus Fv; and 10) FcγRIIb variants plus FcRn variants plus Fv.

DETAILED DESCRIPTION OF EXEMPLARY EMBODIMENTS

Overview of Invention

The in vivo pharmacokinetic properties of therapeutic antibodies can be altered through modification of their Fc domain. Such modifications may include amino acid substitutions, deletions, or additions as well as other modifications such as chemical modifications. In the present invention, modifications that increase affinity of molecules such as antibodies for the inhibitory Fc receptor FcγRIIb (CD32b) are utilized to facilitate rapid in vivo clearance of complexes comprising the antigen and the molecule of the invention. Incorporation of the IIb-enhancing affinity modifications (also referred to herein as "FcγRIIb variants" or "FcγRIIb variations" or grammatical equivalents thereof) into various antibodies leads to a novel phenomenon whereby the antibody-target complex is cleared extremely rapidly while the antibody alone retains a reasonably long half-life. Although much of the discussion herein is directed to antibodies for the sake of clarity, it will be appreciated that discussion of the FcγRIIb variants described herein are applicable to any of the rapid clearance molecules described herein, including polypeptides, antibodies, and Fc fusion proteins.

The present invention provides methods of rapidly lowering the serum concentration of an antigen in a subject by administering an antibody that has both a variable region that binds the antigen and a variant Fc domain that binds the FcγRIIb receptor with increased affinity as compared to an un-modified Fc domain. Without being bound by theory, it appears that an antibody of the invention binds to the antigen to form an antibody-antigen complex that is cleared more rapidly than the unbound antigen. Thus, the free antigen concentration in the patient, e.g. the serum concentration of free antigen in the patient, is rapidly decreased. In other words, the antigen-antibody complex is differentially cleared (e.g. clearance of complex/clearance of antigen ratio is greater than 1). In some cases, the methods and compositions of the present invention clear an antibody-antigen complex at least 2, 5, 10, 15, 20, 30, 40, 50, 60, 70, 80, 90, 100, 150, 200, 250, 300-fold faster than clearance of the antigen alone. In certain cases the methods and compositions of the present invention clear an antibody-antigen complex 5-500, 50-450, 100-400, 200-350, 100-200-fold faster than clearance of the antigen alone. In other cases, clearance rates of 25× faster than antigen alone, 50×, 75× and 100× or more are provided by methods and compositions of the present invention. In some cases, the methods and compositions of the present invention decrease the clearance rate of an antibody-antigen complex by at least 30%, 40%, 50%, 60%, 70%, 80% 90%, 95%, or 99% as compared to the clearance rate of the antigen alone. In some cases, the methods and compositions of the present invention decrease the clearance rate of an antibody-antigen complex by at least 30%, 40%, 50%, 60%, 70%, 80% 90%, 95%, or 99% as compared to the clearance rate mediated by an antibody comprising a parent (un-modified) Fc domain.

Thus, compositions of the present invention include such "rapid clearance" molecules (also referred to as "scrubbers") of the present invention that lead to clearance of the antibody-antigen complex more rapidly than the unbound antigen or antibody alone. Such rapid clearance compositions are generally polypeptides that comprise two domains: an antigen or ligand binding portion and an Fc domain that exhibits increased FcγRIIb binding as compared to a non-engineered Fc region. In some embodiments, as is further described herein, the rapid clearance molecules are antibodies, comprising a standard antigen binding Fv region, and a variant FcγRIIb binding region, e.g. an engineered Fc region. In alternative embodiments, the rapid clearance molecule is an Fc fusion protein, with a binding ligand or receptor as one domain (e.g. a CR domain) and an Fc region with increased FcγRIIb binding. In addition to the faster clearance rates described above as compared to clearance of antigen alone, rapid clearance molecules of the invention further clear the antigen-containing complex more rapidly than IgG antibodies with the same selectivity would mediate.

Application of different FcγRIIb-enhancing Fc amino acid substitutions with varying affinities to the FcγRIIb receptor (e.g. S267E, S267D, L328F, P238D, S267E/L328F, G236N/S267E, and G236D/S267E, as further described herein) can allow some "tuning" of how fast the complex antigen is cleared while maintaining significant half life of the rapid clearance composition of the invention (including antibodies). That is, different amino acid substitutions that alter FcγRIIb binding affinity may lead to different balances between the complex clearance rate and the antibody clearance rate, allowing for tailoring toward optimal therapeutic profile and dosing. This tuning may be accomplished by using amino acid substitutions in the Fc domain that increase binding to FcγRIIb as compared to the parent Fc domain. This increase in binding may be tuned by using Fc variants with 1-100, 5-90, 10-80, 15-70, 20-60, 30-50, 10-20 fold greater affinity as compared to the parent Fc domain. This increase in binding may also be tuned by using Fc variants with 50-200, 60-190, 70-180, 80-170, 90-160, 100-150, 110-140, 120-130, 50-100 greater affinity as compared to the parent Fc domain. In some cases, affinity is measured by Biacore as described in Example 2.

Figure 1B:
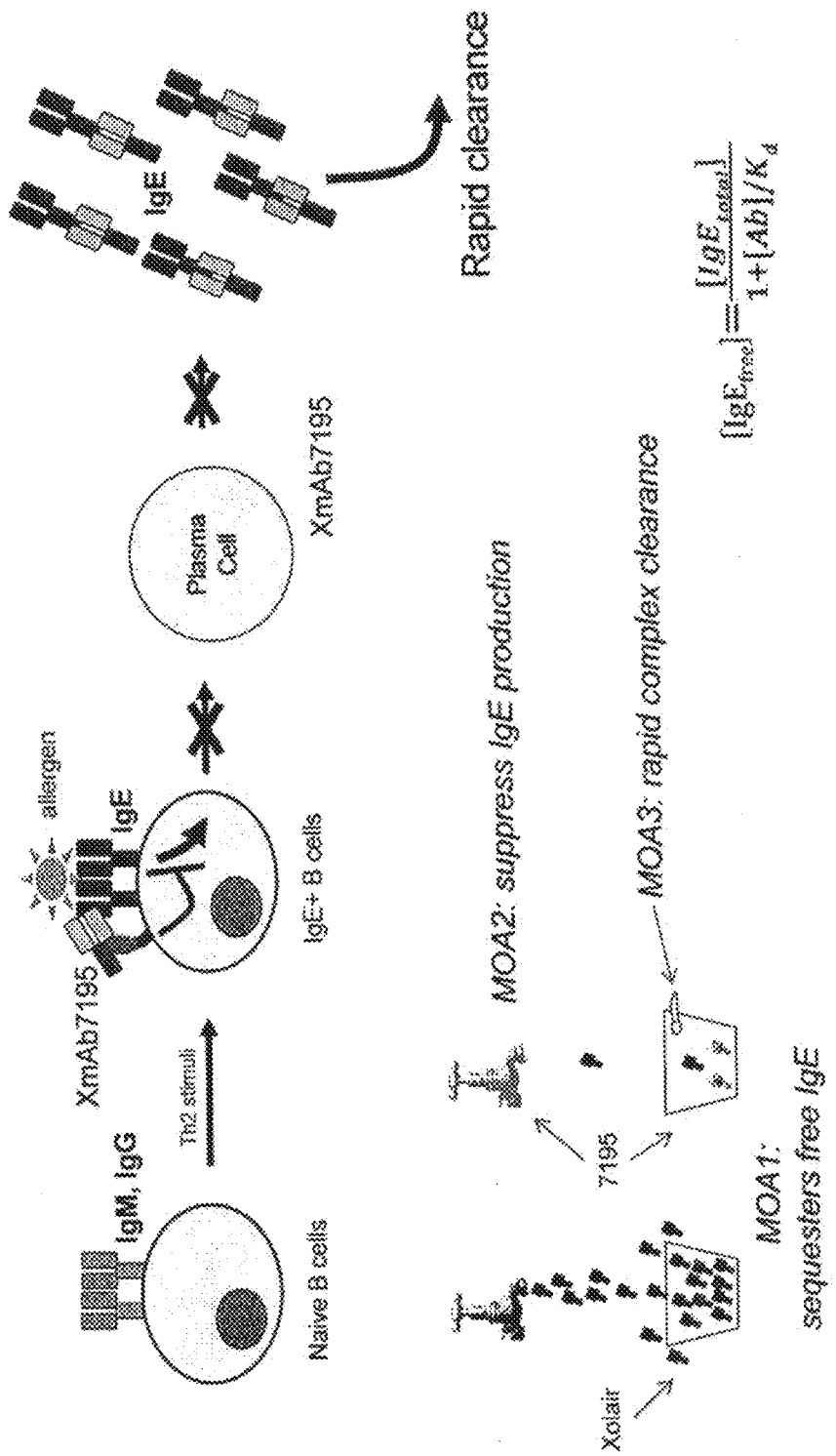
FIG. 1B shows the rapid clearance mechanism, outlining the possible mechanisms of action (MOA): the first is to sequester the free antigen (in the figure this is IgE), secondly the production of the antigen is suppressed, in the case of IgE, and finally the complex of the antigen-antibody is cleared rapidly.

In certain cases, molecules of the invention incorporate FcγRIIb receptor variants that can range from very tight differential binding to FcγRIIb to variants that display increased (as compared to wild type Fc domains) binding affinity but at a lower level. For example, very tight (or heavy) binding to FcγRIIb receptor may include FcγRIIb variants that show at least 50, 75, 100, 125, 150, 175, 200, 225, 250-fold greater affinity to FcγRIIb receptor as compared to the parent Fc domain. In contrast, a lower level (or light, also referred to herein as "lite") increase in binding may include FcγRIIb variants that show no more than 50, 40, 30, 20, 10, 5-fold greater affinity to FcγRIIb receptor as compared to the parent Fc domain.

The effects of molecules of the invention may be further tuned by combining amino acid substitutions that alter FcγRIIb binding affinity with amino acid substitutions that affect binding to FcRn. Proteins with amino acid substitutions that affect binding to FcRn (also referred to herein as "FcRn variants") may in certain situations also increase serum half-life in vivo as compared to the parent protein. As will be appreciated, any combination of Fc and FcRn variants may be used to tune clearance of the antigen-antibody complex. Suitable FcRn variants that may be combined with any of the Fc variants described herein include without limitation 434A, 434S, 428L, 308F, 259I, 428L/434S, 259I/308F, 436I/428L, 436I/434S, 436V/434S, 436V/428L, 252Y, 252Y/254T/256E, and 259I/308F/428L.

Without being bound by theory, it appears that the accelerated clearance of antibodies containing amino acid substitutions that confer high affinity (as compared to the parent Fc domain) to the inhibitory receptor FcγRIIb is likely mediated by interaction with FcγRIIb-expressing cells, possibly liver sinusoidal endothelial cells. In addition, it appears that the accelerated clearance is due to the clearance of the antigen-antibody complex via interactions with the FcγRIIb receptor.

In addition, unexpectedly, administration of antibodies including the FcγRIIb binding affinity variants described herein leads to near instantaneous drops in total antigen levels, whereas administration of other antibodies to the antigen that lack modifications that lead to increased FcγRIIb binding affinity often lead to increases in total antigen levels. Furthermore, the greater reduction in total antigen levels seen with antibodies with increased FcγRIIb binding affinity leads to superior reduction of free antigen relative to levels seen with antibodies that lack the FcγRIIb variants.

In addition, in some cases, compositions and methods of the invention provide sufficient increased affinity to the FcγRIIb receptor to allow for rapid clearance of the antibody-antigen complex while allowing appropriate serum half lives of the unbound antibodies.

The invention is exemplified in the case of XmAb7195. XmAb7195 is an anti-IgE antibody that sequesters IgE and prevents its interaction with FceR1 on mast cells and basophils. The variable region is similar to the variable region of omalizumab (Xolair, an anti-IgE antibody). The XmAb7195 Fc domain was engineered with the S267E/L328F substitutions (Kabat numbering) to confer high affinity to human FcγRIIb. A single 5 mg/kg dose of XmAb7195 was administered via intravenous injection to chimpanzees (n=3) and its effects on free and total IgE were compared to that of omalizumab (anti-IgE with native IgG1 Fc domain). As shown in FIG. 22, the XmAb7195 antibody had a relatively short half-life of approximately 2 days, and the omalizumab exhibited a longer half-life of approximately 11 days.

Unexpectedly, the XmAb7195 antibody also led to a near-instantaneous drop of total IgE levels, whereas the omalizumab treatment led to an increase in total IgE (as observed in humans treated with omalizumab). The XmAb7195-IgE complexes exhibited greatly accelerated clearance presumably via their interaction with FcRIIb. Furthermore, the greater reduction of total IgE using XmAb7195 led to superior reductions of free IgE relative to omalizumab-treated animals. PK/PD simulations suggest that the half-life of the XmAb7195/IgE complexes are on the order of 1 hour—versus an 8 day half-life reported for omalizumab/IgE complexes. Furthermore, the present invention also suggests that rapid recovery of the antigen can occur after cessation of antibody administration.

This surprising and unexpected result, e.g. that adding FcγRIIb variants to existing antibodies can rapidly clear antigen in patients leads to a number of useful applications. Any therapeutic target antigen system in which rapid clearance of the antigen is desired can be subjected to the present invention. For example, disease systems in which the antigen load is high find particular use in the present invention. Similarly, disease systems where rapid recovery of the antigen is desired after antibody administration can be treated with the antibodies of the invention. For example, during the use of TNF antibody inhibitors, patients frequently get infections. Withdrawing the antibody treatment will allow rapid recovery of the TNF to fight the infection. Similarly, these antibodies can be used to treat pathogen infection when rapid pathogen clearance is desired (for example, when a patient scheduled for surgery gets an infection, the present invention can be used to clear the infection rapidly, the therapeutic antibody rapidly clears as well and surgery can progress). In addition, these antibodies may be particularly useful in situations where existing antibodies do not neutralize the antigen, or where pathogens evolve to evade neutralization.

Figure 28:
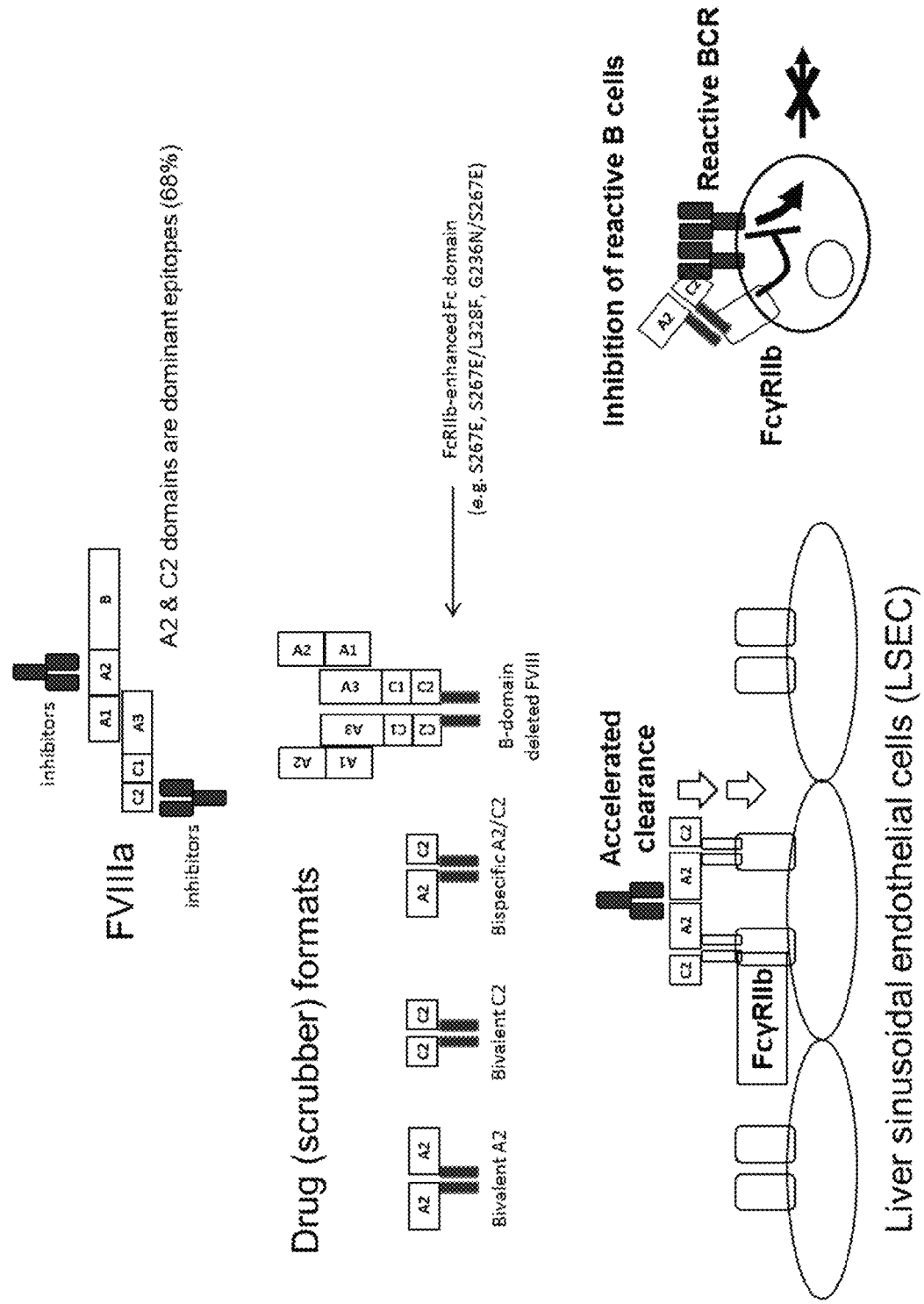
FIG. 28. A Factor VIII fusion embodiment to "scrub" FVIII inhibitor antibodies prior to FVIIIa replacement dosing.
Figure 29:
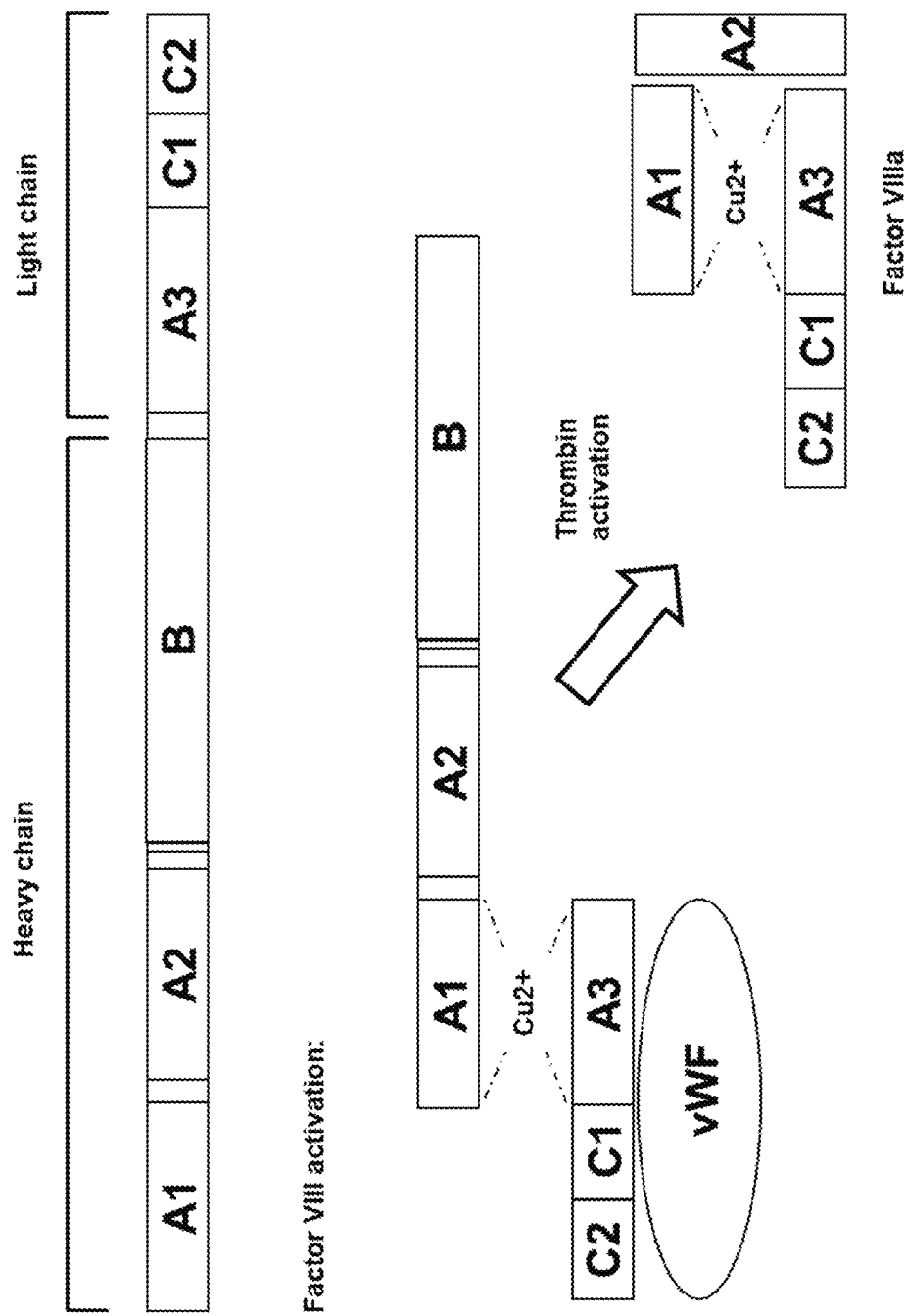
FIG. 29. An illustration of primary structure and domain organization of FVIII.
Figure 31:
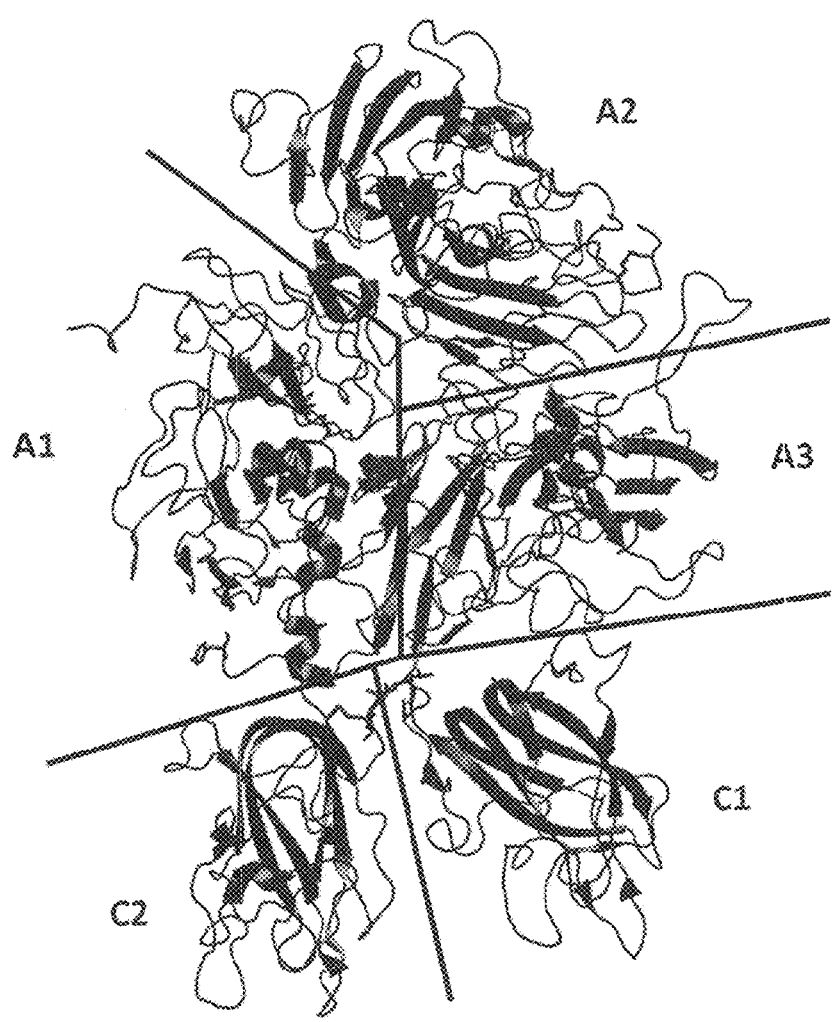
FIG. 31. The structure of B-domain deleted human Factor VIII. Domains A1, A2, A3, C1, and C2 are indicated.
Figure 32:
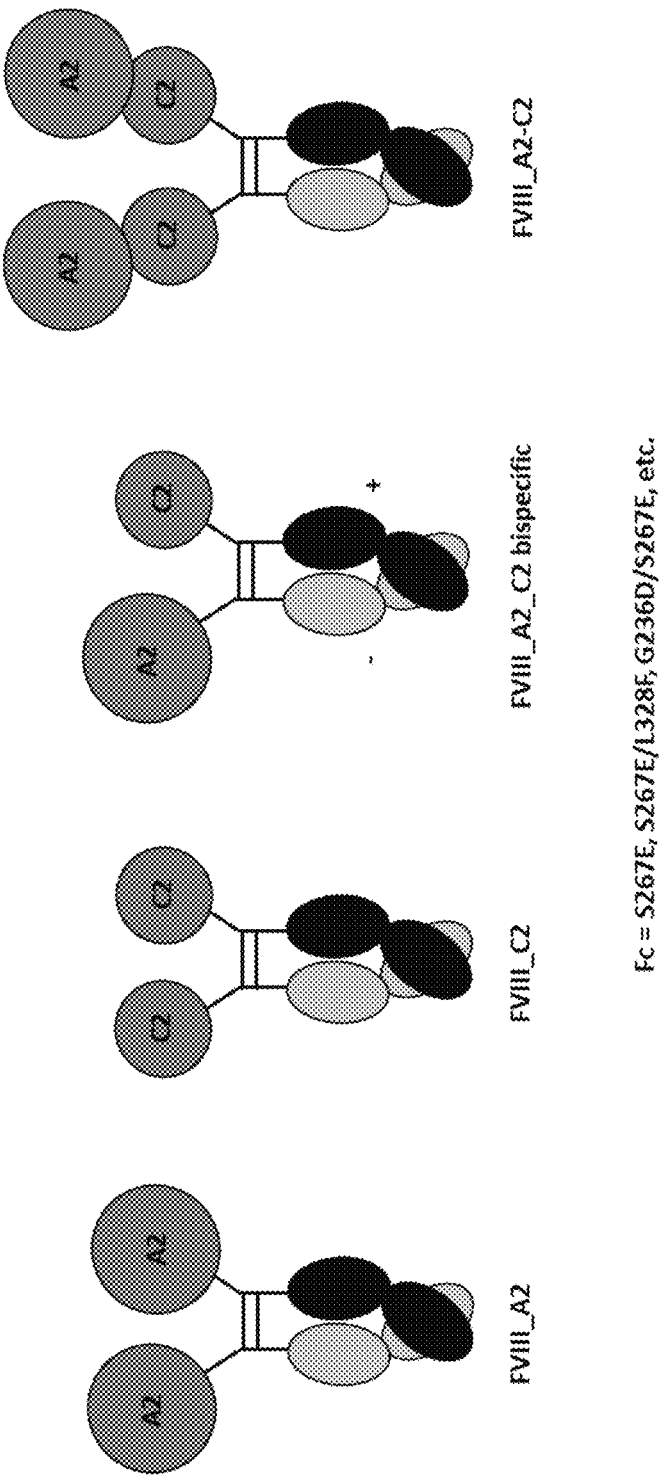
FIG. 32. Diagram showing Factor VIII inhibitor scrubber constructs consisting of FVIII domains A2 and C2 fused to a rapid clearance IIb Fc.
Figure 34:
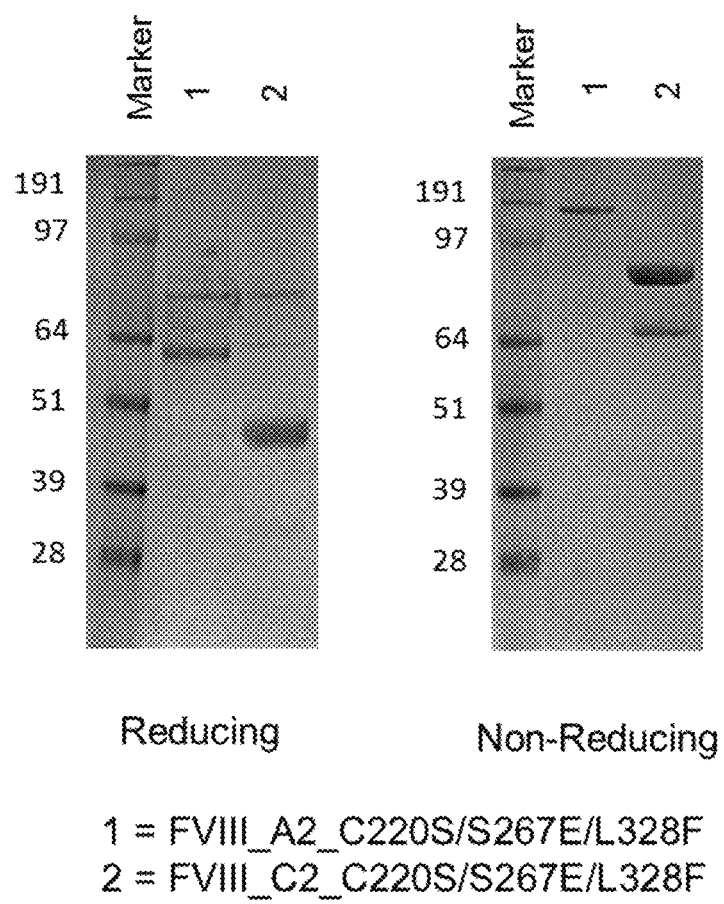
FIG. 34. Reducing and non-reducing SDS-PAGE of Factor VIII inhibitor scrubber constructs FVIII_A2_C220S/S267E/L328F and FVIII_C2_C220S/S267E/L328F.
Figure 35:
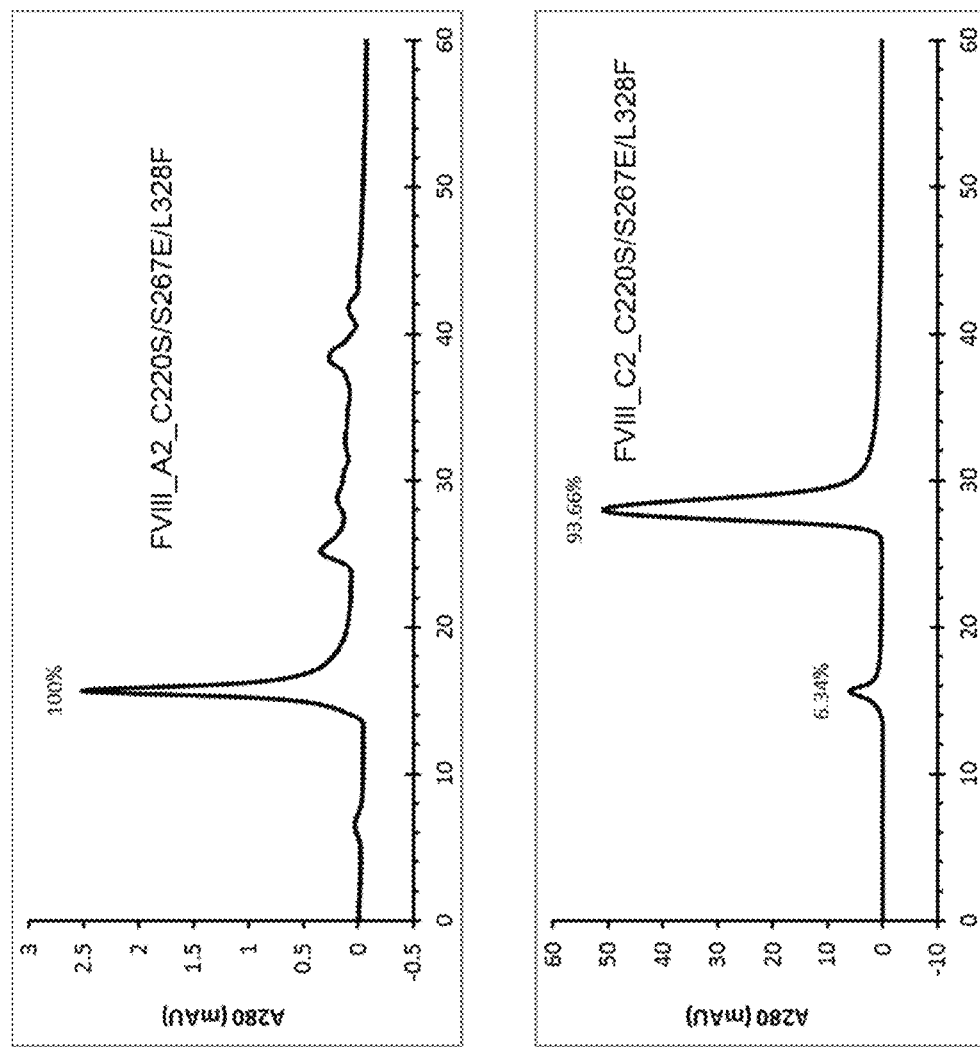
FIG. 35. Size-exclusion chromatography of Factor VIII inhibitor scrubber constructs FVIII_A2_C220S/S267E/L328F and FVIII_C2_C220S/S267E/L328F.
Figure 38:
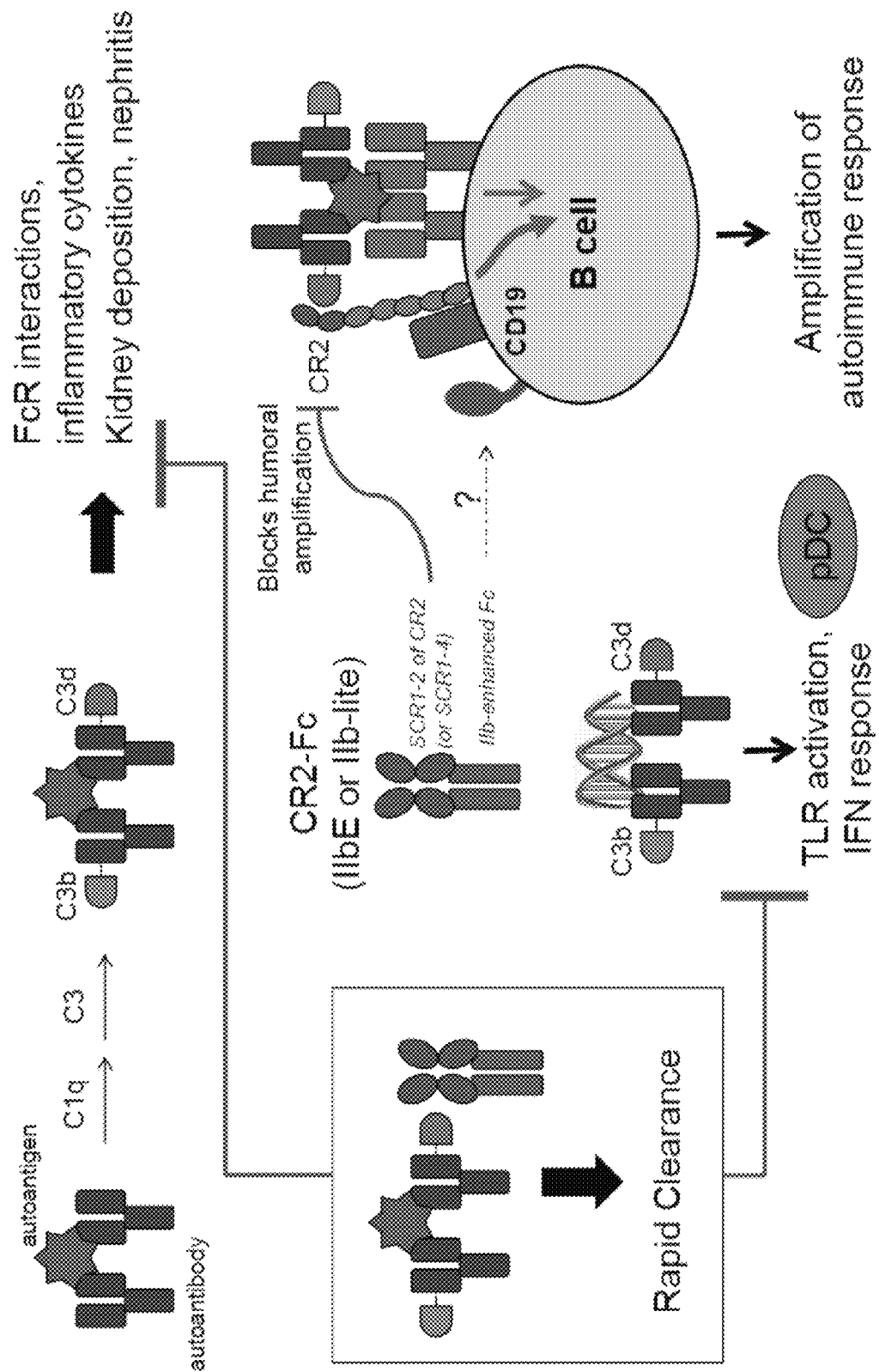
FIG. 38. General overview of the CR2-IIbE embodiment, the "immune complex scrubber" embodiment. As shown, the "rapid clearance" mechanism, utilizing a CR2-Fc fusion, wherein the Fc component of the fusion protein has increased FcγRIIb binding as compared to a wild-type Fc domain (particularly an Fc region from a human IgG1, IgG2, IgG3 or IgG4) and the CR component is as described herein.

In addition, the invention finds use in the treatment of hemophiliacs. One issue with hemophiliacs is the effect that Factor VIII (FVIII (not to be confused with "Fv")) inhibitors play in disease. Currently, these FVIII inhibitors (generally FVIII antibodies, as shown in FIG. 28) are a huge problem for hemophiliacs. The present invention works as generally outlined in FIGS. 28 and 29. Fc fusion proteins, comprising an Fc domain with FcγRIIb amino acid variants, fused to FVIIIa components as outlined herein, will sequester the inhibitor antibodies, rapidly clear the inhibitor antibodies, and will inhibit FVII-reactive B cells (to prohibit the further production of the inhibitors).

The rapid clearance mechanisms of the present invention are also used to remove oxidized low-density lipoprotein (oxidized LDL or oxLDL) from the blood. OxLDL is a key facilitator of atherosclerosis via macrophage uptake and foam cell formation (see FIG. 42). In this embodiment, increased affinity for the inhibitory Fc receptor FcγRIIb (CD32b) is utilized to facilitate rapid in vivo clearance of oxLDL via their interaction with Fc-containing oxLDL-binding proteins. Incorporation of the IIb-enhancing affinity substitutions into various Fc-containing oxLDL-binding proteins leads to a novel phenomenon whereby the complex is cleared extremely rapidly. Application of different IIb-enhancing substitutions (including without limitation S267E, S267D, L328F, P238D, S267E/L328F, G236N/S267E, and G236D/S267E, which are useful for all the rapid clearance molecules herein) may lead to different balances between the complex clearance rate and the Fc-containing oxLDL-binding protein clearance rate, allowing for tailoring toward optimal therapeutic profile and dosing.

In addition, the invention finds use in a variety of diseases or situations where plasmapheresis is typically applied to clear the body of pathogens, autoantibodies, or other pathogenic factors. Such diseases include, but are not limited to, the following: Guillain-Barré syndrome; Chronic inflammatory demyelinating polyneuropathy; Goodpasture's syndrome; Hyperviscosity syndromes: Cryoglobulinemia; Paraproteinemia; Waldenström macroglobulinemia; Myasthenia gravis; Thrombotic thrombocytopenic purpura (TTP)/hemolytic uremic syndrome; Wegener's granulomatosis; Lambert-Eaton Syndrome; Antiphospholipid Antibody Syndrome (APS or APLS); Microscopic polyangiitis; Recurrent focal and segmental glomerulosclerosis in the transplanted kidney; HELLP syndrome; PANDAS syndrome; Refsum disease; Behcet syndrome; HIV-related neuropathy; Graves' disease in infants and neonates; Pemphigus vulgaris; Multiple sclerosis; Rhabdomyolysis; Toxic Epidermal Necrolysis (TEN). That is, by using FcγRIIb antibodies with variable regions specific to these antigens, clearance of the antigens in a rapid manner can occur.

DEFINITIONS

Described herein are several definitions. Such definitions are meant to encompass grammatical equivalents.

By "ablation" herein is meant a decrease or removal of activity. Thus for example, "ablating FcγR binding" means the Fc region amino acid variant has less than 50% starting binding as compared to an Fc region not containing the specific variant, with less than 70-80-90-95-98% loss of activity being preferred, and in general, with the activity being below the level of detectable binding in a Biacore assay. Of particular use in the ablation of FcγR binding is the double variant 236R/328R, and 236R and 328R separately as well.

Figure 41:
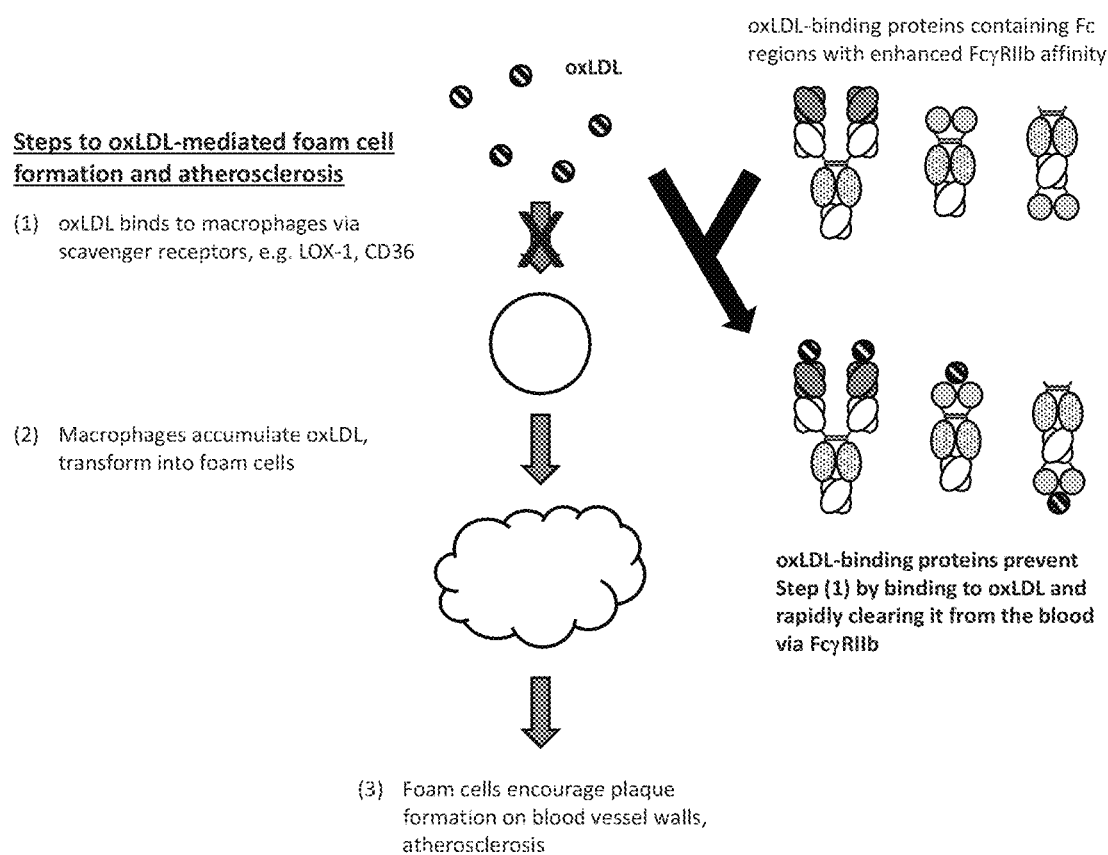
FIG. 41. Schematic describing the generation of atherosclerosis via macrophage uptake of oxLDL and its prevention by Fc-containing oxLDL-binding proteins with enhanced FcγRIIb affinity.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell. The role of high affinity binding to FcγRIIIa to ADCC activity is well established. In some cases, as described herein, amino acid substitutions in the Fc domain can be used to increase or decrease binding to one or more of the FcγR receptors, as is generally outlined in US Publication 2006/0024298, hereby incorporated by reference in its entirety and in particular for the amino acid substitutions disclosed therein, FIG. 41 as well as the other figures and their accompanying legends in particular. In addition, for some embodiments outlined herein, it may be desirable to ablate binding to one or more of the FcγR receptors. For example, the L328F variant ablates FcγRIIIa binding, such that ADCC mechanisms are not triggered. In addition, significant ablatement of FcγR binding to all receptors can be accomplished using 236R/328R variants.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "amino acid modification" herein is meant an amino acid substitution, insertion, and/or deletion in a polypeptide sequence. By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution E272Y refers to a variant polypeptide, in this case an Fc variant, in which the glutamic acid at position 272 is replaced with tyrosine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the recombinant creation of a new gene encoding the same protein, if the protein has the same amino acid at the particular position that it started with, it is not an amino acid substitution. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

By "antibody" herein is meant a protein consisting of one or more polypeptides substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (υ), delta (δ), gamma (γ), sigma (σ), and alpha (α) which encode the IgM, IgD, IgG (IgG1, IgG2, IgG3, and IgG4), IgE, and IgA (IgA1 and IgA2) isotypes respectively. Antibody herein is meant to include full length antibodies and antibody fragments, and may refer to a natural antibody from any organism, an engineered antibody, or an antibody generated recombinantly for experimental, therapeutic, or other purposes.

By "amino acid" and "amino acid identity" as used herein is meant one of the 20 naturally occurring amino acids or any non-natural analogues that may be present at a specific, defined position.

By "CD32b+ cell" or "FcγRIIb+ cell" as used herein is meant any cell or cell type that expresses CD32b (FcγRIIb). CD32b+ cells include but are not limited to B cells, plasma cells, dendritic cells, macrophages, neutrophils, mast cells, basophils, or eosinophils.

By "IgE+ cell" as used herein is meant any cell or cell type that expresses IgE. In preferred embodiments of the invention, IgE+ cells express membrane-anchored IgE (m IgE). IgE+ cells include but are not limited to B cells and plasma cells.

By "CDC" or "complement dependent cytotoxicity" as used herein is meant the reaction wherein one or more complement protein components recognize bound antibody on a target cell and subsequently cause lysis of the target cell.

By "molecule" or grammatical equivalents is meant a bifunctional molecule capable of binding both antigen and FcγRIIb wherein the Kd for binding of the molecule to FcγRIIb is less than about 100 nM on a cell surface resulting in simultaneous binding of both the antigen to which the antibody is directed and FcγRIIb.

By "constant region" of an antibody as defined herein is meant the region of the antibody that is encoded by one of the light or heavy chain immunoglobulin constant region genes. By "constant light chain" or "light chain constant region" as used herein is meant the region of an antibody encoded by the kappa (Cκ) or lambda (Cλ) light chains. The constant light chain typically comprises a single domain, and as defined herein refers to positions 108-214 of Cκ or Cλ, wherein numbering is according to the EU index. By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. For full length IgG antibodies, the constant heavy chain, as defined herein, refers to the N-terminus of the CH1 domain to the C-terminus of the CH3 domain, thus comprising positions 118-447, wherein numbering is according to the EU index.

By "effector function" as used herein is meant a biochemical event that results from the interaction of an antibody Fc region with an Fc receptor or ligand. Effector functions include FcγR-mediated effector functions such as ADCC and ADCP, and complement-mediated effector functions such as CDC.

By "effector cell" as used herein is meant a cell of the immune system that expresses one or more Fc and/or complement receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and γδ T cells, and may be from any organism including but not limited to humans, mice, rats, rabbits, and monkeys.

By "Fab" or "Fab region" as used herein is meant the polypeptides that comprise the VH, CH1, VH, and CL immunoglobulin domains. Fab may refer to this region in isolation, or this region in the context of a full length antibody or antibody fragment.

By "Fc" or "Fc region", as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, as described below.

By "Fc polypeptide" as used herein is meant a polypeptide that comprises all or part of an Fc region. Fc polypeptides include antibodies, Fc fusions, isolated Fcs, and Fc fragments. Immunoglobulins may be Fc polypeptides.

By "Fc fusion" as used herein is meant a protein wherein one or more polypeptides is operably linked to Fc. Fc fusion is herein meant to be synonymous with the terms "immunoadhesin", "Ig fusion", "Ig chimera", and "receptor globulin" (sometimes with dashes) as used in the prior art (Chamow et al., 1996, Trends Biotechnol 14:52-60; Ashkenazi et al., 1997, Curr Opin Immunol 9:195-200, both hereby entirely incorporated by reference). An Fc fusion combines the Fc region of an immunoglobulin with a fusion partner, which in general may be any protein, polypeptide or small molecule. The role of the non-Fc part of an Fc fusion, i.e., the fusion partner, is to mediate target binding, and thus it is functionally analogous to the variable regions of an antibody. Virtually any protein or small molecule may be linked to Fc to generate an Fc fusion. Protein fusion partners may include, but are not limited to, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, e.g., an extracellular receptor that is implicated in disease.

By "Fc gamma receptor" or "FcγR" as used herein is meant any member of the family of proteins that bind the IgG antibody Fc region and are substantially encoded by the FcγR genes. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65, incorporated entirely by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "Fc ligand" or "Fc receptor" as used herein is meant a molecule, e.g., a polypeptide, from any organism that binds to the Fc region of an antibody to form an Fc-ligand complex. Fc ligands include but are not limited to FcγRs, FcγRs, FcγRs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, Immunological Reviews 190:123-136). Fc ligands may include undiscovered molecules that bind Fc.

By "full length antibody" as used herein is meant the structure that constitutes the natural biological form of an antibody, including variable and constant regions. For example, in most mammals, including humans and mice, the full length antibody of the IgG isotype is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3. In some mammals, for example in camels and llamas, IgG antibodies may consist of only two heavy chains, each heavy chain comprising a variable domain attached to the Fc region.

By "immunoglobulin" herein is meant a protein comprising one or more polypeptides substantially encoded by immunoglobulin genes. Immunoglobulins include but are not limited to antibodies (including bispecific antibodies) and Fc fusions. Immunoglobulins may have a number of structural forms, including but not limited to full length antibodies, antibody fragments, and individual immunoglobulin domains.

By "immunoglobulin (Ig) domain" as used herein is meant a region of an immunoglobulin that exists as a distinct structural entity as ascertained by one skilled in the art of protein structure. Ig domains typically have a characteristic β-sandwich folding topology. The known Ig domains in the IgG isotype of antibodies are VH Cγ1, Cγ2, Cγ3, VL, and CL.

By "IgG" or "IgG immunoglobulin" or "immunoglobulin G" as used herein is meant a polypeptide belonging to the class of antibodies that are substantially encoded by a recognized immunoglobulin gamma gene. In humans this class comprises the subclasses or isotypes IgG1, IgG2, IgG3, and IgG4.

By "IgE" or "IgE immunoglobulin" or "immunoglobulin E" as used herein is meant a polypeptide belonging to the class of antibodies that are substantially encoded by a recognized immunoglobulin epsilon gene. IgE may be membrane-anchored (mIgE), or non-membrane-anchored, also referred to herein as circulating IgE.

By "inhibition" of cells or grammatical equivalents is meant preventing or reducing the activation, proliferation, maturation or differentiation of targeted cells.

By "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM, IgD, and IgE.

By "modification" herein is meant an alteration in the physical, chemical, or sequence properties of a protein, polypeptide, antibody, or immunoglobulin. Modifications described herein include amino acid modifications and glycoform modifications.

By "glycoform modification" or "modified glycoform" or "engineered glycoform" as used herein is meant a carbohydrate composition that is covalently attached to a protein, for example an antibody, wherein said carbohydrate composition differs chemically from that of a parent protein. Modified glycoform typically refers to the different carbohydrate or oligosaccharide; thus for example an Fc variant may comprise a modified glycoform. Alternatively, modified glycoform may refer to the Fc variant that comprises the different carbohydrate or oligosaccharide.

By "parent polypeptide", "parent protein", "parent immunoglobulin", "parent Fc domain", "precursor polypeptide", "precursor protein", or "precursor immunoglobulin" as used herein is meant an unmodified polypeptide, protein, Fc domain, or immunoglobulin that is subsequently modified to generate a variant, e.g., any polypeptide, protein or immunoglobulin which serves as a template and/or basis for at least one amino acid modification described herein. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent Fc polypeptide" as used herein is meant an Fc polypeptide that is modified to generate a variant Fc polypeptide, and by "parent antibody" as used herein is meant an antibody that is modified to generate a variant antibody (e.g., a parent antibody may include, but is not limited to, a protein comprising the constant region of a naturally occurring Ig).

By "position" as used herein is meant a location in the sequence of a protein. Positions may be numbered sequentially, or according to an established format, for example the EU index as described in Kabat. For example, position 297 is a position in the human antibody IgG1.

By "polypeptide" or "protein" as used herein is meant at least two covalently attached amino acids, which includes proteins, polypeptides, oligopeptides and peptides.

By "residue" as used herein is meant a position in a protein and its associated amino acid identity. For example, Asparagine 297 (also referred to as Asn297, also referred to as N297) is a residue in the human antibody IgG1.

By "rapid clearance" or grammatical equivalents herein is meant that the antigen-antibody complex composition is cleared from the blood more quickly than either the antigen alone or the antibody, or a complex between the antigen and a parent analog of the antibody. As is understood in the art, antibodies with different Fvs may have different half lives in serum, so the comparison is to the starting antibody (e.g. an anti-IgE antibody without the IIb variants outlined herein) to the IIb engineered antibody. In general, "rapid clearance" are clearance rates of 25× faster than parent antibody, 50×, 75× and 100× or more. For example, as outlined herein, the anti-IgE IIb antibody of the examples shows a one hour clearance rate in chimps as compared to 2 days of either the parent Xolair antibody or an Fc IIb polypeptide that does not contain a binding moiety for IgE. Similarly, "clearance" can be measured as a reduction in free target antigen of 10%, 25%, 50% with 90 to 99% percentage of starting serum antigen concentration being a preferred clearance.

By "target antigen" as used herein is meant the molecule that is bound by the variable region of a given antibody, or the fusion partner of an Fc fusion. A target antigen may be a protein, carbohydrate, lipid, or other chemical compound. An antibody or Fc fusion is said to be "specific" for a given target antigen based on having affinity for the target antigen. A variety of target antigens are listed below.

Virtually any antigen may be targeted by the polypeptides of the invention, including but not limited to proteins, subunits, domains, motifs, and/or epitopes belonging to the following list of target antigens, which includes both soluble factors such as cytokines and membrane-bound factors. Proteins that may be target antigens of the invention include without limitation: IgE (soluble and/or membrane-bound), cytokines, e.g., IL-4, IL-6, IL-13, and TNFα; chemokines, e.g., MCP-1, RANTES, TARC, and MDC; growth factors, e.g., VEGF, HGF, and NGF; also, immune complexes, blood factor inhibitors, e.g. FVIII inhibitors, LDL, oxidized LDL, SOST, and DKK1. Target antigens may also include without limitation: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAM8, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin 0, Cathepsin S, Cathepsin V, Cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11 b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-1 (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxin1, EpCAM, Ephrin B2/EphB4, EPO, ERCC, E-selectin, ET-1, Factor 10a, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein 10b/IIIa (GP 10b/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, I-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bpi, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Mud), MUC18, Muellerian-inhibitin substance, Mug, MuSK, NAIP, NAP, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGJ2, PIN, PLA2, placental alkaline phosphatase (PLAP), P1GF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (DcTRAIL R1 TNFRH1), TNFRSF25 (DR3 Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3 Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (flt-1), VEGF, VEGFR, VEGFR-3 (flt-4), VEGI, VIM, Viral antigens, VLA, VLA-1, VLA-4, VNR integrin, von Willebrands factor, WI F-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors.

As discussed below, target antigens that find use in the particular use of rapid clearance of antibody-antigen complexes are listed below, and include cancer antigens, autoantigens, pathogen antigens, allergy antigens, etc.

By "target cell" as used herein is meant a cell that expresses a target antigen.

By "variable region" as used herein is meant the region of an immunoglobulin that comprises one or more Ig domains substantially encoded by any of the Vκ, Vλ, and/or VH genes that make up the kappa, lambda, and heavy chain immunoglobulin genetic loci respectively.

By "variant polypeptide", "polypeptide variant", or "variant" as used herein is meant a polypeptide sequence that differs from that of a parent polypeptide sequence by virtue of at least one amino acid modification. The parent polypeptide may be a naturally occurring or wild-type (WT) polypeptide, or may be a modified version of a WT polypeptide. Variant polypeptide may refer to the polypeptide itself, a composition comprising the polypeptide, or the amino sequence that encodes it. In some embodiments, variant polypeptides disclosed herein (e.g., variant immunoglobulins) may have at least one amino acid modification compared to the parent polypeptide, e.g. from about one to about ten amino acid modifications, from about one to about five amino acid modifications, etc. compared to the parent. The variant polypeptide sequence herein may possess at least about 80% homology with a parent polypeptide sequence, e.g., at least about 90% homology, 95% homology, etc. Accordingly, by "Fc variant" or "variant Fc" as used herein is meant an Fc sequence that differs from that of a parent Fc sequence by virtue of at least one amino acid modification. An Fc variant may only encompass an Fc region, or may exist in the context of an antibody, Fc fusion, isolated Fc, Fc fragment, or other polypeptide that is substantially encoded by Fc. Fc variant may refer to the Fc polypeptide itself, compositions comprising the Fc variant polypeptide, or the amino acid sequence that encodes it. By "Fc polypeptide variant" or "variant Fc polypeptide" as used herein is meant an Fc polypeptide that differs from a parent Fc polypeptide by virtue of at least one amino acid modification. By "protein variant" or "variant protein" as used herein is meant a protein that differs from a parent protein by virtue of at least one amino acid modification. By "antibody variant" or "variant antibody" as used herein is meant an antibody that differs from a parent antibody by virtue of at least one amino acid modification. By "IgG variant" or "variant IgG" as used herein is meant an antibody that differs from a parent IgG by virtue of at least one amino acid modification. By "immunoglobulin variant" or "variant immunoglobulin" as used herein is meant an immunoglobulin sequence that differs from that of a parent immunoglobulin sequence by virtue of at least one amino acid modification.

By "wild type" or "WT" herein is meant an amino acid sequence or a nucleotide sequence that is found in nature, including allelic variations. A WT protein, polypeptide, antibody, immunoglobulin, IgG, etc. has an amino acid sequence or a nucleotide sequence that has not been intentionally modified.

Rapid Clearance Molecules

The present invention is directed to the use of rapid clearance molecules (also referred to herein as "IIb variants") with high affinity to the FcγRIIb receptor that result in the rapid clearance from serum of the antibody-antigen complex, while retaining significant if not all the serum half-life of the unbound antigen or unbound rapid clearance molecules. In certain embodiments, the rapid clearance molecules of the invention include antibodies or Fc fusion proteins. Although much of the discussion herein is in terms of antibodies for ease of discussion, it will be appreciated that this discussion applies equally to any of the rapid clearance molecules described herein.

In general, rapid clearance molecules of the invention generally comprise a variable region that binds to an antigen and a variant Fc domain comprising one or more amino acid substitutions as compared to a parent Fc domain such that the variant Fc domain binds FcγRIIb with increased affinity as compared to the parent Fc domain.

In certain aspects, the rapid clearance ("RC") antibodies incorporate FcγRIIb receptor variants that can range from very tight differential binding to FcγRIIb to variants that display increased (as compared to wild type Fc domains) binding affinity but at a lower level. For example, very tight (or heavy) binding to FcγRIIb receptor may include FcγRIIb variants that show at least 50, 75, 100, 125, 150, 175, 200, 225, 250-fold greater affinity to FcγRIIb receptor as compared to the parent Fc domain. In contrast, a lower level (or light, also referred to herein as "lite") increase in binding may include FcγRIIb variants that show no more than 50, 40, 30, 20, 10, 5-fold greater affinity to FcγRIIb receptor as compared to the parent Fc domain. In further embodiments, tighter/heavier binding FcγRIIb variants show 50-300, 60-275, 70-250, 80-225, 90-200, 100-175, 110-150-fold greater affinity to FcγRIIb receptor as compared to the parent Fc domain, whereas lower/lighter binding FcγRIIb variants show 2-40, 4-35, 6-30, 8-25, 9-20, 10-15-fold greater affinity to FcγRIIb receptor as compared to the parent Fc domain. In certain embodiments, affinity is measured using Biacore, for example as described in Example 2. As discussed herein, the functional properties of rapid clearance molecules, including rapid clearance antibodies, can be tuned using modifications (such as amino acid substitutions, deletions or additions) that increase binding to FcγRIIb receptor by a tighter/heavier or a lower/lighter degree.

Figure 25:
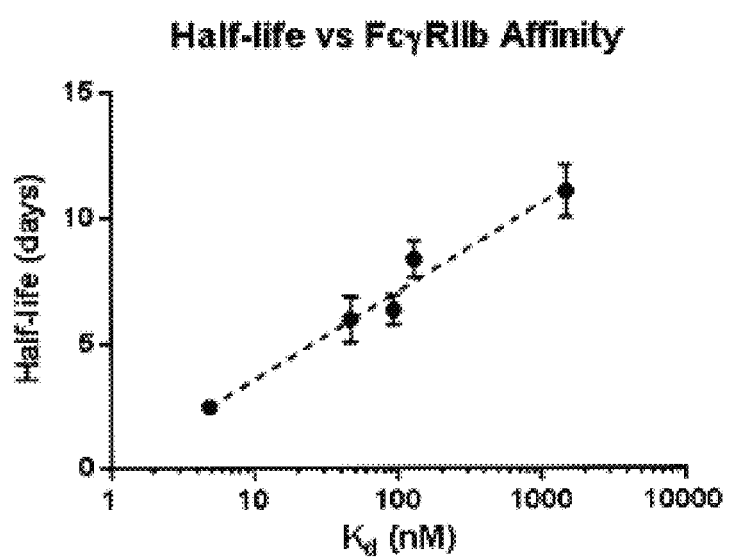
FIG. 25. Plot of test article half-life in human FcγRIIb transgenic mice versus FcγRIIb affinity. A direct relationship is observed.

As shown herein, the binding affinity of the IIb variants can be manipulated to result in different clearance/half life ratios. That is, the IIb variant S267E/L328F shows very high affinity binding to FcγRIIb of the variants discussed herein, and also has a faster clearance rate for antigen-antibody complexes among the variants discussed herein. The binding affinity, antibody half lives and clearance rates can be adjusted using high affinity binding variants or lower affinity binding variants, e.g. S267E, G236N/S267E, etc.). For example, the binding affinity of S267E is about 10× lower than the S267E/L328F variant, with a corresponding increase in half-life of roughly 2×-4× higher. In certain aspects, higher/heavier binding results in decreases in half-life. Thus, clearance rate and half-life can be adjusted by utilizing FcγRIIb-enhancing Fc amino acid substitutions that possess intermediate or lower increases in binding affinity (e.g., these substitutions still result in variants with higher affinity for FcγRIIb receptor than the parent molecules, but the affinities for these variants is not as increased, i.e., is lower/lighter than the heavy binding variants). Correlations between half-life and binding affinity can be measured as known in the art and discussed herein—see for example FIG. 25 and Example 6.

Application of different FcγRIIb-enhancing Fc amino acid substitutions with varying affinities to the FcγRIIb receptor (e.g. S267E/L328F, G236D/S267E, G236N/S267E, and S267E alone, as further described herein) can allow some "tuning" of how fast the complex antigen is cleared while maintaining significant half life of the rapid clearance composition of the invention (including antibodies). That is, different amino acid substitutions that alter FcγRIIb binding affinity may lead to different balances between the complex clearance rate and the antibody clearance rate, allowing for tailoring toward optimal therapeutic profile and dosing. This tuning may be accomplished by using amino acid substitutions in the Fc domain that increase binding to FcγRIIb as compared to the parent Fc domain. This increase in binding may be tuned by using Fc variants with 1-100, 5-90, 10-80, 15-70, 20-60, 30-50, 10-20, 5-15, fold greater affinity as compared to the parent Fc domain. This increase in binding may also be tuned by using Fc variants with 20-500, 30-400, 40-300, 50-200, 60-190, 70-180, 80-170, 90-160, 100-150, 110-140, 120-130, 50-100, 25-75 fold greater affinity to FcγRIIb receptor as compared to the parent Fc domain.

The effects of molecules of the invention may be further tuned by combining amino acid substitutions that alter FcγRIIb binding affinity with amino acid substitutions that affect binding to FcRn. Proteins with amino acid substitutions that affect binding to FcRn (also referred to herein as "FcRn variants") may in certain situations also increase serum half-life in vivo as compared to the parent protein. As will be appreciated, any combination of Fc and FcRn variants may be used to tune clearance of the antigen-antibody complex. Suitable FcRn variants that may be combined with any of the Fc variants described herein that alter binding to FcγRIIb include without limitation 434A, 434S, 428L, 308F, 259I, 428L/434S, 259I/308F, 436I/428L, 436I/434S, 436V/434S, 436V/428L, 252Y, 252Y/254T/256E, and 259I/308F/428L.

In further embodiments, combinations of variants that alter binding to the FcγRIIb are combined with a variety of scaffolds, target antigens and/or FcRn variants to further tune clearance properties or other functional properties (such as binding to FcγRIIa) of the antibodies. Exemplary (non-limiting) combinations are provided in FIG. 48, which provides a matrix of possible combinations, with each variants being independently and optionally combined from the appropriate source Legend: Legend A are suitable FcRn variants: 434A, 434S, 428L, 308F, 259I, 428L/434S, 259I/308F, 436I/428L, 436I or V/434S, 436V/428L, 252Y, 252Y/254T/256E, 259I/308F/428L. Legend B are suitable scaffolds and include IgG1, IgG2, IgG3, IgG4, and IgG1/2. Legend C are suitable exemplary target antigens: IgE (soluble or membrane-bound), IL-4, IL-6, IL-13, TNFα, MCP-1, RANTES, TARC, MDC, VEGF, HGF, and NGF, immune complexes, FVIII inhibitors, LDL, oxidized LDL (OxLDL), Lp(a), SOST, and DKK1. Legend D reflects the following possible combinations, again, with each variant being independently and optionally combined from the appropriate source Legend: 1) FcγRIIb variants plus FcRn variants; 2) FcγRIIb variants plus FcRn variants plus Scaffold; 3) FcγRIIb variants plus FcRn variants plus Scaffold plus Fv; 4) FcγRIIb variants plus Scaffold 5) FcγRIIb variants plus Fv; 6) FcRn variants plus Scaffold; 7) FcRn variants plus Fv; 8) Scaffold plus Fv; 9) FcγRIIb variants plus Scaffold plus Fv; and 10) FcγRIIb variants plus FcRn variants plus Fv. Note that any of these combinations may also include any of the FcγRIIb variants described herein, including those listed in FIGS. 30, 36, 48 as well as those listed in the first column of FIG. 48. Any of these combinations may also include any Fc variants known in the art, including for example variants described in WO 2012/115241; WO2013/125667; U.S. Pat. No. 6,737,056; U.S. Pat. No. 8,435,517; and Mimoto et al., Protein Engineering Design and Selection, vol. 26, No. 10, pp. 589-598 (2013), each of which is hereby incorporated by reference in its entirety for all purposes, and in particular any figures, legends, or discussion related to variants that affect binding to Fcγ receptors, including the FcγRIIb receptor. The combinations described in FIG. 48 may further include selections from additional target antigens known in the art or described herein.

In still further embodiments and in accordance with any of the above, the rapid clearance molecules of the invention reduce the total concentration of free antigen in a patient as compared to the concentration prior to treatment with the rapid clearance molecule. In exemplary embodiments, methods and compositions of the invention reduce the total concentration of antigen by at least 2, 5, 10, 20, 30, 40, 50, 60, 70, 80, 90-fold as compared to the concentration prior to treatment with the rapid clearance molecule.

In yet further embodiments and in accordance with any of the above, rapid clearance molecules include amino acid substitutions (including those described herein) that lead to Fc variants with increased FcγRIIb as compared to the parent Fc domain and further also alates binding to FcγRIIa. Such Fc variants may include the Fc variants described herein as well as Fc variants described herein combined with further substitutions that ablate binding to other FcγR, including without limitation FcγRIIa. As discussed above, "ablation" herein is meant a decrease or removal of activity. Thus for example, "ablating FcγR binding" means the Fc region amino acid variant has less than 50% starting binding as compared to an Fc region not containing the specific variant, with less than 70-80-90-95-98% loss of activity being preferred, and in general, with the activity being below the level of detectable binding in a Biacore assay.

In certain aspects and in accordance with any of the above, accelerated clearance of the antigen containing complexes seen with rapid clearance molecules containing amino acid substitutions that confer high affinity (as compared to the parent Fc domain) to the inhibitory receptor FcγRIIb is likely mediated by interaction with FcγRIIb-expressing cells, possibly liver sinusoidal endothelial cells. In certain embodiments, the accelerated clearance of the antigen containing molecules is not mediated by changes in pH or ionic conditions, such as those encountered within lysosomes.

In general, antibodies of the invention that have engineered Fc domains that result in higher affinity than wild-type antibodies to the FcγRIIb receptor can be directed to a variety of antigens as discussed herein, including cancer antigens, pathogen antigens, allergy antigens, etc.

In further embodiments, rapid clearance antibodies of the invention show functional properties as described in U.S. Provisional Application Ser. No. 61/752,955, filed Jan. 15, 2013; 61/794,164, filed Mar. 15, 2013, 61/794,386, filed Mar. 15, 2013, and 61/833,696, filed Jun. 11, 2013, each of which is expressly incorporated by reference in the entirety and in particular the figures describing such variants, their functional properties, or models of their functional properties (as shown for example in FIGS. 23-26 of U.S. Ser. No. 61/752,955).

Antibodies

The present invention relates to the generation of heterodimeric antibodies, generally therapeutic antibodies, through the use of "heterodimerization amino acid variants". As is discussed below, the term "antibody" is used generally. Antibodies that find use in the present invention can take on a number of formats as described herein, including traditional antibodies as well as antibody derivatives, fragments and mimetics, described below. In general, the term "antibody" includes any polypeptide that includes at least one constant domain, including, but not limited to, CH1, CH2, CH3 and CL.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. The present invention is directed to the IgG class, which has several subclasses, including, but not limited to IgG1, IgG2, IgG3, and IgG4. Thus, "isotype" as used herein is meant any of the subclasses of immunoglobulins defined by the chemical and antigenic characteristics of their constant regions. It should be understood that therapeutic antibodies can also comprise hybrids of isotypes and/or subclasses. For example, as shown herein, the present invention covers heterodimers that can contain one or both chains that are IgG1/G2 hybrids (see SEQ ID NO:6, for example).

The amino-terminal portion of each chain includes a variable region of about 100 to 110 or more amino acids primarily responsible for antigen recognition, generally referred to in the art and herein as the "Fv domain" or "Fv region". In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below.

Throughout the present specification, the Kabat numbering system is generally used when referring to a residue in the variable domain (approximately, residues 1-107 of the light chain variable region and residues 1-113 of the heavy chain variable region) (e.g, Kabat et al., supra (1991)).

The CDRs contribute to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope.

The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide.

Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and nonconformational epitopes may be distinguished in that the binding to the former but not the latter is lost in the presence of denaturing solvents.

An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen, for example "binning."

In some embodiments, the antibodies are full length. By "full length antibody" herein is meant the structure that constitutes the natural biological form of an antibody, including variable and constant regions, including one or more modifications as outlined herein.

Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively.

Antibody Fragments

In one embodiment, the antibody is an antibody fragment. Of particular interest are antibodies that comprise Fc regions, Fc fusions, and the constant region of the heavy chain (CH1-hinge-CH2-CH3), again also including constant heavy region fusions.

Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883, entirely incorporated by reference), (viii) bispecific single chain Fv (WO 03/11161, hereby incorporated by reference) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, all entirely incorporated by reference). The antibody fragments may be modified. For example, the molecules may be stabilized by the incorporation of disulphide bridges linking the VH and VL domains (Reiter et al., 1996, Nature Biotech. 14:1239-1245, entirely incorporated by reference).

Chimeric and Humanized Antibodies

In some embodiments, the scaffold components can be a mixture from different species. As such, if the protein is an antibody, such antibody may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536, all entirely incorporated by reference. "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

In one embodiment, the antibody is a minibody. Minibodies are minimized antibody-like proteins comprising a scFv joined to a CH3 domain. Hu et al., 1996, Cancer Res. 56:3055-3061, entirely incorporated by reference. In some cases, the scFv can be joined to the Fc region, and may include some or the entire hinge region.

Fc Fusion Proteins

In addition to antibody constructs discussed herein, the invention further provides Fc fusion proteins where the Fc region has IIb variants. That is, rather than have the Fc domain of an antibody joined to an antibody variable region, the Fc domain can be joined to other moieties, particularly binding moieties such as ligands. By "Fc fusion" as used herein is meant a protein wherein one or more polypeptides is operably linked to an Fc region. Fc fusion is herein meant to be synonymous with the terms "immunoadhesin", "Ig fusion", "Ig chimera", and "receptor globulin" (sometimes with dashes) as used in the prior art (Chamow et al., 1996, Trends Biotechnol 14:52-60; Ashkenazi et al., 1997, Curr Opin Immunol 9:195-200, both entirely incorporated by reference). An Fc fusion combines the Fc region of an immunoglobulin with a fusion partner, which in general can be any protein or small molecule. Virtually any protein or small molecule may be linked to Fc to generate an Fc fusion. Protein fusion partners may include, but are not limited to, the variable region of any antibody, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferably an extracellular receptor, which is implicated in disease. Thus, the IgG variants can be linked to one or more fusion partners.

FcγRIIb Variants

The compositions and methods of the invention rely on FcγRIIb variants that increase binding to the FcγRIIb receptor. Related applications discuss the FcγRIIb variants in detail. See for example U.S. Ser. Nos. 11/124,620 and 13/294,103, both of which are incorporated by reference in their entirety, and in particular for the amino acid variant positions, accompanying specification description, figures and accompanying legends, and data relating to the variants. Fc variants that find particular use herein include, but are not limited to, those listed in FIG. 30.

FcγRIIb receptor variants that are considered "tight" binding and display the fastest rapid clearance times, include S267E/L328F.

FcγRIIb receptor variants increased binding as compared to wild type Fc domains, e.g. IgG1 domains, but are considered lower affinity and thus can result in longer half lives include, but are not limited to, S267E and G236N/267E and G236D/267E (sometimes referred to as "IIb-lite" variants).

Additional FcγR Variants

In addition to FcγRIIb receptor variants, there are a number of useful Fc substitutions that can be made to alter binding to one or more of the FcγR receptors. Substitutions that result in increased binding as well as decreased binding can be useful. For example, it is known that increased binding to FcγRIIIa generally results in increased ADCC (antibody dependent cell-mediated cytotoxicity; the cell-mediated reaction wherein nonspecific cytotoxic cells that express FcγRs recognize bound antibody on a target cell and subsequently cause lysis of the target cell. Amino acid substitutions that find use in the present invention include those listed in U.S. Ser. No. 11/124,620 (particularly FIG. 41), U.S. Ser. Nos. 11/174,287, 11/396,495, 11/538,406, all of which are expressly incorporated herein by reference in their entirety and specifically for the variants disclosed therein. Particular variants that find use include, but are not limited to, 236A, 239D, 239E, 332E, 332D, 239D/332E, 267D, S267E, L328F, S267E/L328F, 236A/332E, 239D/332E/330Y, 239D, 332E/330L, 243L, 298A and 299T. In some cases ablation variants such as 236R, 328R, and 236R/328R can be made, although this is not preferred in some embodiments. Additional suitable Fc variants are found in FIG. 41 of US 2006/0024298, the figure and legend of which are hereby incorporated by reference in their entirety.

In addition, there are additional Fc substitutions that find use in increased binding to the FcRn receptor and optionally increased serum half life, as specifically disclosed in U.S. Ser. No. 12/341,769, hereby incorporated by reference in its entirety, including, but not limited to, 434S, 434A, 428L, 308F, 259I, 428L/434S, 259I/308F, 436I/428L, 436I or V/434S, 436V/428L and 259I/308F/428L.

IgE-FcγRIIb Molecules

One example of rapid clearance applications are antibodies that contain an antigen binding site to IgE and FcγRIIb variants, resulting in "co-engagement". For example, described herein are variant anti-IgE antibodies engineered such that the Fc domain binds to FcγRIIb with up to ~430-fold greater affinity relative to native IgG1. These FcγRIIb binding-enhanced (IIbE) variants strongly inhibit BCR-induced calcium mobilization and viability in primary human IgE+ B cells. The use of a single molecule, such as an antibody to suppress B cell functions of cognate IgE BCR and FcγRIIb represents a novel approach in the treatment of IgE-mediated diseases. Non-limiting examples of IgE-mediated diseases include allergic responses and asthma and are described in U.S. Ser. No. 12/156,183, hereby incorporated by reference in its entirety, and particularly for the discussion associated with coengagement, and described below.

Factor VIII-FcγRIIb Molecules

In one embodiment, the rapid clearance mechanisms of the present invention are used to treat hemophilia. One issue with hemophiliacs is the effect that Factor VIII (FVIII (not to be confused with "Fv")) inhibitors play in disease. The most significant complication of treatment of hemophilia A is the development of alloantibodies to the therapeutic Factor VIII, that then inhibit the activity of the Factor VIII. Approximately 30% of patients with severe hemophilia A develop these alloantibodies, recognizing the exogenous correct FVIII as "foreign", generally resulting in bleeding episodes that are more difficult to manage.

FIG. 28 shows the structure of the FVIIIa protein, consisting of heterodimeric protein comprising a heavy chain (A1-A2-B, not to be confused with the heavy chain of an antibody) and a light chain (A3-C1-C2) that are associated through a noncovalent divalent metal ion linkage between the A1 and A3 domains. The alloantibodies generally develop to the A2 and C2 domains, which are the dominant epitopes for the alloantibodies, generally accounting for roughly 68% of the alloantibody antigens.

Due to the rapid clearance of antibodies and Fc fusions engineered to bind with high affinity to FcγRIIb, the present invention provides "scrubber" or "drug" Fc fusions, comprising some or all of the domains of FVIIIa, that bind to the FVIIIa inhibitors thereby clearing out the alloantibodies. That is, the FcγRIIb fusions, directed against these inhibitor antibodies will sequester the inhibitor antibodies, rapidly clear the inhibitor antibodies, and will also inhibit FVIII-reactive B cells (to prohibit the further production of the inhibitors).

CR-Fc Fusion Molecules

In one embodiment, the rapid clearance mechanisms of the present invention are used with complement receptor 2 (CR2)-Fc fusions for immune system modulation and accelerated clearance of C3d-tagged immune complexes. These fusion proteins in this context are sometimes referred to herein as "CR2-IIbE". In this embodiment, increased affinity for the inhibitory Fc receptor FcRIIb (CD32b) is utilized to facilitate rapid in vivo clearance of C3-tagged immune complexes via their interaction with CR-IIbE fusions. Incorporation of the IIb-enhancing affinity substitutions into various fusions leads to a novel phenomenon whereby the fusion-target complex is cleared extremely rapidly while the CR-IIbE alone retains a reasonably long half-life. Application of different IIb-enhancing substitutions (e.g. S267E/L328F, G236D/S267E, 236N/267E, or S267E alone, as are useful for all the rapid clearance molecules herein) may lead to different balances between the complex clearance rate and the fusion protein clearance rate, allowing for tailoring toward optimal therapeutic profile and dosing.

In another aspect of the invention, rapid clearance-mediating IIb technology can additionally be applied to other complement system receptors or inhibitors, including but not limited to, CR1, Factor H (fH), CR3, and CRIg. Typically, only the SCR domains required for recognition of the appropriate complement factor will be required, although additional repeats may be included for stability.

In yet another aspect of the invention, rapid clearance-mediating IIb technology can be applied to antibodies that recognize C3 fragments, thereby mimicking the above-described CR-Fc fusions, similar to the IgE and Factor VIII antibody examples. Examples include, but are not limited to, anti-C3d antibodies with engineered Fc regions. See also U.S. Ser. No. 61/752,955, filed Jan. 15, 2013, which is hereby incorporated by reference in its entirety for all purposes and in particular for all teachings, figures and legends related to schemes of complement and antibodies directed to same.

Anti-IgE Antibodies

In some embodiments, the immunoglobulins described herein bind IgE. The anti-IgE antibodies of the invention may comprise any variable region, known or not yet known, that has specificity for IgE. Known anti-IgE antibodies include but are not limited to murine antibodies MaE11, MaE13, and MaE15, humanized and/or engineered versions of these antibodies including E25, E26, and E27, particularly E25, also known as rhuMab-E25, also known as Omalizumab, such as those described in U.S. Pat. No. 6,761,889, U.S. Pat. No. 6,329,509, US20080003218A1, and Presta, L G et al., 1993, J Immunol 151:2623-2632, all herein expressly incorporated by reference. A preferred engineered version of MaE11 is H1 L1 MaE11, described in the Examples herein. Other anti-IgE that may be useful for the invention include murine antibody TES-C21, chimeric TES-C21, also known as CGP51901 (Corne, J et al., 1997, J Clin Invest 99:879-887; Racine-Poon, A et al., 1997, Clin Pharmcol Ther 62:675-690), and humanized and/or engineered versions of this antibody including but not limited to CGP56901, also known as TNX-901, such as those antibodies described in Kolbinger, F et al., 1993, Protein Eng 6:971-980. Other anti-IgE antibodies that may find use for the invention are described in U.S. Pat. No. 6,066,718, U.S. Pat. No. 6,072,035, PCT/US04/02894, U.S. Pat. No. 5,342,924, U.S. Pat. No. 5,091,313, U.S. Pat. No. 5,449,760, U.S. Pat. No. 5,543,144, U.S. Pat. No. 5,342,924, and U.S. Pat. No. 5,614,611, all of which are incorporated herein by reference. Other useful anti-IgE antibodies include the murine antibody BSW17. Amino acid sequences of the variable region VH and VL domains and CDRs of some of these antibodies are provided in FIG. 5.

Fc Variants and Fc Receptor Binding Properties

Immunoglobulins disclosed herein may comprise an Fc variant. An Fc variant comprises one or more amino acid modifications relative to a parent Fc polypeptide, wherein the amino acid modification(s) provide one or more optimized properties. An Fc variant disclosed herein differs in amino acid sequence from its parent by virtue of at least one amino acid modification. Thus Fc variants disclosed herein have at least one amino acid modification compared to the parent. Alternatively, the Fc variants disclosed herein may have more than one amino acid modification as compared to the parent, for example from about one to fifty amino acid modifications, e.g., from about one to ten amino acid modifications, from about one to about five amino acid modifications, etc. compared to the parent. Thus the sequences of the Fc variants and those of the parent Fc polypeptide are substantially homologous. For example, the variant Fc variant sequences herein will possess about 80% homology with the parent Fc variant sequence, e.g., at least about 90% homology, at least about 95% homology, at least about 98% homology, at least about 99% homology, etc. Modifications disclosed herein include amino acid modifications, including insertions, deletions, and substitutions. Modifications disclosed herein also include glycoform modifications. Modifications may be made genetically using molecular biology, or may be made enzymatically or chemically.

Fc variants disclosed herein are defined according to the amino acid modifications that compose them. Thus, for example, S267E is an Fc variant with the substitution S267E relative to the parent Fc polypeptide. Likewise, S267E/L328F defines an Fc variant with the substitutions S267E and L328F relative to the parent Fc polypeptide. The identity of the WT amino acid may be unspecified, in which case the aforementioned variant is referred to as S267E/L328F. It is noted that the order in which substitutions are provided is arbitrary, that is to say that, for example, S267E/L328F is the same Fc variant as L328F/267E, and so on. Unless otherwise noted, positions discussed herein are numbered according to the EU index or EU numbering scheme (Kabat et al., 1991, Sequences of Proteins of Immunological Interest, 5th Ed., United States Public Health Service, National Institutes of Health, Bethesda, hereby entirely incorporated by reference). The EU index or EU index as in Kabat or EU numbering scheme refers to the numbering of the EU antibody (Edelman et al., 1969, Proc Natl Acad Sci USA 63:78-85, hereby entirely incorporated by reference).

In certain embodiments, the Fc variants disclosed herein are based on human IgG sequences, and thus human IgG sequences are used as the "base" sequences against which other sequences are compared, including but not limited to sequences from other organisms, for example rodent and primate sequences. Immunoglobulins may also comprise sequences from other immunoglobulin classes such as IgA, IgE, IgGD, IgGM, and the like. It is contemplated that, although the Fc variants disclosed herein are engineered in the context of one parent IgG, the variants may be engineered in or "transferred" to the context of another, second parent IgG. This is done by determining the "equivalent" or "corresponding" residues and substitutions between the first and second IgG, typically based on sequence or structural homology between the sequences of the first and second IgGs. In order to establish homology, the amino acid sequence of a first IgG outlined herein is directly compared to the sequence of a second IgG. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first immunoglobulin are defined. Alignment of conserved residues may conserve 100% of such residues. However, alignment of greater than 75% or as little as 50% of conserved residues is also adequate to define equivalent residues. Equivalent residues may also be defined by determining structural homology between a first and second IgG that is at the level of tertiary structure for IgGs whose structures have been determined. In this case, equivalent residues are defined as those for which the atomic coordinates of two or more of the main chain atoms of a particular amino acid residue of the parent or precursor (N on N, CA on CA, C on C and O on O) are within about 0.13 nm, after alignment. In another embodiment, equivalent residues are within about 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent IgG in which the IgGs are made, what is meant to be conveyed is that the Fc variants discovered as disclosed herein may be engineered into any second parent IgG that has significant sequence or structural homology with the Fc variant. Thus for example, if a variant antibody is generated wherein the parent antibody is human IgG1, by using the methods described above or other methods for determining equivalent residues, the variant antibody may be engineered in another IgG1 parent antibody that binds a different antigen, a human IgG2 parent antibody, a human IgA parent antibody, a mouse IgG2a or IgG2b parent antibody, and the like. Again, as described above, the context of the parent Fc variant does not affect the ability to transfer the Fc variants disclosed herein to other parent IgGs.

The Fc variants disclosed herein may be optimized for a variety of Fc receptor binding properties. An Fc variant that is engineered or predicted to display one or more optimized properties is herein referred to as an "optimized Fc variant". Properties that may be optimized include but are not limited to enhanced or reduced affinity for an FcγR. In one embodiment, the Fc variants disclosed herein are optimized to possess enhanced affinity for an inhibitory receptor FcγRIIb. In other embodiments, immunoglobulins disclosed herein provide enhanced affinity for FcγRIIb, yet reduced affinity for one or more activating FcγRs, including for example FcγRI, FcγRIIa, FcγRIIIa, and/or FcγRIIIb. The FcγR receptors may be expressed on cells from any organism, including but not limited to human, cynomolgus monkeys, and mice. The Fc variants disclosed herein may be optimized to possess enhanced affinity for human FcγRIIb.

By "greater affinity" or "improved affinity" or "enhanced affinity" or "better affinity" than a parent Fc polypeptide, as used herein is meant that an Fc variant binds to an Fc receptor with a significantly higher equilibrium constant of association (KA or Ka) or lower equilibrium constant of dissociation (KD or Kd) than the parent Fc polypeptide when the amounts of variant and parent polypeptide in the binding assay are essentially the same. For example, the Fc variant with improved Fc receptor binding affinity may display from about 5 fold to about 1000 fold, e.g. from about 10 fold to about 500 fold improvement in Fc receptor binding affinity compared to the parent Fc polypeptide, where Fc receptor binding affinity is determined, for example, by the binding methods disclosed herein, including but not limited to Biacore, by one skilled in the art. Accordingly, by "reduced affinity" as compared to a parent Fc polypeptide as used herein is meant that an Fc variant binds an Fc receptor with significantly lower KA or higher KD than the parent Fc polypeptide. Greater or reduced affinity can also be defined relative to an absolute level of affinity. For example, according to the data herein, WT (native) IgG1 binds FcγRIIb with an affinity of about 2 μM, or about 2000 nM. Furthermore, some Fc variants described herein bind FcγRIIb with an affinity about 10-fold greater to WT IgG1. As disclosed herein, greater or enhanced affinity means having a KD lower than about 100 nM, for example between about 10 nM-about 100 nM, between about 1-about 100 nM, or less than about 1 nM.

Anti-IgE antibodies of the invention preferably have high affinity for FcγRIIb. By high affinity herein is meant that the affinity of the interaction between the antibody and FcγRIIb is stronger than 100 nM. That is to say that the equilibrium dissociation constant Kd for binding of the antibody to FcγRIIb is lower than 100 nM.

In one embodiment, the Fc variants provide selectively enhanced affinity to FcγRIIb relative to one or more activating receptors. Selectively enhanced affinity means either that the Fc variant has improved affinity for FcγRIIb relative to the activating receptor(s) as compared to the parent Fc polypeptide but has reduced affinity for the activating receptor(s) as compared to the parent Fc polypeptide, or it means that the Fc variant has improved affinity for both FcγRIIb and activating receptor(s) as compared to the parent Fc polypeptide, however the improvement in affinity is greater for FcγRIIb than it is for the activating receptor(s). In alternate embodiments, the Fc variants reduce or ablate binding to one or more activating FcγRs, reduce or ablate binding to one or more complement proteins, reduce or ablate one or more FcγR-mediated effector functions, and/or reduce or ablate one or more complement-mediated effector functions.

The presence of different polymorphic forms of FcγRs provides yet another parameter that impacts the therapeutic utility of the Fc variants disclosed herein. Whereas the specificity and selectivity of a given Fc variant for the different classes of FcγRs significantly affects the capacity of an Fc variant to target a given antigen for treatment of a given disease, the specificity or selectivity of an Fc variant for different polymorphic forms of these receptors may in part determine which research or pre-clinical experiments may be appropriate for testing, and ultimately which patient populations may or may not respond to treatment. Thus the specificity or selectivity of Fc variants disclosed herein to Fc receptor polymorphisms, including but not limited to FcγRIIa, FcγRIIIa, and the like, may be used to guide the selection of valid research and pre-clinical experiments, clinical trial design, patient selection, dosing dependence, and/or other aspects concerning clinical trials.

Fc variants disclosed herein may comprise modifications that modulate interaction with Fc receptors other than FcγRs, including but not limited to complement proteins, FcRn, and Fc receptor homologs (FcRHs). FcRHs include but are not limited to FcRH1, FcRH2, FcRH3, FcRH4, FcRH5, and FcRH6 (Davis et al., 2002, Immunol. Reviews 190:123-136).

An important parameter that determines the most beneficial selectivity of a given Fc variant to treat a given disease is the context of the Fc variant. Thus the Fc receptor selectivity or specificity of a given Fc variant will provide different properties depending on whether it composes an antibody, Fc fusion, or Fc variants with a coupled fusion partner. In one embodiment, an Fc receptor specificity of the Fc variant disclosed herein will determine its therapeutic utility. The utility of a given Fc variant for therapeutic purposes will depend on the epitope or form of the target antigen and the disease or indication being treated. For some targets and indications, greater FcγRIIb affinity and reduced activating FcγR-mediated effector functions may be beneficial. For other target antigens and therapeutic applications, it may be beneficial to increase affinity for FcγRIIb, or increase affinity for both FcγRIIb and activating receptors.

Glycoform Modifications

Many polypeptides, including antibodies, are subjected to a variety of posttranslational modifications involving carbohydrate moieties, such as glycosylation with oligosaccharides. There are several factors that can influence glycosylation. The species, tissue and cell type have all been shown to be important in the way that glycosylation occurs. In addition, the extracellular environment, through altered culture conditions such as serum concentration, may have a direct effect on glycosylation (Lifely et al., 1995, Glycobiology 5(8): 813-822).

All antibodies contain carbohydrate at conserved positions in the constant regions of the heavy chain. Each antibody isotype has a distinct variety of N-linked carbohydrate structures. Aside from the carbohydrate attached to the heavy chain, up to 30% of human IgGs have a glycosylated Fab region. IgG has a single N-linked biantennary carbohydrate at Asn297 of the CH2 domain. For IgG from either serum or produced ex vivo in hybridomas or engineered cells, the IgG are heterogeneous with respect to the Asn297 linked carbohydrate (Jefferis et al., 1998, Immunol. Rev. 163:59-76; Wright et al., 1997, Trends Biotech 15:26-32). For human IgG, the core oligosaccharide normally consists of GlcNAc2Man3GlcNAc, with differing numbers of outer residues.

The carbohydrate moieties of immunoglobulins disclosed herein will be described with reference to commonly used nomenclature for the description of oligosaccharides. A review of carbohydrate chemistry which uses this nomenclature is found in Hubbard et al. 1981, Ann. Rev. Biochem. 50:555-583. This nomenclature includes, for instance, Man, which represents mannose; GlcNAc, which represents 2-N- acetylglucosamine; Gal which represents galactose; Fuc for fucose; and Glc, which represents glucose. Sialic acids are described by the shorthand notation NeuNAc, for 5-N-acetylneuraminic acid, and NeuNGc for 5-glycolyl-neuraminic.

The term "glycosylation" means the attachment of oligosaccharides (carbohydrates containing two or more simple sugars linked together e.g. from two to about twelve simple sugars linked together) to a glycoprotein. The oligosaccharide side chains are typically linked to the backbone of the glycoprotein through either N- or O-linkages. The oligosaccharides of immunoglobulins disclosed herein occur generally are attached to a CH2 domain of an Fc region as N-linked oligosaccharides. "N-linked glycosylation" refers to the attachment of the carbohydrate moiety to an asparagine residue in a glycoprotein chain. The skilled artisan will recognize that, for example, each of murine IgG1, IgG2a, IgG2b and IgG3 as well as human IgG1, IgG2, IgG3, IgG4, IgA and IgD CH2 domains have a single site for N-linked glycosylation at amino acid residue 297 (Kabat et al. Sequences of Proteins of Immunological Interest, 1991).

For the purposes herein, a "mature core carbohydrate structure" refers to a processed core carbohydrate structure attached to an Fc region which generally consists of the following carbohydrate structure GlcNAc(Fucose)-GlcNAc-Man-(Man-GlcNAc)2 typical of biantennary oligosaccharides. The mature core carbohydrate structure is attached to the Fc region of the glycoprotein, generally via N-linkage to Asn297 of a CH2 domain of the Fc region. A "bisecting GlcNAc" is a GlcNAc residue attached to the β1,4 mannose of the mature core carbohydrate structure. The bisecting GlcNAc can be enzymatically attached to the mature core carbohydrate structure by a β(1,4)-N-acetylglucosaminyl-transferase III enzyme (GnTIII). CHO cells do not normally express GnTIII (Stanley et al., 1984, J. Biol. Chem. 261: 13370-13378), but may be engineered to do so (Umana et al., 1999, Nature Biotech. 17:176-180).

Described herein are Fc variants that comprise modified glycoforms or engineered glycoforms. By "modified glycoform" or "engineered glycoform" as used herein is meant a carbohydrate composition that is covalently attached to a protein, for example an antibody, wherein said carbohydrate composition differs chemically from that of a parent protein. Engineered glycoforms may be useful for a variety of purposes, including but not limited to enhancing or reducing FcγR-mediated effector function. In one embodiment, the immunoglobulins disclosed herein are modified to control the level of fucosylated and/or bisecting oligosaccharides that are covalently attached to the Fc region.

A variety of methods are well known in the art for generating modified glycoforms (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473); (U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1); (Potelligent™ technology [Biowa, Inc., Princeton, N.J.]; GlycoMAb™ glycosylation engineering technology [GLYCART biotechnology AG, Zürich, Switzerland]; all of which are expressly incorporated by reference). These techniques control the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells), by regulating enzymes involved in the glycosylation pathway (for example FUT8 [α1,6-fucosyltranserase] and/or β1-4-N-acetylglucosaminyltransferase III [GnTIII]), or by modifying carbohydrate(s) after the IgG has been expressed. Other methods for modifying glycoforms of the immunoglobulins disclosed herein include using glycoengineered strains of yeast (Li et al., 2006, Nature Biotechnology 24(2):210-215), moss (Nechansky et al., 2007, Mol Immunjol 44(7):1826-8), and plants (Cox et al., 2006, Nat Biotechnol 24(12):1591-7). The use of a particular method to generate a modified glycoform is not meant to constrain embodiments to that method. Rather, embodiments disclosed herein encompass Fc variants with modified glycoforms irrespective of how they are produced.

In one embodiment, immunoglobulins disclosed herein are glycoengineered to alter the level of sialylation. Higher levels of sialylated Fc glycans in immunoglobulin G molecules can adversely impact functionality (Scallon et al., 2007, Mol Immunol. 44(7):1524-34), and differences in levels of Fc sialylation can result in modified anti-inflammatory activity (Kaneko et al., 2006, Science 313:670-673). Because antibodies may acquire anti-inflammatory properties upon sialylation of Fc core polysaccharide, it may be advantageous to glycoengineer the immunoglobulins disclosed herein for greater or reduced Fc sialic acid content.

Engineered glycoform typically refers to the different carbohydrate or oligosaccharide; thus for example an immunoglobulin may comprise an engineered glycoform. Alternatively, engineered glycoform may refer to the immunoglobulin that comprises the different carbohydrate or oligosaccharide. In one embodiment, a composition disclosed herein comprises a glycosylated Fc variant having an Fc region, wherein about 51-100% of the glycosylated antibody, e.g., 80-100%, 90-100%, 95-100%, etc. of the antibody in the composition comprises a mature core carbohydrate structure which lacks fucose. In another embodiment, the antibody in the composition both comprises a mature core carbohydrate structure that lacks fucose and additionally comprises at least one amino acid modification in the Fc region. In an alternative embodiment, a composition comprises a glycosylated Fc variant having an Fc region, wherein about 51-100% of the glycosylated antibody, 80-100%, or 90-100%, of the antibody in the composition comprises a mature core carbohydrate structure which lacks sialic acid. In another embodiment, the antibody in the composition both comprises a mature core carbohydrate structure that lacks sialic acid and additionally comprises at least one amino acid modification in the Fc region. In yet another embodiment, a composition comprises a glycosylated Fc variant having an Fc region, wherein about 51-100% of the glycosylated antibody, 80-100%, or 90-100%, of the antibody in the composition comprises a mature core carbohydrate structure which contains sialic acid. In another embodiment, the antibody in the composition both comprises a mature core carbohydrate structure that contains sialic acid and additionally comprises at least one amino acid modification in the Fc region. In another embodiment, the combination of engineered glycoform and amino acid modification provides optimal Fc receptor binding properties to the antibody.

Other Modifications

Immunoglobulins disclosed herein may comprise one or more modifications that provide optimized properties that are not specifically related to FcγR- or complement-mediated effector functions per se. Said modifications may be amino acid modifications, or may be modifications that are made enzymatically or chemically. Such modification(s) likely provide some improvement in the immunoglobulin, for example an enhancement in its stability, solubility, function, or clinical use. Disclosed herein are a variety of improvements that may be made by coupling the immunoglobulins disclosed herein with additional modifications.

In one embodiment, the variable region of an antibody disclosed herein may be affinity matured, that is to say that amino acid modifications have been made in the VH and/or VL domains of the antibody to enhance binding of the antibody to its target antigen. Such types of modifications may improve the association and/or the dissociation kinetics for binding to the target antigen. Other modifications include those that improve selectivity for target antigen vs. alternative targets. These include modifications that improve selectivity for antigen expressed on target vs. non-target cells. Other improvements to the target recognition properties may be provided by additional modifications. Such properties may include, but are not limited to, specific kinetic properties (i.e. association and dissociation kinetics), selectivity for the particular target versus alternative targets, and selectivity for a specific form of target versus alternative forms. Examples include full-length versus splice variants, cell-surface vs. soluble forms, selectivity for various polymorphic variants, or selectivity for specific conformational forms of the target antigen. Immunoglobulins disclosed herein may comprise one or more modifications that provide reduced or enhanced internalization of an immunoglobulin.

In one embodiment, modifications are made to improve biophysical properties of the immunoglobulins disclosed herein, including but not limited to stability, solubility, and oligomeric state. Modifications can include, for example, substitutions that provide more favorable intramolecular interactions in the immunoglobulin such as to provide greater stability, or substitution of exposed nonpolar amino acids with polar amino acids for higher solubility. Other modifications to the immunoglobulins disclosed herein include those that enable the specific formation or homodimeric or homomultimeric molecules. Such modifications include but are not limited to engineered disulfides, as well as chemical modifications or aggregation methods which may provide a mechanism for generating covalent homodimeric or homomultimers. Additional modifications to the variants disclosed herein include those that enable the specific formation or heterodimeric, heteromultimeric, bifunctional, and/or multifunctional molecules. Such modifications include, but are not limited to, one or more amino acid substitutions in the CH3 domain, in which the substitutions reduce homodimer formation and increase heterodimer formation. Additional modifications include modifications in the hinge and CH3 domains, in which the modifications reduce the propensity to form dimers.

In further embodiments, the immunoglobulins disclosed herein comprise modifications that remove proteolytic degradation sites. These may include, for example, protease sites that reduce production yields, as well as protease sites that degrade the administered protein in vivo. In one embodiment, additional modifications are made to remove covalent degradation sites such as deamidation (i.e. deamidation of glutaminyl and asparaginyl residues to the corresponding glutamyl and aspartyl residues), oxidation, and proteolytic degradation sites. Deamidation sites that are particular useful to remove are those that have enhance propensity for deamidation, including, but not limited to asparaginyl and glutamyl residues followed by glycines (NG and QG motifs, respectively). In such cases, substitution of either residue can significantly reduce the tendency for deamidation. Common oxidation sites include methionine and cysteine residues. Other covalent modifications, that can either be introduced or removed, include hydroxylation of proline and lysine, phosphorylation of hydroxyl groups of seryl or threonyl residues, methylation of the "-amino groups of lysine, arginine, and histidine side chains (T. E. Creighton, Proteins: Structure and Molecular Properties, W.H. Freeman & Co., San Francisco, pp. 79-86 (1983), incorporated entirely by reference), acetylation of the N-terminal amine, and amidation of any C-terminal carboxyl group. Additional modifications also may include but are not limited to posttranslational modifications such as N-linked or O-linked glycosylation and phosphorylation.

Modifications may include those that improve expression and/or purification yields from hosts or host cells commonly used for production of biologics. These include, but are not limited to various mammalian cell lines (e.g. CHO), yeast cell lines, bacterial cell lines, and plants. Additional modifications include modifications that remove or reduce the ability of heavy chains to form inter-chain disulfide linkages. Additional modifications include modifications that remove or reduce the ability of heavy chains to form intra-chain disulfide linkages.

The immunoglobulins disclosed herein may comprise modifications that include the use of unnatural amino acids incorporated using, for example, the technologies developed by Schultz and colleagues, including but not limited to methods described by Cropp & Shultz, 2004, Trends Genet. 20(12):625-30, Anderson et al., 2004, Proc. Natl. Acad. Sci. U.S.A. 101(2):7566-71, Zhang et al., 2003, 303(5656):371-3, and Chin et al., 2003, Science 301(5635):964-7, all incorporated entirely by reference. In some embodiments, these modifications enable manipulation of various functional, biophysical, immunological, or manufacturing properties discussed above. In additional embodiments, these modifications enable additional chemical modification for other purposes. Other modifications are contemplated herein. For example, the immunoglobulin may be linked to one of a variety of nonproteinaceous polymers, e.g., polyethylene glycol (PEG), polypropylene glycol, polyoxyalkylenes, or copolymers of polyethylene glycol and polypropylene glycol. Additional amino acid modifications may be made to enable specific or non-specific chemical or post-translational modification of the immunoglobulins. Such modifications, include, but are not limited to PEGylation and glycosylation. Specific substitutions that can be utilized to enable PEGylation include, but are not limited to, introduction of novel cysteine residues or unnatural amino acids such that efficient and specific coupling chemistries can be used to attach a PEG or otherwise polymeric moiety. Introduction of specific glycosylation sites can be achieved by introducing novel N-X-T/S sequences into the immunoglobulins disclosed herein.

Modifications to reduce immunogenicity may include modifications that reduce binding of processed peptides derived from the parent sequence to MHC proteins. For example, amino acid modifications would be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an antibody disclosed herein. See for example U.S. Ser. No. 09/903,378, U.S. Ser. No. 10/754,296, U.S. Ser. No. 11/249,692, and references cited therein, all expressly incorporated by reference.

In some embodiments, immunoglobulins disclosed herein may be combined with immunoglobulins that alter FcRn binding. Such variants may provide improved pharmacokinetic properties to the immunoglobulins. Preferred variants that increase binding to FcRn and/or improve pharmacokinetic properties include but are not limited to substitutions at positions 259, 308, 428, and 434, including but not limited to for example 259I, 308F, 428L, 428M, 434S, 434H, 434F, 434Y, and 434M (PCT/US2008/088053, filed Dec. 22, 2008, entitled "Fc Variants with Altered Binding to FcRn", entirely incorporated by reference). Other variants that increase Fc binding to FcRn include but are not limited to: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 286A, 305A, 307A, 311A, 312A, 376A, 378Q, 380A, 382A, 434A (Shields et al, Journal of Biological Chemistry, 2001, 276(9):6591-6604, entirely incorporated by reference), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/434F/436H, 308T/309P/311 S (Dall Acqua et al. Journal of Immunology, 2002, 169:5171-5180, Dall'Acqua et al., 2006, The Journal of biological chemistry 281:23514-23524, entirely incorporated by reference).

Covalent modifications of antibodies are included within the scope of immunoglobulins disclosed herein, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

In some embodiments, the covalent modification of the antibodies disclosed herein comprises the addition of one or more labels. The term "labeling group" means any detectable label. In some embodiments, the labeling group is coupled to the antibody via spacer arms of various lengths to reduce potential steric hindrance. Various methods for labeling proteins are known in the art and may be used in generating immunoglobulins disclosed herein.

Antibody-Drug Conjugates

In some embodiments, the multispecific antibodies of the invention are conjugated with drugs to form antibody-drug conjugates (ADCs). In general, ADCs are used in oncology applications, where the use of antibody-drug conjugates for the local delivery of cytotoxic or cytostatic agents allows for the targeted delivery of the drug moiety to tumors, which can allow higher efficacy, lower toxicity, etc. An overview of this technology is provided in Ducry et al., Bioconjugate Chem., 21:5-13 (2010), Carter et al., Cancer J. 14(3):154 (2008) and Senter, Current Opin. Chem. Biol. 13:235-244 (2009), all of which are hereby incorporated by reference in their entirety.

Thus the invention provides multispecific antibodies conjugated to drugs. Generally, conjugation is done by covalent attachment to the antibody, as further described below, and generally relies on a linker, often a peptide linkage (which, as described below, may be designed to be sensitive to cleavage by proteases at the target site or not). In addition, as described above, linkage of the linker-drug unit (LU-D) can be done by attachment to cysteines within the antibody. As will be appreciated by those in the art, the number of drug moieties per antibody can change, depending on the conditions of the reaction, and can vary from 1:1 to 10:1 drug:antibody. As will be appreciated by those in the art, the actual number is an average.

Thus the invention provides multispecific antibodies conjugated to drugs. As described below, the drug of the ADC can be any number of agents, including but not limited to cytotoxic agents such as chemotherapeutic agents, growth inhibitory agents, toxins (for example, an enzymatically active toxin of bacterial, fungal, plant, or animal origin, or fragments thereof), or a radioactive isotope (that is, a radioconjugate) are provided. In other embodiments, the invention further provides methods of using the ADCs.

Drugs for use in the present invention include cytotoxic drugs, particularly those which are used for cancer therapy. Such drugs include, in general, DNA damaging agents, anti-metabolites, natural products and their analogs. Exemplary classes of cytotoxic agents include the enzyme inhibitors such as dihydrofolate reductase inhibitors, and thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, dolastatins, maytansinoids, differentiation inducers, and taxols.

Members of these classes include, for example, methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, caminomycin, aminopterin, tallysomycin, podophyllotoxin and podophyllotoxin derivatives such as etoposide or etoposide phosphate, vinblastine, vincristine, vindesine, taxanes including taxol, taxotere retinoic acid, butyric acid, N8-acetyl spermidine, camptothecin, calicheamicin, esperamicin, ene-diynes, duocarmycin A, duocarmycin SA, calicheamicin, camptothecin, maytansinoids (including DM1), monomethylauristatin E (MMAE), monomethylauristatin F (MMAF), and maytansinoids (DM4) and their analogues.

Toxins may be used as antibody-toxin conjugates and include bacterial toxins such as diphtheria toxin, plant toxins such as ricin, small molecule toxins such as geldanamycin (Mandler et al (2000) J. Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). Toxins may exert their cytotoxic and cytostatic effects by mechanisms including tubulin binding, DNA binding, or topoisomerase inhibition.

Conjugates of a multispecific antibody and one or more small molecule toxins, such as a maytansinoids, dolastatins, auristatins, a trichothecene, calicheamicin, and CC1065, and the derivatives of these toxins that have toxin activity, are contemplated.

Maytansinoids

Maytansine compounds suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. As described below, drugs may be modified by the incorporation of a functionally active group such as a thiol or amine group for conjugation to the antibody.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides) and those having modifications at other positions Exemplary maytansinoid drug moieties also include those having modifications such as: C-9-SH (U.S. Pat. No. 4,424,219) (prepared by the reaction of maytansinol with H2S or P2S5); C-14-alkoxymethyl(demethoxy/CH2OR) (U.S. Pat. No. 4,331,598); C-14-hydroxymethyl or acyloxymethyl (CH2OH or CH2OAc) (U.S. Pat. No. 4,450,254) (prepared from Nocardia); C-15-hydroxy/acyloxy (U.S. Pat. No. 4,364,866) (prepared by the conversion of maytansinol by Streptomyces); C-15-methoxy (U.S. Pat. Nos. 4,313,946 and 4,315,929) (isolated from Trewia nudiflora); C-18-N-demethyl (U.S. Pat. Nos. 4,362,663 and 4,322,348) (prepared by the demethylation of maytansinol by Streptomyces); and 4,5-deoxy (U.S. Pat. No. 4,371,533) (prepared by the titanium trichloride/LAH reduction of maytansinol).

Of particular use are DM1 (disclosed in U.S. Pat. No. 5,208,020, incorporated by reference) and DM4 (disclosed in U.S. Pat. No. 7,276,497, incorporated by reference). See also a number of additional maytansinoid derivatives and methods in U.S. Pat. No. 5,416,064, WO/01/24763, U.S. Pat. Nos. 7,303,749, 7,601,354, U.S. Ser. No. 12/631,508, WO02/098883, U.S. Pat. Nos. 6,441,163, 7,368,565, WO02/16368 and WO04/1033272, all of which are expressly incorporated by reference in their entirety.

ADCs containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference. Liu et al., Proc. Natl. Acad. Sci. USA 93:8618-8623 (1996) described ADCs comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Chari et al., Cancer Research 52:127-131 (1992) describe ADCs in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses 3×105 HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Auristatins and Dolastatins

In some embodiments, the ADC comprises a multispecific antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Senter et al, Proceedings of the American Association for Cancer Research, Volume 45, Abstract Number 623, presented Mar. 28, 2004 and described in United States Patent Publication No. 2005/0238648, the disclosure of which is expressly incorporated by reference in its entirety.

An exemplary auristatin embodiment is MMAE (see U.S. Pat. No. 6,884,869 expressly incorporated by reference in its entirety).

Another exemplary auristatin embodiment is MMAF (see US 2005/0238649, U.S. Pat. Nos. 5,767,237 and 6,124,431, expressly incorporated by reference in their entirety).

Additional exemplary embodiments comprising MMAE or MMAF and various linker components (described further herein) have the following structures and abbreviations (wherein Ab means antibody and p is 1 to about 8):

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lubke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat Biotechnol 21(7):778-784.

Calicheamicin

In other embodiments, the ADC comprises an antibody of the invention conjugated to one or more calicheamicin molecules. For example, Mylotarg is the first commercial ADC drug and utilizes calicheamicin γ1 as the payload (see U.S. Pat. No. 4,970,198, incorporated by reference in its entirety). Additional calicheamicin derivatives are described in U.S. Pat. Nos. 5,264,586, 5,384,412, 5,550,246, 5,739,116, 5,773,001, 5,767,285 and 5,877,296, all expressly incorporated by reference. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, γ1I, α2I, α2I, N-acetyl-γ1I, PSAG and θI1 (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Duocarmycins

CC-1065 (see U.S. Pat. No. 4,169,888, incorporated by reference) and duocarmycins are members of a family of antitumor antibiotics utilized in ADCs. These antibiotics appear to work through sequence-selectively alkylating DNA at the N3 of adenine in the minor groove, which initiates a cascade of events that result in apoptosis.

Important members of the duocarmycins include duocarmycin A (U.S. Pat. No. 4,923,990, incorporated by reference) and duocarmycin SA (U.S. Pat. No. 5,101,038, incorporated by reference), and a large number of analogues as described in U.S. Pat. Nos. 7,517,903, 7,691,962, 5,101,038;

5,641,780; 5,187,186; 5,070,092; 5,070,092; 5,641,780; 5,101,038; 5,084,468, 5,475,092, 5,585,499, 5,846,545, WO2007/089149, WO2009/017394A1, U.S. Pat. Nos. 5,703,080, 6,989,452, 7,087,600, 7,129,261, 7,498,302, and 7,507,420, all of which are expressly incorporated by reference.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an ADC formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include At211, I131, I125, Y90, Re186, Re188, Sm153, Bi212, P32, Pb212 and radioactive isotopes of Lu.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as Tc99m or I123, Re186, Re188 and In111 can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate Iodine-123. "Monoclonal Antibodies in Immunoscintigraphy" (Chatal, CRC Press 1989) describes other methods in detail.

For compositions comprising a plurality of antibodies, the drug loading is represented by p, the average number of drug molecules per Antibody. Drug loading may range from 1 to 20 drugs (D) per Antibody. The average number of drugs per antibody in preparation of conjugation reactions may be characterized by conventional means such as mass spectroscopy, ELISA assay, and HPLC. The quantitative distribution of Antibody-Drug-Conjugates in terms of p may also be determined.

In some instances, separation, purification, and characterization of homogeneous Antibody-Drug-conjugates where p is a certain value from Antibody-Drug-Conjugates with other drug loadings may be achieved by means such as reverse phase HPLC or electrophoresis. In exemplary embodiments, p is 2, 3, 4, 5, 6, 7, or 8 or a fraction thereof.

The generation of Antibody-drug conjugate compounds can be accomplished by any technique known to the skilled artisan. Briefly, the Antibody-drug conjugate compounds can include a multispecific antibody as the Antibody unit, a drug, and optionally a linker that joins the drug and the binding agent.

A number of different reactions are available for covalent attachment of drugs and/or linkers to binding agents. This is can be accomplished by reaction of the amino acid residues of the binding agent, for example, antibody molecule, including the amine groups of lysine, the free carboxylic acid groups of glutamic and aspartic acid, the sulfhydryl groups of cysteine and the various moieties of the aromatic amino acids. A commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule.

Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates can also be used as coupling agents for covalently attaching drugs to binding agents. Other techniques are known to the skilled artisan and within the scope of the present invention.

In some embodiments, an intermediate, which is the precursor of the linker, is reacted with the drug under appropriate conditions. In other embodiments, reactive groups are used on the drug and/or the intermediate. The product of the reaction between the drug and the intermediate, or the derivatized drug, is subsequently reacted with a multispecific antibody of the invention under appropriate conditions.

It will be understood that chemical modifications may also be made to the desired compound in order to make reactions of that compound more convenient for purposes of preparing conjugates of the invention. For example a functional group e.g. amine, hydroxyl, or sulfhydryl, may be appended to the drug at a position which has minimal or an acceptable effect on the activity or other properties of the drug Linker Units Typically, the antibody-drug conjugate compounds comprise a Linker unit between the drug unit and the antibody unit. In some embodiments, the linker is cleavable under intracellular or extracellular conditions, such that cleavage of the linker releases the drug unit from the antibody in the appropriate environment. For example, solid tumors that secrete certain proteases may serve as the target of the cleavable linker; in other embodiments, it is the intracellular proteases that are utilized. In yet other embodiments, the linker unit is not cleavable and the drug is released, for example, by antibody degradation in lysosomes.

In some embodiments, the linker is cleavable by a cleaving agent that is present in the intracellular environment (for example, within a lysosome or endosome or caveolea). The linker can be, for example, a peptidyl linker that is cleaved by an intracellular peptidase or protease enzyme, including, but not limited to, a lysosomal or endosomal protease. In some embodiments, the peptidyl linker is at least two amino acids long or at least three amino acids long or more.

Cleaving agents can include, without limitation, cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Peptidyl linkers that are cleavable by enzymes that are present in CD38-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker (SEQ ID NO: 96)). Other examples of such linkers are described, e.g., in U.S. Pat. No. 6,214,345, incorporated herein by reference in its entirety and for all purposes.

In some embodiments, the peptidyl linker cleavable by an intracellular protease is a Val-Cit linker or a Phe-Lys linker (see, e.g., U.S. Pat. No. 6,214,345, which describes the synthesis of doxorubicin with the val-cit linker).

In other embodiments, the cleavable linker is pH-sensitive, that is, sensitive to hydrolysis at certain pH values. Typically, the pH-sensitive linker hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) may be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (for example, a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

In other embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker unit is not cleavable and the drug is released by antibody degradation. (See U.S. Publication No. 2005/0238649 incorporated by reference herein in its entirety and for all purposes).

In many embodiments, the linker is self-immolative. As used herein, the term "self-immolative Spacer" refers to a bifunctional chemical moiety that is capable of covalently linking together two spaced chemical moieties into a stable tripartite molecule. It will spontaneously separate from the second chemical moiety if its bond to the first moiety is cleaved. See for example, WO 2007059404A2, WO06110476A2, WO05112919A2, WO2010/062171, WO09/017394, WO07/089149, WO 07/018431, WO04/043493 and WO02/083180, which are directed to drug-cleavable substrate conjugates where the drug and cleavable substrate are optionally linked through a self-immolative linker and which are all expressly incorporated by reference.

Often the linker is not substantially sensitive to the extracellular environment. As used herein, "not substantially sensitive to the extracellular environment," in the context of a linker, means that no more than about 20%, 15%, 10%, 5%, 3%, or no more than about 1% of the linkers, in a sample of antibody-drug conjugate compound, are cleaved when the antibody-drug conjugate compound presents in an extracellular environment (for example, in plasma).

Whether a linker is not substantially sensitive to the extracellular environment can be determined, for example, by incubating with plasma the antibody-drug conjugate compound for a predetermined time period (for example, 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent (that is, in the milieu of the linker-therapeutic agent moiety of the antibody-drug conjugate compound as described herein). In yet other embodiments, the linker promotes cellular internalization when conjugated to both the auristatin compound and the multispecific antibodies of the invention.

A variety of exemplary linkers that can be used with the present compositions and methods are described in WO 2004-010957, U.S. Publication No. 2006/0074008, U.S. Publication No. 20050238649, and U.S. Publication No. 2006/0024317 (each of which is incorporated by reference herein in its entirety and for all purposes).

Drug Loading

Drug loading is represented by p and is the average number of Drug moieties per antibody in a molecule. Drug loading ("p") may be 1, 2, 3, 4, 5, 6, 7, 8, 9, 10, 11, 12, 13, 14, 15, 16, 17, 18, 19, 20 or more moieties (D) per antibody, although frequently the average number is a fraction or a decimal. Generally, drug loading of from 1 to 4 is frequently useful, and from 1 to 2 is also useful. ADCs of the invention include collections of antibodies conjugated with a range of drug moieties, from 1 to 20. The average number of drug moieties per antibody in preparations of ADC from conjugation reactions may be characterized by conventional means such as mass spectroscopy and, ELISA assay.

The quantitative distribution of ADC in terms of p may also be determined. In some instances, separation, purification, and characterization of homogeneous ADC where p is a certain value from ADC with other drug loadings may be achieved by means such as electrophoresis.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the drug loading for an ADC of the invention ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. Indeed, it has been shown that for certain ADCs, the optimal ratio of drug moieties per antibody may be less than 8, and may be about 2 to about 5. See US 2005-0238649 A1 (herein incorporated by reference in its entirety).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety;

indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments (such as thioMab or thioFab prepared as disclosed herein and in WO2006/034488 (herein incorporated by reference in its entirety)).

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography.

In some embodiments, a homogeneous ADC with a single loading value may be isolated from the conjugation mixture by electrophoresis or chromatography.

Methods of Determining Cytotoxic Effect of ADCs

Methods of determining whether a Drug or Antibody-Drug conjugate exerts a cytostatic and/or cytotoxic effect on a cell are known. Generally, the cytotoxic or cytostatic activity of an Antibody Drug conjugate can be measured by: exposing mammalian cells expressing a target protein of the Antibody Drug conjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the Antibody Drug conjugate.

For determining whether an Antibody Drug conjugate exerts a cytostatic effect, a thymidine incorporation assay may be used. For example, cancer cells expressing a target antigen at a density of 5,000 cells/well of a 96-well plated can be cultured for a 72-hour period and exposed to 0.5 µCi of 3H-thymidine during the final 8 hours of the 72-hour period. The incorporation of 3H-thymidine into cells of the culture is measured in the presence and absence of the Antibody Drug conjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that an Antibody Drug conjugate is useful in the treatment of cancers.

Cell viability can be measured by determining in a cell the uptake of a dye such as neutral red, trypan blue, or ALAMAR™ blue (see, e.g., Page et al., 1993, Intl. J. Oncology 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990, J. Natl. Cancer Inst. 82:1107-12).

Alternatively, a tetrazolium salt, such as MTT, is used in a quantitative colorimetric assay for mammalian cell survival and proliferation by detecting living, but not dead, cells (see, e.g., Mosmann, 1983, J. Immunol. Methods 65:55-63).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al. eds., 1992, pp. 3.17.1-3.17.16). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza et al., 1995, Cancer Research 55:3110-16).

In vivo, the effect of a therapeutic composition of the multispecific antibody of the invention can be evaluated in a suitable animal model. For example, xenogenic cancer models can be used, wherein cancer explants or passaged xenograft tissues are introduced into immune compromised animals, such as nude or SCID mice (Klein et al., 1997, Nature Medicine 3: 402-408). Efficacy can be measured using assays that measure inhibition of tumor formation, tumor regression or metastasis, and the like.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16th Edition, A. Osal., Ed., 1980).

Conjugates

In one embodiment, the molecules disclosed herein are antibody "fusion proteins", sometimes referred to herein as "antibody conjugates". The fusion partner or conjugate partner can be proteinaceous or non-proteinaceous; the latter generally being generated using functional groups on the antibody and on the conjugate partner. Conjugate and fusion partners may be any molecule, including small molecule chemical compounds and polypeptides. For example, a variety of antibody conjugates and methods are described in Trail et al., 1999, Curr. Opin. Immunol. 11:584-588, incorporated entirely by reference. Possible conjugate partners include but are not limited to cytokines, cytotoxic agents, toxins, radioisotopes, chemotherapeutic agent, anti-angiogenic agents, a tyrosine kinase inhibitors, and other therapeutically active agents. In some embodiments, conjugate partners may be thought of more as payloads, that is to say that the goal of a conjugate is targeted delivery of the conjugate partner to a targeted cell, for example a cancer cell or immune cell, by the immunoglobulin. Thus, for example, the conjugation of a toxin to an immunoglobulin targets the delivery of said toxin to cells expressing the target antigen. As will be appreciated by one skilled in the art, in reality the concepts and definitions of fusion and conjugate are overlapping. The designation of a fusion or conjugate is not meant to constrain it to any particular embodiment disclosed herein. Rather, these terms are used loosely to convey the broad concept that any immunoglobulin disclosed herein may be linked genetically, chemically, or otherwise, to one or more polypeptides or molecules to provide some desirable property.

Suitable conjugates include, but are not limited to, labels as described below, drugs and cytotoxic agents including, but not limited to, cytotoxic drugs (e.g., chemotherapeutic agents) or toxins or active fragments of such toxins. Suitable toxins and their corresponding fragments include diphtheria A chain, exotoxin A chain, ricin A chain, abrin A chain, curcin, crotin, phenomycin, enomycin and the like. Cytotoxic agents also include radiochemicals made by conjugating radioisotopes to antibodies, or binding of a radionuclide to a chelating agent that has been covalently attached to the antibody. Additional embodiments utilize calicheamicin, auristatins, geldanamycin, maytansine, and duocarmycins and analogs.

In one embodiment, the molecules disclosed herein are fused or conjugated to a cytokine. By "cytokine" as used herein is meant a generic term for proteins released by one cell population that act on another cell as intercellular mediators. For example, as described in Penichet et al., 2001, J. Immunol. Methods 248:91-101, incorporated entirely by reference, cytokines may be fused to antibody to provide an array of desirable properties. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; C5a; and other polypeptide factors including LIF and kit ligand (KL). As used herein, the term cytokine includes proteins from natural sources or from recombinant cell culture, and biologically active equivalents of the native sequence cytokines.

In yet another embodiment, an molecules disclosed herein may be conjugated to a "receptor" (such streptavidin) for utilization in tumor pretargeting wherein the immunoglobulin-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the immunoglobulin is conjugated or operably linked to an enzyme in order to employ Antibody Dependent Enzyme Mediated Prodrug Therapy (ADEPT). ADEPT may be used by conjugating or operably linking the immunoglobulin to a prodrug-activating enzyme that converts a prodrug (e.g. a peptidyl chemotherapeutic agent.

When immunoglobulin partners are used as conjugates, conjugate partners may be linked to any region of an immunoglobulin disclosed herein, including at the N- or C-termini, or at some residue in-between the termini. A variety of linkers may find use in immunoglobulins disclosed herein to covalently link conjugate partners to an immunoglobulin. By "linker", "linker sequence", "spacer", "tethering sequence" or grammatical equivalents thereof, herein is meant a molecule or group of molecules (such as a monomer or polymer) that connects two molecules and often serves to place the two molecules in one configuration. Linkers are known in the art; for example, homo- or heterobifunctional linkers as are well known (see, 1994 Pierce Chemical Company catalog, technical section on cross-linkers, pages 155-200, incorporated entirely by reference). A number of strategies may be used to covalently link molecules together. These include, but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 50 amino acid residues. In one embodiment, the linker is from about 1 to 30 amino acids in length, e.g., a linker may be 1 to 20 amino acids in length. Useful linkers include glycine-serine polymers (including, for example, (GS)n, (GSGGS)n (Set forth as SEQ ID NO:1), (GGGGS)n (Set forth as SEQ ID NO:2) and (GGGS)n (Set forth as SEQ ID NO:3), where n is an integer of at least one), glycine-alanine polymers, alanine-serine polymers, and other flexible linkers, as will be appreciated by those in the art. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers.

Production

Also disclosed herein are methods for producing and experimentally testing the antibodies used in the methods described herein. The disclosed methods are not meant to constrain embodiments to any particular application or theory of operation. Rather, the provided methods are meant to illustrate generally that one or more immunoglobulins may be produced and experimentally tested to obtain immunoglobulins. General methods for antibody molecular biology, expression, purification, and screening are described in Antibody Engineering, edited by Duebel & Kontermann, Springer-Verlag, Heidelberg, 2001; and Hayhurst & Georgiou, 2001, Curr Opin Chem Biol 5:683-689; Maynard & Georgiou, 2000, Annu Rev Biomed Eng 2:339-76; Antibodies: A Laboratory Manual by Harlow & Lane, New York: Cold Spring Harbor Laboratory Press, 1988, all incorporated entirely by reference.

In one embodiment disclosed herein, nucleic acids are created that encode the molecules, and that may then be cloned into host cells, expressed and assayed, if desired. Thus, nucleic acids, and particularly DNA, may be made that encode each protein sequence. These practices are carried out using well-known procedures. For example, a variety of methods that may find use in generating immunoglobulins disclosed herein are described in Molecular Cloning—A Laboratory Manual, 3rd Ed. (Maniatis, Cold Spring Harbor Laboratory Press, New York, 2001), and Current Protocols in Molecular Biology (John Wiley & Sons), both incorporated entirely by reference. As will be appreciated by those skilled in the art, the generation of exact sequences for a library comprising a large number of sequences is potentially expensive and time consuming. By "library" herein is meant a set of variants in any form, including but not limited to a list of nucleic acid or amino acid sequences, a list of nucleic acid or amino acid substitutions at variable positions, a physical library comprising nucleic acids that encode the library sequences, or a physical library comprising the variant proteins, either in purified or unpurified form. Accordingly, there are a variety of techniques that may be used to efficiently generate libraries disclosed herein. Such methods include but are not limited to gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in for generating nucleic acids that encode immunoglobulins.

The molecules disclosed herein may be produced by culturing a host cell transformed with nucleic acid, e.g., an expression vector, containing nucleic acid encoding the molecules, under the appropriate conditions to induce or cause expression of the protein. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, and yeast. For example, a variety of cell lines that may find use in generating immunoglobulins disclosed herein are described in the ATCC® cell line catalog, available from the American Type Culture Collection.

In one embodiment, the molecules are expressed in mammalian expression systems, including systems in which the expression constructs are introduced into the mammalian cells using virus such as retrovirus or adenovirus. Any mammalian cells may be used, e.g., human, mouse, rat, hamster, and primate cells. Suitable cells also include known research cells, including but not limited to Jurkat T cells, NIH3T3, CHO, BHK, COS, HEK293, PER C.6, HeLa, Sp2/0, NS0 cells and variants thereof. In an alternate embodiment, library proteins are expressed in bacterial cells. Bacterial expression systems are well known in the art, and include Escherichia coli (E. coli), Bacillus subtilis, Streptococcus cremoris, and Streptococcus lividans. In alternate embodiments, immunoglobulins are produced in insect cells (e.g. Sf21/Sf9, Trichoplusia ni Bti-Tn5b1-4) or yeast cells (e.g. S. cerevisiae, Pichia, etc). In an alternate embodiment, molecules are expressed in vitro using cell free translation systems. In vitro translation systems derived from both prokaryotic (e.g. E. coli) and eukaryotic (e.g. wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the immunoglobulins may be produced by chemical synthesis methods. Also transgenic expression systems both animal (e.g. cow, sheep or goat milk, embryonated hen's eggs, whole insect larvae, etc.) and plant (e.g. corn, tobacco, duckweed, etc.)

The nucleic acids that encode the molecules disclosed herein may be incorporated into an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which find use in generating immunoglobulins disclosed herein include but are not limited to those which enable protein expression in mammalian cells, bacteria, insect cells, yeast, and in in vitro systems. As is known in the art, a variety of expression vectors are available, commercially or otherwise, that may find use for expressing molecules disclosed herein.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the molecule, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

molecules may be operably linked to a fusion partner to enable targeting of the expressed protein, purification, screening, display, and the like. Fusion partners may be linked to the immunoglobulin sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS. A fusion partner may be a targeting or signal sequence that directs immunoglobulin and any associated fusion partners to a desired cellular location or to the extracellular media. As is known in the art, certain signaling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example H6 and H10 or other tags for use with Immobilized Metal Affinity Chromatography (IMAC) systems (e.g. Ni+2 affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both. For example, an immunoglobulin may be purified using a His-tag by immobilizing it to a Ni+2 affinity column, and then after purification the same His-tag may be used to immobilize the antibody to a Ni+2 coated plate to perform an ELISA or other binding assay (as described below). A fusion partner may enable the use of a selection method to screen immunoglobulins (see below). Fusion partners that enable a variety of selection methods are well-known in the art. For example, by fusing the members of an immunoglobulin library to the gene III protein, phage display can be employed (Kay et al., Phage display of peptides and proteins: a laboratory manual, Academic Press, San Diego, Calif., 1996; Lowman et al., 1991, Biochemistry 30:10832-10838; Smith, 1985, Science 228:1315-1317, incorporated entirely by reference). Fusion partners may enable immunoglobulins to be labeled. Alternatively, a fusion partner may bind to a specific sequence on the expression vector, enabling the fusion partner and associated immunoglobulin to be linked covalently or noncovalently with the nucleic acid that encodes them. The methods of introducing exogenous nucleic acid into host cells are well known in the art, and will vary with the host cell used. Techniques include but are not limited to dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

In one embodiment, molecules are purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use for purification of immunoglobulins disclosed herein. For example, the bacterial proteins A and G bind to the Fc region. Likewise, the bacterial protein L binds to the Fab region of some antibodies, as of course does the antibody's target antigen. Purification can often be enabled by a particular fusion partner. For example, immunoglobulins may be purified using glutathione resin if a GST fusion is employed, Ni+2 affinity chromatography if a His-tag is employed, or immobilized anti-flag antibody if a flag-tag is used. For general guidance in suitable purification techniques, see, e.g. incorporated entirely by reference Protein Purification: Principles and Practice, 3rd Ed., Scopes, Springer-Verlag, NY, 1994, incorporated entirely by reference. The degree of purification necessary will vary depending on the screen or use of the immunoglobulins. In some instances no purification is necessary. For example in one embodiment, if the immunoglobulins are secreted, screening may take place directly from the media. As is well known in the art, some methods of selection do not involve purification of proteins. Thus, for example, if a library of immunoglobulins is made into a phage display library, protein purification may not be performed.

In Vitro Experimentation molecules may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label. The use of fusion partners has been discussed above. By "labeled" herein is meant that the immunoglobulins disclosed herein have one or more elements, isotopes, or chemical compounds attached to enable the detection in a screen. In general, labels fall into three classes: a) immune labels, which may be an epitope incorporated as a fusion partner that is recognized by an antibody, b) isotopic labels, which may be radioactive or heavy isotopes, and c) small molecule labels, which may include fluorescent and colorimetric dyes, or molecules such as biotin that enable other labeling methods. Labels may be incorporated into the compound at any position and may be incorporated in vitro or in vivo during protein expression.

In one embodiment, the functional and/or biophysical properties of molecules are screened in an in vitro assay. In vitro assays may allow a broad dynamic range for screening properties of interest. Properties that may be screened include but are not limited to stability, solubility, and affinity for Fc ligands, for example FcγRs. Multiple properties may be screened simultaneously or individually. Proteins may be purified or unpurified, depending on the requirements of the assay. In one embodiment, the screen is a qualitative or quantitative binding assay for binding of molecules to a protein or nonprotein molecule that is known or thought to bind the molecule. In one embodiment, the screen is a binding assay for measuring binding to the target antigen. In an alternate embodiment, the screen is an assay for binding of molecules to an Fc ligand, including but are not limited to the family of FcγRs, the neonatal receptor FcRn, the complement protein C1q, and the bacterial proteins A and G. Said Fc ligands may be from any organism. In one embodiment, Fc ligands are from humans, mice, rats, rabbits, and/or monkeys. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration. These and other methods may take advantage of some fusion partner or label of the immunoglobulin. Assays may employ a variety of detection methods including but not limited to chromogenic, fluorescent, luminescent, or isotopic labels.

The biophysical properties of molecules, for example stability and solubility, may be tested using a variety of methods known in the art. Protein stability may be determined by measuring the thermodynamic equilibrium between folded and unfolded states. For example, molecules disclosed herein may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of an molecule may be quantitatively or qualitatively determined using a wide range of methods that are known in the art. Methods which may find use for characterizing the biophysical properties of molecules disclosed herein include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising an immunoglobulin could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the molecule's stability and solubility.

In one embodiment, molecules may be tested using one or more cell-based or in vitro assays. For such assays, immunoglobulins, purified or unpurified, are typically added exogenously such that cells are exposed to individual variants or groups of variants belonging to a library. These assays are typically, but not always, based on the biology of the ability of the immunoglobulin to bind to the target antigen and mediate some biochemical event, for example effector functions like cellular lysis, phagocytosis, ligand/receptor binding inhibition, inhibition of growth and/or proliferation, apoptosis and the like. Such assays often involve monitoring the response of cells to immunoglobulin, for example cell survival, cell death, cellular phagocytosis, cell lysis, change in cellular morphology, or transcriptional activation such as cellular expression of a natural gene or reporter gene. For example, such assays may measure the ability of molecules to elicit ADCC, ADCP, or CDC. For some assays additional cells or components, that is in addition to the target cells, may need to be added, for example serum complement, or effector cells such as peripheral blood monocytes (PBMCs), NK cells, macrophages, and the like. Such additional cells may be from any organism, e.g., humans, mice, rat, rabbit, and monkey. Cross-linked or monomeric antibodies may cause apoptosis of certain cell lines expressing the antibody's target antigen, or they may mediate attack on target cells by immune cells which have been added to the assay. Methods for monitoring cell death or viability are known in the art, and include the use of dyes, fluorophores, immunochemical, cytochemical, and radioactive reagents. For example, caspase assays or annexin-flourconjugates may enable apoptosis to be measured, and uptake or release of radioactive substrates (e.g. Chromium-51 release assays) or the metabolic reduction of fluorescent dyes such as alamar blue may enable cell growth, proliferation or activation to be monitored. In one embodiment, the DELFIA® EuTDA-based cytotoxicity assay (Perkin Elmer, MA) is used. Alternatively, dead or damaged target cells may be monitored by measuring the release of one or more natural intracellular proteins, for example lactate dehydrogenase. Transcriptional activation may also serve as a method for assaying function in cell-based assays. In this case, response may be monitored by assaying for natural genes or proteins which may be upregulated or down-regulated, for example the release of certain interleukins may be measured, or alternatively readout may be via a luciferase or GFP-reporter construct. Cell-based assays may also involve the measure of morphological changes of cells as a response to the presence of an immunoglobulin. Cell types for such assays may be prokaryotic or eukaryotic, and a variety of cell lines that are known in the art may be employed. Alternatively, cell-based screens are performed using cells that have been transformed or transfected with nucleic acids encoding the molecules.

In vitro assays include but are not limited to binding assays, ADCC, CDC, cytotoxicity, proliferation, peroxide/ozone release, chemotaxis of effector cells, inhibition of such assays by reduced effector function antibodies; ranges of activities such as >100× improvement or >100× reduction, blends of receptor activation and the assay outcomes that are expected from such receptor profiles.

In Vivo Experimentation

The biological properties of the molecules disclosed herein may be characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. Said animals may be referred to as disease models. With respect to the molecules disclosed herein, a particular challenge arises when using animal models to evaluate the potential for in-human efficacy of candidate polypeptides—this is due, at least in part, to the fact that molecules that have a specific effect on the affinity for a human Fc receptor may not have a similar affinity effect with the orthologous animal receptor. These problems can be further exacerbated by the inevitable ambiguities associated with correct assignment of true orthologues (Mechetina et al., Immunogenetics, 2002 54:463-468, incorporated entirely by reference), and the fact that some orthologues simply do not exist in the animal (e.g. humans possess an FcγRIIa whereas mice do not). Therapeutics are often tested in mice, including but not limited to mouse strains NZB, NOD, BXSB, MRL/lpr, K/BxN and transgenics (including knockins and knockouts). Such mice can develop various autoimmune conditions that resemble human organ specific, systemic autoimmune or inflammatory disease pathologies such as systemic lupus erythematosus (SLE) and rheumatoid arthritis (RA). For example, an immunoglobulin disclosed herein intended for autoimmune diseases may be tested in such mouse models by treating the mice to determine the ability of the immunoglobulin to reduce or inhibit the development of the disease pathology. Because of the incompatibility between the mouse and human Fcγ receptor system, an alternative approach is to use a murine SCID model in which immune deficient mice are engrafted with human PBLs or PBMCs (huPBL-SCID, huPBMC-SCID) providing a semi-functional human immune system with human effector cells and Fc receptors. In such a model, an antigen challenge (such as tetanus toxoid) activates the B cells to differentiate into plasma cells and secrete immunoglobulins, thus reconstituting antigen specific humoral immunity. Therefore, a dual targeting immunoglobulin disclosed herein that specifically binds to IgE and FcγRIIb on B cells may be tested to examine the ability to specifically inhibit B cell differentiation. Such experimentation may provide meaningful data for determination of the potential of said immunoglobulin to be used as a therapeutic. Other organisms, e.g., mammals, may also be used for testing. For example, because of their genetic similarity to humans, monkeys can be suitable therapeutic models, and thus may be used to test the efficacy, toxicity, pharmacokinetics, or other property of the immunoglobulins disclosed herein. Tests of the immunoglobulins disclosed herein in humans are ultimately required for approval as drugs, and thus of course these experiments are contemplated. Thus the immunoglobulins disclosed herein may be tested in humans to determine their therapeutic efficacy, toxicity, pharmacokinetics, and/or other clinical properties.

The molecules disclosed herein may confer superior performance on Fc-containing therapeutics in animal models or in humans. The receptor binding profiles of such immunoglobulins, as described in this specification, may, for example, be selected to increase the potency of cytotoxic drugs or to target specific effector functions or effector cells to improve the selectivity of the drug's action. Further, receptor binding profiles can be selected that may reduce some or all effector functions thereby reducing the side-effects or toxicity of such Fc-containing drug. For example, an immunoglobulin with reduced binding to FcγRIIIa, FcγRI and FcγRIIa can be selected to eliminate most cell-mediated effector function, or an immunoglobulin with reduced binding to C1q may be selected to limit complement-mediated effector functions. In some contexts, such effector functions are known to have potential toxic effects. Therefore eliminating them may increase the safety of the Fc-bearing drug and such improved safety may be characterized in animal models. In some contexts, such effector functions are known to mediate the desirable therapeutic activity. Therefore enhancing them may increase the activity or potency of the Fc-bearing drug and such improved activity or potency may be characterized in animal models.

In some embodiments, molecules disclosed herein may be assessed for efficacy in clinically relevant animal models of various human diseases. In many cases, relevant models include various transgenic animals for specific antigens and receptors.

Relevant transgenic models such as those that express human Fc receptors (e.g., CD32b) could be used to evaluate and test immunoglobulins and Fc-fusions in their efficacy. The evaluation of molecules by the introduction of human genes that directly or indirectly mediate effector function in mice or other rodents may enable physiological studies of efficacy in autoimmune disorders (including SLE, RA and MS). Human Fc receptors such as FcγRIIb may possess polymorphisms such as that in gene promoter (−343 from G to C) or transmembrane domain of the receptor 187 I or T which would further enable the introduction of specific and combinations of human polymorphisms into rodents. The various studies involving polymorphism-specific FcRs is not limited to this section, however encompasses all discussions and applications of FcRs in general as specified in throughout this application. Immunoglobulins disclosed herein may confer superior activity on Fc-containing drugs in such transgenic models, in particular variants with binding profiles optimized for human FcγRIIb mediated activity may show superior activity in transgenic CD32b mice. Similar improvements in efficacy in mice transgenic for the other human Fc receptors, e.g. FcγRIIa, FcγRI, etc., may be observed for molecules with binding profiles optimized for the respective receptors. Mice transgenic for multiple human receptors would show improved activity for immunoglobulins with binding profiles optimized for the corresponding multiple receptors.

Because of the difficulties and ambiguities associated with using animal models to characterize the potential efficacy of candidate therapeutic antibodies in a human patient, some variant polypeptides disclosed herein may find utility as proxies for assessing potential in-human efficacy. Such proxy molecules may mimic—in the animal system—the FcR and/or complement biology of a corresponding candidate human immunoglobulin. This mimicry is most likely to be manifested by relative association affinities between specific immunoglobulins and animal vs. human receptors. For example, if one were using a mouse model to assess the potential in-human efficacy of an Fc variant that has reduced affinity for the inhibitory human FcγRIIb, an appropriate proxy variant would have reduced affinity for mouse FcγRII. It should also be noted that the proxy Fc variants could be created in the context of a human Fc variant, an animal Fc variant, or both.

In one embodiment, the testing of molecules may include study of efficacy in primates (e.g. cynomolgus monkey model) to facilitate the evaluation of depletion of specific target cells harboring the target antigen. Additional primate models include but are not limited to use of the rhesus monkey to assess Fc polypeptides in therapeutic studies of autoimmune, transplantation and cancer.

Toxicity studies are performed to determine antibody or Fc-fusion related-effects that cannot be evaluated in standard pharmacology profiles, or occur only after repeated administration of the agent. Most toxicity tests are performed in two species—a rodent and a non-rodent—to ensure that any unexpected adverse effects are not overlooked before new therapeutic entities are introduced into man. In general, these models may measure a variety of toxicities including genotoxicity, chronic toxicity, immunogenicity, reproductive/developmental toxicity and carcinogenicity. Included within the aforementioned parameters are standard measurement of food consumption, bodyweight, antibody formation, clinical chemistry, and macro- and microscopic examination of standard organs/tissues (e.g. cardiotoxicity). Additional parameters of measurement are injection site trauma and the measurement of neutralizing antibodies, if any. Traditionally, monoclonal antibody therapeutics, naked or conjugated, are evaluated for cross-reactivity with normal tissues, immunogenicity/antibody production, conjugate or linker toxicity and "bystander" toxicity of radiolabelled species. Nonetheless, such studies may have to be individualized to address specific concerns and following the guidance set by ICH S6 (Safety studies for biotechnological products, also noted above). As such, the general principles are that the products are sufficiently well characterized, impurities/contaminants have been removed, that the test material is comparable throughout development, that GLP compliance is maintained.

The pharmacokinetics (PK) of the molecules disclosed herein may be studied in a variety of animal systems, with the most relevant being non-human primates such as the cynomolgus and rhesus monkeys. Single or repeated i.v./s.c. administrations over a dose range of 6000-fold (0.05-300 mg/kg) can be evaluated for half-life (days to weeks) using plasma concentration and clearance. Volume of distribution at a steady state and level of systemic absorbance can also be measured. Examples of such parameters of measurement generally include maximum observed plasma concentration (Cmax), the time to reach Cmax (Tmax), the area under the plasma concentration-time curve from time 0 to infinity [AUC(0-inf] and apparent elimination half-life (T½). Additional measured parameters could include compartmental analysis of concentration-time data obtained following i.v. administration and bioavailability.

The molecules disclosed herein may confer superior pharmacokinetics on Fc-containing therapeutics in animal systems or in humans. For example, increased binding to FcRn may increase the half-life and exposure of the Fc-containing drug. Alternatively, decreased binding to FcRn may decrease the half-life and exposure of the Fc-containing drug in cases where reduced exposure is favorable such as when such drug has side-effects.

It is known in the art that the array of Fc receptors is differentially expressed on various immune cell types, as well as in different tissues. Differential tissue distribution of Fc receptors may ultimately have an impact on the pharmacodynamic (PD) and pharmacokinetic (PK) properties of molecules disclosed herein. Because molecules of the present invention have varying affinities for the array of Fc receptors, further screening of the polypeptides for PD and/or PK properties may be extremely useful for defining the optimal balance of PD, PK, and therapeutic efficacy conferred by each candidate polypeptide.

Pharmacodynamic studies may include, but are not limited to, targeting specific cells or blocking signaling mechanisms, measuring inhibition of antigen-specific antibodies etc. The molecules disclosed herein may target particular effector cell populations and thereby direct Fc-containing drugs to induce certain activities to improve potency or to increase penetration into a particularly favorable physiological compartment. For example, neutrophil activity and localization can be targeted by an molecule that targets FcγRIIIb. Such pharmacodynamic effects may be demonstrated in animal models or in humans.

Use

Once made the molecules as described herein find use in a variety of methods. In a preferred embodiment the method includes contacting a cell that coexpresses IgE and FcγRIIb with a molecule such that both IgE and FcγRIIb are bound by the molecule and the cell is inhibited. By "inhibited" in this context is meant that the molecule is preventing or reducing activation and/or proliferation of IgE+ B cells.

The molecules disclosed herein may find use in a wide range of products. In one embodiment a molecule disclosed herein is a therapeutic, a diagnostic, or a research reagent. The molecules may find use in a composition that is monoclonal or polyclonal. The molecules disclosed herein may be used for therapeutic purposes. As will be appreciated by those in the art, the molecules disclosed herein may be used for any therapeutic purpose that antibodies, and the like may be used for. The molecules may be administered to a patient to treat disorders including but not limited to autoimmune and inflammatory diseases, infectious diseases, and cancer.

A "patient" for the purposes disclosed herein includes both humans and other animals, e.g., other mammals. Thus the molecules disclosed herein have both human therapy and veterinary applications. The term "treatment" or "treating" as disclosed herein is meant to include therapeutic treatment, as well as prophylactic, or suppressive measures for a disease or disorder. Thus, for example, successful administration of an molecule prior to onset of the disease results in treatment of the disease. As another example, successful administration of an optimized molecule after clinical manifestation of the disease to combat the symptoms of the disease comprises treatment of the disease. "Treatment" and "treating" also encompasses administration of an optimized immunoglobulin after the appearance of the disease in order to eradicate the disease. Successful administration of an agent after onset and after clinical symptoms have developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented.

In one embodiment, a molecule disclosed herein is administered to a patient having a disease involving inappropriate expression of a protein or other molecule. Within the scope disclosed herein this is meant to include diseases and disorders characterized by aberrant proteins, due for example to alterations in the amount of a protein present, protein localization, posttranslational modification, conformational state, the presence of a mutant or pathogen protein, etc. Similarly, the disease or disorder may be characterized by alterations molecules including but not limited to polysaccharides and gangliosides. An overabundance may be due to any cause, including but not limited to overexpression at the molecular level, prolonged or accumulated appearance at the site of action, or increased activity of a protein relative to normal. Included within this definition are diseases and disorders characterized by a reduction of a protein. This reduction may be due to any cause, including but not limited to reduced expression at the molecular level, shortened or reduced appearance at the site of action, mutant forms of a protein, or decreased activity of a protein relative to normal. Such an overabundance or reduction of a protein can be measured relative to normal expression, appearance, or activity of a protein, and said measurement may play an important role in the development and/or clinical testing of the immunoglobulins disclosed herein.

Disclosed herein are novel methods of treating IgE-mediated disorders, e.g., food and environmental allergies and allergic asthma. In preferred embodiments, allergic diseases that may be treated by the products and methods of the invention include allergic and atopic asthma, atopic dermatitis and eczema, allergic rhinitis, allergic conjunctivitis and rhinoconjunctivitis, allergic encephalomyelitis, allergic rhinitis, allergic vasculitis, and anaphylactic shock. Environmental and food allergies that may be treated include allergies to dustmite, cockroach, cat and other animals, pollen (including ragweed, Bermuda grass, Russian thistle, oak, rye, and others), molds and fungi (e.g., *Alternaria alternata, Aspergillus* and others), latex, insect stings (bee, wasp, and others), penicillin and other drugs, strawberries and other fruits and vegetables, peanuts, soy, and other legumes, walnuts and other treenuts, shellfish and other seafood, milk and other dairy products, wheat and other grains, and eggs. Indeed, any food allergen, aeroallergen, occupational allergen, or other IgE-mediated environmental allergen may be treated by a therapeutic amount of the products disclosed in this invention. For examples of common allergens, see Arbes et al., Prevalences of positive skin test responses to 10 common allergens in the US population: Results from the Third National Health and Nutrition Examination Survey, Clinical Gastroenterology 116(2), 377-383 (2005).

Also disclosed are diagnostic tests to identify patients who are likely to show a favorable clinical response to a molecule disclosed herein, or who are likely to exhibit a significantly better response when treated with an molecule disclosed herein versus one or more currently used therapeutics. Any of a number of methods for determining FcγR polymorphisms in humans known in the art may be used. Furthermore, also disclosed are prognostic tests performed on clinical samples such as blood and tissue samples. Such tests may assay for activity, regardless of mechanism. Such information may be used to identify patients for inclusion or exclusion in clinical trials, or to inform decisions regarding appropriate dosages and treatment regimens. Such information may also be used to select a drug that contains a particular molecule that shows superior activity in such assay.

Formulation

Pharmaceutical compositions are contemplated wherein an molecule disclosed herein and one or more therapeutically active agents are formulated. Formulations of the molecules disclosed herein are prepared for storage by mixing said immunoglobulin having the desired degree of purity with optional pharmaceutically acceptable carriers, excipients or stabilizers (Remington's Pharmaceutical Sciences 16th edition, Osol, A. Ed., 1980, incorporated entirely by reference), in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN™, PLURONICS™ or polyethylene glycol (PEG). In one embodiment, the pharmaceutical composition that comprises the immunoglobulin disclosed herein may be in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Some embodiments include at least one of the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration may be sterile. This is readily accomplished by filtration through sterile filtration membranes or other methods.

The molecules disclosed herein may also be formulated as immunoliposomes. A liposome is a small vesicle comprising various types of lipids, phospholipids and/or surfactant that is useful for delivery of a therapeutic agent to a mammal. Liposomes containing the immunoglobulin are prepared by methods known in the art. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The molecule and other therapeutically active agents may also be entrapped in microcapsules prepared by methods including but not limited to coacervation techniques, interfacial polymerization (for example using hydroxymethylcellulose or gelatin-microcapsules, or poly-(methylmethacylate) microcapsules), colloidal drug delivery systems (for example, liposomes, albumin microspheres, microemulsions, nano-particles and nanocapsules), and macroemulsions. Such techniques are disclosed in Remington's Pharmaceutical Sciences 16th edition, Osol, A. Ed., 1980, incorporated entirely by reference. Sustained-release preparations may be prepared. Suitable examples of sustained-release preparations include semipermeable matrices of solid hydrophobic polymer, which matrices are in the form of shaped articles, e.g. films, or microcapsules. Examples of sustained-release matrices include polyesters, hydrogels (for example poly(2-hydroxyethyl-methacrylate), or poly(vinylalcohol)), polylactides, copolymers of L-glutamic acid and gamma ethyl-L-glutamate, non-degradable ethylene-vinyl acetate, degradable lactic acid-glycolic acid copolymers such as the Lupron Depot® (which are injectable microspheres composed of lactic acid-glycolic acid copolymer and leuprolide acetate), poly-D-(−)-3-hydroxybutyric acid, and ProLease® (commercially available from Alkermes), which is a microsphere-based delivery system composed of the desired bioactive molecule incorporated into a matrix of poly-DL-lactide-co-glycolide (PLG).

Administration

Administration of the pharmaceutical composition comprising an molecule disclosed herein, e.g., in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. In some instances, for example for the treatment of wounds, inflammation, etc., the immunoglobulin may be directly applied as a solution or spray. As is known in the art, the pharmaceutical composition may be formulated accordingly depending upon the manner of introduction.

Subcutaneous administration may be used in circumstances where the patient may self-administer the pharmaceutical composition. Many protein therapeutics are not sufficiently potent to allow for formulation of a therapeutically effective dose in the maximum acceptable volume for subcutaneous administration. This problem may be addressed in part by the use of protein formulations comprising arginine-HCl, histidine, and polysorbate. Antibodies disclosed herein may be more amenable to subcutaneous administration due to, for example, increased potency, improved serum half-life, or enhanced solubility.

As is known in the art, protein therapeutics are often delivered by IV infusion or bolus. The antibodies disclosed herein may also be delivered using such methods. For example, administration may be by intravenous infusion with 0.9% sodium chloride as an infusion vehicle.

Pulmonary delivery may be accomplished using an inhaler or nebulizer and a formulation comprising an aerosolizing agent. For example, AERx® inhalable technology commercially available from Aradigm, or Inhance™ pulmonary delivery system commercially available from Nektar Therapeutics may be used. Antibodies disclosed herein may be more amenable to intrapulmonary delivery. FcRn is present in the lung, and may promote transport from the lung to the bloodstream (e.g. Syntonix WO 04004798, Bitonti et al. (2004) Proc. Nat. Acad. Sci. 101:9763-8, both incorporated entirely by reference). Accordingly, antibodies that bind FcRn more effectively in the lung or that are released more efficiently in the bloodstream may have improved bioavailability following intrapulmonary administration. Antibodies disclosed herein may also be more amenable to intrapulmonary administration due to, for example, improved solubility or altered isoelectric point.

Furthermore, molecules disclosed herein may be more amenable to oral delivery due to, for example, improved stability at gastric pH and increased resistance to proteolysis. Furthermore, FcRn appears to be expressed in the intestinal epithelia of adults, so antibodies disclosed herein with improved FcRn interaction profiles may show enhanced bioavailability following oral administration. FcRn mediated transport of antibodies may also occur at other mucus membranes such as those in the gastrointestinal, respiratory, and genital tracts.

In addition, any of a number of delivery systems are known in the art and may be used to administer the antibodies disclosed herein. Examples include, but are not limited to, encapsulation in liposomes, microparticles, microspheres (e.g., PLA/PGA microspheres), and the like. Alternatively, an implant of a porous, non-porous, or gelatinous material, including membranes or fibers, may be used. Sustained release systems may comprise a polymeric material or matrix such as polyesters, hydrogels, poly(vinylalcohol), polylactides, copolymers of L-glutamic acid and ethyl-L-glutamate, ethylene-vinyl acetate, lactic acid-glycolic acid copolymers such as the Lupron Depot®, and poly-D-(−)-3-hydroxybutyric acid. It is also possible to administer a nucleic acid encoding an immunoglobulin disclosed herein, for example by retroviral infection, direct injection, or coating with lipids, cell surface receptors, or other transfection agents. In all cases, controlled release systems may be used to release the immunoglobulin at or close to the desired location of action.

Dosing

The dosing amounts and frequencies of administration are, in one embodiment, selected to be therapeutically or prophylactically effective. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

The concentration of the therapeutically active molecule in the formulation may vary from about 0.1 to 100 weight %. In one embodiment, the concentration of the molecule is in the range of 0.003 to 1.0 molar. In order to treat a patient, a therapeutically effective dose of the immunoglobulin disclosed herein may be administered. By "therapeutically effective dose" herein is meant a dose that produces the effects for which it is administered. The exact dose will depend on the purpose of the treatment, and will be ascertainable by one skilled in the art using known techniques. Dosages may range from 0.0001 to 100 mg/kg of body weight or greater, for example 0.1, 1, 10, or 50 mg/kg of body weight. In one embodiment, dosages range from 1 to 10 mg/kg.

In some embodiments, only a single dose of the molecule is used. In other embodiments, multiple doses of the molecule are administered. The elapsed time between administrations may be less than 1 hour, about 1 hour, about 1-2 hours, about 2-3 hours, about 3-4 hours, about 6 hours, about 12 hours, about 24 hours, about 48 hours, about 2-4 days, about 4-6 days, about 1 week, about 2 weeks, or more than 2 weeks.

In other embodiments the molecules disclosed herein are administered in metronomic dosing regimes, either by continuous infusion or frequent administration without extended rest periods. Such metronomic administration may involve dosing at constant intervals without rest periods. Typically such regimens encompass chronic low-dose or continuous infusion for an extended period of time, for example 1-2 days, 1-2 weeks, 1-2 months, or up to 6 months or more. The use of lower doses may minimize side effects and the need for rest periods.

In certain embodiments the molecules disclosed herein and one or more other prophylactic or therapeutic agents are cyclically administered to the patient. Cycling therapy involves administration of a first agent at one time, a second agent at a second time, optionally additional agents at additional times, optionally a rest period, and then repeating this sequence of administration one or more times. The number of cycles is typically from 2-10. Cycling therapy may reduce the development of resistance to one or more agents, may minimize side effects, or may improve treatment efficacy.

Combination Therapies

The molecules disclosed herein may be administered concomitantly with one or more other therapeutic regimens or agents. Additional therapeutic regimes or agents may be used to treat the same disease, to treat an accompanying complication, or may be used to improve the efficacy or safety of the immunoglobulin Particularly preferred co-therapies include those that are approved or are being clinically evaluated for the treatment of IgE-mediated disorders such as allergies and asthma. In particular, the therapeutic compositions of the invention may be used in combination with anti-inflammatories such as corticosteroids, and/or brochodilators such as inhaled β2-agonists, the two major groups of medications. Inhaled corticosteroids include fluticasone, budesonide, flunisolide, mometasone, triamcinolone, and beclomethasone, whereas oral corticosteroids include prednisone, methylprednisolone, and prednisolone. Other steroids include glucocorticoids, dexamethasone, cortisone, hydroxycortisone, azulfidineicosanoids such as prostaglandins, thromboxanes, and leukotrienes, as well as topical steroids such as anthralin, calcipotriene, clobetasol, and tazarotene. Bronchodilators increase the diameter of the air passages and ease the flow to and from the lungs. Brochodilators that may be combined with the therapies of the invention include short-acting bronchodilators such as metaproterenol, ephedrine, terbutaline, and albuterol, and long-acting bronchodilators such as salmeterol, metaproterenol, and theophylline.

The therapies of the invention may be combined with non-steroidal anti-inflammatory drugs (NSAIDs) such as asprin, ibuprofen, celecoxib, diclofenac, etodolac, fenoprofen, indomethacin, ketorolac, oxaprozin, nabumentone, sulindac, tolmentin, rofecoxib, naproxen, ketoprofen, and nabumetone. Co-therapies may include antihistamines such as loratadine, fexofenadine, cetirizine, diphenhydramine, chlorpheniramine maleate, clemastine, and azelastine. Co-therapy may include cromoglycate, cromolyn sodium, and nedrocromil, as well as decongestants, spray or oral, such as oxymetazoline, phenylephrine, and pseudoephedrine. The therapies of the invention may be combined with a class of anti-inflammatories called leukotriene-receptor antagonists such as pranlukast, zafirlukast, and montelukast, and leukotriene-receptor synthesis-inhibitors such as zileuton.

The therapies of the invention may be combined with other immunotherapies, including allergy shots, as well as other antagonists of IgE or FcεRs. The therapies of the invention may be combined with antagonists of chemokines or cytokines, including but not limited to antibodies and Fc fusions, including but not limited to inhibitors of chemokines CCR3, CCR4, CCR8, and CRTH2, and CCR5, and inhibitors of cytokines IL-13, IL-4, IL-5, IL-6, IL-9, IL-10, IL-12, IL-15, IL-18, IL-19, IL-21, Class II family of cytokine receptors, IL-22, IL-23, IL-25, IL-27, IL-31, and IL-33. The therapies of the invention may be combined with modulators of adhesion, transcription factors, and/or intracellular signaling. For example, the immunoglobulins of the invention may be combined with modulators of NF-κb, AP-1, GATA-3, Stat1, Stat-6, c-maf, NFATs, suppressors of cytokine signaling (SOCS), peroxisome proliferator-activated receptors (PPARs), MAP kinase, p38 MAPK, JNK, and sphingosine I-phosphate receptors. The therapies of the invention may be administered with suplatast tolilate, inhibitors of phosphodiesterase 4 (PDE4), calcium channel blockers, and heparin-like molecules. Possible co-therapies for the invention are described further in detail in Caramori et al., 2008, Journal of Occupational Medicine and Toxicology 3-S1-S6.

The therapies of the invention may also be used in conjunction with one or more antibiotics, anti-fungal agents, or antiviral agents. The antibodies disclosed herein may also be combined with other therapeutic regimens such as surgery.

EXAMPLES

Examples are provided below are for illustrative purposes only. These examples are not meant to constrain any embodiment disclosed herein to any particular application or theory of operation.

Example 1. Novel Methods for Inhibiting IgE+ FcγRIIb+ Cells

Immunoglobulin IgE is a central initiator and propagator of allergic response in affected tissue. IgE binds the high affinity receptor for IgE (FcεRI), a key receptor involved in immediate allergic manifestations that is expressed on a variety of effector cells, including mast cells, basophils, eosinophils, as well as other cell types. Cross-linking of FcεRI by immune-complexed IgE-allergen activates these cells, releasing chemical mediators such as histamine, prostaglandins, and leukotrienes, which may lead to the development of a type I hypersensitivity reaction. The approved monoclonal antibody Omalizumab (Xolair) neutralizes IgE by binding to it and blocking engagement with FcεR's. Omalizumab reduces bioactive IgE through sequestration, attenuating the amount of antigen-specific IgE that can bind to and sensitize tissue mast cells and basophils. This neutralization of free circulating IgE, in turn, leads to a decrease in symptoms of allergic diseases. Interestingly, serum IgE levels increase after start of therapy because of omalizumab-IgE complex formation and may remain high up to a year after stopping therapy. Consequently, this issue may lead to false-negatives on diagnostic tests and therefore IgE levels must be routinely checked.

A novel approach to targeting the IgE pathway involves not only blocking free circulating IgE from engaging FcεRs on effector cells, but targeting the source of IgE production. IgE is secreted by IgE-producing plasma cells located in lymph nodes draining the site of antigen entry or locally at the sites of allergic reactions. IgE-producing plasma cells are differentiated from IgE+ B cells. Class switching of B cells to IgE production is induced by two separate signals, both of which can be provided by TH2 cells.

There are two forms of immunoglobulins: the secreted and the membrane-anchored form. The membrane-anchored form differs from the secreted form in that the former has a membrane-anchoring peptide extending from the C terminus of the heavy-chain. Membrane-anchored immunoglobulin on B-cells, also referred to as the B cell receptor (BCR) complex, is critical for B-cell functions. It can transduce signals for resting B cells to differentiate into activated lymphoblasts and Ig-secreting plasma cells.

Differentiated B cells expressing membrane-anchored IgE, referred to here as mIgE+ B cells, possess a natural negatively regulating feedback mechanism—the inhibitory Fc receptor FcγRIIb. FcγRIIb is expressed on a variety of immune cells, including B cells, dendritic cells, monocytes, and macrophages, where it plays a critical role in immune regulation. In its normal role on B cells, FcγRIIb serves as a feedback mechanism to modulate B cell activation through the B cell receptor (BCR). Engagement of BCR by immune complexed antigen on mature B cells activates an intracellular signaling cascade, including calcium mobilization, which leads to cell proliferation and differentiation. However, as IgG antibodies with specificity to the antigen are produced, the associated immune complexes (ICs) can crosslink the BCR with FcγRIIb, whereupon the activation of BCR is inhibited by engagement of FcγRIIb and associated intracellular signaling pathways that interfere with the downstream pathways of BCR activation. The expression of FcγRIIb on the surface of mIgE+ B cells, which use mIgE as their BCR, serves as a negative regulator of these cell types.

A novel strategy for inhibiting IgE-mediated disease, illustrated in FIG. 1, is to inhibit IgE+ B cells (i.e. B cells expressing membrane anchored IgE) by coengaging membrane anchored IgE and the inhibitory receptor FcγRIIb. In B cells that have class-switched to express IgE, mIgE serves as the BCR (referred to herein as mIgE BCR). This approach would potentially mimic the natural biological mechanism of immune complex-mediated suppression of B cell activation, thereby preventing differentiation into IgE-producing plasma cells. IgE-producing plasma cells reside in the bone marrow and probably have a life span of several weeks to several months. Since new IgE-secreting plasma cells go through mIgE-expressing B-cell stages during differentiation, if their generation is abrogated by inhibiting their mIgE+ B cell precursors with this anti-IgE treatment, the existing plasma cells will die off within weeks to months, and thus the production of IgE will also gradually abate. Importantly, inhibition of IgE+ memory B cells, which bear mIgE, would also be inhibited by anti-IgE immunoglobulins that coengage FcγRIIb with high affinity. If this occurs, therapy may have long-term impact on the fundamental disease.

Example 2. Anti-IgE Antibodies with High Affinity for FcγRIIb

Under physiological conditions, bridging of the BCR with FcγRIIb and subsequent B cell suppression occurs via immune complexes of IgGs and cognate antigen. The design strategy was to reproduce this effect using a single cross-linking antibody. Human IgG binds human FcγRIIb with weak affinity (greater than 100 nM for IgG1), and FcγRIIb-mediated inhibition occurs in response to immune-complexed but not monomeric IgG. It was reasoned that high affinity to this receptor (less than 100 nM) would be required for maximal inhibition of B cell activation. In order to enhance the inhibitory activity of the anti-IgE antibodies of the invention, the Fc region was engineered with variants that improve binding to FcγRIIb. Engineered Fc variants have been described that bind to FcγRIIb with improved affinity relative to native IgG1 (U.S. Ser. No. 12/156,183, filed May 30, 2008, entitled "Methods and Compositions for Inhibiting CD32b Expressing cells", herein incorporated expressly by reference).

Variants were originally generated in the context of an antibody targeting the antigen CD19, a regulatory component of the BCR coreceptor complex. The Fv region of this antibody is a humanized and affinity matured version of antibody 4G7, and is referred to herein as HuAM4G7. The Fv genes for this antibody were subcloned into the mammalian expression vector pTT5 (National Research Council Canada). Mutations in the Fc domain were introduced using site-directed mutagenesis (QuikChange, Stratagene, Cedar Creek, Tex.). In addition, control knock out variants with ablated affinity for Fc receptors were generated that comprise the substitutions G236R and L328R (G236R/L328R). This variant is referred to as Fc-KO or Fc knockout. Heavy and light chain constructs were cotransfected into HEK293E cells for expression, and antibodies were purified using protein A affinity chromatography (Pierce Biotechnology, Rockford, Ill.).

Recombinant human FcγRIIb protein for binding studies was obtained from R&D Systems (Minneapolis, Minn.). Genes encoding FcγRIIa and FcγRIIIa receptor proteins were obtained from the Mammalian Gene Collection (ATCC), and subcloned into pTT5 vector (National Research Council Canada) containing 6×His tags. Allelic forms of the receptors (H131 and R131 for FcγRIIa and V158 and F158 for FcγRIIIa) were generated using QuikChange mutagenesis. Vectors encoding the receptors were transfected into HEK293T cells, and proteins were purified using nickel affinity chromatography.

Variants were tested for receptor affinity using Biacore technology, also referred to as Biacore herein, a surface plasmon resonance (SPR) based technology for studying biomolecular interactions in real time. SPR measurements were performed using a Biacore 3000 instrument (Biacore, Piscataway, N.J.). A protein NG (Pierce Biotechnology) CM5 biosensor chip (Biacore) was generated using a standard primary amine coupling protocol. All measurements were performed using HBS-EP buffer (10 mM HEPES pH 7.4, 0.15 M NaCl, 3 mM EDTA, 0.005% vol/vol surfactant P20, Biacore). Antibodies at 20 nM or 50 nM in HBS-EP buffer were immobilized on the protein A/G surface and FcγRs were injected. After each cycle, the surface was regenerated by injecting glycine buffer (10 mM, pH 1.5). Data were processed by zeroing time and response before the injection of FcγR and by subtracting appropriate non-specific signals (response of reference channel and injection of running buffer). Kinetic analyses were performed by global fitting of binding data with a 1:1 Langmuir binding model using BIAevaluation software (Biacore).

Figure 2:
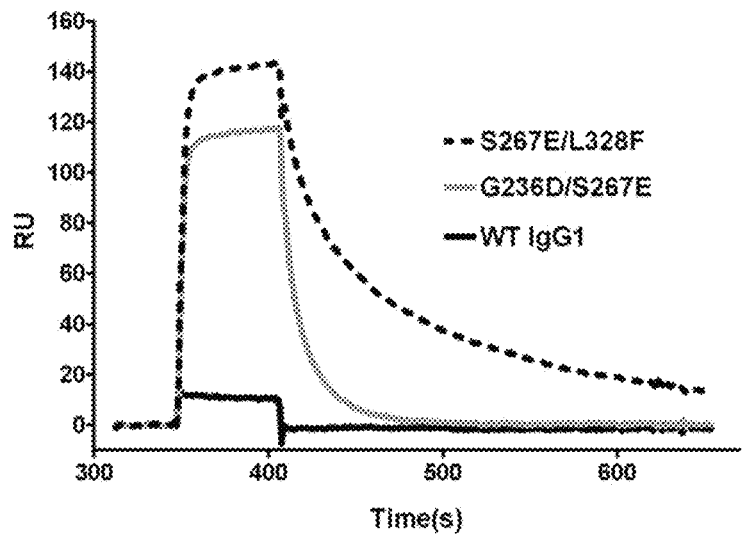
FIG. 2. Biacore surface plasmon resonance sensorgrams showing binding of Fc variant anti-CD19 antibodies to human FcγRIIb.
Figure 3:
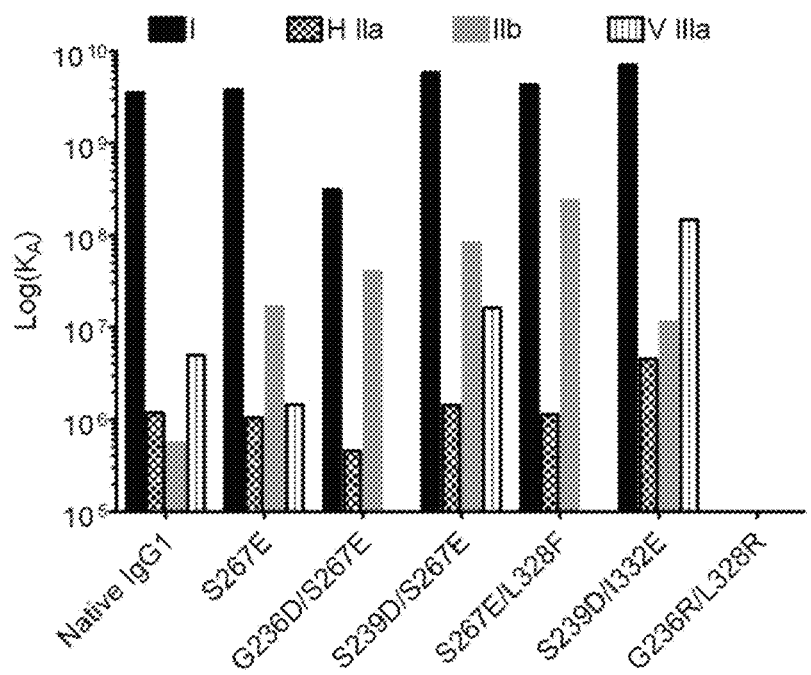
FIG. 3. Affinities of Fc variant antibodies for human FcγRs as determined by Biacore. The graph shows the $\log(K_A)$ for binding of variant and WT IgG1 antibodies to human FcγRI (I), H131 FcγRIIa (H IIa), FcγRIIb (IIb), and V158 FcγRIIIa (VIIIa). Binding of G236D/S267E and S267E/L328F to V158 FcγRIIIa was not detectable. Binding of G236R/L328R (Fc-KO) to all receptors tested was not detectable.

A representative set of sensorgrams for binding of select variant anti-CD19 antibodies to FcγRIIb is shown in FIG. 2. The affinities of all variants and WT (native) IgG1 to all of the FcγRs, obtained from fits of the Biacore binding data, are plotted in FIG. 3 and provided numerically in FIG. 4. Whereas WT IgG1 Fc binds with FcγRIIb with μM affinity ($K_D$=1.8 μM in FIG. 4), a number of variants, for example G236D/S267E, S239D/S267E, and S267E/L328F, have been engineered that bind the inhibitory receptor more tightly. The S239D/I332E variant, as described in U.S. Ser. No. 11/124,620, also has improved affinity for the activating receptors FcγRIIa and FcγRIIIa, and therefore is capable of mediated enhanced antibody-dependent cell-mediated cytotoxicity (ADCC) and phagocytosis (ADCP). The G236R/L328R variant, also referred to Fc-knockout or Fc-KO, lacks binding to the Fc receptors, and is used as a control in the experiments described herein.

Figures 8, 9:
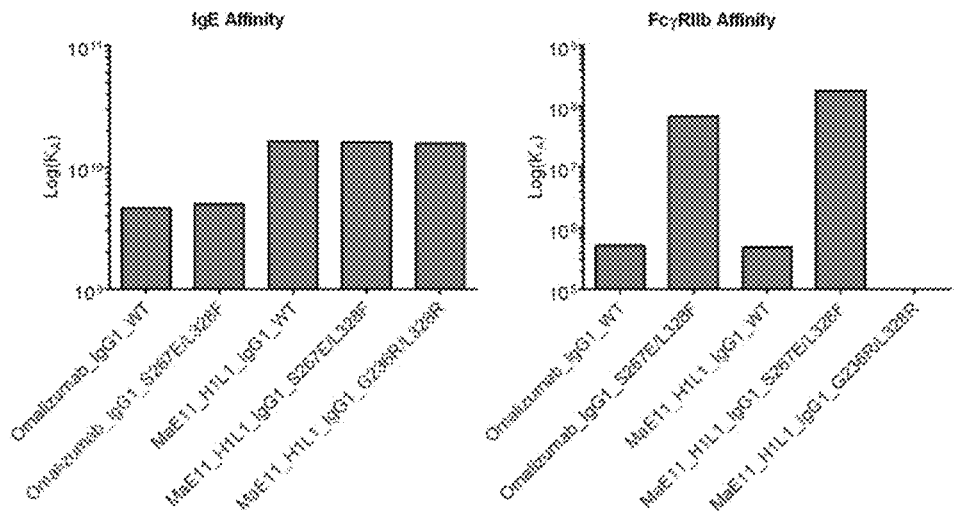
FIG. 8. Table of affinity data for binding of WT and variant anti-IgE antibodies to the IgE Fc region and FcγRIIb.
FIG. 9. Plot of affinity data for binding of WT and variant anti-IgE antibodies to the IgE Fc region and FcγRIIb.

Select variants were constructed in antibodies that target IgE. The heavy and light chain variable regions (VH and VL) of anti-IgE antibodies are provided in FIG. 5. Omalizumab is a humanized antibody that is currently approved for the treatment of allergic asthma, and is marketed under the name Xolair. MaE11 is the murine precursor of Omalizumab. H1L1_MaE11 is a novel humanized version of MaE11. Genes encoding the heavy and light VH and VL domains of these anti-IgE antibodies were synthesized commercially (Blue Heron Biotechnologies). Also synthesized were the variable region VH and VL genes of the anti-respiratory syncytial virus (RSV) antibody motavizumab, used in the experiments described herein as a negative control. VL genes were subcloned into the mammalian expression vector pTT5 (NRC-BRI, Canada) encoding the Ckappa constant chain. VH genes were subcloned into the pTT5 vector encoding native IgG1 and variant constant chains. Amino acid sequences of select constant chains are provided in FIG. 6. All DNA was sequenced to confirm the fidelity of the sequences. The amino acid sequences of the full length heavy and light chains of select antibodies are provided in FIG. 7. As shown in FIG. 9 and discussed in further detail herein, H1L1_MaE11 shows higher affinity to IgE than Omalizumab.

Plasmids containing heavy and light chain genes were co-transfected into HEK293E cells using lipofectamine (Invitrogen) and grown in FreeStyle 293 media (Invitrogen). After 5 days of growth, the antibodies were purified from the culture supernatant by protein A affinity using MabSelect resin (GE Healthcare).

Variant and native IgG1 anti-IgE antibodies were tested for binding to IgE and to FcγRIIb using Biacore. DNA encoding the Fc region of IgE, which contains the binding site for the anti-IgE antibodies used, was synthesized (Blue Heron Biotechnologies) and subcloned into the pTT5 vector. IgE Fc was expressed in 293E cells and purified using protein A as described above. SPR measurements were performed using the protein A/antibody capture method described above, except that analyte was either FcγRIIb or the Fc region of IgE. Data acquisition and fitting are as described above. FIG. 8 provides the resulting equilibrium binding constants (KDs) obtained from these binding experiments, as well as the fold affinity relative to native IgG1 for binding to FcγRIIb. FIG. 9 shows plots of these data. The results confirm the high of affinity of the antibodies for IgE, and that the S267E/L328F variant improves binding to FcγRIIb over two orders of magnitude, consistent with previous results.

The use of particular variants, for example S267E/L328F and S239D/I332E, are meant here as proof of concept for the mechanism as described herein, and are not meant to constrain the invention to their particular use. The data provided in U.S. Ser. No. 12/156,183 and U.S. Ser. No. 11/124,620 indicate that a number of engineered variants, at specific Fc positions, provide the targeted properties. Substitutions to enhance FcγR affinity, in particular to FcγRIIb, include: 234, 235, 236, 237, 239, 266, 267, 268, 325, 326, 327, 328, and 332. In some embodiments, substitutions are made to at least one or more of the nonlimiting following positions to enhance affinity to FcγRIIb: 235, 236, 239, 266, 267, 268, and 328.

Nonlimiting combinations of positions for making substitutions to enhance affinity to FcγRIIb include: 234/239, 234/267, 234/328, 235/236, 235/239, 235/267, 235/268, 235/328, 236/239, 236/267, 236/268, 236/328, 237/267, 239/267, 239/268, 239/327, 239/328, 239/332, 266/267, 267/268, 267/325, 267/327, 267/328, 267/332, 268/327, 268/328, 268/332, 326/328, 327/328, and 328/332. In some embodiments, combinations of positions for making substitutions to enhance affinity to FcγRIIb include, but are not limited to: 235/267, 236/267, 239/268, 239/267, 267/268, and 267/328.

Substitutions for enhancing affinity to FcγRIIb include: 234D, 234E, 234W, 235D, 235F, 235R, 235Y, 236D, 236N, 237D, 237N, 239D, 239E, 266M, 267D, S267E, 268D, 268E, 327D, 327E, L328F, 328W, 328Y, and 332E. In some embodiments, combination of positions for making substitutions for enhancing affinity to FcγRIIb include, but are not limited to: 235Y, 236D, 239D, 266M, S267E, 268D, 268E, L328F, 328W, and 328Y.

Combinations of substitutions for enhancing affinity to FcγRIIb include: L234D/S267E, L234E/S267E, L234F/ S267E, L234E/L328F, L234W/S239D, L234W/S239E, L234W/S267E, L234W/L328Y, L235D/S267E, L235D/ L328F, L235F/5239D, L235F/S267E, L235F/L328Y, L235Y/G236D, L235Y/S239D, L235Y/S267D, L235Y/ S267E, L235Y/H268E, L235Y/L328F, G236D/S239D, G236D/S267E, G236D/H268E, G236D/L328F, G236N/ S267E, G237D/S267E, G237N/S267E, S239D/S267D, S239D/S267E, S239D/H268D, S239D/H268E, S239D/ A327D, S239D/L328F, S239D/L328W, S239D/L328Y, S239D/I332E, S239E/S267E, V266M/S267E, S267D/ H268E, S267E/H268D, S267E/H268E, S267E/N325L, S267E/A327D, S267E/A327E, S267E/L328F, S267E/ L328I, S267E/L328Y, S267E/I332E, H268D/A327D, H268D/L328F, H268D/L328W, H268D/L328Y, H268D/ I332E, H268E/L328F, H268E/L328Y, A327D/L328Y, L328F/I332E, L328W/I332E, and L328Y/I332E. In some embodiments, combinations of substitutions for enhancing affinity to FcγRIIb include, but are not limited to: L235Y/ S267E, G236D/S267E, S239D/H268D, S239D/S267E, S267E/H268D, S267E/H268E, and S267E/L328F.

Example 3. In Vitro Inhibition of IgE+ B Cells by Anti-IgE Antibodies with High Affinity to FcγRIIb An enzyme-linked immunosorbent assay (ELISA) was established to detect IgE. Flat bottom plates were prepared by coating with pH 9.4 Na Bicarbonate buffer, followed by adherence with anti-IgE capture antibodies at 10 ug/ml overnight in pH 9.4 (0.1 M NaBicarbonate buffer). After overnight, the plate was blocked with 3% BSA/PBS, and serial dilutions of IgE (from a human IgE ELISA kit, Bethyl Laboratories) was added 3× to 1 ug/ml. After 3 hours, plates were washed 3× (200 µl) with TTBS, and bound IgE was measured. HRP-conjugated goat polyclonal anti-human IgE antibody (Bethyl Laboratories) was added at (1:5000) for 1 hour in 1% BSA/PBS. Samples were washed 3× and IgE was detected with TMB peroxidase substrate (KPL, Inc 50-76-00). Reactions were stopped with 50 µl 2N $H_2SO_4$ and read at 450 nm.

Figure 10:
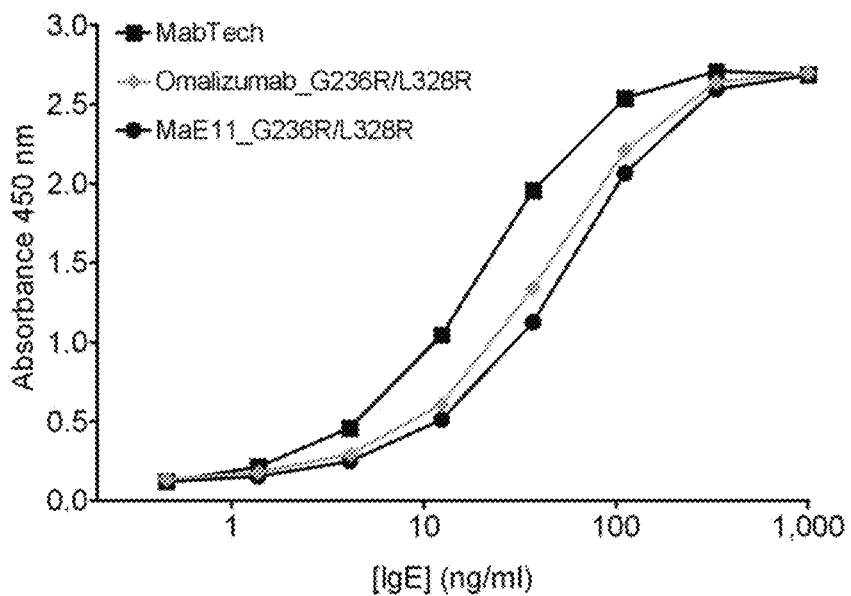
FIG. 10. IgE ELISA using commercial (MabTech) and in-house (Omalizumab and MaE11) anti-IgE antibodies as capture reagents.
Figure 11:
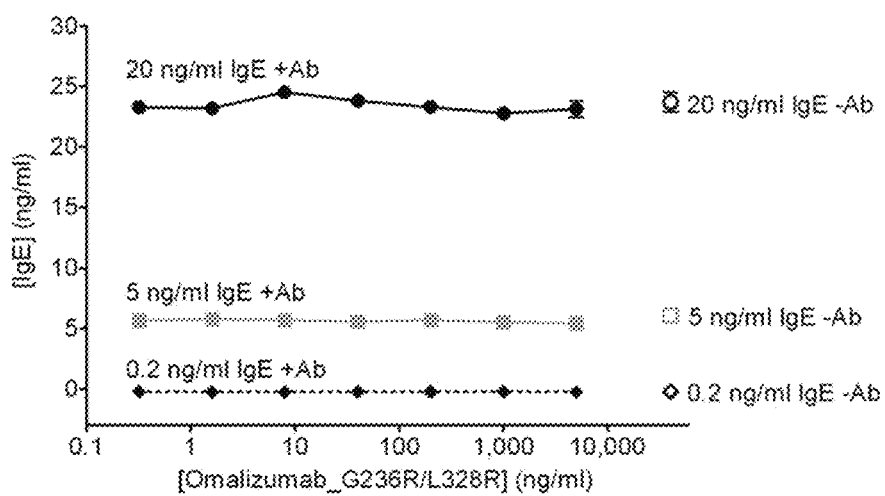
FIG. 11. The variable region of the anti-IgE antibody omalizumab does not compete with MabTech capture antibody for IgE detection in the ELISA protocol.

FIG. 10 shows capture of IgE with various anti-human IgE antibodies, including a pool of three monoclonal anti-IgE antibodies (MabTech; 107/182/101), MaE11_IgG1_G236R/L328R, and Omalizumab_IgG1_G236R/L328R. The data show that the commercial anti-IgE antibody reagent (MabTech), Omalizumab, and its parent chimeric antibody MaE11 are able to capture IgE. In order to use this assay to detect IgE, it was necessary to determine whether MaE11 and omalizumab antibodies would interfere with IgE capture by the MabTech anti-IgE reagent. The assay was repeated as described above, and concentration of IgE from absorbance was calculated using a standard curve. FIG. 11 shows that anti-IgE antibody omalizumab_G236R/L328R does not compete with the MabTech anti-IgE antibody in the current ELISA protocol.

Figure 12:
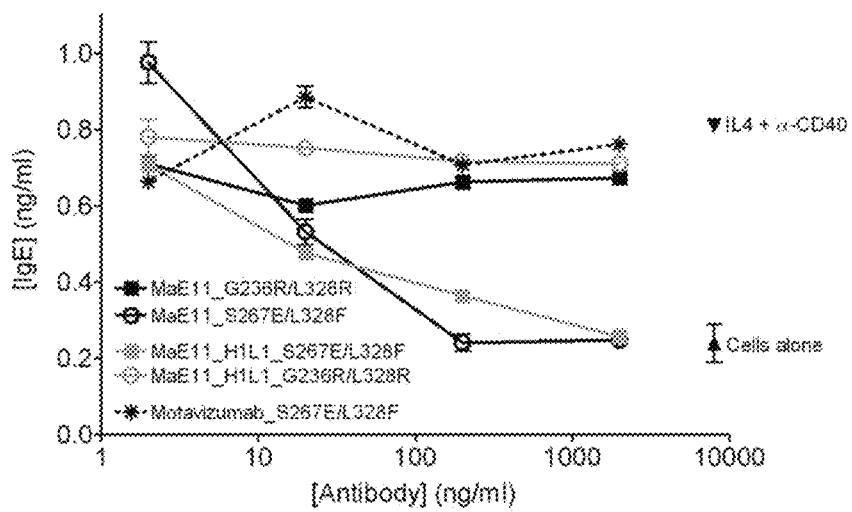
FIG. 12. Inhibition of class-switched IgE+ B cells with variant anti-IgE antibodies enhanced for FcγRIIb affinity, but not antibodies lacking FcγR binding (Fc variant G236R/L328R) or lacking binding to IgE (motavizumab). The plot shows the concentration of IgE released from PBMCs after 12 days incubation with IL-4, anti-CD40 (α-CD40) agonist antibody, and varying concentrations of the antibodies shown.
Figure 13:
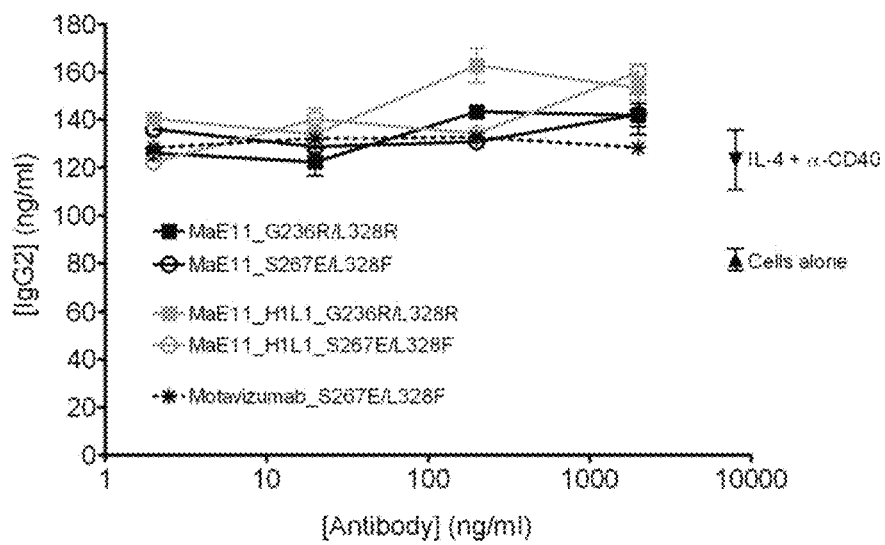
FIG. 13. Variant anti-IgE antibodies do not inhibit class-switched IgG2+ B cells. The plot shows the concentration of IgG2 released from PBMCs after 12 days incubation with IL-4, α-CD40, and varying concentrations of the antibodies shown.

Fc variant anti-IgE antibodies were tested for their capacity to inhibit IgE+ B cells. Human PBMCs were induced to class switch to IgE producing B cells by adding 5 ng/ml interleukin-4 (IL-4) and 100 ng/ml anti-CD40 antibody (clone G28.5 IgG1). The anti-CD40 antibody is an agonist of CD40, and thus mimics the activity of the co-activator CD40L. Varying concentration of anti-IgE antibodies were added, and the samples were incubated for 12 days. ELISA plates were prepared and blocked as described above, using 5 ug/ml Mabtech anti-IgE as the capture antibody. 100 µl of the PBMC samples were added and incubated >3 hours, and then washed with TTBS 3× (200 µl). Antibody-HRP conjugated antibody was added and detected as described above. Absorbance at 450 nm was converted to IgE concentration using a standard curve. The results are shown in FIG. 12. Antibodies lacking FcγR binding (G236R/L328R variants) or having no specificity for IgE (Motavizumab anti-RSV antibody) had no effect on IgE production from differentiated B cells. In contrast, variant antibodies with greater affinity for FcγRIIb inhibited IgE production. These data suggest that co-engagement of surface IgE and the inhibitory FcγR receptor FcγRIIb inhibits class-switched B cells of that immunoglobulin type. Inhibition of IgE+ B cells reduces the number of IgE expressing plasma cells, which in turn reduces the amount of IgE detected. To evaluate the selectivity of this activity for IgE producing B cells, human IgG2 was measured from the same samples using an IgG2 ELISA (Bethyl Laboratories). FIG. 13 shows that IgG2 secretion was not inhibited, indicating that the inhibitory activity of anti-IgE antibodies with high FcγRIIb affinity is selective for IgE+ class-switched cells. Repeat of this experiment using variant versions of the approved anti-IgE antibody Omalizumab showed similar inhibitory results by the variant with high FcγRIIb affinity (FIG. 14).

Figure 16:
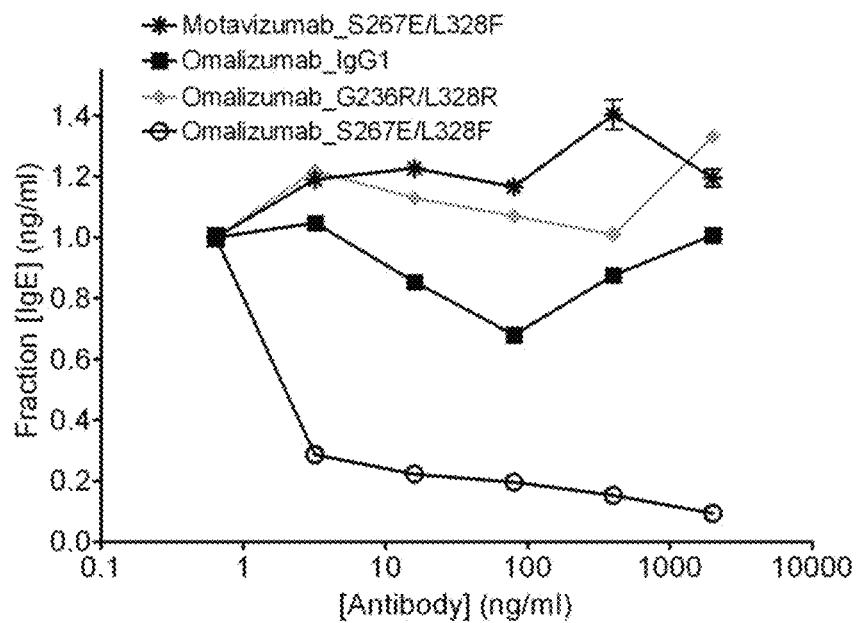
FIG. 16. Inhibition of class-switched IgE+ B cells with variant anti-IgE antibodies enhanced for FcγRIIb affinity. The plot shows the concentration of IgE released from PBMCs after 14 days incubation with IL-4, anti-CD40 (α-CD40) agonist antibody, anti-mu BCR cross-linking antibody, and varying concentrations of the antibodies shown. Data were normalized to the lowest concentration of antibody.

The capacity of anti-IgE antibodies with high FcγRIIb affinity to inhibit IgE production was evaluated in the presence of mIgE BCR stimulation. The above assay was repeated, with class-switching to IgE promoted by IL-4 and α-CD40 agonist antibody, and in addition the B cells were activated using either anti-mu or anti-CD79b antibody. These antibodies cross-link the BCR, thereby providing a signal similar to immune-complexed antigen. Anti-mu antibody cross-links membrane-anchored IgM, and anti-CD79b cross-links CD79b, which is a signaling component of the BCR complex. PBMCs were incubated for 14 days with IL-4, α-CD40, and either anti-CD79b or anti-mu, and IgE was detected as described above. The results for anti-CD79b (FIG. 15) and anti-mu (FIG. 16) show that the anti-IgE antibodies with high affinity for FcγRIIb are capable of inhibiting IgE production when B cells are stimulated via BCR cross-linking.

Figure 17:
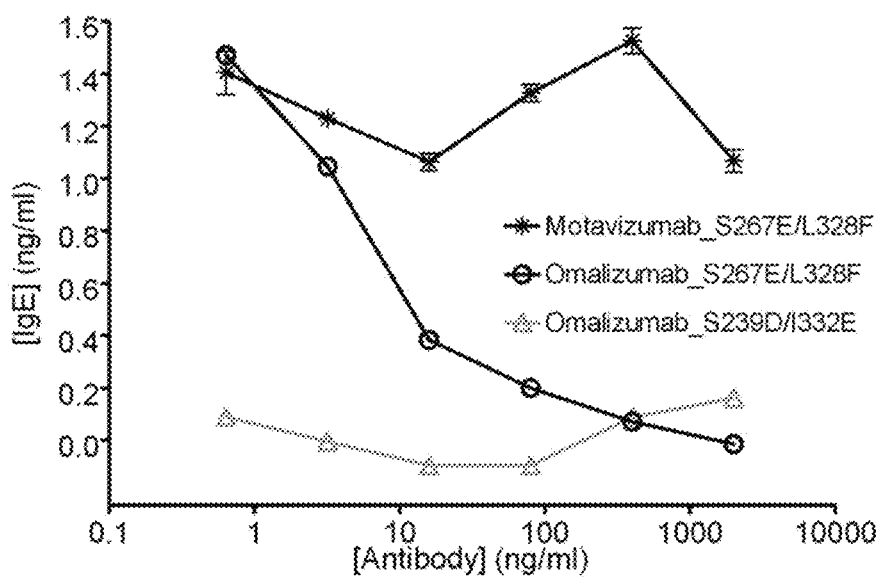
FIG. 17. Inhibition of class-switched IgE+ B cells with variant anti-IgE antibodies enhanced for FcγRIIb affinity. The plot shows the concentration of IgE released from PBMCs after 14 days incubation with IL-4, anti-CD40 (α-CD40) agonist antibody, anti-CD79b BCR cross-linking antibody, and varying concentrations of the antibodies shown.
Figure 18:
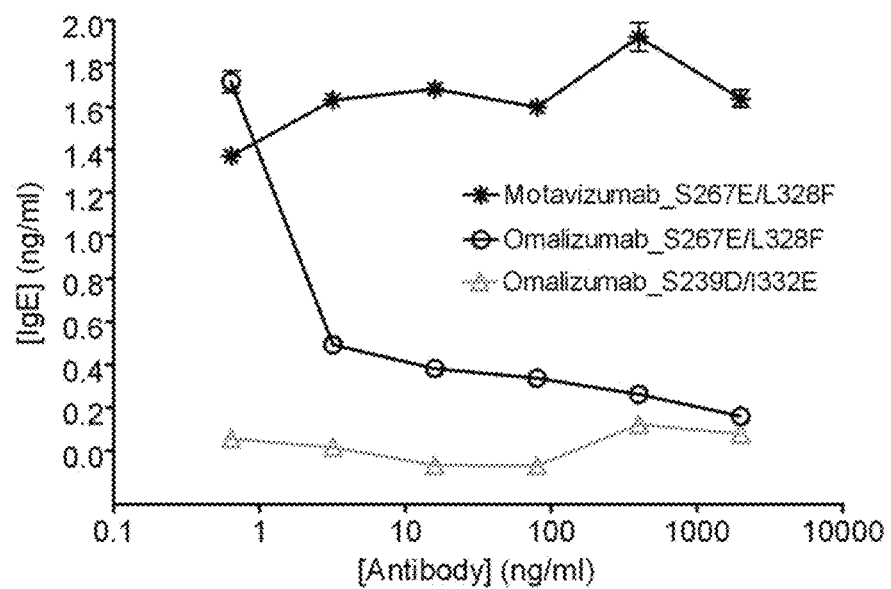
FIG. 18. Inhibition of class-switched IgE+ B cells with variant anti-IgE antibodies enhanced for FcγRIIb affinity. The plot shows the concentration of IgE released from PBMCs after 14 days incubation with IL-4, anti-CD40 (α-CD40) agonist antibody, anti-mu BCR cross-linking antibody, and varying concentrations of the antibodies shown.
Figure 19:
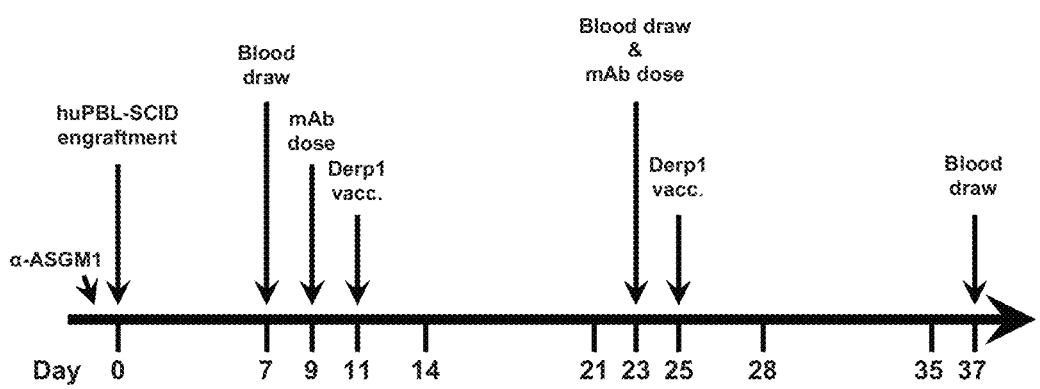
FIG. 19. Protocol for huPBL-SCID in vivo study to test activity of anti-IgE antibodies. The indicated days reflect the number of days after engraftment of PBMCs from a donor testing positive for IgE antibodies specific for Der p 1. Derp1 vacc. indicates vaccination with Der p 1 antigen.

An additional strategy for inhibiting IgE+ B cells is to deplete them. This may be carried out using an anti-IgE antibody that is enhanced for effector function. The variant S239D/I332E increases binding to activating receptor FcγRIIa and FcγRIIIa (FIG. 3 and FIG. 4), and thus improves ADCC and ADCP effector functions. The above B cell assay was carried out using a S239D/I332E variant of the anti-IgE antibody Omalizumab. PBMCs were incubated for 14 days with IL-4, α-CD40, and either anti-CD79b (FIG. 17) or anti-mu (FIG. 18), and IgE was detected as described above. The results (FIGS. 17 and 18) show that anti-IgE antibodies with optimized effector function are able to inhibit IgE production from class-switched IgE+ B cells.

Example 4. In Vivo Inhibition of IgE+ B Cells by Anti-IgE Antibodies with High Affinity to FcγRIIb The immunoglobulins disclosed herein were assessed using a huPBL-SCID mouse model as a proxy for therapeutic activity in humans. This study examined the capacity of the anti-IgE antibodies described here to inhibit B cell activity and plasma cell development in response to a common human allergen—dust mite protein Der p 1. In this method, human peripheral blood leukocytes (PBLs) from a blood donor with allergic response to Der p 1 were engrafted to immune-deficient SCID mice and treated with the native or variant anti-IgE antibodies. The mice were challenged with an antigen to stimulate an immune response, and production of immunoglobulins was measured to examine the course of B cell development into plasma cells.

Blood donors were screened for allergy to dust mite antigen based on the presence of anti-IgE antibodies against Der p 1. A donor with positive reactivity was leukapheresed to obtained peripheral blood mononuclear cells (PBMCs). The protocol for the study is provided in FIG. 20. One day prior to PBMC injection, mice were given intraperitoneal (i.p.) injections with 100 μl of anti-asialo GM antibody (Wako, Richmond, Va.) to deplete murine natural killer (NK) cells. The next day, mice were injected i.p. with $3 \times 10^7$ PBLs in a 0.5 ml volume. After PBMC injection, mice were assigned to 5 different groups of mice with 7 mice in each group. On day 7 post PBMC injection, blood was collected from all mice via retro-orbital sinus/plexus (OSP) puncture for determination of human IgG and IgE levels by ELISA (ZeptoMetrix, Buffalo, N.Y.). Two days later (day 9), mice were injected i.p. with 10 mg/kg antibody or PBS. On day 11, mice were injected i.p. with 15 ug dustmite antigen Der p 1 (LoTox Natural Der p 1, Indoor Biotechnologies, Charlottesville, Va.). On day 23 (12 days post antigen vaccination), blood was collected from all mice for determination of human IgG and IgE antibodies. On the same day, mice received a second injection i.p. with 10 mg/kg antibody or PBS. Two days later (day 25), mice received a boost vaccination i.p. of 10 ug dustmite antigen Der p 1. On day 37 (12 days post antigen boost), blood was collected by OSP for human immunoglobulin determination. Human IgG and IgE concentrations were measured using ELISA methods similar to those described above.

Figure 20:
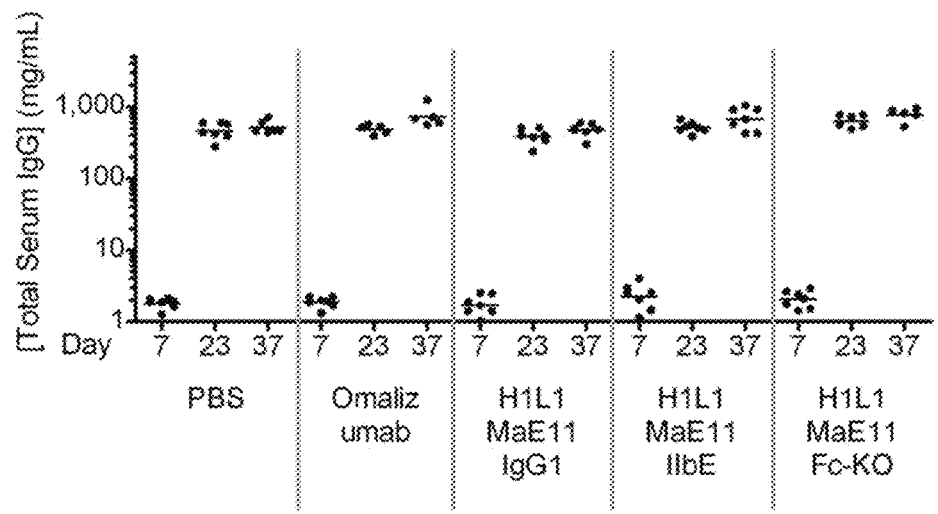
FIG. 20. Total serum IgG levels from the huPBL-SCID in vivo model for each treatment group. The indicated days (7, 23, and 37) reflect the blood draws outlined in the protocol in FIG. 19. PBS indicates the untreated vehicle group, Omalizumab indicates the group treated with Omalizumab_IgG1, and the 3 H1 L1 MaE11 groups indicate groups treated with humanized MaE11 comprising either a WT IgG1 (IgG1), S267E/L328F variant (IIbE), or G236R/L328R (Fc-KO) Fc region.
Figure 21:
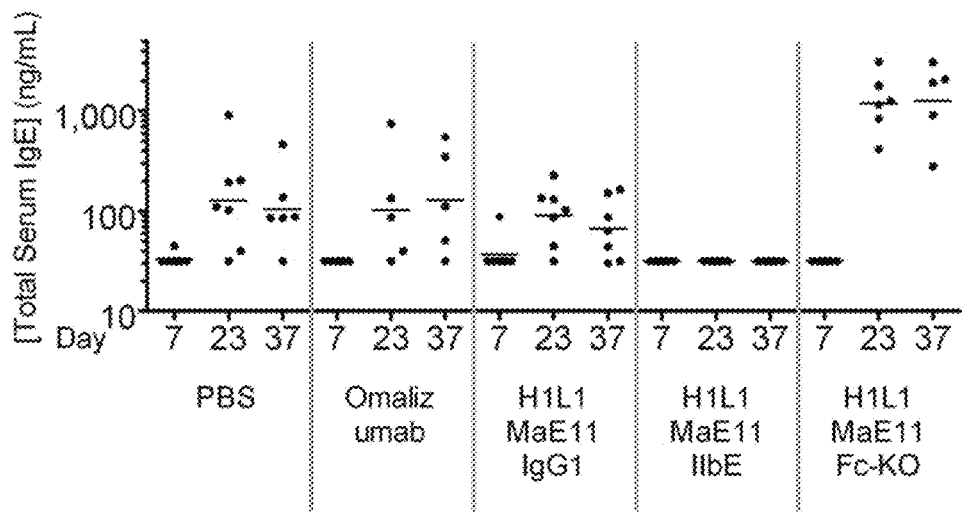
FIG. 21. Total serum IgE levels from the huPBL-SCID in vivo model for each treatment group. The indicated days (7, 23, and 37) reflect the blood draws outlined in the protocol in FIG. 19. PBS indicates the untreated vehicle group, Omalizumab indicates the group treated with Omalizumab_IgG1, and the 3 H1 L1 MaE11 groups indicate groups treated with humanized MaE11 comprising either a WT IgG1 (IgG1), S267E/L328F variant (IIbE), or G236R/L328R (Fc-KO) Fc region. The limit of quantitation for the ELISA method was 31.6 ng/mL; samples that were below this limit were reported as 31.6 ng/mL in the plot.

The results are shown in FIGS. 20 and 21 for serum IgG and IgE levels respectively. Before the allergen challenge, the levels of human IgG and IgE antibodies were low in all the groups. After Der p 1 immunization, all groups showed high levels of human IgG, indicating a robust immune response by engrafted human B cells to either the vaccinated Der p 1 antigen or endogenous mouse antigens. In contrast to IgG response, the treatment groups differed significantly in their production of IgE antibodies. Omalizumab and the IgG1 version of H1 L1 MaE11 were equivalent to vehicle in their capacity to inhibit production of human IgE. However the FcγRIIb-enhanced (IIbE, S267E/L328F) version of H1 L1 MaE11 showed no detectable levels of human IgE. The Fc-KO (variant G236R/L328R) version of H1L1 MaE11, which lacks binding to all FcγRs, showed an enhancement in human IgE production. This is possibly due to its ability to cross-link human mIgE and thus activate IgE+ B cells, yet its complete lack of FcγRIIb inhibitory or FcγRIIa/IIIa cytotoxic activities such as those possessed by the IgG1 and IIbE versions of the antibody. These in vivo data show that anti-IgE antibodies with high affinity for FcγRIIb are capable of inhibiting human IgE+ B cell activation and immunoglobulin secreting plasma cell differentiation, and thus support the potential of the immunoglobulins disclosed herein for treating IgE-mediated disorders.

Example 5. Comparative PK/PD Model of XmAb7195 Vs. Omalizumab Effect on Free and Total IgE in Chimpanzees XmAb7195 (anti-human IgE, S267E/L328F) was evaluated for its pharmacokinetics and pharmacodynamics (free and total IgE) in chimpanzees following a single intravenous dose of 5 mg/kg. Chimpanzees and humans have similar FcγRIIb structure at the critical binding region (Arginine at position 131, or 131-R), in contrast to macaques which do not have the relevant contact amino acid. The comparator antibody in this study was commercially available omalizumab (Xolair®. Genentech, USA), an anti-human IgE antibody with a wild type human IgG1 Fc domain.

The purpose of this study was two-fold. The first objective was to evaluate the pharmacokinetic behavior of XmAb7195 in chimpanzees. Sequence differences among primate species lead to significant differences in receptor affinities for XmAb7195. The receptor-mediated clearance of XmAb7195 may involve Fc-gamma receptors type II (a and b). PK experiments in other non-human primates have been performed, but may not be predictive since macaques do not have arginine at position 131 of the Fc gamma type II receptors. PK in chimpanzees, which have the appropriate genotype, may be more predictive of the PK/PD profile expected in human clinical studies. The second purpose of the study was to evaluate the pharmacodynamic effect of a single dose of XmAb7195 on the sequestration, production, and clearance of IgE. In each of these objectives, we used omalizumab as a comparator molecule in order to evaluate the effect that the engineered Fc had on PK/PD parameters.

Figure 22A:
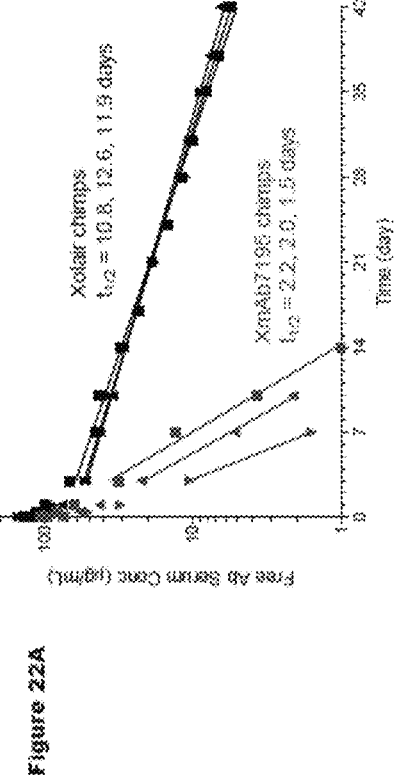
FIG. 22 A-C. Data from a chimp study of XmAb7195, described herein, that shows a rapid and unprecedented reduction in total IgE. The dosage was a single 5 mg/kg dose, mean baseline IgE level is ~3 ug/ml. LLOQ is the lower limit of quantification. This contrasts with a known Xolair side effect that the concentration of total IgE is increased upon administration.
Figure 22C:
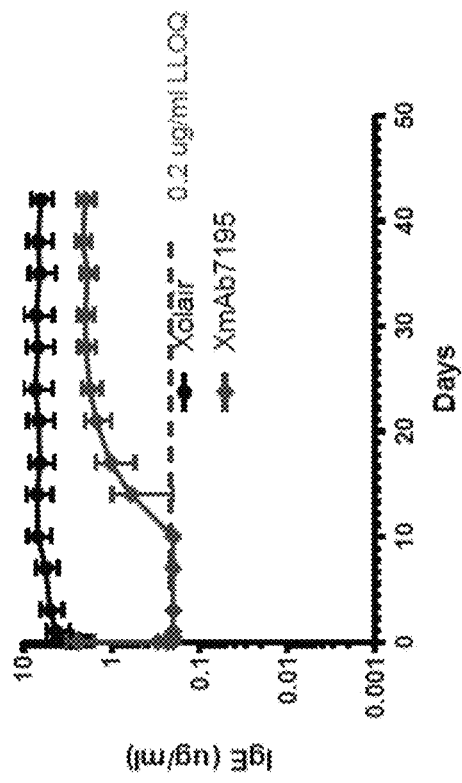
Figure 22B:
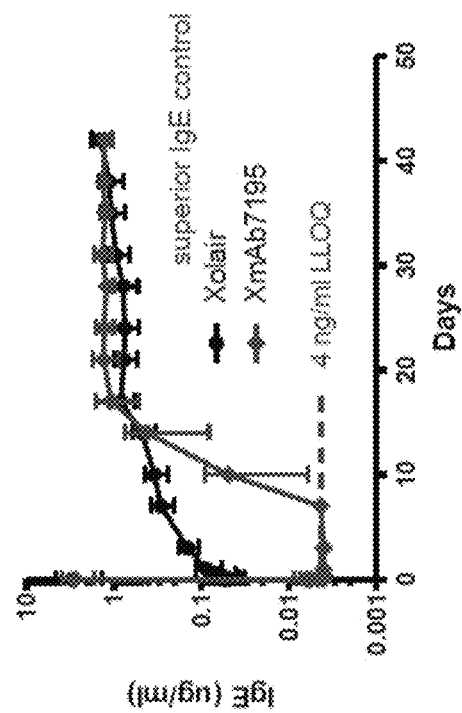

The results of free drug concentrations as a function of time are presented in FIG. 22A. Notably, XmAb7195 has a shorter half-life of approximately 2 days compared to the approximately 11 days observed for omalizumab. Analysis of free and total IgE was undertaken on serum samples at each of the PK time points. Free IgE levels exhibited a rapid drop immediately after dosing. The nadir of free IgE concentrations for the omalizumab-treated chimps averaged approximately 50 ng/ml at one hour post dosing. XmAb7195 caused a more significant reduction of free IgE, reaching levels below the lower limit of quantitation (LLOQ) of 4 ng/ml almost immediately after dosing and remaining below the LLOQ up to day 10. (FIG. 22B) Omalizumab increased total IgE for a period of weeks, similar to its observed effects in humans. XmAb7195 caused a rapid disappearance of total IgE—reaching the LLOQ within 1 hour post-dosing and lasting for 10 days—followed by a gradual return to baseline levels over a period of weeks. FIG. 22C shows group mean total IgE levels versus time for chimpanzees treated with omalizumab or XmAb7195 (anti-IgE, S267E/L328F). The lower limit of quantification was 0.2 µg/ml.

Example 6. PK/PD of Anti-IgE Antibodies in Human FcγRIIb Transgenic Mice

Several anti-mouse IgE antibodies with different FcγRIIb-enhancing Fc substitutions were produced for comparison of their ability to modulate total IgE concentrations in vivo. The first, XENP8253, comprises the R1E4 Fv domain (anti-mouse IgE) and an Fc domain containing the S267E/L328F substitutions. The second, XENP8252, is a surrogate for omalizumab, comprising the R1E4 Fv domain with a native human IgG1 backbone. Additional Fc variants—S267E, G236D/S267E, and G236N/S267E were also characterized to examine the relationship between human FcγRIIb affinity and pharmacokinetics and pharmacodynamics.

Figure 23:
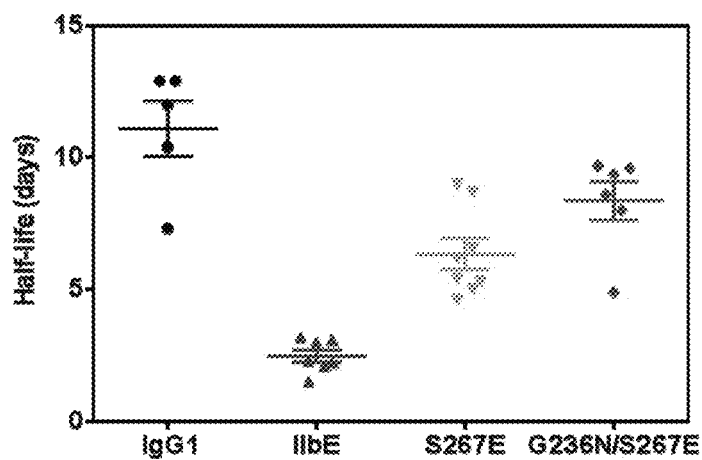
FIG. 23. A scatter plot of calculated half-lives for individual mice treated with variant anti-IgE antibodies (IIbE=S267E/L328F).
Figure 24:
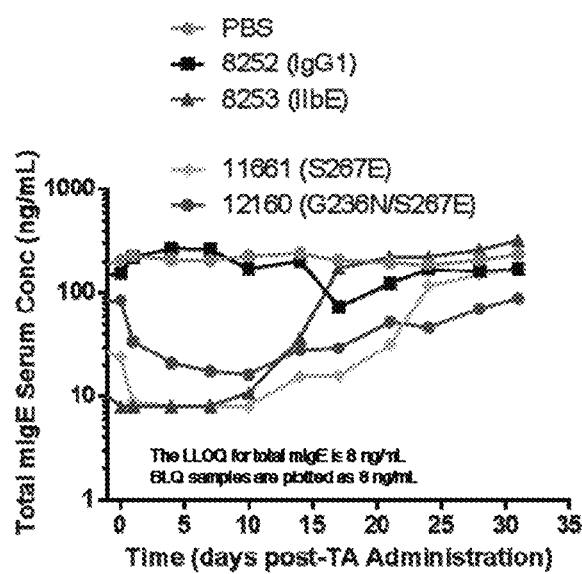
FIG. 24. Serum total IgE concentration as a function of time in human FcγRIIb transgenic mice treated with anti-mouse IgE antibodies. The lower limit of quantification of the IgE assay was 13 ng/ml.

A single 2 mg/kg dose of all anti-IgE antibodies sequestered serum IgE and reduced free IgE serum levels by several orders of magnitude within hours of the treatment. Their effect on total IgE, however, was very different. The omalizumab surrogate (XENP8252), which contains an unmodified IgG1 Fc domain, had no discernible effect on total IgE relative to the PBS control. In contrast, the high FcγRIIb affinity variant S267E/L328F reduced total IgE within hours, and caused sustained reduction of total IgE relative to both the PBS group and the XENP8252-treated mice. The extremely rapid onset of the total IgE reduction in this model system indicates (without being bound by theory) that anti-IgE antibodies with enhanced affinity for FcγRIIb increase the rate of drug:IgE complex clearance. This hypothesis is consistent with the observation that the S267E/L328F (IIbE) variant has reduced half-life (approximately 2.5 days) relative to the IgG1 antibody (XENP8252) (approximately 11 days). (FIG. 23). FIG. 24 shows serum total IgE concentration as a function of time in the human FcγRIIb transgenic mice treated with anti-mouse IgE antibodies. The lower limit of quantification of this IgE assay was 13 ng/ml.

The additional variant antibodies—S267E, G236D/S267E, and G236N/S267E, with FcγRIIb affinities intermediate between IgG1 and S267E/L328, have intermediate half-lives and intermediate effects on total IgE, revealing a direct relationship between FcγRIIb affinity and clearance rates of either antibody alone or antibody complexed with antigen. (See FIG. 25).

Example 7. Antibody:IgE Complex Internalization by Liver Sinusoidal Endothelial Cells (LSEC) from FcγRIIb Transgenic Mice A hypothesis tested was that much of the in vivo accelerated clearance of antibody and antibody:IgE complexes is mediated by liver sinusoidal endothelial cells (LSEC). Anderson and colleagues (Ganesan et al., J Immunol 2012) published a study demonstrating that three quarters of mouse FcγRIIb is expressed in the liver, with 90% of it being expressed in LSEC. Moreover, the authors demonstrated that clearance of radiolabeled small immune complexes (SIC) is significantly impaired in an FcγRIIb knockout strain compared to wild-type mice.

An LSEC enrichment protocol was adopted from Katz et al, (Katz et al., (2004) J Immunol "Liver sinusoidal endothelial cells are insufficient to activate T cells," 173(1): 230-235) for non-parenchymal cell isolation. Briefly, mouse liver was infused with 1 ml of 1% (w/v) collagenase D in 1×HBSS using syringe and needle. Then, the liver was quickly minced in 20 ml of 1% collagenase D and incubated at 37° C. for 20 minutes with stirring to keep the cells in suspension. The cell suspension was passed through a 100 µm cell strainer filter mesh and spun 3× at low speed (30×g, 10 minutes) to remove the bulk of parenchymal hepatocytes. The final enriched non-parenchymal liver cell pellet (300×g, 10 minutes) was washed twice with PBS (300×g, 10 minutes) and used in internalization assays.

Figure 26:
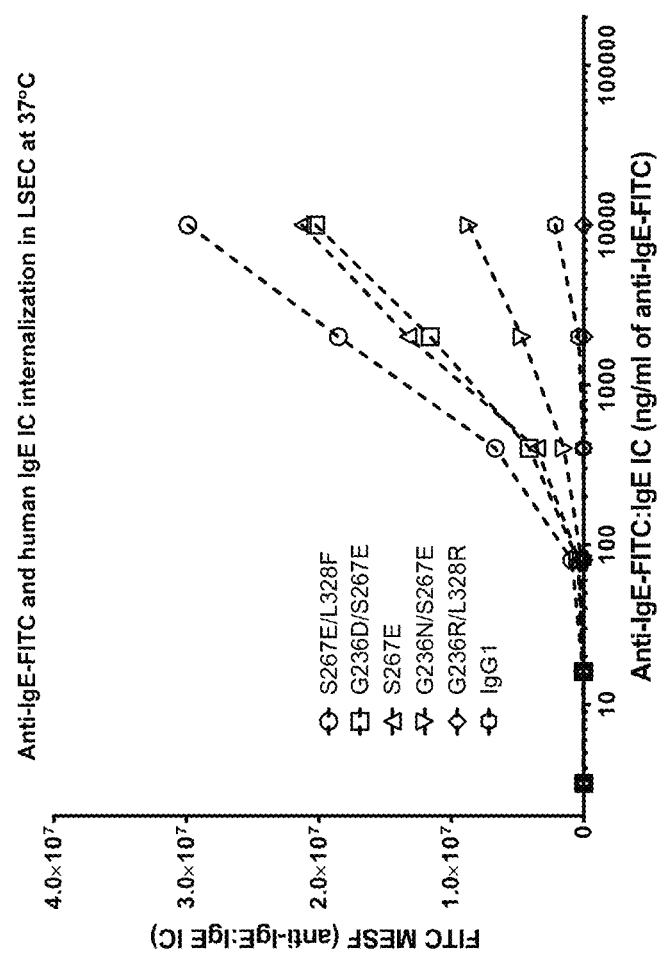
FIG. 26. Plot in vitro internalization of antibody:IgE complexes into LSEC isolated from FcγRIIb transgenic mice.

FITC conjugated anti-IgE antibodies plus human IgE pre-formed IC were incubated with enriched LSEC's for 60 minutes at 37° C., washed with low pH "Acid" wash buffer (glycine, NaCl, pH=2.7) and stained with anti-CD146 and anti-CD45 antibodies. The internalized signal (FITC MFI) was quantified from CD146+CD45low LSEC's and MESF normalized values are plotted. As shown in FIG. 26, IgE complexes formed with the anti-IgE antibody containing the high IIb affinity variant S267E/L328 internalize into LSEC more substantially than either anti-IgE IgG1 or anti-IgE with Fc knockout substitutions (G236R/L328R). Variants with intermediate IIb affinity—S267E, G236D/S267E, and G236N/S267E—displayed intermediate internalization corresponding with their relative affinities.

Example 8. Whole Body Imaging Study of IgE Biodistribution

A study was designed to evaluate the biodistribution and specific hepatic uptake of XmAb7195 (anti-IgE-S267E/

L328F) as compared to saline controls and control antibody XENP6728 (anti-IgE-IgG1), when administered intravenously together with $^{89}$Zr-IgE to female FcγRIIb transgenic mice.

Treatment began on Day 0. Animals were first injected intravenously with $^{89}$Zr-labeled IgE in the range of 0.10 to 0.13 mCi. This was immediately followed by an intravenous injection of saline, 10 mg/kg XmAb7195, or 10 mg/kg XENP6728.

Animals were induced with 3.0% isoflurane in air (2.0 L/min) and were maintained during imaging procedures at 1.0-2.0% isoflurane in air (2.0 L/min). Animals were positioned inside the Siemens Inveon PET ring, and the PET acquisition was initiated and data was acquired continuously for 2 hours for the first acquisition.

Figure 27:
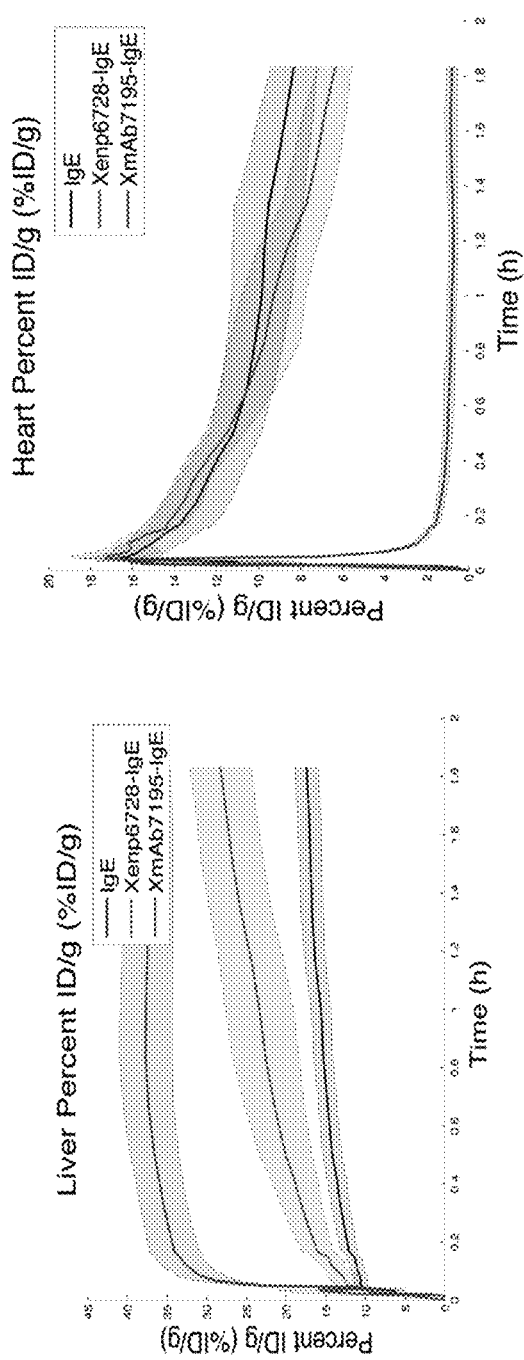
FIG. 27. Liver and heart distribution of $^{89}$Zr-IgE upon co-administration of saline, XmAb7195 (S267E/L328F), or XENP6782 (IgG1).

Administration of XmAb7195 was associated with significantly greater, more rapid and more sustained accumulation of $^{89}$Zr-IgE in the liver, compared with saline and compared with the IgG1 analog XENP6728. Correspondingly, administration of XmAb7195 was associated with significantly reduced accumulation of $^{89}$Zr-IgE in the heart, which is representative of the amount of labeled IgE in bulk circulation. (FIG. 27).

Example 9. CR2-Fc Fusions with High Affinity for FcγRIIb

Soluble CRs and CR-Fc fusions have been described for therapeutic purposes. These include CR1, CR2-Fc (U.S. Pat. No. 6,458,360), CR2-fH (CR2-factor H), and others. However, while these approaches generally block interaction of C3-tagged ICs with their associated receptors, they do not necessarily remove the immune complexes from circulation. Most of the complement receptors and regulatory proteins are composed of one or more so-called short complement repeat (SCR) domains, also called complement control protein (CCP) modules or Sushi domains. Typically, only a subset of the domains is involved in direct recognition of the associated complement fragment ligand. For example, it has been demonstrated that only the first two SCRs of CR2 are essential for C3d binding. The SCR domains are stable and well-behaved, making them suitable for use in the development of therapeutic proteins.

Genes encoding the first two (SCR1-2) or first four (SCR1-4) SCR domains from human and mouse were synthesized commercially (Blue Heron Biotechnologies). Genes were subcloned into the mammalian expression vector pTT5 (NRC-BRI, Canada) encoding the human IgG1 Fc (hinge-CH2-CH3 domains). The SCR domains were also subcloned into pTT5 vectors encoding variant IgG1 Fc domains containing S267E, G236D/L328F, G236N/L328F, S267E/L328F (high FcRIIb binding), or G236R/L328R (ablated FcR binding or Fc knockout; also shown as FcKO) substitutions. All DNA was sequenced to confirm the fidelity of the sequences. Amino acid sequences of select CR2-Fc variants are provided in FIG. 40. Plasmids containing heavy and light chain genes were co-transfected into HEK293E cells using lipofectamine (Invitrogen) and grown in FreeStyle 293 media (Invitrogen). After 5 days of growth, the antibodies were purified from the culture supernatant by protein A affinity using MabSelect resin (GE Healthcare).

SPR measurements were performed using a Biacore 3000 instrument (Biacore, Piscataway, N.J.). A protein A (Pierce Biotechnology) CM5 biosensor chip (Biacore) was generated using a standard primary amine coupling protocol. All measurements were performed using HBS-EP buffer (10 mM HEPES pH 7.4, 0.15 M NaCl, 3 mM EDTA, 0.005% vol/vol surfactant P20, Biacore). CR2-Fc variants at 25 nM in HBS-EP buffer were immobilized on the protein A surface and then 100 nM purified human C3d (Alpha Diagnostic cat# C3D18-N-25) was injected. After each cycle, the surface was regenerated by injecting glycine buffer (10 mM, pH 1.5). Data were processed by zeroing time and response before the injection of C3d and by subtracting appropriate nonspecific signals (response of reference channel and injection of running buffer). Kinetic analyses were performed by global fitting of binding data with a 1:1 Langmuir binding model using BIAevaluation software (Biacore). Example binding curves are shown in FIG. 39A.

Binding of CR2-Fc constructs to recombinant C3d-Fc was evaluated using ELISA. XENP12561 or XENP12562 (hSCR1-2 or hSCR1-4 Fc fusion) were coated to plates followed by adding varying concentrations of XENP12704, which is an anti-IgE antibody containing human C3d fused to the C-terminus of Ckappa. Anti-C1q antibody and no plate coating were used as controls. Plates were incubated overnight at 4° C. and an anti-IgG-F(ab')2-specific-HRP antibody was used for ELISA detection. Results are shown in FIG. 39B. XENP12561 and XENP12562 showed clear binding to recombinant C3d, with XENP12562 (containing hSCR1-4 domains) showing slightly stronger binding. A similar ELISA format was also used to evaluate the binding of CR2-Fc constructs to C3d-tagged immune complexes (IC) present in normal and rheumatoid arthritis (RA) patient sera. RA patients have autoimmune antibodies present and their sera are expected to contain a higher amount of C3d-tagged IC of these antibodies compared to normal subjects. XENP12561 or XENP12562 (hSCR1-2 or hSCR1-4 Fc fusion) were coated to plates followed by adding varying concentrations of normal or RA patient sera. Plates were incubated overnight at 4° C. and an anti-IgG-F(ab')2-specific-HRP antibody was used for ELISA detection. Results are shown in FIG. 39C. XENP12561 and XENP12562 showed strong binding to c3d-tagged IC present in both normal and RA patient sera. These results show that there is approximately 100-fold higher amount of IC in RA patient sera compared to normal sera.

Figure 44:
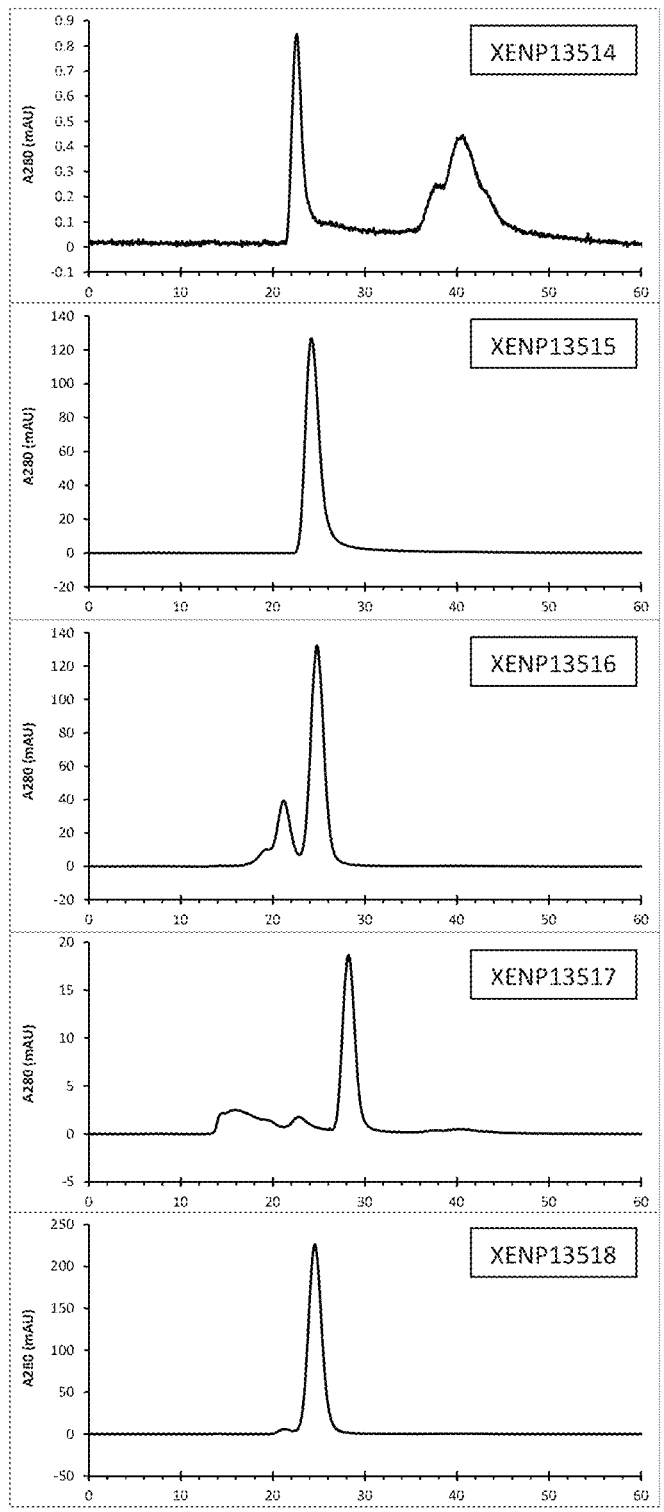
FIG. 44. Size-exclusion chromatograms for expressed and purified Fc-containing oxLDL-binding proteins.

Example 10. Design of Fc-Containing oxLDL-Binding Proteins with Enhanced FcγRIIb Affinity OxLDL is bound naturally by scavenger receptors such as LOX-1 (also known as OLR1) and CD36. Amino acid sequences for human and mouse versions of these receptors are listed in FIG. 43. LOX-1 and CD36 Fc fusions can be designed (XENP13516, XENP13517, XENP13518, sequences are listed in FIG. 44A-B). An Fc region is desirable to increase serum half-life, stability, and expression yields, while also serving as a scaffold for the inclusion of Fc variants for enhancing FcγRIIb affinity. Also, monoclonal antibodies that bind oxLDL are known in the art (XENP13514 and XENP13515, sequences are listed in FIG. 44A-B).

Plasmids containing appropriate genes were transfected or co-transfected into HEK293E cells using lipofectamine (Invitrogen) and grown in FreeStyle 293 media (Invitrogen). After 5 days of growth, the proteins were purified from the culture supernatant by protein A affinity using MabSelect resin (GE Healthcare). The resulting proteins were examined by size-exclusion chromatography (see FIG. 45).

Based on these results, amino acid sequences were designed for Fc-containing oxLDL-binding proteins containing the S267E/L328F Fc variant that confers enhanced FcγRIIb affinity (FIG. 46). Alternative Fc variants with various levels of FcγRIIb affinity can also be used as mentioned above, e.g., G236N/S236E, G236D/S267E, and S267E. These variants allow for the rapid clearance of oxLDL from the blood.

The EO6 antibody can be humanized to reduce its immunogenicity as a therapeutic in humans. Sequences of humanized variable regions derived from the EO6 parental sequence can be found in FIG. 47.

All cited references are herein expressly incorporated by reference in their entirety.

Whereas particular embodiments have been described above for purposes of illustration, it will be appreciated by those skilled in the art that numerous variations of the details may be made without departing from the invention as described in the appended claims.

---

We claim:

1. A method of treating atherosclerosis in a patient by rapidly lowering serum concentration of oxidized low-density lipoprotein (oxLDL) in said patient, said method comprising:
   a) administering a rapid clearance molecule comprising:
      i) a domain that binds said oxLDL; and
      ii) a variant human IgG Fc domain comprising an amino acid substitution as compared to a parent human IgG Fc domain, wherein said variant Fc domain binds FcγRIIb with increased affinity as compared to said parent Fc domain;
   wherein said rapid clearance molecule binds to said oxLDL to form a molecule-oxLDL complex and said complex is cleared at least two fold faster than oxLDL alone.

2. A method according to claim 1, wherein said variant Fc domain comprises amino acid substitutions selected from the group consisting of S267E, S267D, L328F, P238D, S267E/L328F, G236N/S267E, and G236D/S267E, wherein numbering is according to EU index as in Kabat.

3. A method according to claim 1, wherein said rapid clearance molecule is an antibody or an Fc fusion protein.

4. A method according to claim 3, wherein said rapid clearance molecule is an anti-oxLDL antibody.

5. A method according to claim 3, wherein said rapid clearance molecule is a LOX-1 Fc fusion protein.

6. A method according to claim 3, wherein said rapid clearance molecule is a CD36 Fc fusion protein.

7. A method according to claim 1, wherein said variant Fc domain comprises amino acid substitutions selected from the group consisting of: N434A, N434S, M428L, V308F, V259I, M428L/N434S, V259I/V308F, Y436I/M428L, Y436I or V/N434S, Y436V/M428L, M252Y, M252Y/S254T/T256E and V259I/V308F/M428L, wherein numbering is according to EU index as in Kabat.

8. A method according to claim 1, wherein said variant Fc domain is a variant of a parent human IgG1 Fc domain.

* * * * *

SEQUENCE LISTING

```
<160> NUMBER OF SEQ ID NOS: 96

<210> SEQ ID NO 1
<211> LENGTH: 121
<212> TYPE: PRT
<213> ORGANISM: Artificial Sequence
<220> FEATURE:
<223> OTHER INFORMATION: Omalizumab variable heavy chain sequence

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Asn Pro Ser Val
    50                  55                  60

Lys Gly Arg Ile Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Ser His Tyr Phe Gly His Trp His Phe Ala Val Trp Gly
            100                 105                 110

Gln Gly Thr Leu Val Thr Val Ser Ser
        115                 120

<210> SEQ ID NO 2
<211> LENGTH: 9
<212> TYPE: PRT
<213> ORGANISM: Artificial Sequence
<220> FEATURE:
<223> OTHER INFORMATION: Omalizumab variable heavy chain sequence CDR1

<400> SEQUENCE: 2

Tyr Ser Ile Thr Ser Gly Tyr Ser Trp
1               5

<210> SEQ ID NO 3
<211> LENGTH: 5
<212> TYPE: PRT
<213> ORGANISM: Artificial Sequence
<220> FEATURE:
<223> OTHER INFORMATION: Omalizumab variable heavy chain sequence CDR2

<400> SEQUENCE: 3

Thr Tyr Asp Gly Ser
1               5

<210> SEQ ID NO 4
<211> LENGTH: 12
<212> TYPE: PRT
<213> ORGANISM: Artificial Sequence
```

```
<220> FEATURE:
<223> OTHER INFORMATION: Omalizumab variable heavy chain sequence CDR3

<400> SEQUENCE: 4

Gly Ser His Tyr Phe Gly His Trp His Phe Ala Val
1               5                   10

<210> SEQ ID NO 5
<211> LENGTH: 111
<212> TYPE: PRT
<213> ORGANISM: Artificial Sequence
<220> FEATURE:
<223> OTHER INFORMATION: Omalizumab variable light chain sequence

<400> SEQUENCE: 5

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
                20                  25                  30

Gly Asp Ser Tyr Met Asn Trp Tyr Gln Gln Lys Pro Gly Lys Ala Pro
            35                  40                  45

Lys Leu Leu Ile Tyr Ala Ala Ser Tyr Leu Glu Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys
            100                 105                 110

<210> SEQ ID NO 6
<211> LENGTH: 10
<212> TYPE: PRT
<213> ORGANISM: Artificial Sequence
<220> FEATURE:
<223> OTHER INFORMATION: Omalizumab variable light chain sequence CDR1

<400> SEQUENCE: 6

Gln Ser Val Asp Tyr Asp Gly Asp Ser Tyr
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Omalizumab variable light chain sequence CDR2

<400> SEQUENCE: 7

Ala Ala Ser Tyr Leu Glu Ser
1               5

<210> SEQ ID NO 8
<211> LENGTH: 7
<212> TYPE: PRT
<213> ORGANISM: Artificial Sequence
<220> FEATURE:
<223> OTHER INFORMATION: Omalizumab variable light chain sequence CDR3

<400> SEQUENCE: 8

Ser His Glu Asp Pro Tyr Thr
1               5
```

<210> SEQ ID NO 9
<211> LENGTH: 121
<212> TYPE: PRT
<213> ORGANISM: Artificial Sequence
<220> FEATURE:
<223> OTHER INFORMATION: MaE11 variable heavy chain sequence

<400> SEQUENCE: 9

Asp Val Gln Leu Gln Glu Ser Gly Pro Gly Leu Val Lys Pro Ser Gln
1               5                   10                  15

Ser Leu Ser Leu Ala Cys Ser Val Thr Gly Tyr Ser Ile Thr Ser Gly
            20                  25                  30

Tyr Ser Trp Asn Trp Ile Arg Gln Phe Pro Gly Asn Lys Leu Glu Trp
        35                  40                  45

Met Gly Ser Ile Thr Tyr Asp Gly Ser Ser Asn Tyr Asn Pro Ser Leu
    50                  55                  60

Lys Asn Arg Ile Ser Val Thr Arg Asp Thr Ser Gln Asn Gln Phe Phe
65                  70                  75                  80

Leu Lys Leu Asn Ser Ala Thr Ala Glu Asp Thr Ala Thr Tyr Tyr Cys
                85                  90                  95

Ala Arg Gly Ser His Tyr Phe Gly His Trp His Phe Ala Val Trp Gly
            100                 105                 110

Ala Gly Thr Thr Val Thr Val Ser Ser
        115                 120

<210> SEQ ID NO 10
<211> LENGTH: 9
<212> TYPE: PRT
<213> ORGANISM: Artificial Sequence
<220> FEATURE:
<223> OTHER INFORMATION: MaE11 variable heavy chain sequence CDR1

<400> SEQUENCE: 10

Tyr Ser Ile Thr Ser Gly Tyr Ser Trp
1               5

<210> SEQ ID NO 11
<211> LENGTH: 5
<212> TYPE: PRT
<213> ORGANISM: Artificial Sequence
<220> FEATURE:
<223> OTHER INFORMATION: MaE11 variable heavy chain sequence CDR2

<400> SEQUENCE: 11

Thr Tyr Asp Gly Ser
1               5

<210> SEQ ID NO 12
<211> LENGTH: 12
<212> TYPE: PRT
<213> ORGANISM: Artificial Sequence
<220> FEATURE:
<223> OTHER INFORMATION: MaE11 variable heavy chain sequence CDR3

<400> SEQUENCE: 12

Gly Ser His Tyr Phe Gly His Trp His Phe Ala Val
1               5                   10

<210> SEQ ID NO 13
<211> LENGTH: 111
<212> TYPE: PRT
<213> ORGANISM: Artificial Sequence
<220> FEATURE:
<223> OTHER INFORMATION: MaE11 variable light chain sequence

<400> SEQUENCE: 13

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Ile Leu Leu Ile Tyr Ala Ala Ser Tyr Leu Gly Ser Glu Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Phe Tyr Cys Gln Gln Ser His
                85                  90                  95

Glu Asp Pro Tyr Thr Phe Gly Ala Gly Thr Lys Leu Glu Ile Lys
            100                 105                 110

<210> SEQ ID NO 14
<211> LENGTH: 10
<212> TYPE: PRT
<213> ORGANISM: Artificial Sequence
<220> FEATURE:
<223> OTHER INFORMATION: MaE11 variable light chain sequence CDR1

<400> SEQUENCE: 14

Gln Ser Val Asp Tyr Asp Gly Asp Ser Tyr
1               5                   10

<210> SEQ ID NO 15
<211> LENGTH: 7
<212> TYPE: PRT
<213> ORGANISM: Artificial Sequence
<220> FEATURE:
<223> OTHER INFORMATION: MaE11 variable light chain sequence CDR2

<400> SEQUENCE: 15

Ala Ala Ser Tyr Leu Gly Ser
1               5

<210> SEQ ID NO 16
<211> LENGTH: 7
<212> TYPE: PRT
<213> ORGANISM: Artificial Sequence
<220> FEATURE:
<223> OTHER INFORMATION: MaE11 variable light chain sequence CDR3

<400> SEQUENCE: 16

Ser His Glu Asp Pro Tyr Thr
1               5

<210> SEQ ID NO 17
<211> LENGTH: 121
<212> TYPE: PRT
<213> ORGANISM: Artificial Sequence
<220> FEATURE:
<223> OTHER INFORMATION: H1L1MaE11 variable heavy chain sequence

<400> SEQUENCE: 17

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Gly
            20                  25                  30

```
Tyr Ser Trp Asn Trp Ile Arg Gln Pro Pro Gly Lys Lys Leu Glu Trp
            35                  40                  45

Ile Gly Ser Ile Thr Tyr Asp Gly Ser Ser Asn Tyr Asn Pro Ser Leu
 50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Ser His Tyr Phe Gly His Trp His Phe Ala Val Trp Gly
                100                 105                 110

Ala Gly Thr Leu Val Thr Val Ser Ser
            115                 120
```

<210> SEQ ID NO 18
<211> LENGTH: 9
<212> TYPE: PRT
<213> ORGANISM: Artificial Sequence
<220> FEATURE:
<223> OTHER INFORMATION: H1L1MaE11 variable heavy chain sequence CDR1

<400> SEQUENCE: 18

```
Tyr Ser Ile Thr Ser Gly Tyr Ser Trp
 1               5
```

<210> SEQ ID NO 19
<211> LENGTH: 5
<212> TYPE: PRT
<213> ORGANISM: Artificial Sequence
<220> FEATURE:
<223> OTHER INFORMATION: H1L1MaE11 variable heavy chain sequence CDR2

<400> SEQUENCE: 19

```
Thr Tyr Asp Gly Ser
 1               5
```

<210> SEQ ID NO 20
<211> LENGTH: 12
<212> TYPE: PRT
<213> ORGANISM: Artificial Sequence
<220> FEATURE:
<223> OTHER INFORMATION: H1L1MaE11 variable heavy chain sequence CDR3

<400> SEQUENCE: 20

```
Gly Ser His Tyr Phe Gly His Trp His Phe Ala Val
 1               5                  10
```

<210> SEQ ID NO 21
<211> LENGTH: 111
<212> TYPE: PRT
<213> ORGANISM: Artificial Sequence
<220> FEATURE:
<223> OTHER INFORMATION: H1L1MaE11 variable light chain sequence

<400> SEQUENCE: 21

```
Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Ser Val Asp Tyr Asp
                 20                  25                  30

Gly Asp Ser Tyr Met Asn Trp Tyr Gln Gln Lys Pro Gly Gln Pro Pro
                 35                  40                  45

Lys Leu Leu Ile Tyr Ala Ala Ser Tyr Leu Gly Ser Glu Ile Pro Ala
 50                  55                  60
```

```
Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser His
                 85                  90                  95

Glu Asp Pro Tyr Thr Phe Gly Ala Gly Thr Lys Leu Glu Ile Lys
            100                 105                 110
```

<210> SEQ ID NO 22
<211> LENGTH: 10
<212> TYPE: PRT
<213> ORGANISM: Artificial Sequence
<220> FEATURE:
<223> OTHER INFORMATION: H1L1MaE11 variable light chain sequence CDR1

<400> SEQUENCE: 22

```
Gln Ser Val Asp Tyr Asp Gly Asp Ser Tyr
 1               5                  10
```

<210> SEQ ID NO 23
<211> LENGTH: 7
<212> TYPE: PRT
<213> ORGANISM: Artificial Sequence
<220> FEATURE:
<223> OTHER INFORMATION: H1L1MaE11 variable light chain sequence CDR2

<400> SEQUENCE: 23

```
Ala Ala Ser Tyr Leu Gly Ser
 1               5
```

<210> SEQ ID NO 24
<211> LENGTH: 7
<212> TYPE: PRT
<213> ORGANISM: Artificial Sequence
<220> FEATURE:
<223> OTHER INFORMATION: H1L1MaE11 variable light chain sequence CDR3

<400> SEQUENCE: 24

```
Ser His Glu Asp Pro Tyr Thr
 1               5
```

<210> SEQ ID NO 25
<211> LENGTH: 123
<212> TYPE: PRT
<213> ORGANISM: Artificial Sequence
<220> FEATURE:
<223> OTHER INFORMATION: TES-C21 variable heavy chain sequence

<400> SEQUENCE: 25

```
Gln Val Gln Leu Gln Gln Ser Gly Ala Glu Leu Met Lys Pro Gly Ala
 1               5                  10                  15

Ser Val Lys Ile Ser Cys Lys Thr Thr Gly Tyr Thr Phe Ser Met Tyr
                20                  25                  30

Trp Leu Glu Trp Val Lys Gln Arg Pro Gly His Gly Leu Glu Trp Val
            35                  40                  45

Gly Glu Ile Ser Pro Gly Thr Phe Thr Thr Asn Tyr Asn Glu Lys Phe
     50                  55                  60

Lys Ala Lys Ala Thr Phe Thr Ala Asp Thr Ser Ser Asn Thr Ala Tyr
 65                  70                  75                  80

Leu Gln Leu Ser Gly Leu Thr Ser Glu Asp Ser Ala Val Tyr Phe Cys
                 85                  90                  95

Ala Arg Phe Ser His Phe Ser Gly Ser Asn Tyr Asp Tyr Phe Asp Tyr
            100                 105                 110
```

Trp Gly Gln Gly Thr Ser Leu Thr Val Ser Ser
        115                 120

<210> SEQ ID NO 26
<211> LENGTH: 7
<212> TYPE: PRT
<213> ORGANISM: Artificial Sequence
<220> FEATURE:
<223> OTHER INFORMATION: TES-C21 variable heavy chain sequence CDR1

<400> SEQUENCE: 26

Tyr Thr Phe Ser Met Tyr Trp
1               5

<210> SEQ ID NO 27
<211> LENGTH: 6
<212> TYPE: PRT
<213> ORGANISM: Artificial Sequence
<220> FEATURE:
<223> OTHER INFORMATION: TES-C21 variable heavy chain sequence CDR2

<400> SEQUENCE: 27

Ser Pro Gly Thr Phe Thr
1               5

<210> SEQ ID NO 28
<211> LENGTH: 14
<212> TYPE: PRT
<213> ORGANISM: Artificial Sequence
<220> FEATURE:
<223> OTHER INFORMATION: TES-C21 variable heavy chain sequence CDR3

<400> SEQUENCE: 28

Phe Ser His Phe Ser Gly Ser Asn Tyr Asp Tyr Phe Asp Tyr
1               5                   10

<210> SEQ ID NO 29
<211> LENGTH: 107
<212> TYPE: PRT
<213> ORGANISM: Artificial Sequence
<220> FEATURE:
<223> OTHER INFORMATION: TES-C21 variable light chain sequence

<400> SEQUENCE: 29

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asp Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Glu Phe Thr Leu Asn Ile Asn Ser Val Glu Ser
65                  70                  75                  80

Glu Asp Ile Ala Asp Tyr Tyr Cys Gln Gln Ser Asp Ser Trp Pro Thr
                85                  90                  95

Thr Phe Gly Gly Gly Thr Lys Leu Glu Ile Lys
            100                 105

<210> SEQ ID NO 30
<211> LENGTH: 6
<212> TYPE: PRT
<213> ORGANISM: Artificial Sequence
<220> FEATURE:

<223> OTHER INFORMATION: TES-C21 variable light chain sequence CDR1

<400> SEQUENCE: 30

Gln Ser Ile Gly Thr Asn
1               5

<210> SEQ ID NO 31
<211> LENGTH: 7
<212> TYPE: PRT
<213> ORGANISM: Artificial Sequence
<220> FEATURE:
<223> OTHER INFORMATION: TES-C21 variable light chain sequence CDR2

<400> SEQUENCE: 31

Tyr Ala Ser Glu Ser Ile Ser
1               5

<210> SEQ ID NO 32
<211> LENGTH: 7
<212> TYPE: PRT
<213> ORGANISM: Artificial Sequence
<220> FEATURE:
<223> OTHER INFORMATION: TES-C21 variable light chain sequence CDR3

<400> SEQUENCE: 32

Ser Asp Ser Trp Pro Thr Thr
1               5

<210> SEQ ID NO 33
<211> LENGTH: 107
<212> TYPE: PRT
<213> ORGANISM: Artificial Sequence
<220> FEATURE:
<223> OTHER INFORMATION: Ckappa light chain

<400> SEQUENCE: 33

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 34
<211> LENGTH: 330
<212> TYPE: PRT
<213> ORGANISM: Artificial Sequence
<220> FEATURE:
<223> OTHER INFORMATION: Native IgG1 constant chain

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 35
<211> LENGTH: 330
<212> TYPE: PRT
<213> ORGANISM: Artificial Sequence
<220> FEATURE:
<223> OTHER INFORMATION: S267E/L328F IgG1 constant chain

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Phe Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 36
<211> LENGTH: 330
<212> TYPE: PRT
<213> ORGANISM: Artificial Sequence
<220> FEATURE:
<223> OTHER INFORMATION: G236D/S267E IgG1 constant chain

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95
```

Lys Val Glu Pro Lys Ser Cys Asp Lys Thr His Thr Cys Pro Pro Cys
            100                 105                 110

Pro Ala Pro Glu Leu Leu Asp Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 37
<211> LENGTH: 218
<212> TYPE: PRT
<213> ORGANISM: Artificial Sequence
<220> FEATURE:
<223> OTHER INFORMATION: Omalizumab light chain (VH-C )

<400> SEQUENCE: 37

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

```
Leu Lys Ser Gly Thr Ala Ser Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
        210                 215

<210> SEQ ID NO 38
<211> LENGTH: 451
<212> TYPE: PRT
<213> ORGANISM: Artificial Sequence
<220> FEATURE:
<223> OTHER INFORMATION: Omalizumab IgG1 heavy chain

<400> SEQUENCE: 38

Glu Val Gln Leu Val Glu Ser Gly Gly Gly Leu Val Gln Pro Gly Gly
1               5                   10                  15
Ser Leu Arg Leu Ser Cys Ala Val Ser Gly Tyr Ser Ile Thr Ser Gly
            20                  25                  30
Tyr Ser Trp Asn Trp Ile Arg Gln Ala Pro Gly Lys Gly Leu Glu Trp
        35                  40                  45
Val Ala Ser Ile Thr Tyr Asp Gly Ser Thr Asn Tyr Asn Pro Ser Val
    50                  55                  60
Lys Gly Arg Ile Thr Ile Ser Arg Asp Asp Ser Lys Asn Thr Phe Tyr
65                  70                  75                  80
Leu Gln Met Asn Ser Leu Arg Ala Glu Asp Thr Ala Val Tyr Tyr Cys
                85                  90                  95
Ala Arg Gly Ser His Tyr Phe Gly His Trp His Phe Ala Val Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
```

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 39
<211> LENGTH: 451
<212> TYPE: PRT
<213> ORGANISM: Artificial Sequence
<220> FEATURE:
<223> OTHER INFORMATION: Omalizumab S267E/L328F heavy chain

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Asn Pro Ser Val
    50                  55                  60

Lys Gly Arg Ile Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Ser His Tyr Phe Gly His Trp His Phe Ala Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

-continued

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Glu His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Phe Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 40
<211> LENGTH: 218
<212> TYPE: PRT
<213> ORGANISM: Artificial Sequence
<220> FEATURE:
<223> OTHER INFORMATION: H1L1 MaE11 light chain (VH-C )

<400> SEQUENCE: 40

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Tyr Leu Gly Ser Glu Ile Pro Ala
    50                  55                  60

Arg Phe Ser Gly Ser Gly Ser Gly Thr Asp Phe Thr Leu Thr Ile Ser
65                  70                  75                  80

```
Ser Leu Gln Pro Glu Asp Phe Ala Thr Tyr Tyr Cys Gln Gln Ser His
                85                  90                  95

Glu Asp Pro Tyr Thr Phe Gly Ala Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 41
<211> LENGTH: 451
<212> TYPE: PRT
<213> ORGANISM: Artificial Sequence
<220> FEATURE:
<223> OTHER INFORMATION: H1L1 MaE11 IgG1 heavy chain

<400> SEQUENCE: 41

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Gly
            20                  25                  30

Tyr Ser Trp Asn Trp Ile Arg Gln Pro Pro Gly Lys Lys Leu Glu Trp
        35                  40                  45

Ile Gly Ser Ile Thr Tyr Asp Gly Ser Ser Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Ser His Tyr Phe Gly His Trp His Phe Ala Val Trp Gly
            100                 105                 110

Ala Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 42
<211> LENGTH: 451
<212> TYPE: PRT
<213> ORGANISM: Artificial Sequence
<220> FEATURE:
<223> OTHER INFORMATION: H1L1 MaE11 S267E/L328F heavy chain

<400> SEQUENCE: 42

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Gly
            20                  25                  30

Tyr Ser Trp Asn Trp Ile Arg Gln Pro Pro Gly Lys Lys Leu Glu Trp
        35                  40                  45

Ile Gly Ser Ile Thr Tyr Asp Gly Ser Ser Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Gly Ser His Tyr Phe Gly His Trp His Phe Ala Val Trp Gly
        100                 105                 110

Ala Gly Thr Leu Val Thr Val Ser Ser Ala Ser Thr Lys Gly Pro Ser
    115                 120                 125

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Glu His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Phe Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 43
<211> LENGTH: 573
<212> TYPE: PRT
<213> ORGANISM: Artificial Sequence
<220> FEATURE:
<223> OTHER INFORMATION: FVIII_A2_IgG1_C220S/S267E/L328F

<400> SEQUENCE: 43

Ser Val Ala Lys Lys His Pro Lys Thr Trp Val His Tyr Ile Ala Ala
1               5                   10                  15

Glu Glu Glu Asp Trp Asp Tyr Ala Pro Leu Val Leu Ala Pro Asp Asp
            20                  25                  30
```

```
Arg Ser Tyr Lys Ser Gln Tyr Leu Asn Asn Gly Pro Gln Arg Ile Gly
         35                  40                  45

Arg Lys Tyr Lys Lys Val Arg Phe Met Ala Tyr Thr Asp Glu Thr Phe
 50                  55                  60

Lys Thr Arg Glu Ala Ile Gln His Glu Ser Gly Ile Leu Gly Pro Leu
 65                  70                  75                  80

Leu Tyr Gly Glu Val Gly Asp Thr Leu Leu Ile Ile Phe Lys Asn Gln
                 85                  90                  95

Ala Ser Arg Pro Tyr Asn Ile Tyr Pro His Gly Ile Thr Asp Val Arg
             100                 105                 110

Pro Leu Tyr Ser Arg Arg Leu Pro Lys Gly Val Lys His Leu Lys Asp
             115                 120                 125

Phe Pro Ile Leu Pro Gly Glu Ile Phe Lys Tyr Lys Trp Thr Val Thr
             130                 135                 140

Val Glu Asp Gly Pro Thr Lys Ser Asp Pro Arg Cys Leu Thr Arg Tyr
145                 150                 155                 160

Tyr Ser Ser Phe Val Asn Met Glu Arg Asp Leu Ala Ser Gly Leu Ile
                 165                 170                 175

Gly Pro Leu Leu Ile Cys Tyr Lys Glu Ser Val Asp Gln Arg Gly Asn
             180                 185                 190

Gln Ile Met Ser Asp Lys Arg Asn Val Ile Leu Phe Ser Val Phe Asp
             195                 200                 205

Glu Asn Arg Ser Trp Tyr Leu Thr Glu Asn Ile Gln Arg Phe Leu Pro
             210                 215                 220

Asn Pro Ala Gly Val Gln Leu Glu Asp Pro Glu Phe Gln Ala Ser Asn
225                 230                 235                 240

Ile Met His Ser Ile Asn Gly Tyr Val Phe Asp Ser Leu Gln Leu Ser
                 245                 250                 255

Val Cys Leu His Glu Val Ala Tyr Trp Tyr Ile Leu Ser Ile Gly Ala
             260                 265                 270

Gln Thr Asp Phe Leu Ser Val Phe Phe Ser Gly Tyr Thr Phe Lys His
             275                 280                 285

Lys Met Val Tyr Glu Asp Thr Leu Thr Leu Phe Pro Phe Ser Gly Glu
             290                 295                 300

Thr Val Phe Met Ser Met Glu Asn Pro Gly Leu Trp Ile Leu Gly Cys
305                 310                 315                 320

His Asn Ser Asp Phe Arg Asn Arg Gly Met Thr Ala Leu Leu Lys Val
                 325                 330                 335

Ser Ser Cys Asp Lys Glu Pro Lys Ser Ser Asp Lys Thr His Thr Cys
             340                 345                 350

Pro Pro Cys Pro Ala Pro Glu Leu Leu Gly Gly Pro Ser Val Phe Leu
             355                 360                 365

Phe Pro Pro Lys Pro Lys Asp Thr Leu Met Ile Ser Arg Thr Pro Glu
             370                 375                 380

Val Thr Cys Val Val Val Asp Val Glu His Glu Asp Pro Glu Val Lys
385                 390                 395                 400

Phe Asn Trp Tyr Val Asp Gly Val Glu Val His Asn Ala Lys Thr Lys
                 405                 410                 415

Pro Arg Glu Glu Gln Tyr Asn Ser Thr Tyr Arg Val Val Ser Val Leu
             420                 425                 430

Thr Val Leu His Gln Asp Trp Leu Asn Gly Lys Glu Tyr Lys Cys Lys
             435                 440                 445
```

-continued

```
Val Ser Asn Lys Ala Phe Pro Ala Pro Ile Glu Lys Thr Ile Ser Lys
450                 455                 460

Ala Lys Gly Gln Pro Arg Glu Pro Gln Val Tyr Thr Leu Pro Pro Ser
465                 470                 475                 480

Arg Glu Glu Met Thr Lys Asn Gln Val Ser Leu Thr Cys Leu Val Lys
            485                 490                 495

Gly Phe Tyr Pro Ser Asp Ile Ala Val Glu Trp Glu Ser Asn Gly Gln
            500                 505                 510

Pro Glu Asn Asn Tyr Lys Thr Thr Pro Pro Val Leu Asp Ser Asp Gly
            515                 520                 525

Ser Phe Phe Leu Tyr Ser Lys Leu Thr Val Asp Lys Ser Arg Trp Gln
530                 535                 540

Gln Gly Asn Val Phe Ser Cys Ser Val Met His Glu Ala Leu His Asn
545                 550                 555                 560

His Tyr Thr Gln Lys Ser Leu Ser Leu Ser Pro Gly Lys
            565                 570

<210> SEQ ID NO 44
<211> LENGTH: 395
<212> TYPE: PRT
<213> ORGANISM: Artificial Sequence
<220> FEATURE:
<223> OTHER INFORMATION: FVIII_C2_IgG1_C220S/S267E/L328F

<400> SEQUENCE: 44

Asp Leu Asn Ser Cys Ser Met Pro Leu Gly Met Glu Ser Lys Ala Ile
1               5                   10                  15

Ser Asp Ala Gln Ile Thr Ala Ser Ser Tyr Phe Thr Asn Met Phe Ala
            20                  25                  30

Thr Trp Ser Pro Ser Lys Ala Arg Leu His Leu Gln Gly Arg Ser Asn
        35                  40                  45

Ala Trp Arg Pro Gln Val Asn Asn Pro Lys Glu Trp Leu Gln Val Asp
    50                  55                  60

Phe Gln Lys Thr Met Lys Val Thr Gly Val Thr Thr Gln Gly Val Lys
65                  70                  75                  80

Ser Leu Leu Thr Ser Met Tyr Val Lys Glu Phe Leu Ile Ser Ser Ser
                85                  90                  95

Gln Asp Gly His Gln Trp Thr Leu Phe Phe Gln Asn Gly Lys Val Lys
            100                 105                 110

Val Phe Gln Gly Asn Gln Asp Ser Phe Thr Pro Val Val Asn Ser Leu
        115                 120                 125

Asp Pro Pro Leu Leu Thr Arg Tyr Leu Arg Ile His Pro Gln Ser Trp
130                 135                 140

Val His Gln Ile Ala Leu Arg Met Glu Val Leu Gly Cys Glu Ala Gln
145                 150                 155                 160

Asp Leu Tyr Glu Pro Lys Ser Ser Asp Lys Thr His Thr Cys Pro Pro
                165                 170                 175

Cys Pro Ala Pro Glu Leu Leu Gly Gly Pro Ser Val Phe Leu Phe Pro
            180                 185                 190

Pro Lys Pro Lys Asp Thr Leu Met Ile Ser Arg Thr Pro Glu Val Thr
        195                 200                 205

Cys Val Val Val Asp Val Glu His Glu Asp Pro Glu Val Lys Phe Asn
    210                 215                 220

Trp Tyr Val Asp Gly Val Glu Val His Asn Ala Lys Thr Lys Pro Arg
225                 230                 235                 240
```

-continued

Glu Glu Gln Tyr Asn Ser Thr Tyr Arg Val Val Ser Val Leu Thr Val
            245                 250                 255

Leu His Gln Asp Trp Leu Asn Gly Lys Glu Tyr Lys Cys Lys Val Ser
        260                 265                 270

Asn Lys Ala Phe Pro Ala Pro Ile Glu Lys Thr Ile Ser Lys Ala Lys
        275                 280                 285

Gly Gln Pro Arg Glu Pro Gln Val Tyr Thr Leu Pro Pro Ser Arg Glu
290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
            325                 330                 335

Asn Asn Tyr Lys Thr Thr Pro Pro Val Leu Asp Ser Asp Gly Ser Phe
            340                 345                 350

Phe Leu Tyr Ser Lys Leu Thr Val Asp Lys Ser Arg Trp Gln Gln Gly
        355                 360                 365

Asn Val Phe Ser Cys Ser Val Met His Glu Ala Leu His Asn His Tyr
        370                 375                 380

Thr Gln Lys Ser Leu Ser Leu Ser Pro Gly Lys
385                 390                 395

<210> SEQ ID NO 45
<211> LENGTH: 572
<212> TYPE: PRT
<213> ORGANISM: Artificial Sequence
<220> FEATURE:
<223> OTHER INFORMATION: heavy chain sequence

<400> SEQUENCE: 45

Ser Val Ala Lys Lys His Pro Lys Thr Trp Val His Tyr Ile Ala Ala
1               5                   10                  15

Glu Glu Glu Asp Trp Asp Tyr Ala Pro Leu Val Leu Ala Pro Asp Asp
            20                  25                  30

Arg Ser Tyr Lys Ser Gln Tyr Leu Asn Asn Gly Pro Gln Arg Ile Gly
        35                  40                  45

Arg Lys Tyr Lys Lys Val Arg Phe Met Ala Tyr Thr Asp Glu Thr Phe
50                  55                  60

Lys Thr Arg Glu Ala Ile Gln His Glu Ser Gly Ile Leu Gly Pro Leu
65                  70                  75                  80

Leu Tyr Gly Glu Val Gly Asp Thr Leu Leu Ile Ile Phe Lys Asn Gln
            85                  90                  95

Ala Ser Arg Pro Tyr Asn Ile Tyr Pro His Gly Ile Thr Asp Val Arg
        100                 105                 110

Pro Leu Tyr Ser Arg Arg Leu Pro Lys Gly Val Lys His Leu Lys Asp
        115                 120                 125

Phe Pro Ile Leu Pro Gly Glu Ile Phe Lys Tyr Lys Trp Thr Val Thr
130                 135                 140

Val Glu Asp Gly Pro Thr Lys Ser Asp Pro Arg Cys Leu Thr Arg Tyr
145                 150                 155                 160

Tyr Ser Ser Phe Val Asn Met Glu Arg Asp Leu Ala Ser Gly Leu Ile
            165                 170                 175

Gly Pro Leu Leu Ile Cys Tyr Lys Glu Ser Val Asp Gln Arg Gly Asn
        180                 185                 190

Gln Ile Met Ser Asp Lys Arg Asn Val Ile Leu Phe Ser Val Phe Asp
        195                 200                 205

-continued

Glu Asn Arg Ser Trp Tyr Leu Thr Glu Asn Ile Gln Arg Phe Leu Pro
            210                 215                 220

Asn Pro Ala Gly Val Gln Leu Glu Asp Pro Glu Phe Gln Ala Ser Asn
225                 230                 235                 240

Ile Met His Ser Ile Asn Gly Tyr Val Phe Asp Ser Leu Gln Leu Ser
                245                 250                 255

Val Cys Leu His Glu Val Ala Tyr Trp Tyr Ile Leu Ser Ile Gly Ala
            260                 265                 270

Gln Thr Asp Phe Leu Ser Val Phe Ser Gly Tyr Thr Phe Lys His
            275                 280                 285

Lys Met Val Tyr Glu Asp Thr Leu Thr Leu Phe Pro Phe Ser Gly Glu
290                 295                 300

Thr Val Phe Met Ser Met Glu Asn Pro Gly Leu Trp Ile Leu Gly Cys
305                 310                 315                 320

His Asn Ser Asp Phe Arg Asn Arg Gly Met Thr Ala Leu Leu Lys Val
                325                 330                 335

Ser Ser Cys Asp Lys Glu Pro Lys Ser Ser Asp Lys Thr His Thr Cys
            340                 345                 350

Pro Pro Cys Pro Ala Pro Glu Leu Leu Gly Gly Pro Ser Val Phe Leu
            355                 360                 365

Phe Pro Pro Lys Pro Lys Asp Thr Leu Met Ile Ser Arg Thr Pro Glu
370                 375                 380

Val Thr Cys Val Val Val Asp Val Glu His Glu Asp Pro Glu Val Gln
385                 390                 395                 400

Phe Asn Trp Tyr Val Asp Gly Val Glu Val His Asn Ala Lys Thr Lys
                405                 410                 415

Pro Arg Glu Glu Gln Tyr Asn Ser Thr Tyr Arg Val Val Ser Val Leu
            420                 425                 430

Thr Val Leu His Gln Asp Trp Leu Asn Gly Lys Glu Tyr Lys Cys Lys
            435                 440                 445

Val Ser Asn Lys Ala Phe Pro Ala Pro Ile Glu Lys Thr Ile Ser Lys
        450                 455                 460

Ala Lys Gly Gln Pro Arg Glu Pro Gln Val Tyr Thr Leu Pro Pro Ser
465                 470                 475                 480

Gln Glu Glu Met Thr Lys Asn Gln Val Ser Leu Thr Cys Leu Val Lys
                485                 490                 495

Gly Phe Tyr Pro Ser Asp Ile Ala Val Glu Trp Glu Ser Ser Gly Gln
            500                 505                 510

Pro Glu Asn Asn Tyr Asn Thr Thr Pro Pro Met Leu Asp Ser Asp Gly
            515                 520                 525

Ser Phe Phe Leu Tyr Ser Lys Leu Thr Val Asp Lys Ser Arg Trp Gln
530                 535                 540

Glu Gly Asn Val Phe Ser Cys Ser Val Met His Glu Ala Leu His Asn
545                 550                 555                 560

His Tyr Thr Gln Lys Ser Leu Ser Leu Ser Pro Gly
            565                 570

<210> SEQ ID NO 46
<211> LENGTH: 395
<212> TYPE: PRT
<213> ORGANISM: Artificial Sequence
<220> FEATURE:
<223> OTHER INFORMATION: heavy chain sequence

<400> SEQUENCE: 46

```
Asp Leu Asn Ser Cys Ser Met Pro Leu Gly Met Glu Ser Lys Ala Ile
1               5                   10                  15
Ser Asp Ala Gln Ile Thr Ala Ser Ser Tyr Phe Thr Asn Met Phe Ala
            20                  25                  30
Thr Trp Ser Pro Ser Lys Ala Arg Leu His Leu Gln Gly Arg Ser Asn
        35                  40                  45
Ala Trp Arg Pro Gln Val Asn Asn Pro Lys Glu Trp Leu Gln Val Asp
    50                  55                  60
Phe Gln Lys Thr Met Lys Val Thr Gly Val Thr Thr Gln Gly Val Lys
65                  70                  75                  80
Ser Leu Leu Thr Ser Met Tyr Val Lys Glu Phe Leu Ile Ser Ser Ser
                85                  90                  95
Gln Asp Gly His Gln Trp Thr Leu Phe Phe Gln Asn Gly Lys Val Lys
            100                 105                 110
Val Phe Gln Gly Asn Gln Asp Ser Phe Thr Pro Val Asn Ser Leu
        115                 120                 125
Asp Pro Pro Leu Leu Thr Arg Tyr Leu Arg Ile His Pro Gln Ser Trp
    130                 135                 140
Val His Gln Ile Ala Leu Arg Met Glu Val Leu Gly Cys Glu Ala Gln
145                 150                 155                 160
Asp Leu Tyr Glu Pro Lys Ser Ser Asp Lys Thr His Thr Cys Pro Pro
                165                 170                 175
Cys Pro Ala Pro Glu Leu Leu Gly Gly Pro Ser Val Phe Leu Phe Pro
            180                 185                 190
Pro Lys Pro Lys Asp Thr Leu Met Ile Ser Arg Thr Pro Glu Val Thr
        195                 200                 205
Cys Val Val Val Asp Val Glu His Glu Asp Pro Glu Val Lys Phe Lys
210                 215                 220
Trp Tyr Val Asp Gly Val Glu Val His Asn Ala Lys Thr Lys Pro Arg
225                 230                 235                 240
Glu Glu Gln Tyr Asn Ser Thr Tyr Arg Val Val Ser Val Leu Thr Val
                245                 250                 255
Leu His Gln Asp Trp Leu Asn Gly Lys Glu Tyr Lys Cys Lys Val Ser
            260                 265                 270
Asn Lys Ala Phe Pro Ala Pro Ile Glu Lys Thr Ile Ser Lys Ala Lys
        275                 280                 285
Gly Gln Pro Arg Glu Pro Gln Val Tyr Thr Leu Pro Pro Ser Arg Glu
    290                 295                 300
Glu Met Thr Lys Asn Gln Val Ser Leu Thr Cys Leu Val Lys Gly Phe
305                 310                 315                 320
Tyr Pro Ser Asp Ile Ala Val Glu Trp Glu Ser Asn Gly Gln Pro Glu
                325                 330                 335
Asn Asn Tyr Lys Thr Thr Pro Pro Val Leu Asp Ser Asp Gly Ser Phe
            340                 345                 350
Phe Leu Tyr Ser Lys Leu Thr Val Asp Lys Ser Arg Trp Gln Gln Gly
        355                 360                 365
Asn Val Phe Ser Cys Ser Val Met His Glu Ala Leu His Asn His Tyr
    370                 375                 380
Thr Gln Lys Ser Leu Ser Leu Ser Pro Gly Lys
385                 390                 395

<210> SEQ ID NO 47
<211> LENGTH: 747
<212> TYPE: PRT
```

<213> ORGANISM: Artificial Sequence
<220> FEATURE:
<223> OTHER INFORMATION: FVIII_A2-C2_IgG1_C220S/S267E/L328F

<400> SEQUENCE: 47

```
Ser Val Ala Lys Lys His Pro Lys Thr Trp Val His Tyr Ile Ala Ala
1               5                   10                  15

Glu Glu Glu Asp Trp Asp Tyr Ala Pro Leu Val Leu Ala Pro Asp Asp
            20                  25                  30

Arg Ser Tyr Lys Ser Gln Tyr Leu Asn Asn Gly Pro Gln Arg Ile Gly
        35                  40                  45

Arg Lys Tyr Lys Lys Val Arg Phe Met Ala Tyr Thr Asp Glu Thr Phe
    50                  55                  60

Lys Thr Arg Glu Ala Ile Gln His Glu Ser Gly Ile Leu Gly Pro Leu
65                  70                  75                  80

Leu Tyr Gly Glu Val Gly Asp Thr Leu Leu Ile Ile Phe Lys Asn Gln
                85                  90                  95

Ala Ser Arg Pro Tyr Asn Ile Tyr Pro His Gly Ile Thr Asp Val Arg
            100                 105                 110

Pro Leu Tyr Ser Arg Arg Leu Pro Lys Gly Val Lys His Leu Lys Asp
        115                 120                 125

Phe Pro Ile Leu Pro Gly Glu Ile Phe Lys Tyr Lys Trp Thr Val Thr
    130                 135                 140

Val Glu Asp Gly Pro Thr Lys Ser Asp Pro Arg Cys Leu Thr Arg Tyr
145                 150                 155                 160

Tyr Ser Ser Phe Val Asn Met Glu Arg Asp Leu Ala Ser Gly Leu Ile
                165                 170                 175

Gly Pro Leu Leu Ile Cys Tyr Lys Glu Ser Val Asp Gln Arg Gly Asn
            180                 185                 190

Gln Ile Met Ser Asp Lys Arg Asn Val Ile Leu Phe Ser Val Phe Asp
        195                 200                 205

Glu Asn Arg Ser Trp Tyr Leu Thr Glu Asn Ile Gln Arg Phe Leu Pro
    210                 215                 220

Asn Pro Ala Gly Val Gln Leu Glu Asp Pro Glu Phe Gln Ala Ser Asn
225                 230                 235                 240

Ile Met His Ser Ile Asn Gly Tyr Val Phe Asp Ser Leu Gln Leu Ser
                245                 250                 255

Val Cys Leu His Glu Val Ala Tyr Trp Tyr Ile Leu Ser Ile Gly Ala
            260                 265                 270

Gln Thr Asp Phe Leu Ser Val Phe Phe Ser Gly Tyr Thr Phe Lys His
        275                 280                 285

Lys Met Val Tyr Glu Asp Thr Leu Thr Leu Phe Pro Phe Ser Gly Glu
    290                 295                 300

Thr Val Phe Met Ser Met Glu Asn Pro Gly Leu Trp Ile Leu Gly Cys
305                 310                 315                 320

His Asn Ser Asp Phe Arg Asn Arg Gly Met Thr Ala Leu Leu Lys Val
                325                 330                 335

Ser Ser Cys Asp Lys Asn Thr Gly Asp Tyr Tyr Glu Asp Ser Tyr Glu
            340                 345                 350

Asp Leu Asn Ser Cys Ser Met Pro Leu Gly Met Glu Ser Lys Ala Ile
        355                 360                 365

Ser Asp Ala Gln Ile Thr Ala Ser Ser Tyr Phe Thr Asn Met Phe Ala
    370                 375                 380

Thr Trp Ser Pro Ser Lys Ala Arg Leu His Leu Gln Gly Arg Ser Asn
```

```
            385                 390                 395                 400
Ala Trp Arg Pro Gln Val Asn Asn Pro Lys Glu Trp Leu Gln Val Asp
                405                 410                 415
Phe Gln Lys Thr Met Lys Val Thr Gly Val Thr Thr Gln Gly Val Lys
            420                 425                 430
Ser Leu Leu Thr Ser Met Tyr Val Lys Glu Phe Leu Ile Ser Ser Ser
            435                 440                 445
Gln Asp Gly His Gln Trp Thr Leu Phe Phe Gln Asn Gly Lys Val Lys
        450                 455                 460
Val Phe Gln Gly Asn Gln Asp Ser Phe Thr Pro Val Val Asn Ser Leu
465                 470                 475                 480
Asp Pro Pro Leu Leu Thr Arg Tyr Leu Arg Ile His Pro Gln Ser Trp
                485                 490                 495
Val His Gln Ile Ala Leu Arg Met Glu Val Leu Gly Cys Glu Ala Gln
            500                 505                 510
Asp Leu Tyr Glu Pro Lys Ser Ser Asp Lys Thr His Thr Cys Pro Pro
            515                 520                 525
Cys Pro Ala Pro Glu Leu Leu Gly Gly Pro Ser Val Phe Leu Phe Pro
        530                 535                 540
Pro Lys Pro Lys Asp Thr Leu Met Ile Ser Arg Thr Pro Glu Val Thr
545                 550                 555                 560
Cys Val Val Val Asp Val Glu His Glu Asp Pro Glu Val Lys Phe Asn
                565                 570                 575
Trp Tyr Val Asp Gly Val Glu Val His Asn Ala Lys Thr Lys Pro Arg
            580                 585                 590
Glu Glu Gln Tyr Asn Ser Thr Tyr Arg Val Val Ser Val Leu Thr Val
            595                 600                 605
Leu His Gln Asp Trp Leu Asn Gly Lys Glu Tyr Lys Cys Lys Val Ser
        610                 615                 620
Asn Lys Ala Phe Pro Ala Pro Ile Glu Lys Thr Ile Ser Lys Ala Lys
625                 630                 635                 640
Gly Gln Pro Arg Glu Pro Gln Val Tyr Thr Leu Pro Pro Ser Arg Glu
                645                 650                 655
Glu Met Thr Lys Asn Gln Val Ser Leu Thr Cys Leu Val Lys Gly Phe
            660                 665                 670
Tyr Pro Ser Asp Ile Ala Val Glu Trp Glu Ser Asn Gly Gln Pro Glu
            675                 680                 685
Asn Asn Tyr Lys Thr Thr Pro Pro Val Leu Asp Ser Asp Gly Ser Phe
        690                 695                 700
Phe Leu Tyr Ser Lys Leu Thr Val Asp Lys Ser Arg Trp Gln Gln Gly
705                 710                 715                 720
Asn Val Phe Ser Cys Ser Val Met His Glu Ala Leu His Asn His Tyr
                725                 730                 735
Thr Gln Lys Ser Leu Ser Leu Ser Pro Gly Lys
            740                 745

<210> SEQ ID NO 48
<211> LENGTH: 148
<212> TYPE: PRT
<213> ORGANISM: Artificial Sequence
<220> FEATURE:
<223> OTHER INFORMATION: Human CR2 SCR1-2 domains

<400> SEQUENCE: 48

Met Gly Ala Ala Gly Leu Leu Gly Val Phe Leu Ala Leu Val Ala Pro
```

```
1               5                   10                  15
Gly Val Leu Gly Ile Ser Cys Gly Ser Pro Pro Ile Leu Asn Gly
            20                  25                  30

Arg Ile Ser Tyr Tyr Ser Thr Pro Ile Ala Val Gly Thr Val Ile Arg
            35                  40                  45

Tyr Ser Cys Ser Gly Thr Phe Arg Leu Ile Gly Glu Lys Ser Leu Leu
            50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
                100                 105                 110

Ser Val Thr Phe Ala Cys Lys Thr Asn Phe Ser Met Asn Gly Asn Lys
            115                 120                 125

Ser Val Trp Cys Gln Ala Asn Asn Met Trp Gly Pro Thr Arg Leu Pro
            130                 135                 140

Thr Cys Val Ser
145
```

<210> SEQ ID NO 49
<211> LENGTH: 273
<212> TYPE: PRT
<213> ORGANISM: Artificial Sequence
<220> FEATURE:
<223> OTHER INFORMATION: Human CR2 SCR1-4 domains

<400> SEQUENCE: 49

```
Met Gly Ala Ala Gly Leu Leu Gly Val Phe Leu Ala Leu Val Ala Pro
1               5                   10                  15

Gly Val Leu Gly Ile Ser Cys Gly Ser Pro Pro Ile Leu Asn Gly
            20                  25                  30

Arg Ile Ser Tyr Tyr Ser Thr Pro Ile Ala Val Gly Thr Val Ile Arg
            35                  40                  45

Tyr Ser Cys Ser Gly Thr Phe Arg Leu Ile Gly Glu Lys Ser Leu Leu
            50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
                100                 105                 110

Ser Val Thr Phe Ala Cys Lys Thr Asn Phe Ser Met Asn Gly Asn Lys
            115                 120                 125

Ser Val Trp Cys Gln Ala Asn Asn Met Trp Gly Pro Thr Arg Leu Pro
            130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175

Leu Ser Val Thr Tyr Ser Cys Glu Ser Gly Tyr Leu Leu Val Gly Glu
                180                 185                 190

Lys Ile Ile Asn Cys Leu Ser Ser Gly Lys Trp Ser Ala Val Pro Pro
                195                 200                 205

Thr Cys Glu Glu Ala Arg Cys Lys Ser Leu Gly Arg Phe Pro Asn Gly
```

```
            210                 215                 220
Lys Val Lys Glu Pro Pro Ile Leu Arg Val Gly Val Thr Ala Asn Phe
225                 230                 235                 240

Phe Cys Asp Glu Gly Tyr Arg Leu Gln Gly Pro Pro Ser Ser Arg Cys
                245                 250                 255

Val Ile Ala Gly Gln Gly Val Ala Trp Thr Lys Met Pro Val Cys Glu
                260                 265                 270

Glu

<210> SEQ ID NO 50
<211> LENGTH: 140
<212> TYPE: PRT
<213> ORGANISM: Artificial Sequence
<220> FEATURE:
<223> OTHER INFORMATION: Mouse CR2 SCR1-2 domains

<400> SEQUENCE: 50

Met Leu Thr Trp Phe Leu Phe Tyr Phe Ser Glu Ile Ser Cys Asp Pro
1               5                   10                  15

Pro Pro Glu Val Lys Asn Ala Arg Lys Pro Tyr Tyr Ser Leu Pro Ile
                20                  25                  30

Val Pro Gly Thr Val Leu Arg Tyr Thr Cys Ser Pro Ser Tyr Arg Leu
            35                  40                  45

Ile Gly Glu Lys Ala Ile Phe Cys Ile Ser Glu Asn Gln Val His Ala
        50                  55                  60

Thr Trp Asp Lys Ala Pro Pro Ile Cys Glu Ser Val Asn Lys Thr Ile
65                  70                  75                  80

Ser Cys Ser Asp Pro Ile Val Pro Gly Gly Phe Met Asn Lys Gly Ser
                85                  90                  95

Lys Ala Pro Phe Arg His Gly Asp Ser Val Thr Phe Thr Cys Lys Ala
                100                 105                 110

Asn Phe Thr Met Lys Gly Ser Lys Thr Val Trp Cys Gln Ala Asn Glu
            115                 120                 125

Met Trp Gly Pro Thr Ala Leu Pro Val Cys Glu Ser
        130                 135                 140

<210> SEQ ID NO 51
<211> LENGTH: 265
<212> TYPE: PRT
<213> ORGANISM: Artificial Sequence
<220> FEATURE:
<223> OTHER INFORMATION: Mouse CR2 SCR1-4 domains

<400> SEQUENCE: 51

Met Leu Thr Trp Phe Leu Phe Tyr Phe Ser Glu Ile Ser Cys Asp Pro
1               5                   10                  15

Pro Pro Glu Val Lys Asn Ala Arg Lys Pro Tyr Tyr Ser Leu Pro Ile
                20                  25                  30

Val Pro Gly Thr Val Leu Arg Tyr Thr Cys Ser Pro Ser Tyr Arg Leu
            35                  40                  45

Ile Gly Glu Lys Ala Ile Phe Cys Ile Ser Glu Asn Gln Val His Ala
        50                  55                  60

Thr Trp Asp Lys Ala Pro Pro Ile Cys Glu Ser Val Asn Lys Thr Ile
65                  70                  75                  80

Ser Cys Ser Asp Pro Ile Val Pro Gly Gly Phe Met Asn Lys Gly Ser
                85                  90                  95

Lys Ala Pro Phe Arg His Gly Asp Ser Val Thr Phe Thr Cys Lys Ala
```

```
              100                 105                 110
Asn Phe Thr Met Lys Gly Ser Lys Thr Val Trp Cys Gln Ala Asn Glu
            115                 120                 125

Met Trp Gly Pro Thr Ala Leu Pro Val Cys Glu Ser Asp Phe Pro Leu
130                 135                 140

Glu Cys Pro Ser Leu Pro Thr Ile His Asn Gly His His Thr Gly Gln
145                 150                 155                 160

His Val Asp Gln Phe Val Ala Gly Leu Ser Val Thr Tyr Ser Cys Glu
                165                 170                 175

Pro Gly Tyr Leu Leu Thr Gly Lys Lys Thr Ile Lys Cys Leu Ser Ser
            180                 185                 190

Gly Asp Trp Asp Gly Val Ile Pro Thr Cys Lys Glu Ala Gln Cys Glu
            195                 200                 205

His Pro Gly Lys Phe Pro Asn Gly Gln Val Lys Glu Pro Leu Ser Leu
            210                 215                 220

Gln Val Gly Thr Thr Val Tyr Phe Ser Cys Asn Glu Gly Tyr Gln Leu
225                 230                 235                 240

Gln Gly Gln Pro Ser Ser Gln Cys Val Ile Val Glu Gln Lys Ala Ile
                245                 250                 255

Trp Thr Lys Lys Pro Val Cys Lys Glu
            260                 265

<210> SEQ ID NO 52
<211> LENGTH: 380
<212> TYPE: PRT
<213> ORGANISM: Artificial Sequence
<220> FEATURE:
<223> OTHER INFORMATION: Human CR2 SCR1-2 IgG1

<400> SEQUENCE: 52

Met Gly Ala Ala Gly Leu Leu Gly Val Phe Leu Ala Leu Val Ala Pro
1               5                   10                  15

Gly Val Leu Gly Ile Ser Cys Gly Ser Pro Pro Pro Ile Leu Asn Gly
            20                  25                  30

Arg Ile Ser Tyr Tyr Ser Thr Pro Ile Ala Val Gly Thr Val Ile Arg
        35                  40                  45

Tyr Ser Cys Ser Gly Thr Phe Arg Leu Ile Gly Glu Lys Ser Leu Leu
    50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
        115                 120                 125

Ser Val Trp Cys Gln Ala Asn Asn Met Trp Gly Pro Thr Arg Leu Pro
    130                 135                 140

Thr Cys Val Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
```

```
                195                 200                 205
Asn Trp Tyr Val Asp Gly Val Glu Val His Asn Ala Lys Thr Lys Pro
210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Glu Glu Met Thr Lys Asn Gln Val Ser Leu Thr Cys Leu Val Lys Gly
    290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly Lys
    370                 375                 380

<210> SEQ ID NO 53
<211> LENGTH: 380
<212> TYPE: PRT
<213> ORGANISM: Artificial Sequence
<220> FEATURE:
<223> OTHER INFORMATION: Human CR2 SCR1-2 IgG1 S267E

<400> SEQUENCE: 53

Met Gly Ala Ala Gly Leu Leu Gly Val Phe Leu Ala Leu Val Ala Pro
1               5                   10                  15

Gly Val Leu Gly Ile Ser Cys Gly Ser Pro Pro Pro Ile Leu Asn Gly
            20                  25                  30

Arg Ile Ser Tyr Tyr Ser Thr Pro Ile Ala Val Gly Thr Val Ile Arg
        35                  40                  45

Tyr Ser Cys Ser Gly Thr Phe Arg Leu Ile Gly Glu Lys Ser Leu Leu
    50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
        115                 120                 125

Ser Val Trp Cys Gln Ala Asn Asn Met Trp Gly Pro Thr Arg Leu Pro
    130                 135                 140

Thr Cys Val Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
```

```
            180                 185                 190
Thr Cys Val Val Asp Val Glu His Glu Asp Pro Glu Val Lys Phe
        195                 200                 205
Asn Trp Tyr Val Asp Gly Val Glu Val His Asn Ala Lys Thr Lys Pro
        210                 215                 220
Arg Glu Glu Gln Tyr Asn Ser Thr Tyr Arg Val Val Ser Val Leu Thr
225                 230                 235                 240
Val Leu His Gln Asp Trp Leu Asn Gly Lys Glu Tyr Lys Cys Lys Val
                245                 250                 255
Ser Asn Lys Ala Leu Pro Ala Pro Ile Glu Lys Thr Ile Ser Lys Ala
            260                 265                 270
Lys Gly Gln Pro Arg Glu Pro Gln Val Tyr Thr Leu Pro Pro Ser Arg
            275                 280                 285
Glu Glu Met Thr Lys Asn Gln Val Ser Leu Thr Cys Leu Val Lys Gly
            290                 295                 300
Phe Tyr Pro Ser Asp Ile Ala Val Glu Trp Glu Ser Asn Gly Gln Pro
305                 310                 315                 320
Glu Asn Asn Tyr Lys Thr Thr Pro Pro Val Leu Asp Ser Asp Gly Ser
                325                 330                 335
Phe Phe Leu Tyr Ser Lys Leu Thr Val Asp Lys Ser Arg Trp Gln Gln
                340                 345                 350
Gly Asn Val Phe Ser Cys Ser Val Met His Glu Ala Leu His Asn His
            355                 360                 365
Tyr Thr Gln Lys Ser Leu Ser Leu Ser Pro Gly Lys
            370                 375                 380

<210> SEQ ID NO 54
<211> LENGTH: 380
<212> TYPE: PRT
<213> ORGANISM: Artificial Sequence
<220> FEATURE:
<223> OTHER INFORMATION: Human CR2 SCR1-2 IgG1 S267E/L328F

<400> SEQUENCE: 54

Met Gly Ala Ala Gly Leu Leu Gly Val Phe Leu Ala Leu Val Ala Pro
1               5                   10                  15
Gly Val Leu Gly Ile Ser Cys Gly Ser Pro Pro Pro Ile Leu Asn Gly
            20                  25                  30
Arg Ile Ser Tyr Tyr Ser Thr Pro Ile Ala Val Gly Thr Val Ile Arg
        35                  40                  45
Tyr Ser Cys Ser Gly Thr Phe Arg Leu Ile Gly Glu Lys Ser Leu Leu
50                  55                  60
Cys Ile Thr Lys Asp Lys Val Asp Gly Thr Trp Asp Lys Pro Ala Pro
65                  70                  75                  80
Lys Cys Glu Tyr Phe Asn Lys Tyr Ser Ser Cys Pro Glu Pro Ile Val
                85                  90                  95
Pro Gly Gly Tyr Lys Ile Arg Gly Ser Thr Pro Tyr Arg His Gly Asp
            100                 105                 110
Ser Val Thr Phe Ala Cys Lys Thr Asn Phe Ser Met Asn Gly Asn Lys
            115                 120                 125
Ser Val Trp Cys Gln Ala Asn Asn Met Trp Gly Pro Thr Arg Leu Pro
            130                 135                 140
Thr Cys Val Ser Glu Pro Lys Ser Ser Asp Lys Thr His Thr Cys Pro
145                 150                 155                 160
Pro Cys Pro Ala Pro Glu Leu Leu Gly Gly Pro Ser Val Phe Leu Phe
```

```
            165                 170                 175
Pro Pro Lys Pro Lys Asp Thr Leu Met Ile Ser Arg Thr Pro Glu Val
            180                 185                 190

Thr Cys Val Val Asp Val Glu His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Phe Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Glu Glu Met Thr Lys Asn Gln Val Ser Leu Thr Cys Leu Val Lys Gly
    290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly Lys
    370                 375                 380

<210> SEQ ID NO 55
<211> LENGTH: 380
<212> TYPE: PRT
<213> ORGANISM: Artificial Sequence
<220> FEATURE:
<223> OTHER INFORMATION: Human CR2 SCR1-2 IgG1 G236N/S267E

<400> SEQUENCE: 55

Met Gly Ala Ala Gly Leu Leu Gly Val Phe Leu Ala Leu Val Ala Pro
1               5                   10                  15

Gly Val Leu Gly Ile Ser Cys Gly Ser Pro Pro Pro Ile Leu Asn Gly
            20                  25                  30

Arg Ile Ser Tyr Tyr Ser Thr Pro Ile Ala Val Gly Thr Val Ile Arg
        35                  40                  45

Tyr Ser Cys Ser Gly Thr Phe Arg Leu Ile Gly Glu Lys Ser Leu Leu
    50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
        115                 120                 125

Ser Val Trp Cys Gln Ala Asn Asn Met Trp Gly Pro Thr Arg Leu Pro
    130                 135                 140

Thr Cys Val Ser Glu Pro Lys Ser Ser Asp Lys Thr His Thr Cys Pro
```

```
145                 150                 155                 160
Pro Cys Pro Ala Pro Glu Leu Leu Asn Gly Pro Ser Val Phe Leu Phe
                165                 170                 175

Pro Pro Lys Pro Lys Asp Thr Leu Met Ile Ser Arg Thr Pro Glu Val
                180                 185                 190

Thr Cys Val Val Val Asp Val Glu His Glu Asp Pro Glu Val Lys Phe
                195                 200                 205

Asn Trp Tyr Val Asp Gly Val Glu Val His Asn Ala Lys Thr Lys Pro
                210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
                260                 265                 270

Lys Gly Gln Pro Arg Glu Pro Gln Val Tyr Thr Leu Pro Pro Ser Arg
                275                 280                 285

Glu Glu Met Thr Lys Asn Gln Val Ser Leu Thr Cys Leu Val Lys Gly
                290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
                340                 345                 350

Gly Asn Val Phe Ser Cys Ser Val Met His Glu Ala Leu His Asn His
                355                 360                 365

Tyr Thr Gln Lys Ser Leu Ser Leu Ser Pro Gly Lys
                370                 375                 380

<210> SEQ ID NO 56
<211> LENGTH: 380
<212> TYPE: PRT
<213> ORGANISM: Artificial Sequence
<220> FEATURE:
<223> OTHER INFORMATION: Human CR2 SCR1-2 IgG1 G236D/S267E

<400> SEQUENCE: 56

Met Gly Ala Ala Gly Leu Leu Gly Val Phe Leu Ala Leu Val Ala Pro
1               5                   10                  15

Gly Val Leu Gly Ile Ser Cys Gly Ser Pro Pro Pro Ile Leu Asn Gly
                20                  25                  30

Arg Ile Ser Tyr Tyr Ser Thr Pro Ile Ala Val Gly Thr Val Ile Arg
                35                  40                  45

Tyr Ser Cys Ser Gly Thr Phe Arg Leu Ile Gly Glu Lys Ser Leu Leu
            50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
                100                 105                 110

Ser Val Thr Phe Ala Cys Lys Thr Asn Phe Ser Met Asn Gly Asn Lys
                115                 120                 125

Ser Val Trp Cys Gln Ala Asn Asn Met Trp Gly Pro Thr Arg Leu Pro
```

```
                    130                 135                 140
Thr Cys Val Ser Glu Pro Lys Ser Ser Asp Lys Thr His Thr Cys Pro
145                 150                 155                 160

Pro Cys Pro Ala Pro Glu Leu Leu Asp Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Glu His Glu Asp Pro Glu Val Lys Phe
                195                 200                 205

Asn Trp Tyr Val Asp Gly Val Glu Val His Asn Ala Lys Thr Lys Pro
210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Glu Glu Met Thr Lys Asn Gln Val Ser Leu Thr Cys Leu Val Lys Gly
290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly Lys
    370                 375                 380

<210> SEQ ID NO 57
<211> LENGTH: 380
<212> TYPE: PRT
<213> ORGANISM: Artificial Sequence
<220> FEATURE:
<223> OTHER INFORMATION: Human CR2 SCR1-2 IgG1 G236R/L328R

<400> SEQUENCE: 57

Met Gly Ala Ala Gly Leu Leu Gly Val Phe Leu Ala Leu Val Ala Pro
1               5                   10                  15

Gly Val Leu Gly Ile Ser Cys Gly Ser Pro Pro Pro Ile Leu Asn Gly
                20                  25                  30

Arg Ile Ser Tyr Tyr Ser Thr Pro Ile Ala Val Gly Thr Val Ile Arg
            35                  40                  45

Tyr Ser Cys Ser Gly Thr Phe Arg Leu Ile Gly Glu Lys Ser Leu Leu
50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
```

```
            115                 120                 125
Ser Val Trp Cys Gln Ala Asn Asn Met Trp Gly Pro Thr Arg Leu Pro
        130                 135                 140

Thr Cys Val Ser Glu Pro Lys Ser Ser Asp Lys Thr His Thr Cys Pro
145                 150                 155                 160

Pro Cys Pro Ala Pro Glu Leu Leu Arg Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Arg Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Glu Glu Met Thr Lys Asn Gln Val Ser Leu Thr Cys Leu Val Lys Gly
    290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly Lys
    370                 375                 380

<210> SEQ ID NO 58
<211> LENGTH: 505
<212> TYPE: PRT
<213> ORGANISM: Artificial Sequence
<220> FEATURE:
<223> OTHER INFORMATION: Human CR2 SCR1-4 IgG1

<400> SEQUENCE: 58

Met Gly Ala Ala Gly Leu Leu Gly Val Phe Leu Ala Leu Val Ala Pro
1               5                   10                  15

Gly Val Leu Gly Ile Ser Cys Gly Ser Pro Pro Pro Ile Leu Asn Gly
            20                  25                  30

Arg Ile Ser Tyr Tyr Ser Thr Pro Ile Ala Val Gly Thr Val Ile Arg
        35                  40                  45

Tyr Ser Cys Ser Gly Thr Phe Arg Leu Ile Gly Glu Lys Ser Leu Leu
    50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
```

```
              100                 105                 110
Ser Val Thr Phe Ala Cys Lys Thr Asn Phe Ser Met Asn Gly Asn Lys
            115                 120                 125

Ser Val Trp Cys Gln Ala Asn Asn Met Trp Gly Pro Thr Arg Leu Pro
            130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175

Leu Ser Val Thr Tyr Ser Cys Glu Ser Gly Tyr Leu Leu Val Gly Glu
                180                 185                 190

Lys Ile Ile Asn Cys Leu Ser Ser Gly Lys Trp Ser Ala Val Pro Pro
                195                 200                 205

Thr Cys Glu Glu Ala Arg Cys Lys Ser Leu Gly Arg Phe Pro Asn Gly
            210                 215                 220

Lys Val Lys Glu Pro Pro Ile Leu Arg Val Gly Val Thr Ala Asn Phe
225                 230                 235                 240

Phe Cys Asp Glu Gly Tyr Arg Leu Gln Gly Pro Pro Ser Ser Arg Cys
                245                 250                 255

Val Ile Ala Gly Gln Gly Val Ala Trp Thr Lys Met Pro Val Cys Glu
                260                 265                 270

Glu Glu Pro Lys Ser Ser Asp Lys Thr His Thr Cys Pro Pro Cys Pro
            275                 280                 285

Ala Pro Glu Leu Leu Gly Gly Pro Ser Val Phe Leu Phe Pro Pro Lys
            290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
                340                 345                 350

Gln Tyr Asn Ser Thr Tyr Arg Val Val Ser Val Leu Thr Val Leu His
            355                 360                 365

Gln Asp Trp Leu Asn Gly Lys Glu Tyr Lys Cys Lys Val Ser Asn Lys
            370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Glu Glu Met
                405                 410                 415

Thr Lys Asn Gln Val Ser Leu Thr Cys Leu Val Lys Gly Phe Tyr Pro
                420                 425                 430

Ser Asp Ile Ala Val Glu Trp Glu Ser Asn Gly Gln Pro Glu Asn Asn
            435                 440                 445

Tyr Lys Thr Thr Pro Pro Val Leu Asp Ser Asp Gly Ser Phe Phe Leu
            450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly Lys
                500                 505

<210> SEQ ID NO 59
```

<211> LENGTH: 505
<212> TYPE: PRT
<213> ORGANISM: Artificial Sequence
<220> FEATURE:
<223> OTHER INFORMATION: Human CR2 SCR1-4 IgG1 S267E

<400> SEQUENCE: 59

```
Met Gly Ala Ala Gly Leu Leu Gly Val Phe Leu Ala Leu Val Ala Pro
 1               5                  10                  15

Gly Val Leu Gly Ile Ser Cys Gly Ser Pro Pro Pro Ile Leu Asn Gly
             20                  25                  30

Arg Ile Ser Tyr Tyr Ser Thr Pro Ile Ala Val Gly Thr Val Ile Arg
         35                  40                  45

Tyr Ser Cys Ser Gly Thr Phe Arg Leu Ile Gly Glu Lys Ser Leu Leu
     50                  55                  60

Cys Ile Thr Lys Asp Lys Val Asp Gly Thr Trp Asp Lys Pro Ala Pro
 65                  70                  75                  80

Lys Cys Glu Tyr Phe Asn Lys Tyr Ser Ser Cys Pro Glu Pro Ile Val
                 85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
        115                 120                 125

Ser Val Trp Cys Gln Ala Asn Asn Met Trp Gly Pro Thr Arg Leu Pro
    130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175

Leu Ser Val Thr Tyr Ser Cys Glu Ser Gly Tyr Leu Leu Val Gly Glu
            180                 185                 190

Lys Ile Ile Asn Cys Leu Ser Ser Gly Lys Trp Ser Ala Val Pro Pro
        195                 200                 205

Thr Cys Glu Glu Ala Arg Cys Lys Ser Leu Gly Arg Phe Pro Asn Gly
    210                 215                 220

Lys Val Lys Glu Pro Pro Ile Leu Arg Val Gly Val Thr Ala Asn Phe
225                 230                 235                 240

Phe Cys Asp Glu Gly Tyr Arg Leu Gln Gly Pro Pro Ser Ser Arg Cys
                245                 250                 255

Val Ile Ala Gly Gln Gly Val Ala Trp Thr Lys Met Pro Val Cys Glu
            260                 265                 270

Glu Glu Pro Lys Ser Ser Asp Lys Thr His Thr Cys Pro Pro Cys Pro
        275                 280                 285

Ala Pro Glu Leu Leu Gly Gly Pro Ser Val Phe Leu Phe Pro Pro Lys
    290                 295                 300

Pro Lys Asp Thr Leu Met Ile Ser Arg Thr Pro Glu Val Thr Cys Val
305                 310                 315                 320

Val Val Asp Val Glu His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
    370                 375                 380
```

```
Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Glu Glu Met
            405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
            435                 440                 445

Tyr Lys Thr Thr Pro Pro Val Leu Asp Ser Asp Gly Ser Phe Phe Leu
    450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly Lys
                500                 505

<210> SEQ ID NO 60
<211> LENGTH: 505
<212> TYPE: PRT
<213> ORGANISM: Artificial Sequence
<220> FEATURE:
<223> OTHER INFORMATION: Human CR2 SCR1-4 IgG1 S267E/L328F

<400> SEQUENCE: 60

Met Gly Ala Ala Gly Leu Leu Gly Val Phe Leu Ala Leu Val Ala Pro
1               5                   10                  15

Gly Val Leu Gly Ile Ser Cys Gly Ser Pro Pro Pro Ile Leu Asn Gly
            20                  25                  30

Arg Ile Ser Tyr Tyr Ser Thr Pro Ile Ala Val Gly Thr Val Ile Arg
        35                  40                  45

Tyr Ser Cys Ser Gly Thr Phe Arg Leu Ile Gly Glu Lys Ser Leu Leu
    50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
        115                 120                 125

Ser Val Trp Cys Gln Ala Asn Asn Met Trp Gly Pro Thr Arg Leu Pro
    130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175

Leu Ser Val Thr Tyr Ser Cys Glu Ser Gly Tyr Leu Leu Val Gly Glu
            180                 185                 190

Lys Ile Ile Asn Cys Leu Ser Ser Gly Lys Trp Ser Ala Val Pro Pro
        195                 200                 205

Thr Cys Glu Glu Ala Arg Cys Lys Ser Leu Gly Arg Phe Pro Asn Gly
    210                 215                 220

Lys Val Lys Glu Pro Pro Ile Leu Arg Val Gly Val Thr Ala Asn Phe
225                 230                 235                 240
```

-continued

```
Phe Cys Asp Glu Gly Tyr Arg Leu Gln Gly Pro Ser Ser Arg Cys
                245                 250                 255

Val Ile Ala Gly Gln Gly Val Ala Trp Thr Lys Met Pro Val Cys Glu
            260                 265                 270

Glu Glu Pro Lys Ser Ser Asp Lys Thr His Thr Cys Pro Pro Cys Pro
            275                 280                 285

Ala Pro Glu Leu Leu Gly Gly Pro Ser Val Phe Leu Phe Pro Pro Lys
        290                 295                 300

Pro Lys Asp Thr Leu Met Ile Ser Arg Thr Pro Glu Val Thr Cys Val
305                 310                 315                 320

Val Val Asp Val Glu His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
    370                 375                 380

Ala Phe Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Glu Glu Met
                405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
        435                 440                 445

Tyr Lys Thr Thr Pro Pro Val Leu Asp Ser Asp Gly Ser Phe Phe Leu
    450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly Lys
            500                 505
```

<210> SEQ ID NO 61
<211> LENGTH: 505
<212> TYPE: PRT
<213> ORGANISM: Artificial Sequence
<220> FEATURE:
<223> OTHER INFORMATION: Human CR2 SCR1-4 IgG1 G236N/S267E

<400> SEQUENCE: 61

```
Met Gly Ala Ala Gly Leu Leu Gly Val Phe Leu Ala Leu Val Ala Pro
1               5                   10                  15

Gly Val Leu Gly Ile Ser Cys Gly Ser Pro Pro Pro Ile Leu Asn Gly
            20                  25                  30

Arg Ile Ser Tyr Tyr Ser Thr Pro Ile Ala Val Gly Thr Val Ile Arg
        35                  40                  45

Tyr Ser Cys Ser Gly Thr Phe Arg Leu Ile Gly Glu Lys Ser Leu Leu
    50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95
```

```
Pro Gly Gly Tyr Lys Ile Arg Gly Ser Thr Pro Tyr Arg His Gly Asp
            100                 105                 110
Ser Val Thr Phe Ala Cys Lys Thr Asn Phe Ser Met Asn Gly Asn Lys
            115                 120                 125
Ser Val Trp Cys Gln Ala Asn Asn Met Trp Gly Pro Thr Arg Leu Pro
            130                 135                 140
Thr Cys Val Ser Val Phe Pro Leu Glu Cys Pro Ala Leu Pro Met Ile
145                 150                 155                 160
His Asn Gly His His Thr Ser Glu Asn Val Gly Ser Ile Ala Pro Gly
                165                 170                 175
Leu Ser Val Thr Tyr Ser Cys Glu Ser Gly Tyr Leu Leu Val Gly Glu
            180                 185                 190
Lys Ile Ile Asn Cys Leu Ser Ser Gly Lys Trp Ser Ala Val Pro Pro
            195                 200                 205
Thr Cys Glu Glu Ala Arg Cys Lys Ser Leu Gly Arg Phe Pro Asn Gly
            210                 215                 220
Lys Val Lys Glu Pro Pro Ile Leu Arg Val Gly Val Thr Ala Asn Phe
225                 230                 235                 240
Phe Cys Asp Glu Gly Tyr Arg Leu Gln Gly Pro Pro Ser Ser Arg Cys
                245                 250                 255
Val Ile Ala Gly Gln Gly Val Ala Trp Thr Lys Met Pro Val Cys Glu
            260                 265                 270
Glu Glu Pro Lys Ser Ser Asp Lys Thr His Thr Cys Pro Pro Cys Pro
            275                 280                 285
Ala Pro Glu Leu Leu Asn Gly Pro Ser Val Phe Leu Phe Pro Pro Lys
            290                 295                 300
Pro Lys Asp Thr Leu Met Ile Ser Arg Thr Pro Glu Val Thr Cys Val
305                 310                 315                 320
Val Val Asp Val Glu His Glu Asp Pro Glu Val Lys Phe Asn Trp Tyr
                325                 330                 335
Val Asp Gly Val Glu Val His Asn Ala Lys Thr Lys Pro Arg Glu Glu
            340                 345                 350
Gln Tyr Asn Ser Thr Tyr Arg Val Val Ser Val Leu Thr Val Leu His
            355                 360                 365
Gln Asp Trp Leu Asn Gly Lys Glu Tyr Lys Cys Lys Val Ser Asn Lys
            370                 375                 380
Ala Leu Pro Ala Pro Ile Glu Lys Thr Ile Ser Lys Ala Lys Gly Gln
385                 390                 395                 400
Pro Arg Glu Pro Gln Val Tyr Thr Leu Pro Pro Ser Arg Glu Glu Met
                405                 410                 415
Thr Lys Asn Gln Val Ser Leu Thr Cys Leu Val Lys Gly Phe Tyr Pro
            420                 425                 430
Ser Asp Ile Ala Val Glu Trp Glu Ser Asn Gly Gln Pro Glu Asn Asn
            435                 440                 445
Tyr Lys Thr Thr Pro Pro Val Leu Asp Ser Asp Gly Ser Phe Phe Leu
            450                 455                 460
Tyr Ser Lys Leu Thr Val Asp Lys Ser Arg Trp Gln Gln Gly Asn Val
465                 470                 475                 480
Phe Ser Cys Ser Val Met His Glu Ala Leu His Asn His Tyr Thr Gln
                485                 490                 495
Lys Ser Leu Ser Leu Ser Pro Gly Lys
            500                 505
```

<210> SEQ ID NO 62
<211> LENGTH: 505
<212> TYPE: PRT
<213> ORGANISM: Artificial Sequence
<220> FEATURE:
<223> OTHER INFORMATION: Human CR2 SCR1-4 IgG1 G236D/S267E

<400> SEQUENCE: 62

```
Met Gly Ala Ala Gly Leu Leu Gly Val Phe Leu Ala Leu Val Ala Pro
1               5                   10                  15

Gly Val Leu Gly Ile Ser Cys Gly Ser Pro Pro Pro Ile Leu Asn Gly
            20                  25                  30

Arg Ile Ser Tyr Tyr Ser Thr Pro Ile Ala Val Gly Thr Val Ile Arg
        35                  40                  45

Tyr Ser Cys Ser Gly Thr Phe Arg Leu Ile Gly Glu Lys Ser Leu Leu
    50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
        115                 120                 125

Ser Val Trp Cys Gln Ala Asn Asn Met Trp Gly Pro Thr Arg Leu Pro
    130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175

Leu Ser Val Thr Tyr Ser Cys Glu Ser Gly Tyr Leu Leu Val Gly Glu
            180                 185                 190

Lys Ile Ile Asn Cys Leu Ser Ser Gly Lys Trp Ser Ala Val Pro Pro
        195                 200                 205

Thr Cys Glu Glu Ala Arg Cys Lys Ser Leu Gly Arg Phe Pro Asn Gly
    210                 215                 220

Lys Val Lys Glu Pro Pro Ile Leu Arg Val Gly Val Thr Ala Asn Phe
225                 230                 235                 240

Phe Cys Asp Glu Gly Tyr Arg Leu Gln Gly Pro Pro Ser Ser Arg Cys
                245                 250                 255

Val Ile Ala Gly Gln Gly Val Ala Trp Thr Lys Met Pro Val Cys Glu
            260                 265                 270

Glu Glu Pro Lys Ser Ser Asp Lys Thr His Thr Cys Pro Pro Cys Pro
        275                 280                 285

Ala Pro Glu Leu Leu Asp Gly Pro Ser Val Phe Leu Phe Pro Pro Lys
    290                 295                 300

Pro Lys Asp Thr Leu Met Ile Ser Arg Thr Pro Glu Val Thr Cys Val
305                 310                 315                 320

Val Val Asp Val Glu His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365
```

```
Gln Asp Trp Leu Asn Gly Lys Glu Tyr Lys Cys Lys Val Ser Asn Lys
    370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Glu Glu Met
                405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
        435                 440                 445

Tyr Lys Thr Thr Pro Pro Val Leu Asp Ser Asp Gly Ser Phe Phe Leu
    450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly Lys
            500                 505

<210> SEQ ID NO 63
<211> LENGTH: 505
<212> TYPE: PRT
<213> ORGANISM: Artificial Sequence
<220> FEATURE:
<223> OTHER INFORMATION: Human CR2 SCR1-4 IgG1 G236R/L328R

<400> SEQUENCE: 63

Met Gly Ala Ala Gly Leu Leu Gly Val Phe Leu Ala Leu Val Ala Pro
1               5                   10                  15

Gly Val Leu Gly Ile Ser Cys Gly Ser Pro Pro Pro Ile Leu Asn Gly
                20                  25                  30

Arg Ile Ser Tyr Tyr Ser Thr Pro Ile Ala Val Gly Thr Val Ile Arg
            35                  40                  45

Tyr Ser Cys Ser Gly Thr Phe Arg Leu Ile Gly Glu Lys Ser Leu Leu
    50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
                100                 105                 110

Ser Val Thr Phe Ala Cys Lys Thr Asn Phe Ser Met Asn Gly Asn Lys
            115                 120                 125

Ser Val Trp Cys Gln Ala Asn Asn Met Trp Gly Pro Thr Arg Leu Pro
    130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175

Leu Ser Val Thr Tyr Ser Cys Glu Ser Gly Tyr Leu Leu Val Gly Glu
            180                 185                 190

Lys Ile Ile Asn Cys Leu Ser Ser Gly Lys Trp Ser Ala Val Pro Pro
    195                 200                 205

Thr Cys Glu Glu Ala Arg Cys Lys Ser Leu Gly Arg Phe Pro Asn Gly
210                 215                 220
```

```
Lys Val Lys Glu Pro Pro Ile Leu Arg Val Gly Thr Ala Asn Phe
225                 230                 235                 240

Phe Cys Asp Glu Gly Tyr Arg Leu Gln Gly Pro Pro Ser Ser Arg Cys
            245                 250                 255

Val Ile Ala Gly Gln Gly Val Ala Trp Thr Lys Met Pro Val Cys Glu
            260                 265                 270

Glu Glu Pro Lys Ser Ser Asp Lys Thr His Thr Cys Pro Pro Cys Pro
            275                 280                 285

Ala Pro Glu Leu Leu Arg Gly Pro Ser Val Phe Leu Phe Pro Pro Lys
            290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
            325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
            355                 360                 365

Gln Asp Trp Leu Asn Gly Lys Glu Tyr Lys Cys Lys Val Ser Asn Lys
370                 375                 380

Ala Arg Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Glu Glu Met
            405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
            435                 440                 445

Tyr Lys Thr Thr Pro Pro Val Leu Asp Ser Asp Gly Ser Phe Phe Leu
450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
            485                 490                 495

Lys Ser Leu Ser Leu Ser Pro Gly Lys
            500                 505

<210> SEQ ID NO 64
<211> LENGTH: 372
<212> TYPE: PRT
<213> ORGANISM: Artificial Sequence
<220> FEATURE:
<223> OTHER INFORMATION: Mouse CR2 SCR1-2 IgG1

<400> SEQUENCE: 64

Met Leu Thr Trp Phe Leu Phe Tyr Phe Ser Glu Ile Ser Cys Asp Pro
1               5                   10                  15

Pro Pro Glu Val Lys Asn Ala Arg Lys Pro Tyr Tyr Ser Leu Pro Ile
            20                  25                  30

Val Pro Gly Thr Val Leu Arg Tyr Thr Cys Ser Pro Ser Tyr Arg Leu
            35                  40                  45

Ile Gly Glu Lys Ala Ile Phe Cys Ile Ser Glu Asn Gln Val His Ala
        50                  55                  60

Thr Trp Asp Lys Ala Pro Pro Ile Cys Glu Ser Val Asn Lys Thr Ile
65                  70                  75                  80
```

-continued

```
Ser Cys Ser Asp Pro Ile Val Pro Gly Gly Phe Met Asn Lys Gly Ser
            85                  90                  95

Lys Ala Pro Phe Arg His Gly Asp Ser Val Thr Phe Thr Cys Lys Ala
        100                 105                 110

Asn Phe Thr Met Lys Gly Ser Lys Thr Val Trp Cys Gln Ala Asn Glu
        115                 120                 125

Met Trp Gly Pro Thr Ala Leu Pro Val Cys Glu Ser Glu Pro Lys Ser
        130                 135                 140

Ser Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
    370

<210> SEQ ID NO 65
<211> LENGTH: 372
<212> TYPE: PRT
<213> ORGANISM: Artificial Sequence
<220> FEATURE:
<223> OTHER INFORMATION: Mouse CR2 SCR1-2 IgG1 S267E

<400> SEQUENCE: 65

Met Leu Thr Trp Phe Leu Phe Tyr Phe Ser Glu Ile Ser Cys Asp Pro
1               5                   10                  15

Pro Pro Glu Val Lys Asn Ala Arg Lys Pro Tyr Tyr Ser Leu Pro Ile
            20                  25                  30

Val Pro Gly Thr Val Leu Arg Tyr Thr Cys Ser Pro Ser Tyr Arg Leu
        35                  40                  45

Ile Gly Glu Lys Ala Ile Phe Cys Ile Ser Glu Asn Gln Val His Ala
    50                  55                  60
```

```
Thr Trp Asp Lys Ala Pro Pro Ile Cys Glu Ser Val Asn Lys Thr Ile
 65                  70                  75                  80

Ser Cys Ser Asp Pro Ile Val Pro Gly Gly Phe Met Asn Lys Gly Ser
                 85                  90                  95

Lys Ala Pro Phe Arg His Gly Asp Ser Val Thr Phe Thr Cys Lys Ala
            100                 105                 110

Asn Phe Thr Met Lys Gly Ser Lys Thr Val Trp Cys Gln Ala Asn Glu
        115                 120                 125

Met Trp Gly Pro Thr Ala Leu Pro Val Cys Glu Ser Glu Pro Lys Ser
    130                 135                 140

Ser Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Glu
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
    370

<210> SEQ ID NO 66
<211> LENGTH: 372
<212> TYPE: PRT
<213> ORGANISM: Artificial Sequence
<220> FEATURE:
<223> OTHER INFORMATION: Mouse CR2 SCR1-2 IgG1 S267E/L328F

<400> SEQUENCE: 66

Met Leu Thr Trp Phe Leu Phe Tyr Phe Ser Glu Ile Ser Cys Asp Pro
  1               5                  10                  15

Pro Pro Glu Val Lys Asn Ala Arg Lys Pro Tyr Tyr Ser Leu Pro Ile
                 20                  25                  30

Val Pro Gly Thr Val Leu Arg Tyr Thr Cys Ser Pro Ser Tyr Arg Leu
             35                  40                  45
```

```
Ile Gly Glu Lys Ala Ile Phe Cys Ile Ser Glu Asn Gln Val His Ala
 50                  55                  60
Thr Trp Asp Lys Ala Pro Pro Ile Cys Glu Ser Val Asn Lys Thr Ile
 65                  70                  75                  80
Ser Cys Ser Asp Pro Ile Val Pro Gly Phe Met Asn Lys Gly Ser
                 85                  90                  95
Lys Ala Pro Phe Arg His Gly Asp Ser Val Thr Phe Thr Cys Lys Ala
                100                 105                 110
Asn Phe Thr Met Lys Gly Ser Lys Thr Val Trp Cys Gln Ala Asn Glu
                115                 120                 125
Met Trp Gly Pro Thr Ala Leu Pro Val Cys Glu Ser Glu Pro Lys Ser
130                 135                 140
Ser Asp Lys Thr His Thr Cys Pro Pro Cys Pro Ala Pro Glu Leu Leu
145                 150                 155                 160
Gly Gly Pro Ser Val Phe Leu Phe Pro Pro Lys Pro Lys Asp Thr Leu
                165                 170                 175
Met Ile Ser Arg Thr Pro Glu Val Thr Cys Val Val Val Asp Val
                180                 185                 190
His Glu Asp Pro Glu Val Lys Phe Asn Trp Tyr Val Asp Gly Val Glu
                195                 200                 205
Val His Asn Ala Lys Thr Lys Pro Arg Glu Glu Gln Tyr Asn Ser Thr
210                 215                 220
Tyr Arg Val Val Ser Val Leu Thr Val Leu His Gln Asp Trp Leu Asn
225                 230                 235                 240
Gly Lys Glu Tyr Lys Cys Lys Val Ser Asn Lys Ala Phe Pro Ala Pro
                245                 250                 255
Ile Glu Lys Thr Ile Ser Lys Ala Lys Gly Gln Pro Arg Glu Pro Gln
                260                 265                 270
Val Tyr Thr Leu Pro Pro Ser Arg Glu Glu Met Thr Lys Asn Gln Val
                275                 280                 285
Ser Leu Thr Cys Leu Val Lys Gly Phe Tyr Pro Ser Asp Ile Ala Val
                290                 295                 300
Glu Trp Glu Ser Asn Gly Gln Pro Glu Asn Asn Tyr Lys Thr Thr Pro
305                 310                 315                 320
Pro Val Leu Asp Ser Asp Gly Ser Phe Phe Leu Tyr Ser Lys Leu Thr
                325                 330                 335
Val Asp Lys Ser Arg Trp Gln Gln Gly Asn Val Phe Ser Cys Ser Val
                340                 345                 350
Met His Glu Ala Leu His Asn His Tyr Thr Gln Lys Ser Leu Ser Leu
                355                 360                 365
Ser Pro Gly Lys
    370

<210> SEQ ID NO 67
<211> LENGTH: 372
<212> TYPE: PRT
<213> ORGANISM: Artificial Sequence
<220> FEATURE:
<223> OTHER INFORMATION: Mouse CR2 SCR1-2 IgG1 G236N/S267E

<400> SEQUENCE: 67

Met Leu Thr Trp Phe Leu Phe Tyr Phe Ser Glu Ile Ser Cys Asp Pro
 1                5                  10                  15
Pro Pro Glu Val Lys Asn Ala Arg Lys Pro Tyr Tyr Ser Leu Pro Ile
                 20                  25                  30
```

Val Pro Gly Thr Val Leu Arg Tyr Thr Cys Ser Pro Ser Tyr Arg Leu
            35                  40                  45

Ile Gly Glu Lys Ala Ile Phe Cys Ile Ser Glu Asn Gln Val His Ala
 50                  55                  60

Thr Trp Asp Lys Ala Pro Pro Ile Cys Glu Ser Val Asn Lys Thr Ile
 65                  70                  75                  80

Ser Cys Ser Asp Pro Ile Val Pro Gly Gly Phe Met Asn Lys Gly Ser
                 85                  90                  95

Lys Ala Pro Phe Arg His Gly Asp Ser Val Thr Phe Thr Cys Lys Ala
            100                 105                 110

Asn Phe Thr Met Lys Gly Ser Lys Thr Val Trp Cys Gln Ala Asn Glu
            115                 120                 125

Met Trp Gly Pro Thr Ala Leu Pro Val Cys Glu Ser Glu Pro Lys Ser
    130                 135                 140

Ser Asp Lys Thr His Thr Cys Pro Pro Cys Pro Ala Pro Glu Leu Leu
145                 150                 155                 160

Asn Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Glu
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
    370

<210> SEQ ID NO 68
<211> LENGTH: 372
<212> TYPE: PRT
<213> ORGANISM: Artificial Sequence
<220> FEATURE:
<223> OTHER INFORMATION: Mouse CR2 SCR1-2 IgG1 G236D/S267E

<400> SEQUENCE: 68

Met Leu Thr Trp Phe Leu Phe Tyr Phe Ser Glu Ile Ser Cys Asp Pro
 1               5                  10                  15

```
Pro Pro Glu Val Lys Asn Ala Arg Lys Pro Tyr Tyr Ser Leu Pro Ile
             20                  25                  30

Val Pro Gly Thr Val Leu Arg Tyr Thr Cys Ser Pro Ser Tyr Arg Leu
         35                  40                  45

Ile Gly Glu Lys Ala Ile Phe Cys Ile Ser Glu Asn Gln Val His Ala
     50                  55                  60

Thr Trp Asp Lys Ala Pro Pro Ile Cys Glu Ser Val Asn Lys Thr Ile
 65                  70                  75                  80

Ser Cys Ser Asp Pro Ile Val Pro Gly Gly Phe Met Asn Lys Gly Ser
                 85                  90                  95

Lys Ala Pro Phe Arg His Gly Asp Ser Val Thr Phe Thr Cys Lys Ala
            100                 105                 110

Asn Phe Thr Met Lys Gly Ser Lys Thr Val Trp Cys Gln Ala Asn Glu
        115                 120                 125

Met Trp Gly Pro Thr Ala Leu Pro Val Cys Glu Ser Glu Pro Lys Ser
    130                 135                 140

Ser Asp Lys Thr His Thr Cys Pro Pro Cys Pro Ala Pro Glu Leu Leu
145                 150                 155                 160

Asp Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Glu
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
    370

<210> SEQ ID NO 69
<211> LENGTH: 372
<212> TYPE: PRT
<213> ORGANISM: Artificial Sequence
<220> FEATURE:
<223> OTHER INFORMATION: Mouse CR2 SCR1-2 IgG1 G236R/L328R

<400> SEQUENCE: 69
```

```
Met Leu Thr Trp Phe Leu Phe Tyr Phe Ser Glu Ile Ser Cys Asp Pro
1               5                   10                  15

Pro Pro Glu Val Lys Asn Ala Arg Lys Pro Tyr Tyr Ser Leu Pro Ile
            20                  25                  30

Val Pro Gly Thr Val Leu Arg Tyr Thr Cys Ser Pro Ser Tyr Arg Leu
            35                  40                  45

Ile Gly Glu Lys Ala Ile Phe Cys Ile Ser Glu Asn Gln Val His Ala
        50                  55                  60

Thr Trp Asp Lys Ala Pro Ile Cys Glu Ser Val Asn Lys Thr Ile
65                  70                  75                  80

Ser Cys Ser Asp Pro Ile Val Pro Gly Gly Phe Met Asn Lys Gly Ser
                85                  90                  95

Lys Ala Pro Phe Arg His Gly Asp Ser Val Thr Phe Thr Cys Lys Ala
            100                 105                 110

Asn Phe Thr Met Lys Gly Ser Lys Thr Val Trp Cys Gln Ala Asn Glu
            115                 120                 125

Met Trp Gly Pro Thr Ala Leu Pro Val Cys Ser Glu Pro Lys Ser
130                 135                 140

Ser Asp Lys Thr His Thr Cys Pro Pro Cys Pro Ala Pro Glu Leu Leu
145                 150                 155                 160

Arg Gly Pro Ser Val Phe Leu Phe Pro Pro Lys Pro Lys Asp Thr Leu
            165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
            195                 200                 205

Val His Asn Ala Lys Thr Lys Pro Arg Glu Glu Gln Tyr Asn Ser Thr
210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Arg Pro Ala Pro
            245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
            275                 280                 285

Ser Leu Thr Cys Leu Val Lys Gly Phe Tyr Pro Ser Asp Ile Ala Val
            290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
            325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
            355                 360                 365

Ser Pro Gly Lys
    370

<210> SEQ ID NO 70
<211> LENGTH: 497
<212> TYPE: PRT
<213> ORGANISM: Artificial Sequence
<220> FEATURE:
<223> OTHER INFORMATION: Mouse CR2 SCR1-4 IgG1
```

<400> SEQUENCE: 70

```
Met Leu Thr Trp Phe Leu Phe Tyr Phe Ser Glu Ile Ser Cys Asp Pro
1               5                   10                  15

Pro Pro Glu Val Lys Asn Ala Arg Lys Pro Tyr Tyr Ser Leu Pro Ile
            20                  25                  30

Val Pro Gly Thr Val Leu Arg Tyr Thr Cys Ser Pro Ser Tyr Arg Leu
        35                  40                  45

Ile Gly Glu Lys Ala Ile Phe Cys Ile Ser Glu Asn Gln Val His Ala
    50                  55                  60

Thr Trp Asp Lys Ala Pro Pro Ile Cys Glu Ser Val Asn Lys Thr Ile
65                  70                  75                  80

Ser Cys Ser Asp Pro Ile Val Pro Gly Gly Phe Met Asn Lys Gly Ser
                85                  90                  95

Lys Ala Pro Phe Arg His Gly Asp Ser Val Thr Phe Thr Cys Lys Ala
                100                 105                 110

Asn Phe Thr Met Lys Gly Ser Lys Thr Val Trp Cys Gln Ala Asn Glu
            115                 120                 125

Met Trp Gly Pro Thr Ala Leu Pro Val Cys Glu Ser Asp Phe Pro Leu
130                 135                 140

Glu Cys Pro Ser Leu Pro Thr Ile His Asn Gly His His Thr Gly Gln
145                 150                 155                 160

His Val Asp Gln Phe Val Ala Gly Leu Ser Val Thr Tyr Ser Cys Glu
                165                 170                 175

Pro Gly Tyr Leu Leu Thr Gly Lys Lys Thr Ile Lys Cys Leu Ser Ser
                180                 185                 190

Gly Asp Trp Asp Gly Val Ile Pro Thr Cys Lys Glu Ala Gln Cys Glu
            195                 200                 205

His Pro Gly Lys Phe Pro Asn Gly Gln Val Lys Glu Pro Leu Ser Leu
210                 215                 220

Gln Val Gly Thr Thr Val Tyr Phe Ser Cys Asn Glu Gly Tyr Gln Leu
225                 230                 235                 240

Gln Gly Gln Pro Ser Ser Gln Cys Val Ile Val Glu Gln Lys Ala Ile
                245                 250                 255

Trp Thr Lys Lys Pro Val Cys Lys Glu Glu Pro Lys Ser Ser Asp Lys
                260                 265                 270

Thr His Thr Cys Pro Pro Cys Pro Ala Pro Glu Leu Leu Gly Gly Pro
            275                 280                 285

Ser Val Phe Leu Phe Pro Pro Lys Pro Lys Asp Thr Leu Met Ile Ser
290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
                340                 345                 350

Val Ser Val Leu Thr Val Leu His Gln Asp Trp Leu Asn Gly Lys Glu
            355                 360                 365

Tyr Lys Cys Lys Val Ser Asn Lys Ala Leu Pro Ala Pro Ile Glu Lys
            370                 375                 380

Thr Ile Ser Lys Ala Lys Gly Gln Pro Arg Glu Pro Gln Val Tyr Thr
385                 390                 395                 400

Leu Pro Pro Ser Arg Glu Glu Met Thr Lys Asn Gln Val Ser Leu Thr
```

-continued

```
                405                 410                 415
Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 71
<211> LENGTH: 497
<212> TYPE: PRT
<213> ORGANISM: Artificial Sequence
<220> FEATURE:
<223> OTHER INFORMATION: Mouse CR2 SCR1-4 IgG1 S267E

<400> SEQUENCE: 71

Met Leu Thr Trp Phe Leu Phe Tyr Phe Ser Glu Ile Ser Cys Asp Pro
1               5                   10                  15

Pro Pro Glu Val Lys Asn Ala Arg Lys Pro Tyr Tyr Ser Leu Pro Ile
            20                  25                  30

Val Pro Gly Thr Val Leu Arg Tyr Thr Cys Ser Pro Ser Tyr Arg Leu
        35                  40                  45

Ile Gly Glu Lys Ala Ile Phe Cys Ile Ser Glu Asn Gln Val His Ala
    50                  55                  60

Thr Trp Asp Lys Ala Pro Pro Ile Cys Glu Ser Val Asn Lys Thr Ile
65                  70                  75                  80

Ser Cys Ser Asp Pro Ile Val Pro Gly Gly Phe Met Asn Lys Gly Ser
                85                  90                  95

Lys Ala Pro Phe Arg His Gly Asp Ser Val Thr Phe Thr Cys Lys Ala
            100                 105                 110

Asn Phe Thr Met Lys Gly Ser Lys Thr Val Trp Cys Gln Ala Asn Glu
        115                 120                 125

Met Trp Gly Pro Thr Ala Leu Pro Val Cys Glu Ser Asp Phe Pro Leu
    130                 135                 140

Glu Cys Pro Ser Leu Pro Thr Ile His Asn Gly His His Thr Gly Gln
145                 150                 155                 160

His Val Asp Gln Phe Val Ala Gly Leu Ser Val Thr Tyr Ser Cys Glu
                165                 170                 175

Pro Gly Tyr Leu Leu Thr Gly Lys Lys Thr Ile Lys Cys Leu Ser Ser
            180                 185                 190

Gly Asp Trp Asp Gly Val Ile Pro Thr Cys Lys Glu Ala Gln Cys Glu
        195                 200                 205

His Pro Gly Lys Phe Pro Asn Gly Gln Val Lys Glu Pro Leu Ser Leu
    210                 215                 220

Gln Val Gly Thr Thr Val Tyr Phe Ser Cys Asn Glu Gly Tyr Gln Leu
225                 230                 235                 240

Gln Gly Gln Pro Ser Ser Gln Cys Val Ile Val Glu Gln Lys Ala Ile
                245                 250                 255

Trp Thr Lys Lys Pro Val Cys Lys Glu Glu Pro Lys Ser Ser Asp Lys
            260                 265                 270
```

-continued

```
Thr His Thr Cys Pro Pro Cys Pro Ala Pro Glu Leu Leu Gly Gly Pro
            275                 280                 285

Ser Val Phe Leu Phe Pro Pro Lys Pro Lys Asp Thr Leu Met Ile Ser
290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
            355                 360                 365

Tyr Lys Cys Lys Val Ser Asn Lys Ala Leu Pro Ala Pro Ile Glu Lys
            370                 375                 380

Thr Ile Ser Lys Ala Lys Gly Gln Pro Arg Glu Pro Gln Val Tyr Thr
385                 390                 395                 400

Leu Pro Pro Ser Arg Glu Glu Met Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
            435                 440                 445

Asp Ser Asp Gly Ser Phe Phe Leu Tyr Ser Lys Leu Thr Val Asp Lys
450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 72
<211> LENGTH: 497
<212> TYPE: PRT
<213> ORGANISM: Artificial Sequence
<220> FEATURE:
<223> OTHER INFORMATION: Mouse CR2 SCR1-4 IgG1 S267E/L328F

<400> SEQUENCE: 72

Met Leu Thr Trp Phe Leu Phe Tyr Phe Ser Glu Ile Ser Cys Asp Pro
1               5                   10                  15

Pro Pro Glu Val Lys Asn Ala Arg Lys Pro Tyr Tyr Ser Leu Pro Ile
                20                  25                  30

Val Pro Gly Thr Val Leu Arg Tyr Thr Cys Ser Pro Ser Tyr Arg Leu
            35                  40                  45

Ile Gly Glu Lys Ala Ile Phe Cys Ile Ser Glu Asn Gln Val His Ala
    50                  55                  60

Thr Trp Asp Lys Ala Pro Pro Ile Cys Glu Ser Val Asn Lys Thr Ile
65                  70                  75                  80

Ser Cys Ser Asp Pro Ile Val Pro Gly Gly Phe Met Asn Lys Gly Ser
                85                  90                  95

Lys Ala Pro Phe Arg His Gly Asp Ser Val Thr Phe Thr Cys Lys Ala
            100                 105                 110

Asn Phe Thr Met Lys Gly Ser Lys Thr Val Trp Cys Gln Ala Asn Glu
        115                 120                 125
```

Met Trp Gly Pro Thr Ala Leu Pro Val Cys Glu Ser Asp Phe Pro Leu
        130                 135                 140
Glu Cys Pro Ser Leu Pro Thr Ile His Asn Gly His Thr Gly Gln
145                 150                 155                 160
His Val Asp Gln Phe Val Ala Gly Leu Ser Val Thr Tyr Ser Cys Glu
                165                 170                 175
Pro Gly Tyr Leu Leu Thr Gly Lys Lys Thr Ile Lys Cys Leu Ser Ser
                180                 185                 190
Gly Asp Trp Asp Gly Val Ile Pro Thr Cys Lys Glu Ala Gln Cys Glu
            195                 200                 205
His Pro Gly Lys Phe Pro Asn Gly Gln Val Lys Glu Pro Leu Ser Leu
210                 215                 220
Gln Val Gly Thr Thr Val Tyr Phe Ser Cys Asn Glu Gly Tyr Gln Leu
225                 230                 235                 240
Gln Gly Gln Pro Ser Ser Gln Cys Val Ile Val Glu Gln Lys Ala Ile
                245                 250                 255
Trp Thr Lys Lys Pro Val Cys Lys Glu Glu Pro Lys Ser Ser Asp Lys
            260                 265                 270
Thr His Thr Cys Pro Pro Cys Pro Ala Pro Glu Leu Leu Gly Gly Pro
        275                 280                 285
Ser Val Phe Leu Phe Pro Pro Lys Pro Lys Asp Thr Leu Met Ile Ser
290                 295                 300
Arg Thr Pro Glu Val Thr Cys Val Val Val Asp Val Glu His Glu Asp
305                 310                 315                 320
Pro Glu Val Lys Phe Asn Trp Tyr Val Asp Gly Val Glu Val His Asn
                325                 330                 335
Ala Lys Thr Lys Pro Arg Glu Glu Gln Tyr Asn Ser Thr Tyr Arg Val
            340                 345                 350
Val Ser Val Leu Thr Val Leu His Gln Asp Trp Leu Asn Gly Lys Glu
        355                 360                 365
Tyr Lys Cys Lys Val Ser Asn Lys Ala Phe Pro Ala Pro Ile Glu Lys
370                 375                 380
Thr Ile Ser Lys Ala Lys Gly Gln Pro Arg Glu Pro Gln Val Tyr Thr
385                 390                 395                 400
Leu Pro Pro Ser Arg Glu Glu Met Thr Lys Asn Gln Val Ser Leu Thr
                405                 410                 415
Cys Leu Val Lys Gly Phe Tyr Pro Ser Asp Ile Ala Val Glu Trp Glu
            420                 425                 430
Ser Asn Gly Gln Pro Glu Asn Asn Tyr Lys Thr Thr Pro Pro Val Leu
        435                 440                 445
Asp Ser Asp Gly Ser Phe Phe Leu Tyr Ser Lys Leu Thr Val Asp Lys
450                 455                 460
Ser Arg Trp Gln Gln Gly Asn Val Phe Ser Cys Ser Val Met His Glu
465                 470                 475                 480
Ala Leu His Asn His Tyr Thr Gln Lys Ser Leu Ser Leu Ser Pro Gly
                485                 490                 495
Lys

<210> SEQ ID NO 73
<211> LENGTH: 497
<212> TYPE: PRT
<213> ORGANISM: Artificial Sequence
<220> FEATURE:
<223> OTHER INFORMATION: Mouse CR2 SCR1-4 IgG1 G236N/S267E

<400> SEQUENCE: 73

```
Met Leu Thr Trp Phe Leu Phe Tyr Phe Ser Glu Ile Ser Cys Asp Pro
1               5                   10                  15

Pro Pro Glu Val Lys Asn Ala Arg Lys Pro Tyr Tyr Ser Leu Pro Ile
            20                  25                  30

Val Pro Gly Thr Val Leu Arg Tyr Thr Cys Ser Pro Ser Tyr Arg Leu
        35                  40                  45

Ile Gly Glu Lys Ala Ile Phe Cys Ile Ser Glu Asn Gln Val His Ala
    50                  55                  60

Thr Trp Asp Lys Ala Pro Pro Ile Cys Glu Ser Val Asn Lys Thr Ile
65                  70                  75                  80

Ser Cys Ser Asp Pro Ile Val Pro Gly Gly Phe Met Asn Lys Gly Ser
                85                  90                  95

Lys Ala Pro Phe Arg His Gly Asp Ser Val Thr Phe Thr Cys Lys Ala
            100                 105                 110

Asn Phe Thr Met Lys Gly Ser Lys Thr Val Trp Cys Gln Ala Asn Glu
            115                 120                 125

Met Trp Gly Pro Thr Ala Leu Pro Val Cys Glu Ser Asp Phe Pro Leu
            130                 135                 140

Glu Cys Pro Ser Leu Pro Thr Ile His Asn Gly His His Thr Gly Gln
145                 150                 155                 160

His Val Asp Gln Phe Val Ala Gly Leu Ser Val Thr Tyr Ser Cys Glu
                165                 170                 175

Pro Gly Tyr Leu Leu Thr Gly Lys Lys Thr Ile Lys Cys Leu Ser Ser
            180                 185                 190

Gly Asp Trp Asp Gly Val Ile Pro Thr Cys Lys Glu Ala Gln Cys Glu
            195                 200                 205

His Pro Gly Lys Phe Pro Asn Gly Gln Val Lys Glu Pro Leu Ser Leu
            210                 215                 220

Gln Val Gly Thr Thr Val Tyr Phe Ser Cys Asn Glu Gly Tyr Gln Leu
225                 230                 235                 240

Gln Gly Gln Pro Ser Ser Gln Cys Val Ile Val Glu Gln Lys Ala Ile
                245                 250                 255

Trp Thr Lys Lys Pro Val Cys Lys Glu Glu Pro Lys Ser Ser Asp Lys
            260                 265                 270

Thr His Thr Cys Pro Pro Cys Pro Ala Pro Glu Leu Leu Asn Gly Pro
            275                 280                 285

Ser Val Phe Leu Phe Pro Pro Lys Pro Lys Asp Thr Leu Met Ile Ser
            290                 295                 300

Arg Thr Pro Glu Val Thr Cys Val Val Val Asp Val Glu His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
            355                 360                 365

Tyr Lys Cys Lys Val Ser Asn Lys Ala Leu Pro Ala Pro Ile Glu Lys
            370                 375                 380

Thr Ile Ser Lys Ala Lys Gly Gln Pro Arg Glu Pro Gln Val Tyr Thr
385                 390                 395                 400

Leu Pro Pro Ser Arg Glu Glu Met Thr Lys Asn Gln Val Ser Leu Thr
                405                 410                 415
```

```
Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 74
<211> LENGTH: 497
<212> TYPE: PRT
<213> ORGANISM: Artificial Sequence
<220> FEATURE:
<223> OTHER INFORMATION: Mouse CR2 SCR1-4 IgG1 G236D/S267E

<400> SEQUENCE: 74

Met Leu Thr Trp Phe Leu Phe Tyr Phe Ser Glu Ile Ser Cys Asp Pro
1               5                   10                  15

Pro Pro Glu Val Lys Asn Ala Arg Lys Pro Tyr Tyr Ser Leu Pro Ile
            20                  25                  30

Val Pro Gly Thr Val Leu Arg Tyr Thr Cys Ser Pro Ser Tyr Arg Leu
        35                  40                  45

Ile Gly Glu Lys Ala Ile Phe Cys Ile Ser Glu Asn Gln Val His Ala
50                  55                  60

Thr Trp Asp Lys Ala Pro Pro Ile Cys Glu Ser Val Asn Lys Thr Ile
65                  70                  75                  80

Ser Cys Ser Asp Pro Ile Val Pro Gly Gly Phe Met Asn Lys Gly Ser
                85                  90                  95

Lys Ala Pro Phe Arg His Gly Asp Ser Val Thr Phe Thr Cys Lys Ala
            100                 105                 110

Asn Phe Thr Met Lys Gly Ser Lys Thr Val Trp Cys Gln Ala Asn Glu
        115                 120                 125

Met Trp Gly Pro Thr Ala Leu Pro Val Cys Glu Ser Asp Phe Pro Leu
130                 135                 140

Glu Cys Pro Ser Leu Pro Thr Ile His Asn Gly His His Thr Gly Gln
145                 150                 155                 160

His Val Asp Gln Phe Val Ala Gly Leu Ser Val Thr Tyr Ser Cys Glu
                165                 170                 175

Pro Gly Tyr Leu Leu Thr Gly Lys Lys Thr Ile Lys Cys Leu Ser Ser
            180                 185                 190

Gly Asp Trp Asp Gly Val Ile Pro Thr Cys Lys Glu Ala Gln Cys Glu
        195                 200                 205

His Pro Gly Lys Phe Pro Asn Gly Gln Val Lys Glu Pro Leu Ser Leu
210                 215                 220

Gln Val Gly Thr Thr Val Tyr Phe Ser Cys Asn Glu Gly Tyr Gln Leu
225                 230                 235                 240

Gln Gly Gln Pro Ser Ser Gln Cys Val Ile Val Glu Gln Lys Ala Ile
                245                 250                 255

Trp Thr Lys Lys Pro Val Cys Lys Glu Glu Pro Lys Ser Ser Asp Lys
            260                 265                 270
```

```
Thr His Thr Cys Pro Pro Cys Pro Ala Pro Glu Leu Leu Asp Gly Pro
            275                 280                 285

Ser Val Phe Leu Phe Pro Lys Pro Lys Asp Thr Leu Met Ile Ser
290                 295                 300

Arg Thr Pro Glu Val Thr Cys Val Val Val Asp Val Glu His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
355                 360                 365

Tyr Lys Cys Lys Val Ser Asn Lys Ala Leu Pro Ala Pro Ile Glu Lys
            370                 375                 380

Thr Ile Ser Lys Ala Lys Gly Gln Pro Arg Glu Pro Gln Val Tyr Thr
385                 390                 395                 400

Leu Pro Pro Ser Arg Glu Glu Met Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
435                 440                 445

Asp Ser Asp Gly Ser Phe Phe Leu Tyr Ser Lys Leu Thr Val Asp Lys
            450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 75
<211> LENGTH: 497
<212> TYPE: PRT
<213> ORGANISM: Artificial Sequence
<220> FEATURE:
<223> OTHER INFORMATION: Mouse CR2 SCR1-4 IgG1 G236R/L328R

<400> SEQUENCE: 75

Met Leu Thr Trp Phe Leu Phe Tyr Phe Ser Glu Ile Ser Cys Asp Pro
1               5                   10                  15

Pro Pro Glu Val Lys Asn Ala Arg Lys Pro Tyr Tyr Ser Leu Pro Ile
                20                  25                  30

Val Pro Gly Thr Val Leu Arg Tyr Thr Cys Ser Pro Ser Tyr Arg Leu
            35                  40                  45

Ile Gly Glu Lys Ala Ile Phe Cys Ile Ser Glu Asn Gln Val His Ala
50                  55                  60

Thr Trp Asp Lys Ala Pro Pro Ile Cys Glu Ser Val Asn Lys Thr Ile
65                  70                  75                  80

Ser Cys Ser Asp Pro Ile Val Pro Gly Gly Phe Met Asn Lys Gly Ser
                85                  90                  95

Lys Ala Pro Phe Arg His Gly Asp Ser Val Thr Phe Thr Cys Lys Ala
            100                 105                 110

Asn Phe Thr Met Lys Gly Ser Lys Thr Val Trp Cys Gln Ala Asn Glu
            115                 120                 125

Met Trp Gly Pro Thr Ala Leu Pro Val Cys Glu Ser Asp Phe Pro Leu
```

```
                130                 135                 140
Glu Cys Pro Ser Leu Pro Thr Ile His Asn Gly His His Thr Gly Gln
145                 150                 155                 160

His Val Asp Gln Phe Val Ala Gly Leu Ser Val Thr Tyr Ser Cys Glu
                165                 170                 175

Pro Gly Tyr Leu Leu Thr Gly Lys Lys Thr Ile Lys Cys Leu Ser Ser
            180                 185                 190

Gly Asp Trp Asp Gly Val Ile Pro Thr Cys Lys Glu Ala Gln Cys Glu
        195                 200                 205

His Pro Gly Lys Phe Pro Asn Gly Gln Val Lys Glu Pro Leu Ser Leu
    210                 215                 220

Gln Val Gly Thr Thr Val Tyr Phe Ser Cys Asn Glu Gly Tyr Gln Leu
225                 230                 235                 240

Gln Gly Gln Pro Ser Ser Gln Cys Val Ile Val Glu Gln Lys Ala Ile
                245                 250                 255

Trp Thr Lys Lys Pro Val Cys Lys Glu Glu Pro Lys Ser Ser Asp Lys
            260                 265                 270

Thr His Thr Cys Pro Pro Cys Pro Ala Pro Glu Leu Leu Arg Gly Pro
        275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Arg Pro Ala Pro Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Arg Glu Glu Met Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 76
<211> LENGTH: 273
<212> TYPE: PRT
<213> ORGANISM: Artificial Sequence
<220> FEATURE:
<223> OTHER INFORMATION: Human LOX-1

<400> SEQUENCE: 76
```

```
Met Thr Phe Asp Asp Leu Lys Ile Gln Thr Val Lys Asp Gln Pro Asp
1               5                   10                  15

Glu Lys Ser Asn Gly Lys Lys Ala Lys Gly Leu Gln Phe Leu Tyr Ser
            20                  25                  30

Pro Trp Trp Cys Leu Ala Ala Thr Leu Gly Val Leu Cys Leu Gly
        35                  40                  45

Leu Val Val Thr Ile Met Val Leu Gly Met Gln Leu Ser Gln Val Ser
    50                  55                  60

Asp Leu Leu Thr Gln Glu Gln Ala Asn Leu Thr His Gln Lys Lys Lys
65                  70                  75                  80

Leu Glu Gly Gln Ile Ser Ala Arg Gln Gln Ala Glu Glu Ala Ser Gln
                85                  90                  95

Glu Ser Glu Asn Glu Leu Lys Glu Met Ile Glu Thr Leu Ala Arg Lys
                100                 105                 110

Leu Asn Glu Lys Ser Lys Glu Gln Met Glu Leu His His Gln Asn Leu
            115                 120                 125

Asn Leu Gln Glu Thr Leu Lys Arg Val Ala Asn Cys Ser Ala Pro Cys
    130                 135                 140

Pro Gln Asp Trp Ile Trp His Gly Glu Asn Cys Tyr Leu Phe Ser Ser
145                 150                 155                 160

Gly Ser Phe Asn Trp Glu Lys Ser Gln Glu Lys Cys Leu Ser Leu Asp
            165                 170                 175

Ala Lys Leu Leu Lys Ile Asn Ser Thr Ala Asp Leu Asp Phe Ile Gln
            180                 185                 190

Gln Ala Ile Ser Tyr Ser Ser Phe Pro Phe Trp Met Gly Leu Ser Arg
            195                 200                 205

Arg Asn Pro Ser Tyr Pro Trp Leu Trp Glu Asp Gly Ser Pro Leu Met
    210                 215                 220

Pro His Leu Phe Arg Val Arg Gly Ala Val Ser Gln Thr Tyr Pro Ser
225                 230                 235                 240

Gly Thr Cys Ala Tyr Ile Gln Arg Gly Ala Val Tyr Ala Glu Asn Cys
                245                 250                 255

Ile Leu Ala Ala Phe Ser Ile Cys Gln Lys Ala Asn Leu Arg Ala
                260                 265                 270

Gln

<210> SEQ ID NO 77
<211> LENGTH: 363
<212> TYPE: PRT
<213> ORGANISM: Artificial Sequence
<220> FEATURE:
<223> OTHER INFORMATION: Mouse LOX-1

<400> SEQUENCE: 77

Met Thr Phe Asp Asp Lys Met Lys Pro Ala Asn Asp Glu Pro Asp Gln
1               5                   10                  15

Lys Ser Cys Gly Lys Lys Pro Lys Gly Leu His Leu Ser Ser Pro
            20                  25                  30

Trp Trp Phe Pro Ala Ala Met Thr Leu Val Ile Leu Cys Leu Val Leu
        35                  40                  45

Ser Val Thr Leu Ile Val Gln Trp Thr Gln Leu Arg Gln Val Ser Asp
    50                  55                  60

Leu Leu Lys Gln Tyr Gln Ala Asn Leu Thr Gln Gln Asp Arg Ile Leu
65                  70                  75                  80
```

```
Glu Gly Gln Met Leu Ala Gln Gln Lys Ala Asn Ala Ser Gln Glu
                85                  90                  95

Ser Lys Lys Glu Leu Lys Gly Lys Ile Asp Thr Leu Thr Gln Lys Leu
            100                 105                 110

Asn Glu Lys Ser Lys Glu Gln Glu Glu Leu Leu Gln Lys Asn Gln Asn
            115                 120                 125

Leu Gln Glu Ala Leu Gln Arg Ala Ala Asn Ser Ser Glu Glu Ser Gln
            130                 135                 140

Arg Glu Leu Lys Gly Lys Ile Asp Thr Ile Thr Arg Lys Leu Asp Glu
145                 150                 155                 160

Lys Ser Lys Glu Gln Glu Glu Leu Leu Gln Met Ile Gln Asn Leu Gln
                165                 170                 175

Glu Ala Leu Gln Arg Ala Ala Asn Ser Ser Glu Glu Ser Gln Arg Glu
            180                 185                 190

Leu Lys Gly Lys Ile Asp Thr Leu Thr Leu Lys Leu Asn Glu Lys Ser
            195                 200                 205

Lys Glu Gln Glu Glu Leu Leu Gln Lys Asn Gln Asn Leu Gln Glu Ala
            210                 215                 220

Leu Gln Arg Ala Ala Asn Phe Ser Gly Pro Cys Pro Gln Asp Trp Leu
225                 230                 235                 240

Trp His Lys Glu Asn Cys Tyr Leu Phe His Gly Pro Phe Ser Trp Glu
                245                 250                 255

Lys Asn Arg Gln Thr Cys Gln Ser Leu Gly Gly Gln Leu Leu Gln Ile
            260                 265                 270

Asn Gly Ala Asp Asp Leu Thr Phe Ile Leu Gln Ala Ile Ser His Thr
            275                 280                 285

Thr Ser Pro Phe Trp Ile Gly Leu His Arg Lys Lys Pro Gly Gln Pro
            290                 295                 300

Trp Leu Trp Glu Asn Gly Thr Pro Leu Asn Phe Gln Phe Lys Thr
305                 310                 315                 320

Arg Gly Val Ser Leu Gln Leu Tyr Ser Ser Gly Asn Cys Ala Tyr Leu
                325                 330                 335

Gln Asp Gly Ala Val Phe Ala Glu Asn Cys Ile Leu Ile Ala Phe Ser
            340                 345                 350

Ile Cys Gln Lys Lys Thr Asn His Leu Gln Ile
            355                 360

<210> SEQ ID NO 78
<211> LENGTH: 472
<212> TYPE: PRT
<213> ORGANISM: Artificial Sequence
<220> FEATURE:
<223> OTHER INFORMATION: Human CD36

<400> SEQUENCE: 78

Met Gly Cys Asp Arg Asn Cys Gly Leu Ile Ala Gly Ala Val Ile Gly
1               5                   10                  15

Ala Val Leu Ala Val Phe Gly Gly Ile Leu Met Pro Val Gly Asp Leu
                20                  25                  30

Leu Ile Gln Lys Thr Ile Lys Lys Gln Val Val Leu Glu Glu Gly Thr
            35                  40                  45

Ile Ala Phe Lys Asn Trp Val Lys Thr Gly Thr Glu Val Tyr Arg Gln
        50                  55                  60

Phe Trp Ile Phe Asp Val Gln Asn Pro Gln Glu Val Met Met Asn Ser
65                  70                  75                  80
```

Ser Asn Ile Gln Val Lys Gln Arg Gly Pro Tyr Thr Tyr Arg Val Arg
            85                  90                  95

Phe Leu Ala Lys Glu Asn Val Thr Gln Asp Ala Glu Asp Asn Thr Val
            100                 105                 110

Ser Phe Leu Gln Pro Asn Gly Ala Ile Phe Glu Pro Ser Leu Ser Val
            115                 120                 125

Gly Thr Glu Ala Asp Asn Phe Thr Val Leu Asn Leu Ala Val Ala Ala
130                 135                 140

Ala Ser His Ile Tyr Gln Asn Gln Phe Val Gln Met Ile Leu Asn Ser
145                 150                 155                 160

Leu Ile Asn Lys Ser Lys Ser Ser Met Phe Gln Val Arg Thr Leu Arg
            165                 170                 175

Glu Leu Leu Trp Gly Tyr Arg Asp Pro Phe Leu Ser Leu Val Pro Tyr
            180                 185                 190

Pro Val Thr Thr Thr Val Gly Leu Phe Tyr Pro Tyr Asn Asn Thr Ala
            195                 200                 205

Asp Gly Val Tyr Lys Val Phe Asn Gly Lys Asp Asn Ile Ser Lys Val
            210                 215                 220

Ala Ile Ile Asp Thr Tyr Lys Gly Lys Arg Asn Leu Ser Tyr Trp Glu
225                 230                 235                 240

Ser His Cys Asp Met Ile Asn Gly Thr Asp Ala Ala Ser Phe Pro Pro
            245                 250                 255

Phe Val Glu Lys Ser Gln Val Leu Gln Phe Phe Ser Ser Asp Ile Cys
            260                 265                 270

Arg Ser Ile Tyr Ala Val Phe Glu Ser Asp Val Asn Leu Lys Gly Ile
            275                 280                 285

Pro Val Tyr Arg Phe Val Leu Pro Ser Lys Ala Phe Ala Ser Pro Val
            290                 295                 300

Glu Asn Pro Asp Asn Tyr Cys Phe Cys Thr Glu Lys Ile Ile Ser Lys
305                 310                 315                 320

Asn Cys Thr Ser Tyr Gly Val Leu Asp Ile Ser Lys Cys Lys Glu Gly
            325                 330                 335

Arg Pro Val Tyr Ile Ser Leu Pro His Phe Leu Tyr Ala Ser Pro Asp
            340                 345                 350

Val Ser Glu Pro Ile Asp Gly Leu Asn Pro Asn Glu Glu His Arg
            355                 360                 365

Thr Tyr Leu Asp Ile Glu Pro Ile Thr Gly Phe Thr Leu Gln Phe Ala
            370                 375                 380

Lys Arg Leu Gln Val Asn Leu Leu Val Lys Pro Ser Glu Lys Ile Gln
385                 390                 395                 400

Val Leu Lys Asn Leu Lys Arg Asn Tyr Ile Val Pro Ile Leu Trp Leu
            405                 410                 415

Asn Glu Thr Gly Thr Ile Gly Asp Glu Lys Ala Asn Met Phe Arg Ser
            420                 425                 430

Gln Val Thr Gly Lys Ile Asn Leu Leu Gly Leu Ile Glu Met Ile Leu
            435                 440                 445

Leu Ser Val Gly Val Val Met Phe Val Ala Phe Met Ile Ser Tyr Cys
450                 455                 460

Ala Cys Arg Ser Lys Thr Ile Lys
465                 470

<210> SEQ ID NO 79
<211> LENGTH: 472
<212> TYPE: PRT

<213> ORGANISM: Artificial Sequence
<220> FEATURE:
<223> OTHER INFORMATION: Mouse CD36

<400> SEQUENCE: 79

```
Met Gly Cys Asp Arg Asn Cys Gly Leu Ile Ala Gly Ala Val Ile Gly
1               5                   10                  15

Ala Val Leu Ala Val Phe Gly Gly Ile Leu Met Pro Val Gly Asp Met
            20                  25                  30

Leu Ile Glu Lys Thr Ile Lys Arg Glu Val Val Leu Glu Gly Thr
        35                  40                  45

Thr Ala Phe Lys Asn Trp Val Lys Thr Gly Thr Thr Val Tyr Arg Gln
    50                  55                  60

Phe Trp Ile Phe Asp Val Gln Asn Pro Asp Asp Val Ala Lys Asn Ser
65                  70                  75                  80

Ser Lys Ile Lys Val Lys Gln Arg Gly Pro Tyr Thr Tyr Arg Val Arg
                85                  90                  95

Tyr Leu Ala Lys Glu Asn Ile Thr Gln Asp Pro Glu Asp His Thr Val
            100                 105                 110

Ser Phe Val Gln Pro Asn Gly Ala Ile Phe Glu Pro Ser Leu Ser Val
        115                 120                 125

Gly Thr Glu Asp Asp Asn Phe Thr Val Leu Asn Leu Ala Val Ala Ala
130                 135                 140

Ala Pro His Ile Tyr Gln Asn Ser Phe Val Gln Val Leu Asn Ser
145                 150                 155                 160

Leu Ile Lys Lys Ser Lys Ser Ser Met Phe Gln Thr Arg Ser Leu Lys
                165                 170                 175

Glu Leu Leu Trp Gly Tyr Lys Asp Pro Phe Leu Ser Leu Val Pro Tyr
            180                 185                 190

Pro Ile Ser Thr Thr Val Gly Val Phe Tyr Pro Tyr Asn Asp Thr Val
        195                 200                 205

Asp Gly Val Tyr Lys Val Phe Asn Gly Lys Asp Asn Ile Ser Lys Val
210                 215                 220

Ala Ile Ile Glu Ser Tyr Lys Gly Lys Arg Asn Leu Ser Tyr Trp Pro
225                 230                 235                 240

Ser Tyr Cys Asp Met Ile Asn Gly Thr Asp Ala Ala Ser Phe Pro Pro
                245                 250                 255

Phe Val Glu Lys Ser Arg Thr Leu Arg Phe Phe Ser Ser Asp Ile Cys
            260                 265                 270

Arg Ser Ile Tyr Ala Val Phe Gly Ser Glu Ile Asp Leu Lys Gly Ile
        275                 280                 285

Pro Val Tyr Arg Phe Val Leu Pro Ala Asn Ala Phe Ala Ser Pro Leu
        290                 295                 300

Gln Asn Pro Asp Asn His Cys Phe Cys Thr Glu Lys Val Ile Ser Asn
305                 310                 315                 320

Asn Cys Thr Ser Tyr Gly Val Leu Asp Ile Gly Lys Cys Lys Glu Gly
                325                 330                 335

Lys Pro Val Tyr Ile Ser Leu Pro His Phe Leu His Ala Ser Pro Asp
            340                 345                 350

Val Ser Glu Pro Ile Glu Gly Leu His Pro Asn Glu Asp Glu His Arg
        355                 360                 365

Thr Tyr Leu Asp Val Glu Pro Ile Thr Gly Phe Thr Leu Gln Phe Ala
        370                 375                 380

Lys Arg Leu Gln Val Asn Ile Leu Val Lys Pro Ala Arg Lys Ile Glu
```

```
                385                 390                 395                 400
Ala Leu Lys Asn Leu Lys Arg Pro Tyr Ile Val Pro Ile Leu Trp Leu
                405                 410                 415

Asn Glu Thr Gly Thr Ile Gly Asp Glu Lys Ala Glu Met Phe Lys Thr
                420                 425                 430

Gln Val Thr Gly Lys Ile Lys Leu Leu Gly Met Val Glu Met Ala Leu
                435                 440                 445

Leu Gly Ile Gly Val Val Met Phe Val Ala Phe Met Ile Ser Tyr Cys
                450                 455                 460

Ala Cys Lys Ser Lys Asn Gly Lys
465                 470

<210> SEQ ID NO 80
<211> LENGTH: 453
<212> TYPE: PRT
<213> ORGANISM: Artificial Sequence
<220> FEATURE:
<223> OTHER INFORMATION: EO6_H0L0_IgG1_WT heavy chain

<400> SEQUENCE: 80

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
                20                  25                  30

Tyr Met Glu Trp Val Arg Gln Pro Pro Gly Lys Arg Leu Glu Trp Ile
            35                  40                  45

Ala Ala Ser Arg Asn Lys Ala Asn Asp Tyr Thr Thr Glu Tyr Ser Ala
        50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp Tyr Tyr Gly Ser Ser Tyr Trp Tyr Phe Asp Val
            100                 105                 110

Trp Gly Ala Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
```

```
                275                 280                 285
Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 81
<211> LENGTH: 220
<212> TYPE: PRT
<213> ORGANISM: Artificial Sequence
<220> FEATURE:
<223> OTHER INFORMATION: EO6_H0L0_IgG1_WT light chain

<400> SEQUENCE: 81

Asp Ile Val Met Thr Gln Ser Pro Thr Phe Leu Ala Val Thr Ala Ser
1               5                   10                  15

Lys Lys Val Thr Ile Ser Cys Thr Ala Ser Glu Ser Leu Tyr Ser Ser
                20                  25                  30

Lys His Lys Val His Tyr Leu Ala Trp Tyr Gln Lys Lys Pro Glu Gln
            35                  40                  45

Ser Pro Lys Leu Leu Ile Tyr Gly Ala Ser Asn Arg Tyr Ile Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Val Glu Asp Leu Thr His Tyr Tyr Cys Ala Gln
                85                  90                  95

Phe Tyr Ser Tyr Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
```

```
            180             185             190
Glu Lys His Lys Val Tyr Ala Cys Glu Val Thr His Gln Gly Leu Ser
        195             200             205

Ser Pro Val Thr Lys Ser Phe Asn Arg Gly Glu Cys
    210             215             220

<210> SEQ ID NO 82
<211> LENGTH: 451
<212> TYPE: PRT
<213> ORGANISM: Artificial Sequence
<220> FEATURE:
<223> OTHER INFORMATION: 2D03_H0L0_IgG1_WT heavy chain

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Ser Ile Ser Val Gly Gly His Arg Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Arg Val Gly Pro Ser Gly Gly Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
```

```
                  325                 330                 335
Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
            450

<210> SEQ ID NO 83
<211> LENGTH: 216
<212> TYPE: PRT
<213> ORGANISM: Artificial Sequence
<220> FEATURE:
<223> OTHER INFORMATION: 2D03_H0L0_IgG1_WT light chain

<400> SEQUENCE: 83

Gln Ser Val Leu Thr Gln Pro Pro Ser Ala Ser Gly Thr Pro Gly Gln
1               5                   10                  15

Arg Val Thr Ile Ser Cys Ser Gly Ser Asn Thr Asn Ile Gly Lys Asn
            20                  25                  30

Tyr Val Ser Trp Tyr Gln Gln Leu Pro Gly Thr Ala Pro Lys Leu Leu
        35                  40                  45

Ile Tyr Ala Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Ala Ser Leu
                85                  90                  95

Asn Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

-continued

```
<210> SEQ ID NO 84
<211> LENGTH: 379
<212> TYPE: PRT
<213> ORGANISM: Artificial Sequence
<220> FEATURE:
<223> OTHER INFORMATION: huLOX1(137-237)-(G4S)2-Fc(216)_IgG1_C220S

<400> SEQUENCE: 84

Val Ala Asn Cys Ser Ala Pro Cys Pro Gln Asp Trp Ile Trp His Gly
1               5                   10                  15

Glu Asn Cys Tyr Leu Phe Ser Ser Gly Ser Phe Asn Trp Glu Lys Ser
            20                  25                  30

Gln Glu Lys Cys Leu Ser Leu Asp Ala Lys Leu Leu Lys Ile Asn Ser
        35                  40                  45

Thr Ala Asp Leu Asp Phe Ile Gln Gln Ala Ile Ser Tyr Ser Ser Phe
    50                  55                  60

Pro Phe Trp Met Gly Leu Ser Arg Arg Asn Pro Ser Tyr Pro Trp Leu
65                  70                  75                  80

Trp Glu Asp Gly Ser Pro Leu Met Pro His Leu Phe Arg Val Arg Gly
                85                  90                  95

Ala Val Ser Gln Thr Tyr Pro Ser Gly Thr Cys Ala Tyr Ile Gln Arg
            100                 105                 110

Gly Ala Val Tyr Ala Glu Asn Cys Ile Leu Ala Ala Phe Ser Ile Cys
        115                 120                 125

Gln Lys Lys Ala Asn Leu Arg Ala Gln Gly Gly Gly Gly Ser Gly Gly
    130                 135                 140

Gly Gly Ser Glu Pro Lys Ser Ser Asp Lys Thr His Thr Cys Pro Pro
145                 150                 155                 160

Cys Pro Ala Pro Glu Leu Leu Gly Gly Pro Ser Val Phe Leu Phe Pro
                165                 170                 175

Pro Lys Pro Lys Asp Thr Leu Met Ile Ser Arg Thr Pro Glu Val Thr
            180                 185                 190

Cys Val Val Val Asp Val Ser His Glu Asp Pro Glu Val Lys Phe Asn
        195                 200                 205

Trp Tyr Val Asp Gly Val Glu Val His Asn Ala Lys Thr Lys Pro Arg
    210                 215                 220

Glu Glu Gln Tyr Asn Ser Thr Tyr Arg Val Val Ser Val Leu Thr Val
225                 230                 235                 240

Leu His Gln Asp Trp Leu Asn Gly Lys Glu Tyr Lys Cys Lys Val Ser
                245                 250                 255

Asn Lys Ala Leu Pro Ala Pro Ile Glu Lys Thr Ile Ser Lys Ala Lys
            260                 265                 270

Gly Gln Pro Arg Glu Pro Gln Val Tyr Thr Leu Pro Pro Ser Arg Glu
        275                 280                 285

Glu Met Thr Lys Asn Gln Val Ser Leu Thr Cys Leu Val Lys Gly Phe
    290                 295                 300

Tyr Pro Ser Asp Ile Ala Val Glu Trp Glu Ser Asn Gly Gln Pro Glu
305                 310                 315                 320

Asn Asn Tyr Lys Thr Thr Pro Pro Val Leu Asp Ser Asp Gly Ser Phe
                325                 330                 335

Phe Leu Tyr Ser Lys Leu Thr Val Asp Lys Ser Arg Trp Gln Gln Gly
            340                 345                 350

Asn Val Phe Ser Cys Ser Val Met His Glu Ala Leu His Asn His Tyr
        355                 360                 365

Thr Gln Lys Ser Leu Ser Leu Ser Pro Gly Lys
```

<210> SEQ ID NO 85
<211> LENGTH: 652
<212> TYPE: PRT
<213> ORGANISM: Artificial Sequence
<220> FEATURE:
<223> OTHER INFORMATION: huCD36(30-439)-(G4S)2-Fc(216)_IgG1_C220S

<400> SEQUENCE: 85

Gly Asp Leu Leu Ile Gln Lys Thr Ile Lys Lys Gln Val Val Leu Glu
1               5                   10                  15

Glu Gly Thr Ile Ala Phe Lys Asn Trp Val Lys Thr Gly Thr Glu Val
            20                  25                  30

Tyr Arg Gln Phe Trp Ile Phe Asp Val Gln Asn Pro Gln Glu Val Met
        35                  40                  45

Met Asn Ser Ser Asn Ile Gln Val Lys Gln Arg Gly Pro Tyr Thr Tyr
    50                  55                  60

Arg Val Arg Phe Leu Ala Lys Glu Asn Val Thr Gln Asp Ala Glu Asp
65                  70                  75                  80

Asn Thr Val Ser Phe Leu Gln Pro Asn Gly Ala Ile Phe Glu Pro Ser
                85                  90                  95

Leu Ser Val Gly Thr Glu Ala Asp Asn Phe Thr Val Leu Asn Leu Ala
            100                 105                 110

Val Ala Ala Ala Ser His Ile Tyr Gln Asn Gln Phe Val Gln Met Ile
        115                 120                 125

Leu Asn Ser Leu Ile Asn Lys Ser Lys Ser Ser Met Phe Gln Val Arg
130                 135                 140

Thr Leu Arg Glu Leu Leu Trp Gly Tyr Arg Asp Pro Phe Leu Ser Leu
145                 150                 155                 160

Val Pro Tyr Pro Val Thr Thr Thr Val Gly Leu Phe Tyr Pro Tyr Asn
                165                 170                 175

Asn Thr Ala Asp Gly Val Tyr Lys Val Phe Asn Gly Lys Asp Asn Ile
            180                 185                 190

Ser Lys Val Ala Ile Ile Asp Thr Tyr Lys Gly Lys Arg Asn Leu Ser
        195                 200                 205

Tyr Trp Glu Ser His Cys Asp Met Ile Asn Gly Thr Asp Ala Ala Ser
210                 215                 220

Phe Pro Pro Phe Val Glu Lys Ser Gln Val Leu Gln Phe Phe Ser Ser
225                 230                 235                 240

Asp Ile Cys Arg Ser Ile Tyr Ala Val Phe Glu Ser Asp Val Asn Leu
                245                 250                 255

Lys Gly Ile Pro Val Tyr Arg Phe Val Leu Pro Ser Lys Ala Phe Ala
            260                 265                 270

Ser Pro Val Glu Asn Pro Asp Asn Tyr Cys Phe Cys Thr Glu Lys Ile
        275                 280                 285

Ile Ser Lys Asn Cys Thr Ser Tyr Gly Val Leu Asp Ile Ser Lys Cys
290                 295                 300

Lys Glu Gly Arg Pro Val Tyr Ile Ser Leu Pro His Phe Leu Tyr Ala
305                 310                 315                 320

Ser Pro Asp Val Ser Glu Pro Ile Asp Gly Leu Asn Pro Asn Glu Glu
                325                 330                 335

Glu His Arg Thr Tyr Leu Asp Ile Glu Pro Ile Thr Gly Phe Thr Leu
            340                 345                 350

Gln Phe Ala Lys Arg Leu Gln Val Asn Leu Leu Val Lys Pro Ser Glu 355                 360                 365
Lys Ile Gln Val Leu Lys Asn Leu Lys Arg Asn Tyr Ile Val Pro Ile
            370                 375                 380
Leu Trp Leu Asn Glu Thr Gly Thr Ile Gly Asp Glu Lys Ala Asn Met
385                 390                 395                 400
Phe Arg Ser Gln Val Thr Gly Lys Ile Asn Gly Gly Gly Ser Gly
                405                 410                 415
Gly Gly Gly Ser Glu Pro Lys Ser Ser Asp Lys Thr His Thr Cys Pro
            420                 425                 430
Pro Cys Pro Ala Pro Glu Leu Leu Gly Gly Pro Ser Val Phe Leu Phe
        435                 440                 445
Pro Pro Lys Pro Lys Asp Thr Leu Met Ile Ser Arg Thr Pro Glu Val
450                 455                 460
Thr Cys Val Val Val Asp Val Ser His Glu Asp Pro Glu Val Lys Phe
465                 470                 475                 480
Asn Trp Tyr Val Asp Gly Val Glu Val His Asn Ala Lys Thr Lys Pro
                485                 490                 495
Arg Glu Glu Gln Tyr Asn Ser Thr Tyr Arg Val Val Ser Val Leu Thr
            500                 505                 510
Val Leu His Gln Asp Trp Leu Asn Gly Lys Glu Tyr Lys Cys Lys Val
        515                 520                 525
Ser Asn Lys Ala Leu Pro Ala Pro Ile Glu Lys Thr Ile Ser Lys Ala
    530                 535                 540
Lys Gly Gln Pro Arg Glu Pro Gln Val Tyr Thr Leu Pro Pro Ser Arg
545                 550                 555                 560
Glu Glu Met Thr Lys Asn Gln Val Ser Leu Thr Cys Leu Val Lys Gly
                565                 570                 575
Phe Tyr Pro Ser Asp Ile Ala Val Glu Trp Glu Ser Asn Gly Gln Pro
            580                 585                 590
Glu Asn Asn Tyr Lys Thr Thr Pro Pro Val Leu Asp Ser Asp Gly Ser
        595                 600                 605
Phe Phe Leu Tyr Ser Lys Leu Thr Val Asp Lys Ser Arg Trp Gln Gln
    610                 615                 620
Gly Asn Val Phe Ser Cys Ser Val Met His Glu Ala Leu His Asn His
625                 630                 635                 640
Tyr Thr Gln Lys Ser Leu Ser Leu Ser Pro Gly Lys
                645                 650

<210> SEQ ID NO 86
<211> LENGTH: 379
<212> TYPE: PRT
<213> ORGANISM: Artificial Sequence
<220> FEATURE:
<223> OTHER INFORMATION: empty-Fc(216)_IgG1_C220S-(G4S)2-huLOX1(137-237)

<400> SEQUENCE: 86

Glu Pro Lys Ser Ser Asp Lys Thr His Thr Cys Pro Pro Cys Pro Ala
1               5                   10                  15
Pro Glu Leu Leu Gly Gly Pro Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
    50                  55                  60
Asp Gly Val Glu Val His Asn Ala Lys Thr Lys Pro Arg Glu Glu Gln

```
                65                  70                  75                  80
Tyr Asn Ser Thr Tyr Arg Val Val Ser Val Leu Thr Val Leu His Gln
                    85                  90                  95
Asp Trp Leu Asn Gly Lys Glu Tyr Lys Cys Lys Val Ser Asn Lys Ala
                    100                 105                 110
Leu Pro Ala Pro Ile Glu Lys Thr Ile Ser Lys Ala Lys Gly Gln Pro
                    115                 120                 125
Arg Glu Pro Gln Val Tyr Thr Leu Pro Pro Ser Arg Glu Glu Met Thr
            130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                    165                 170                 175
Lys Thr Thr Pro Pro Val Leu Asp Ser Asp Gly Ser Phe Phe Leu Tyr
                    180                 185                 190
Ser Lys Leu Thr Val Asp Lys Ser Arg Trp Gln Gln Gly Asn Val Phe
                    195                 200                 205
Ser Cys Ser Val Met His Glu Ala Leu His Asn His Tyr Thr Gln Lys
                    210                 215                 220
Ser Leu Ser Leu Ser Pro Gly Lys Gly Gly Gly Ser Gly Gly Gly
225                 230                 235                 240
Gly Ser Val Ala Asn Cys Ser Ala Pro Cys Pro Gln Asp Trp Ile Trp
                    245                 250                 255
His Gly Glu Asn Cys Tyr Leu Phe Ser Ser Gly Ser Phe Asn Trp Glu
                    260                 265                 270
Lys Ser Gln Glu Lys Cys Leu Ser Leu Asp Ala Lys Leu Leu Lys Ile
                    275                 280                 285
Asn Ser Thr Ala Asp Leu Asp Phe Ile Gln Gln Ala Ile Ser Tyr Ser
                    290                 295                 300
Ser Phe Pro Phe Trp Met Gly Leu Ser Arg Arg Asn Pro Ser Tyr Pro
305                 310                 315                 320
Trp Leu Trp Glu Asp Gly Ser Pro Leu Met Pro His Leu Phe Arg Val
                    325                 330                 335
Arg Gly Ala Val Ser Gln Thr Tyr Pro Ser Gly Thr Cys Ala Tyr Ile
                    340                 345                 350
Gln Arg Gly Ala Val Tyr Ala Glu Asn Cys Ile Leu Ala Ala Phe Ser
                    355                 360                 365
Ile Cys Gln Lys Lys Ala Asn Leu Arg Ala Gln
    370                 375

<210> SEQ ID NO 87
<211> LENGTH: 453
<212> TYPE: PRT
<213> ORGANISM: Artificial Sequence
<220> FEATURE:
<223> OTHER INFORMATION: E06_H0L0_IgG1_S267E/L328F heavy chain sequence

<400> SEQUENCE: 87

Glu Val Lys Leu Val Glu Ser Gly Gly Gly Leu Val Gln Pro Gly Gly
1               5                   10                  15
Ser Leu Arg Leu Ser Cys Ala Thr Ser Gly Phe Thr Phe Ser Asp Phe
                    20                  25                  30
Tyr Met Glu Trp Val Arg Gln Pro Pro Gly Lys Arg Leu Glu Trp Ile
                    35                  40                  45
Ala Ala Ser Arg Asn Lys Ala Asn Asp Tyr Thr Thr Glu Tyr Ser Ala
```

```
                    50                  55                  60
Ser Val Lys Gly Arg Phe Ile Val Ser Arg Asp Thr Ser Gln Ser Ile
 65                  70                  75                  80

Leu Tyr Leu Gln Met Asn Ala Leu Arg Ala Glu Asp Thr Ala Ile Tyr
                     85                  90                  95

Tyr Cys Ala Arg Asp Tyr Tyr Gly Ser Ser Tyr Trp Tyr Phe Asp Val
                100                 105                 110

Trp Gly Ala Gly Thr Thr Val Thr Val Ser Ser Ala Ser Thr Lys Gly
                115                 120                 125

Pro Ser Val Phe Pro Leu Ala Pro Ser Ser Lys Ser Thr Ser Gly Gly
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Phe Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
                450

<210> SEQ ID NO 88
```

```
<211> LENGTH: 451
<212> TYPE: PRT
<213> ORGANISM: Artificial Sequence
<220> FEATURE:
<223> OTHER INFORMATION: 2D03_H0L0_IgG1_S267E/L328F heavy chain sequence

<400> SEQUENCE: 88
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Ser Ile Ser Val Gly Gly His Arg Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Arg Val Gly Pro Ser Gly Gly Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Glu His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Phe Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 89
<211> LENGTH: 379
<212> TYPE: PRT
<213> ORGANISM: Artificial Sequence
<220> FEATURE:
<223> OTHER INFORMATION:
      huLOX1(137-237)-(G4S)2-Fc(216)_IgG1_C220S/S267E/L328F

<400> SEQUENCE: 89

Val Ala Asn Cys Ser Ala Pro Cys Pro Gln Asp Trp Ile Trp His Gly
1               5                   10                  15

Glu Asn Cys Tyr Leu Phe Ser Ser Gly Ser Phe Asn Trp Glu Lys Ser
            20                  25                  30

Gln Glu Lys Cys Leu Ser Leu Asp Ala Lys Leu Leu Lys Ile Asn Ser
        35                  40                  45

Thr Ala Asp Leu Asp Phe Ile Gln Gln Ala Ile Ser Tyr Ser Ser Phe
50                  55                  60

Pro Phe Trp Met Gly Leu Ser Arg Arg Asn Pro Ser Tyr Pro Trp Leu
65                  70                  75                  80

Trp Glu Asp Gly Ser Pro Leu Met Pro His Leu Phe Arg Val Arg Gly
                85                  90                  95

Ala Val Ser Gln Thr Tyr Pro Ser Gly Thr Cys Ala Tyr Ile Gln Arg
            100                 105                 110

Gly Ala Val Tyr Ala Glu Asn Cys Ile Leu Ala Ala Phe Ser Ile Cys
        115                 120                 125

Gln Lys Lys Ala Asn Leu Arg Ala Gln Gly Gly Gly Gly Ser Gly Gly
130                 135                 140

Gly Gly Ser Glu Pro Lys Ser Ser Asp Lys Thr His Thr Cys Pro Pro
145                 150                 155                 160

Cys Pro Ala Pro Glu Leu Leu Gly Gly Pro Ser Val Phe Leu Phe Pro
                165                 170                 175

Pro Lys Pro Lys Asp Thr Leu Met Ile Ser Arg Thr Pro Glu Val Thr
            180                 185                 190

Cys Val Val Val Asp Val Glu His Glu Asp Pro Glu Val Lys Phe Asn
        195                 200                 205

Trp Tyr Val Asp Gly Val Glu Val His Asn Ala Lys Thr Lys Pro Arg
    210                 215                 220

Glu Glu Gln Tyr Asn Ser Thr Tyr Arg Val Val Ser Val Leu Thr Val
225                 230                 235                 240

Leu His Gln Asp Trp Leu Asn Gly Lys Glu Tyr Lys Cys Lys Val Ser
                245                 250                 255

Asn Lys Ala Phe Pro Ala Pro Ile Glu Lys Thr Ile Ser Lys Ala Lys
            260                 265                 270

Gly Gln Pro Arg Glu Pro Gln Val Tyr Thr Leu Pro Pro Ser Arg Glu

```
                    275                 280                 285
Glu Met Thr Lys Asn Gln Val Ser Leu Thr Cys Leu Val Lys Gly Phe
    290                 295                 300

Tyr Pro Ser Asp Ile Ala Val Glu Trp Glu Ser Asn Gly Gln Pro Glu
305                 310                 315                 320

Asn Asn Tyr Lys Thr Thr Pro Pro Val Leu Asp Ser Asp Gly Ser Phe
                325                 330                 335

Phe Leu Tyr Ser Lys Leu Thr Val Asp Lys Ser Arg Trp Gln Gln Gly
            340                 345                 350

Asn Val Phe Ser Cys Ser Val Met His Glu Ala Leu His Asn His Tyr
        355                 360                 365

Thr Gln Lys Ser Leu Ser Leu Ser Pro Gly Lys
    370                 375

<210> SEQ ID NO 90
<211> LENGTH: 652
<212> TYPE: PRT
<213> ORGANISM: Artificial Sequence
<220> FEATURE:
<223> OTHER INFORMATION:
    huCD36(30-439)-(G4S)2-Fc(216)_IgG1_C220S/S267E/L328F

<400> SEQUENCE: 90

Gly Asp Leu Leu Ile Gln Lys Thr Ile Lys Lys Gln Val Val Leu Glu
1               5                   10                  15

Glu Gly Thr Ile Ala Phe Lys Asn Trp Val Lys Thr Gly Thr Glu Val
            20                  25                  30

Tyr Arg Gln Phe Trp Ile Phe Asp Val Gln Asn Pro Gln Glu Val Met
        35                  40                  45

Met Asn Ser Ser Asn Ile Gln Val Lys Gln Arg Gly Pro Tyr Thr Tyr
    50                  55                  60

Arg Val Arg Phe Leu Ala Lys Glu Asn Val Thr Gln Asp Ala Glu Asp
65                  70                  75                  80

Asn Thr Val Ser Phe Leu Gln Pro Asn Gly Ala Ile Phe Glu Pro Ser
                85                  90                  95

Leu Ser Val Gly Thr Glu Ala Asp Asn Phe Thr Val Leu Asn Leu Ala
            100                 105                 110

Val Ala Ala Ala Ser His Ile Tyr Gln Asn Gln Phe Val Gln Met Ile
        115                 120                 125

Leu Asn Ser Leu Ile Asn Lys Ser Lys Ser Ser Met Phe Gln Val Arg
    130                 135                 140

Thr Leu Arg Glu Leu Leu Trp Gly Tyr Arg Asp Pro Phe Leu Ser Leu
145                 150                 155                 160

Val Pro Tyr Pro Val Thr Thr Thr Val Gly Leu Phe Tyr Pro Tyr Asn
                165                 170                 175

Asn Thr Ala Asp Gly Val Tyr Lys Val Phe Asn Gly Lys Asp Asn Ile
            180                 185                 190

Ser Lys Val Ala Ile Ile Asp Thr Tyr Lys Gly Lys Arg Asn Leu Ser
        195                 200                 205

Tyr Trp Glu Ser His Cys Asp Met Ile Asn Gly Thr Asp Ala Ala Ser
    210                 215                 220

Phe Pro Pro Phe Val Glu Lys Ser Gln Val Leu Gln Phe Phe Ser Ser
225                 230                 235                 240

Asp Ile Cys Arg Ser Ile Tyr Ala Val Phe Glu Ser Asp Val Asn Leu
                245                 250                 255
```

-continued

Lys Gly Ile Pro Val Tyr Arg Phe Val Leu Pro Ser Lys Ala Phe Ala
            260             265             270

Ser Pro Val Glu Asn Pro Asp Asn Tyr Cys Phe Cys Thr Glu Lys Ile
            275             280             285

Ile Ser Lys Asn Cys Thr Ser Tyr Gly Val Leu Asp Ile Ser Lys Cys
    290             295             300

Lys Glu Gly Arg Pro Val Tyr Ile Ser Leu Pro His Phe Leu Tyr Ala
305             310             315             320

Ser Pro Asp Val Ser Glu Pro Ile Asp Gly Leu Asn Pro Asn Glu Glu
                325             330             335

Glu His Arg Thr Tyr Leu Asp Ile Glu Pro Ile Thr Gly Phe Thr Leu
            340             345             350

Gln Phe Ala Lys Arg Leu Gln Val Asn Leu Leu Val Lys Pro Ser Glu
            355             360             365

Lys Ile Gln Val Leu Lys Asn Leu Lys Arg Asn Tyr Ile Val Pro Ile
370             375             380

Leu Trp Leu Asn Glu Thr Gly Thr Ile Gly Asp Glu Lys Ala Asn Met
385             390             395             400

Phe Arg Ser Gln Val Thr Gly Lys Ile Asn Gly Gly Gly Ser Gly
            405             410             415

Gly Gly Gly Ser Glu Pro Lys Ser Ser Asp Lys Thr His Thr Cys Pro
            420             425             430

Pro Cys Pro Ala Pro Glu Leu Leu Gly Gly Pro Ser Val Phe Leu Phe
            435             440             445

Pro Pro Lys Pro Lys Asp Thr Leu Met Ile Ser Arg Thr Pro Glu Val
450             455             460

Thr Cys Val Val Val Asp Val Glu His Glu Asp Pro Glu Val Lys Phe
465             470             475             480

Asn Trp Tyr Val Asp Gly Val Glu Val His Asn Ala Lys Thr Lys Pro
            485             490             495

Arg Glu Glu Gln Tyr Asn Ser Thr Tyr Arg Val Val Ser Val Leu Thr
            500             505             510

Val Leu His Gln Asp Trp Leu Asn Gly Lys Glu Tyr Lys Cys Lys Val
            515             520             525

Ser Asn Lys Ala Phe Pro Ala Pro Ile Glu Lys Thr Ile Ser Lys Ala
530             535             540

Lys Gly Gln Pro Arg Glu Pro Gln Val Tyr Thr Leu Pro Pro Ser Arg
545             550             555             560

Glu Glu Met Thr Lys Asn Gln Val Ser Leu Thr Cys Leu Val Lys Gly
            565             570             575

Phe Tyr Pro Ser Asp Ile Ala Val Glu Trp Glu Ser Asn Gly Gln Pro
            580             585             590

Glu Asn Asn Tyr Lys Thr Thr Pro Pro Val Leu Asp Ser Asp Gly Ser
            595             600             605

Phe Phe Leu Tyr Ser Lys Leu Thr Val Asp Lys Ser Arg Trp Gln Gln
            610             615             620

Gly Asn Val Phe Ser Cys Ser Val Met His Glu Ala Leu His Asn His
625             630             635             640

Tyr Thr Gln Lys Ser Leu Ser Leu Ser Pro Gly Lys
            645             650

<210> SEQ ID NO 91
<211> LENGTH: 379
<212> TYPE: PRT

<213> ORGANISM: Artificial Sequence
<220> FEATURE:
<223> OTHER INFORMATION:
    empty-Fc(216)_IgG1_C220S/S267E/L328F-(G4S)2-huLOX1(137-237)

<400> SEQUENCE: 91

| | | | | | | | | | | | | | | | |
|---|---|---|---|---|---|---|---|---|---|---|---|---|---|---|---|
| Glu | Pro | Lys | Ser | Ser | Asp | Lys | Thr | His | Thr | Cys | Pro | Pro | Cys | Pro | Ala |
| 1 | | | | 5 | | | | | 10 | | | | | 15 | |
| Pro | Glu | Leu | Leu | Gly | Gly | Pro | Ser | Val | Phe | Leu | Phe | Pro | Pro | Lys | Pro |
| | | | 20 | | | | | 25 | | | | | 30 | | |
| Lys | Asp | Thr | Leu | Met | Ile | Ser | Arg | Thr | Pro | Glu | Val | Thr | Cys | Val | Val |
| | | 35 | | | | | 40 | | | | | 45 | | | |
| Val | Asp | Val | Glu | His | Glu | Asp | Pro | Glu | Val | Lys | Phe | Asn | Trp | Tyr | Val |
| 50 | | | | | 55 | | | | | 60 | | | | | |
| Asp | Gly | Val | Glu | Val | His | Asn | Ala | Lys | Thr | Lys | Pro | Arg | Glu | Glu | Gln |
| 65 | | | | | 70 | | | | | 75 | | | | | 80 |
| Tyr | Asn | Ser | Thr | Tyr | Arg | Val | Val | Ser | Val | Leu | Thr | Val | Leu | His | Gln |
| | | | | 85 | | | | | 90 | | | | | 95 | |
| Asp | Trp | Leu | Asn | Gly | Lys | Glu | Tyr | Lys | Cys | Lys | Val | Ser | Asn | Lys | Ala |
| | | | 100 | | | | | 105 | | | | | 110 | | |
| Phe | Pro | Ala | Pro | Ile | Glu | Lys | Thr | Ile | Ser | Lys | Ala | Lys | Gly | Gln | Pro |
| | | 115 | | | | | 120 | | | | | 125 | | | |
| Arg | Glu | Pro | Gln | Val | Tyr | Thr | Leu | Pro | Pro | Ser | Arg | Glu | Glu | Met | Thr |
| 130 | | | | | 135 | | | | | 140 | | | | | |
| Lys | Asn | Gln | Val | Ser | Leu | Thr | Cys | Leu | Val | Lys | Gly | Phe | Tyr | Pro | Ser |
| 145 | | | | | 150 | | | | | 155 | | | | | 160 |
| Asp | Ile | Ala | Val | Glu | Trp | Glu | Ser | Asn | Gly | Gln | Pro | Glu | Asn | Asn | Tyr |
| | | | | 165 | | | | | 170 | | | | | 175 | |
| Lys | Thr | Thr | Pro | Pro | Val | Leu | Asp | Ser | Asp | Gly | Ser | Phe | Phe | Leu | Tyr |
| | | | 180 | | | | | 185 | | | | | 190 | | |
| Ser | Lys | Leu | Thr | Val | Asp | Lys | Ser | Arg | Trp | Gln | Gln | Gly | Asn | Val | Phe |
| | | 195 | | | | | 200 | | | | | 205 | | | |
| Ser | Cys | Ser | Val | Met | His | Glu | Ala | Leu | His | Asn | His | Tyr | Thr | Gln | Lys |
| 210 | | | | | 215 | | | | | 220 | | | | | |
| Ser | Leu | Ser | Leu | Ser | Pro | Gly | Lys | Gly | Gly | Gly | Ser | Gly | Gly | Gly | Gly |
| 225 | | | | | 230 | | | | | 235 | | | | | 240 |
| Gly | Ser | Val | Ala | Asn | Cys | Ser | Ala | Pro | Cys | Pro | Gln | Asp | Trp | Ile | Trp |
| | | | | 245 | | | | | 250 | | | | | 255 | |
| His | Gly | Glu | Asn | Cys | Tyr | Leu | Phe | Ser | Ser | Gly | Ser | Phe | Asn | Trp | Glu |
| | | | 260 | | | | | 265 | | | | | 270 | | |
| Lys | Ser | Gln | Glu | Lys | Cys | Leu | Ser | Leu | Asp | Ala | Lys | Leu | Leu | Lys | Ile |
| | | 275 | | | | | 280 | | | | | 285 | | | |
| Asn | Ser | Thr | Ala | Asp | Leu | Asp | Phe | Ile | Gln | Gln | Ala | Ile | Ser | Tyr | Ser |
| 290 | | | | | 295 | | | | | 300 | | | | | |
| Ser | Phe | Pro | Phe | Trp | Met | Gly | Leu | Ser | Arg | Arg | Asn | Pro | Ser | Tyr | Pro |
| 305 | | | | | 310 | | | | | 315 | | | | | 320 |
| Trp | Leu | Trp | Glu | Asp | Gly | Ser | Pro | Leu | Met | Pro | His | Leu | Phe | Arg | Val |
| | | | | 325 | | | | | 330 | | | | | 335 | |
| Arg | Gly | Ala | Val | Ser | Gln | Thr | Tyr | Pro | Ser | Gly | Thr | Cys | Ala | Tyr | Ile |
| | | | 340 | | | | | 345 | | | | | 350 | | |
| Gln | Arg | Gly | Ala | Val | Tyr | Ala | Glu | Asn | Cys | Ile | Leu | Ala | Ala | Phe | Ser |
| | | 355 | | | | | 360 | | | | | 365 | | | |
| Ile | Cys | Gln | Lys | Lys | Ala | Asn | Leu | Arg | Ala | Gln |
| | | 370 | | | | | 375 | | | |

<210> SEQ ID NO 92
<211> LENGTH: 123
<212> TYPE: PRT
<213> ORGANISM: Artificial Sequence
<220> FEATURE:
<223> OTHER INFORMATION: E06_H1 variable heavy chain sequence

<400> SEQUENCE: 92

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Ala Pro Gly Lys Gly Leu Glu Trp Val
        35                  40                  45

Gly Ala Ser Arg Asn Lys Ala Asn Asp Tyr Thr Thr Glu Tyr Ser Ala
    50                  55                  60

Ser Val Lys Gly Arg Phe Thr Ile Thr Arg Asp Thr Ser Ala Ser Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Tyr Tyr Gly Ser Ser Tyr Trp Tyr Phe Asp Val
            100                 105                 110

Trp Gly Ala Gly Thr Leu Val Thr Val Ser Ser
        115                 120
```

<210> SEQ ID NO 93
<211> LENGTH: 123
<212> TYPE: PRT
<213> ORGANISM: Artificial Sequence
<220> FEATURE:
<223> OTHER INFORMATION: E06_H2 variable heavy chain sequence

<400> SEQUENCE: 93

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Ala Pro Gly Gln Arg Leu Glu Trp Val
        35                  40                  45

Gly Ala Ser Arg Asn Lys Ala Asn Asp Tyr Thr Thr Glu Tyr Ser Ala
    50                  55                  60

Ser Val Lys Gly Arg Phe Thr Ile Ser Arg Asp Thr Ser Lys Ser Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Tyr Tyr Gly Ser Ser Tyr Trp Tyr Phe Asp Val
            100                 105                 110

Trp Gly Ala Gly Thr Leu Val Thr Val Ser Ser
        115                 120
```

<210> SEQ ID NO 94
<211> LENGTH: 113
<212> TYPE: PRT
<213> ORGANISM: Artificial Sequence
<220> FEATURE:
<223> OTHER INFORMATION: E06_L1 variable light chain sequence

<400> SEQUENCE: 94

```
Asp Ile Val Met Thr Gln Ser Pro Leu Ser Leu Pro Val Thr Pro Gly
```

```
                1               5                  10                 15
Glu Pro Ala Ser Ile Ser Cys Arg Ala Ser Glu Ser Leu Tyr Ser Ser
                    20                 25                 30

Lys His Lys Val His Tyr Leu Ala Trp Tyr Gln Lys Lys Pro Gly Gln
        35                 40                 45

Ser Pro Gln Leu Leu Ile Tyr Gly Ala Ser Asn Arg Tyr Ile Gly Val
    50                 55                 60

Pro Asp Arg Phe Thr Gly Ser Gly Ser Gly Thr Asp Phe Thr Leu Lys
65                  70                 75                 80

Ile Ser Arg Val Glu Ala Glu Asp Val Gly Val Tyr Tyr Cys Ala Gln
                85                 90                 95

Phe Tyr Ser Tyr Pro Leu Thr Phe Gly Ala Gly Thr Lys Leu Glu Ile
                100                105                110

Lys

<210> SEQ ID NO 95
<211> LENGTH: 113
<212> TYPE: PRT
<213> ORGANISM: Artificial Sequence
<220> FEATURE:
<223> OTHER INFORMATION: E06_L2 variable light chain sequence

<400> SEQUENCE: 95

Asp Ile Val Met Thr Gln Ser Pro Ser Ser Leu Ser Ala Ser Val Gly
1               5                  10                 15

Asp Arg Val Thr Ile Thr Cys Arg Ala Ser Glu Ser Leu Tyr Ser Ser
                20                 25                 30

Lys His Lys Val His Tyr Leu Ala Trp Tyr Gln Lys Lys Pro Gly Lys
        35                 40                 45

Ser Pro Lys Leu Leu Ile Tyr Gly Ala Ser Asn Arg Tyr Ile Gly Val
    50                 55                 60

Pro Asp Arg Phe Thr Gly Ser Gly Ser Gly Thr Asp Phe Thr Leu Thr
65                  70                 75                 80

Ile Ser Ser Leu Gln Pro Glu Asp Phe Ala Thr Tyr Tyr Cys Ala Gln
                85                 90                 95

Phe Tyr Ser Tyr Pro Leu Thr Phe Gly Ala Gly Thr Lys Leu Glu Ile
                100                105                110

Lys

<210> SEQ ID NO 96
<211> LENGTH: 4
<212> TYPE: PRT
<213> ORGANISM: Artificial Sequence
<220> FEATURE:
<223> OTHER INFORMATION: sequence linker

<400> SEQUENCE: 96

Gly Phe Leu Gly
1
```